US012435369B2

(12) United States Patent
Graham et al.

(10) Patent No.: US 12,435,369 B2
(45) Date of Patent: Oct. 7, 2025

(54) NUCLEOTIDE ANALOGS AND USES THEREOF

(71) Applicant: Singular Genomics Systems, Inc., San Diego, CA (US)

(72) Inventors: Ronald Graham, Carlsbad, CA (US); Surya Adhikari, San Diego, CA (US); Ada Tong, San Diego, CA (US); Zachary Terranova, San Diego, CA (US)

(73) Assignee: Singular Genomcis Systems, Inc., San Diego, CA (US)

( * ) Notice: Subject to any disclaimer, the term of this patent is extended or adjusted under 35 U.S.C. 154(b) by 637 days.

(21) Appl. No.: 17/887,289

(22) Filed: Aug. 12, 2022

(65) Prior Publication Data

US 2023/0119408 A1 Apr. 20, 2023

Related U.S. Application Data

(60) Provisional application No. 63/301,780, filed on Jan. 21, 2022, provisional application No. 63/276,430, filed on Nov. 5, 2021, provisional application No. 63/232,950, filed on Aug. 13, 2021.

(51) Int. Cl.
*C07H 19/10* (2006.01)
*C12Q 1/6874* (2018.01)

(52) U.S. Cl.
CPC .......... *C12Q 1/6874* (2013.01); *C07H 19/10* (2013.01)

(58) Field of Classification Search
CPC .................................................. C07H 19/10
See application file for complete search history.

(56) References Cited

U.S. PATENT DOCUMENTS

| | | | |
|---|---|---|---|
| 5,034,506 | A | 7/1991 | Summerton et al. |
| 5,235,033 | A | 8/1993 | Summerton et al. |
| 6,664,079 | B2 | 12/2003 | Ju et al. |
| 10,738,072 | B1 | 8/2020 | Graham et al. |
| 11,174,281 | B1 | 11/2021 | Graham et al. |
| 2006/0003383 | A1 | 1/2006 | Graham |
| 2007/0009980 | A1 | 1/2007 | Graham |
| 2009/0047699 | A1 | 2/2009 | Graham |
| 2016/0002721 | A1 | 1/2016 | Liu et al. |

FOREIGN PATENT DOCUMENTS

| | | | |
|---|---|---|---|
| WO | WO2001092284 | A1 * | 12/2001 |
| WO | WO-2015/148402 | A1 | 10/2015 |
| WO | WO-2018/148723 | A1 | 8/2018 |
| WO | WO-2020/056044 | A1 | 3/2020 |

OTHER PUBLICATIONS

Bentley, D. R. et al. (Nov. 6, 2008). "Accurate whole human genome sequencing using reversible terminator chemistry," *Nature* 456(7218): 53-59.

Bergen, K. et al. (Jun. 3, 2013). "Structures of KOD and 9 N DNA polymerases complexed with primer template duplex," *ChemBioChem* 14(9): 1058-1062.

Binauld, S. et al. (Mar. 14, 2013, e-published Dec. 10, 2012). "Acid-degradable polymers for drug delivery: a decade of innovation." *Chemical Communications* 49(21): 2082-2102.

Feeney, R. E. et al. (Apr. 1, 1982). "Chemical modification of proteins: An overview," *Advances in Chemistry Series* 182: 3-55.

Franzini, R. M. et al. (Jun. 13, 2008). "Organometallic activation of a fluorogen for templated nucleic acid detection," *Organic Letters* 10(14): 2935-2938.

Fuller, C. W. et al. (Apr. 18, 2016). "Real-time single-molecule electronic DNA sequencing by synthesis using polymer-tagged nucleotides on a nanopore array," *Proceedings of the National Academy of Sciences* 113(19): 5233-5238.

Grabowski, J. et al. (Feb. 13, 2018). "Preparation of acetals from aldehydes and alcohols under basic conditions," *Organic & Biomolecular Chemistry* 16(17): 3114-3120.

Guo, J. et al. (Jul. 8, 2008, e-published Jun. 30, 2008). "Four-color DNA sequencing with 3'- O-modified nucleotide reversible terminators and chemically cleavable fluorescent dideoxynucleotides," *PNAS USA* 105(27):9145-9150.

Hutter, D. et al. (e-published Dec. 1, 2010). "Labeled nucleoside triphosphates with reversibly terminating aminoalkoxyl groups," *Nucleosides, Nucleotides and Nucleic Acids* 29(11-12): 879-895.

Ju, J. et al. (Dec. 26, 2006). "Four-color DNA sequencing by synthesis using cleavable fluorescent nucleotide reversible terminators," *Proceedings of the National Academy of Sciences* 103(52): 19635-19640.

Kumar, S. et al. (Aug. 29, 2012, e-published Sep. 21, 2012). "PEG-labeled nucleotides and nanopore detection for single molecule DNA sequencing by synthesis," *Scientific Reports* 2:684.

Leriche, G. et al. (Aug. 2, 2010). "Optimization of the azobenzene scaffold for reductive cleavage by dithionite; development of an azobenzene cleavable linker for proteomic applications," *European Journal of Organic Chemistry* 23: 4360-4364.

Mag, M. et al. (Nov. 24, 1992). "Synthesis and selective cleavage of an oligodeoxynucleotide containing a bridged non-chiral internucleotide 3'-phosphoramidate linkage," *Tetrahedron letters* 33(48): 7319-7322.

Matikonda, S. S. et al. (Jul. 3, 2020). "Core remodeling leads to long wavelength fluoro-coumarins," *Chemical science* 11: 7302-7307.

Meguro, Y. et al. (Aug. 6, 2020). "Efficient generation of thiolate sugars from glycosyl Bunte salts and its application to S-glycoside synthesis," *Tetrahedron Letters* 61(32): 152198.

Omura, M. et al. (e-published Mar. 10, 2007). "One-pot synthesis of α-alkoxy azides from carbonyl compounds catalyzed by iron (III) chloride," *Chemistry letters* 36(4): 532-533.

Rathod, K. M. et al. (2013). "Synthesis and antimicrobial activity of azo compounds containing m-cresol moiety," *Chemical Science Transactions* 2(1): 25-28.

Rosenblum, B. B. et al. (Nov. 1, 1997). "New dye-labeled terminators for improved DNA sequencing patterns," *Nucleic acids research* 25(22): 4500-4504.

Ruparel, H. et al. (Apr. 13, 2005). "Design and synthesis of a 3'-O-allyl photocleavable fluorescent nucleotide as a reversible terminator for DNA sequencing by synthesis," *Proceedings of the National Academy of Sciences* 102(17): 5932-5937.

(Continued)

*Primary Examiner* — Adam C Milligan
*Assistant Examiner* — Karen Cheng
(74) *Attorney, Agent, or Firm* — Mintz, Levin, Cohn, Ferris, Glovsky and Popeo, P.C.; Zachary L. Terranova

(57) ABSTRACT

Disclosed herein, inter alia, are compounds, modified nucleotides, compositions, and methods of using the same.

16 Claims, 7 Drawing Sheets

(56) References Cited

OTHER PUBLICATIONS

Seio, K. et al. (Nov. 1, 2002). "A new protecting group for 5'-hydroxyl function of nucleotides in oligonucleotide synthesis without acid treatment utilizing unique properties of tritylthio group," *Nucleic acids symposium series* 2(1): 27-28.

Seliger, H. (2000). "Protection of 5'-Hydroxy Functions of Nucleosides," *Current protocols in nucleic acid chemistry* 2.3.1-2.3.34.

Shenoi, R. A. et al. (Aug. 20, 2012). "Branched multifunctional polyether polyketals: variation of ketal group structure enables unprecedented control over polymer degradation in solution and within cells," *Journal of the American Chemical Society* 134(36): 14945-14957.

Southworth, M.W. et al. (May 28, 1996). "Cloning of thermostable DNA polymerases from hyperthermophilic marine Archaea with emphasis on *Thermococcus* sp. 9° N-7 and mutations affecting 3'-5' exonuclease activity," *PNAS USA* 93(11):5281-5285.

Walker, J. W. et al. (Oct. 1, 1988) "Photolabile 1-(2-nitrophenyl) ethyl phosphate esters of adenine nucleotide analogs. Synthesis and mechanism of photolysis," *Journal of the American Chemical Society* 110(21): 7170-7177.

Wu, J. et al. (Oct. 16, 2007). "3'-O-modified nucleotides as reversible terminators for pyrosequencing," *Proceedings of the National Academy of Sciences* 104(42): 16462-16467.

Zhu, Z. et al. (Aug. 25, 1994) "Directly labeled DNA probes using fluorescent nucleotides with different length linkers." Nucleic acids research 22(16): 3418-3422.

Franzini, R. M. et al. (Nov. 11, 2009, e-published Jul. 14, 2009). "Efficient nucleic acid detection by templated reductive quencher release," Journal of the American Chemical Society 131(44): 16021-16023.

* cited by examiner rxn1 rxn2 rxn3 rxn4

RT#1

RT#12

RT#1

RT#12

NUCLEOTIDE ANALOGS AND USES THEREOF

CROSS-REFERENCES TO RELATED APPLICATIONS

This application claims the benefit of U.S. Provisional Application No. 63/232,950, filed Aug. 13, 2021, U.S. Provisional Application No. 63/276,430, filed Nov. 5, 2021 and U.S. Provisional Application No. 63/301,780, filed Jan. 21, 2022, which are all incorporated herein by reference in its entirety and for all purposes.

BACKGROUND

DNA sequencing is a fundamental tool in biological and medical research; it is an essential technology for the paradigm of personalized precision medicine. Among various new DNA sequencing methods, sequencing by synthesis (SBS) is the leading method for realizing the goal of the $1,000 genome. Accordingly, there is a need for modified nucleotides and nucleosides that are effectively recognized as substrates by DNA polymerases, that are efficiently and accurately incorporated into growing DNA chains during SBS. Disclosed herein, inter alia, are solutions to these and other problems in the art.

BRIEF SUMMARY

In an aspect is provided a compound having the formula:

(I)

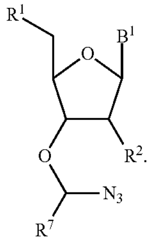

$B^1$ is a nucleobase. $R^1$ is a polyphosphate moiety, 5'-O-nucleoside protecting group, monophosphate moiety, nucleic acid moiety, hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a polymerase-compatible cleavable moiety. $R^7$ is substituted or unsubstituted cycloalkyl, substituted or unsubstituted heterocycloalkyl, substituted or unsubstituted aryl, or substituted or unsubstituted heteroaryl.

In an aspect is provided a nucleic acid polymerase complex including a nucleic acid polymerase, wherein the nucleic acid polymerase is bound to a compound as described herein, including embodiments.

In an aspect is provided a method for sequencing a nucleic acid, including: (i) incorporating in series with a nucleic acid polymerase, within a reaction vessel, one of four different compounds into a primer to create an extension strand, wherein the primer is hybridized to the nucleic acid and wherein each of the four different compounds comprises a unique detectable label; and (ii) detecting the unique detectable label of each incorporated compound, so as to thereby identify each incorporated compound in the extension strand, thereby sequencing the nucleic acid; wherein each of the four different compounds is independently a compound as described herein, including embodiments.

In another aspect is provided a method of incorporating a compound into a primer, the method including combining a polymerase, a primer hybridized to nucleic acid template and the compound within a reaction vessel and allowing the polymerase to incorporate the compound into the primer thereby forming an extended primer, wherein the compound is a compound as described herein, including embodiments.

In another aspect is provided a method of preparing or synthesizing a compound of Formula (I)

(I)

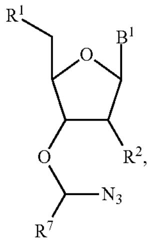

the method including mixing compound (A), compound (B), and an azide salt together in a reaction vessel, wherein compound (A) has the formula:

(A)

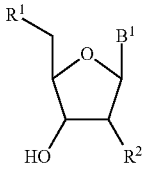

and compound (B) has the formula:

(B)

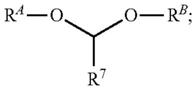

wherein $B^1$, $R^1$, $R^2$, and $R^7$ are as described herein. $R^A$ and $R^B$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

BRIEF DESCRIPTION OF THE DRAWINGS

FIG. 1B illustrates the overall enthalpic contribution to the four different subreactions.

FIG. 3A), second reaction (rxn2; FIG. 3B), third reaction (rxn3; FIG. 3C), and fourth reaction (rnx4; FIG. 3D) for a variety of reversible terminators. Including a resonance-stabilizing moiety (e.g., a cyclic moiety, such as an aromatic or heteroaromatic moiety found in RT #8-RT #19) affects the reaction enthalpy, in particular for rxn3 and rxn4.

DETAILED DESCRIPTION

Figure 1A:
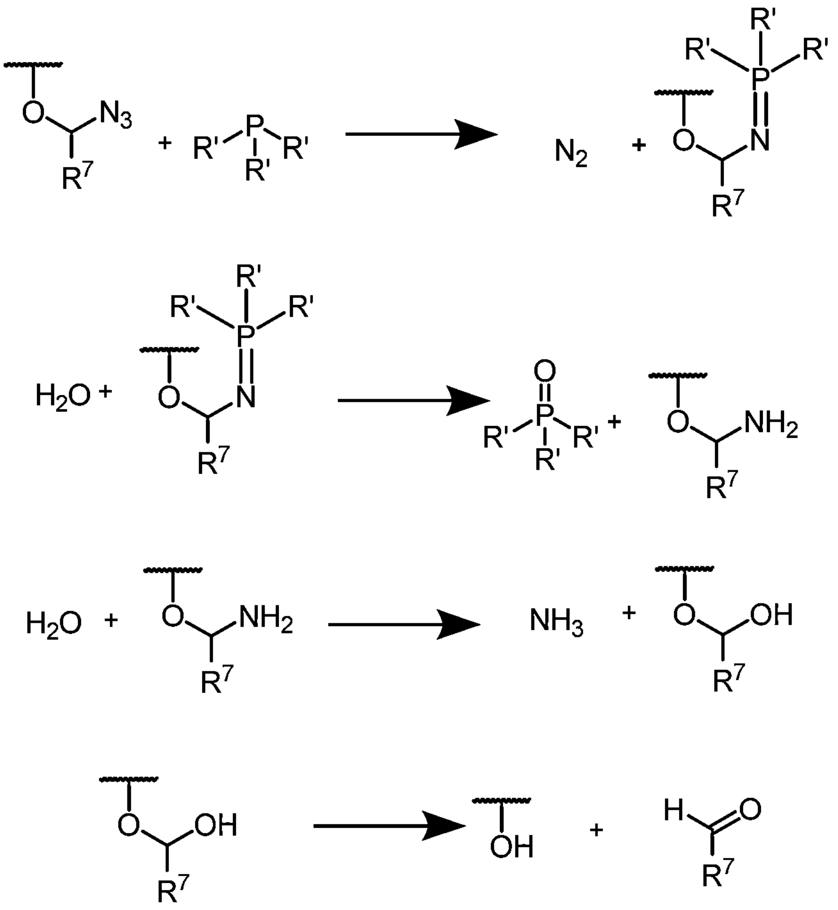
FIGS. 1A-1B. Reaction scheme depicting the removal of an azido-containing reversible terminator. Briefly, the 3' oxygen is protected with an R-substituted methylene azide, wherein R is as described herein (e.g., as $R^7$). A phosphine-containing reducing agent (e.g., tris(2-carboxyethyl)phosphine (TCEP)), depicted as $P(R')_3$, contacts the reversible terminator to generate $N_2$ and a phosphine imide (rxn1). The resulting phosphine imide hydrolyzes to form an amine (rxn2), which further evolves to an acetal releasing ammonia (rxn3). Finally, the acetal hydrolyzes to form an aldehyde and a 3' OH on the nucleotide (rxn4).

The aspects and embodiments described herein relate to novel nucleotide analogues.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkenyl includes one or more double bonds. An alkynyl includes one or more triple bonds.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne. The term "alkynylene" by itself or as part of another substituent, means, unless otherwise stated, a divalent radical derived from an alkyne. In embodiments, the alkylene is fully saturated. In embodiments, the alkylene is monounsaturated. In embodiments, the alkylene is polyunsaturated. An alkenylene includes one or more double bonds. An alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—S—CH_2$, $—S(O)—CH_3$, $—CH_2—CH_2—S(O)_2—CH_3$, $—CH{=}CHO—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P).

A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. A heteroalkenylene includes one or more double bonds. A heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. In embodiments, a bicyclic or multicyclic cycloalkyl ring system refers to multiple rings fused together or multiple spirocyclic rings wherein at least one of the fused or spirocyclic rings is a cycloalkyl ring and wherein the multiple rings are attached to the parent molecular moiety through any carbon atom contained within a cycloalkyl ring of the multiple rings.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, a bicyclic or multicyclic cycloalkenyl ring system refers to multiple rings fused together or multiple spirocyclic rings wherein at least one of the fused or spirocyclic rings is a cycloalkenyl ring and wherein the multiple rings are attached to the parent molecular moiety through any carbon atom contained within a cycloalkenyl ring of the multiple rings.

In embodiments, the term "heterocycloalkyl" means a monocyclic, bicyclic, or a multicyclic heterocycloalkyl ring system. In embodiments, heterocycloalkyl groups are fully saturated. In embodiments, a bicyclic or multicyclic heterocycloalkyl ring system refers to multiple rings fused together or multiple spirocyclic rings wherein at least one of the fused or spirocyclic rings is a heterocycloalkyl ring and wherein the multiple rings are attached to the parent molecular moiety through any atom contained within a heterocycloalkyl ring of the multiple rings.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. A bicyclic or multicyclic cycloalkyl ring system refers to multiple rings fused together wherein at least one of the fused rings is a cycloalkyl ring and wherein the multiple rings are attached to the parent molecular moiety through any carbon atom contained within a cycloalkyl ring of the multiple rings.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. A bicyclic or multicyclic cycloalkenyl ring system refers to multiple rings fused together wherein at least one of the fused rings is a cycloalkenyl ring and wherein the multiple rings are attached to the parent molecular moiety through any carbon atom contained within a cycloalkenyl ring of the multiple rings.

In embodiments, the term "heterocycloalkyl" means a monocyclic, bicyclic, or a multicyclic heterocycloalkyl ring system. In embodiments, heterocycloalkyl groups are fully saturated. A bicyclic or multicyclic heterocycloalkyl ring system refers to multiple rings fused together wherein at least one of the fused rings is a heterocycloalkyl ring and wherein the multiple rings are attached to the parent molecular moiety through any atom contained within a heterocycloalkyl ring of the multiple rings.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring and wherein the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom (s) are optionally quaternized. Thus, the term "heteroaryl" includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "~" denotes the point of attachment of a chemical moiety to the remainder of a molecule or chemical formula. The term "oxo," as used herein, means an oxygen that is double bonded to a carbon atom.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NR$SO_2$R', —NR'NR"R"', —ONR'R", —NR'C(O)NR"NR"'R"", —CN, —$NO_2$, —NR'$SO_2$R", —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')═NR"", —NR—C(NR'R")═NR"', —S(O)R', —S(O)$_2$R', —S(O)$_2$NR'R", —NRSO$_2$R', —NR'NR"R"', —ONR'R", —NR'C(O)NR"NR"'R"", —CN, —$NO_2$, —R', —$N_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$—$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_5$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and/or each substituted or unsubstituted heteroaryl is a substituted or unsubstituted 5 to 6 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In some embodiments, the compound (e.g., nucleotide analogue) is a chemical species set forth in the Examples section, claims, embodiments, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers. As used herein, the term "isomers" refers to compounds having the same number and kind of atoms, and hence the same molecular weight, but differing in respect to the structural arrangement or configuration of the atoms. The term "tautomer," as used herein, refers to one of two or more structural isomers which exist in equilibrium and which are readily converted from one isomeric form to another. It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure. The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," "analogue" or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent," "detectable compound," "detectable label," or "detectable moiety" is a substance (e.g., element), molecule, or composition detectable by spectroscopic, photochemical, biochemical, immunochemical, chemical, magnetic resonance imaging, or other physical means. For example, detectable agents include $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$ $^{189}Re$, $^{194}r$ $^{198}Au$, $^{199}Au$, $^{211}At$, $^{211}Pb$, $^{212}B^{1}$, $^{212}Pb$, $^{213}B^{1}$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, $^{32}P$, fluorophore (e.g., fluorescent dyes), modified oligonucleotides (e.g., moieties described in PCT/US2015/022063, which is incorporated herein by reference), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. In embodiments, a detectable moiety is a moiety (e.g., monovalent form) of a detectable agent.

The terms "fluorophore" or "fluorescent agent" or "fluorescent dye" are used interchangeably and refer to a substance, compound, agent (e.g., a detectable agent), or composition (e.g., compound) that can absorb light at one or more wavelengths and re-emit light at one or more longer wavelengths, relative to the one or more wavelengths of absorbed light. Examples of fluorophores that may be included in the compounds and compositions described herein include fluorescent proteins, xanthene derivatives (e.g., fluorescein, rhodamine, Oregon green, eosin, or Texas red), cyanine and derivatives (e.g., cyanine, indocarbocyanine, oxacarbocyanine, thiacarbocyanine, or merocyanine), napththalene derivatives (e.g., dansyl or prodan derivatives), coumarin and derivatives, oxadiazole derivatives (e.g., pyridyloxazole, nitrobenzoxadiazole or benzoxadiazole), anthracene derivatives (e.g., anthraquinones, DRAQ5, DRAQ7, or CyTRAK Orange), pyrene derivatives (e.g., cascade blue and derivatives), oxazine derivatives (e.g., Nile red, Nile blue, cresyl violet, or oxazine 170), acridine derivatives (e.g., proflavin, acridine orange, acridine yellow), arylmethine derivatives (e.g., auramine, crystal violet, or malachite green), tetrapyrrole derivatives (e.g., porphin, phthalocyanine, bilirubin), CF Dye™, DRAQ™, CyTRAK™, BODIPY™, Alexa Fluor™, DyLight Fluor™, Atto™, Tracy™ FluoProbes™, Abberior Dyes™, DY™ dyes, MegaStokes Dyes™, Sulfo Cy™, Seta™ dyes, SeTau™ dyes, Square Dyes™, Quasar™ dyes, Cal Fluor™ dyes, SureLight Dyes™, PerCP™ Phycobilisomes™, APC™, APCXL™, RPE™, and/or BPE™. A fluorescent moiety is a radical of a fluorescent agent. The emission from the fluorophores can be detected by any number of methods, including but not limited to, fluorescence spectroscopy, fluorescence microscopy, fluorimeters, fluorescent plate readers, infrared scanner analysis, laser scanning confocal microscopy, automated confocal nanoscanning, laser spectrophotometers, fluorescent-activated cell sorters (FACS), image-based analyzers and fluorescent scanners (e.g., gel/membrane scanners). In embodiments, the fluorophore is an aromatic (e.g., polyaromatic) moiety having a conjugated 7r-electron system. In embodiments, the fluorophore is a fluorescent dye moiety, that is, a monovalent fluorophore.

Radioactive substances (e.g., radioisotopes) that may be used as imaging and/or labeling agents in accordance with the embodiments of the disclosure include, but are not limited to, $^{18}F$, $^{32}P$, $^{33}P$, $^{45}Ti$, $^{47}SC$, $^{52}Fe$, $^{62}Cu$, $^{64}Cu$, $^{67}Cu$, $^{67}Ga$ $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$ $^{161}Tb$, $^{166}Dy$ $^{166}Ho$, $^{169}Er$, $^{175}Lu$, $^{177}Lu$, $^{186}Re$, $^{188}Re$, $^{189}Re$, $^{194}Ir$ $^{198}Au$, $^{199}Au$, $^{211}At$, $^{211}Pb$, $^{212}B^1$, $^{212}Pb$, $^{213}B^1$, $^{223}Ra$ and $^{225}Ac$. Paramagnetic ions that may be used as additional imaging agents in accordance with the embodiments of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Examples of detectable agents include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent moiety or fluorescent dye moiety. In embodiments, the detectable moiety is a fluorescein isothiocyanate moiety, tetramethylrhodamine-5-(and 6)-isothiocyanate moiety, Cy2 moiety, Cy3 moiety, Cy5 moiety, Cy7 moiety, 4',6-diamidino-2-phenylindole moiety, Hoechst 33258 moiety, Hoechst 33342 moiety, Hoechst 34580 moiety, propidium-iodide moiety, or acridine orange moiety. In embodiments, the detectable moiety is a Indo-1, Ca saturated moiety, Indo-1 Ca2+ moiety, Cascade Blue BSA pH 7.0 moiety, Cascade Blue moiety, LysoTracker Blue moiety, Alexa 405 moiety, LysoSensor Blue pH 5.0 moiety, LysoSensor Blue moiety, DyLight 405 moiety, DyLight 350 moiety, BFP (Blue Fluorescent Protein) moiety, Alexa 350 moiety, 7-Amino-4-methylcoumarin pH 7.0 moiety, Amino Coumarin moiety, AMCA conjugate moiety, Coumarin moiety, 7-Hydroxy-4-methylcoumarin moiety, 7-Hydroxy-4-methylcoumarin pH 9.0 moiety, 6,8-Difluoro-7-hydroxy-4-methylcoumarin pH 9.0 moiety, Hoechst 33342 moiety, Pacific Blue moiety, Hoechst 33258 moiety, Hoechst 33258-DNA moiety, Pacific Blue antibody conjugate pH 8.0 moiety, PO—PRO-1 moiety, PO—PRO-1-DNA moiety, POPO-1 moiety, POPO-1-DNA moiety, DAPI-DNA moiety, DAPI moiety, Marina Blue moiety, SYTOX Blue-DNA moiety, CFP (Cyan Fluorescent Protein) moiety, eCFP (Enhanced Cyan Fluorescent Protein) moiety, 1-Anilinonaphthalene-8-sulfonic acid (1,8-ANS) moiety, Indo-1, Ca free moiety, 1,8-ANS (1-Anilinonaphthalene-8-sulfonic acid) moiety, BO-PRO-1-DNA moiety, BOPRO-1 moiety, BOBO-1-DNA moiety, SYTO 45-DNA moiety, evoglow-Ppl moiety, evoglow-Bs1 moiety, evoglow-Bs2 moiety, Auramine O moiety, DiO moiety, LysoSensor Green pH 5.0 moiety, Cy 2 moiety, LysoSensor Green moiety, Fura-2, high Ca moiety, Fura-2 Ca2+sup> moiety, SYTO 13-DNA moiety, YO-PRO-1-DNA moiety, YOYO-1-DNA moiety, eGFP (Enhanced Green Fluorescent Protein) moiety, LysoTracker Green moiety, GFP (S65T) moiety, BODIPY FL, MeOH moiety, Sapphire moiety, BODIPY FL conjugate moiety, MitoTracker Green moiety, MitoTracker Green FM, MeOH moiety, Fluorescein 0.1 M NaOH moiety, Calcein pH 9.0 moiety, Fluorescein pH 9.0 moiety, Calcein moiety, Fura-2, no Ca moiety, Fluo-4 moiety, FDA moiety, DTAF moiety, Fluorescein moiety, CFDA moiety, FITC moiety, Alexa Fluor 488 hydrazide-water moiety, DyLight 488 moiety, 5-FAM pH 9.0 moiety, Alexa 488 moiety, Rhodamine 110 moiety, Rhodamine 110 pH 7.0 moiety, Acridine Orange moiety, BCECF pH 5.5 moiety, PicoGreendsDNA quantitation reagent moiety, SYBR Green I moiety, Rhodaminen Green pH 7.0 moiety, CyQUANT GR-DNA moiety, NeuroTrace 500/525, green fluorescent Nissl stain-RNA moiety, DansylCadaverine moiety, Fluoro-Emerald moiety, Nissl moiety, Fluorescein dextran pH 8.0 moiety, Rhodamine Green moiety, 5-(and -6)-Carboxy-2',7'-dichlorofluorescein pH 9.0 moiety, DansylCadaverine, MeOH moiety, eYFP (Enhanced Yellow Fluorescent Protein) moiety, Oregon Green 488 moiety, Fluo-3 moiety, BCECF pH 9.0 moiety, SBFI-Na+ moiety, Fluo-3 Ca2+ moiety, Rhodamine 123 MeOH moiety, FlAsH moiety, Calcium Green-1 Ca2+ moiety, Magnesium Green moiety, DM-NERF pH 4.0 moiety, Calcium Green moiety, Citrine moiety, LysoSensor Yellow pH 9.0 moiety, TO—PRO-1-DNA moiety, Magnesium Green Mg2+ moiety, Sodium Green Na+ moiety, TOTO-1-DNA moiety, Oregon Green 514 moiety, Oregon Green 514 antibody conjugate pH 8.0 moiety, NBD-X moiety, DM-NERF pH 7.0 moiety, NBD-X, MeOH moiety, CI-NERF pH 6.0 moiety, Alexa 430 moiety, CI-NERF pH 2.5 moiety, Lucifer Yellow, CH moiety, LysoSensor Yellow pH 3.0 moiety, 6-TET, SE pH 9.0 moiety, Eosin antibody conjugate pH 8.0 moiety, Eosin moiety, 6-Carboxyrhodamine 6G pH 7.0 moiety, 6-Carboxyrhodamine 6G, hydrochloride moiety, Bodipy R6G SE moiety, BODIPY R6G MeOH moiety, 6 JOE moiety, Cascade Yellow moiety, mBanana moiety, Alexa 532 moiety, Erythrosin-5-isothiocyanate pH 9.0 moiety, 6-HEX, SE pH 9.0 moiety, mOrange moiety, mHoneydew moiety, Cy 3 moiety, Rhodamine B moiety, DiI moiety, 5-TAMRA-MeOH moiety, Alexa 555 moiety, DyLight 549 moiety, BODIPY TMR-X, SE moiety, BODIPY TMR-X MeOH moiety, PO—PRO-3-DNA moiety, PO—PRO-3 moiety, Rhodamine moiety, POPO-3 moiety, Alexa 546 moiety, Calcium Orange Ca2+ moiety, TRITC moiety, Calcium Orange moiety, Rhodaminephalloidin pH 7.0 moiety, MitoTracker Orange moiety, MitoTracker Orange MeOH moiety, Phycoerythrin moiety, Magnesium Orange moiety, R-Phycoerythrin pH 7.5 moiety, 5-TAMRA pH 7.0 moiety, 5-TAMRA moiety, Rhod-2 moiety, FM 1-43 moiety, Rhod-2 Ca2+ moiety, FM 1-43 lipid moiety, LOLO-1-DNA moiety, dTomato moiety, DsRed moiety, Dapoxyl (2-aminoethyl) sulfonamide moiety, Tetramethylrhodamine dextran pH 7.0 moiety, Fluor-Ruby moiety, Resorufin moiety, Resorufin pH 9.0 moiety, mTangerine moiety, LysoTracker Red moiety, Lissaminerhodamine moiety, Cy 3.5 moiety, Rhodamine Red-X antibody conjugate pH 8.0 moiety, Sulforhodamine 101 EtOH moiety, JC-1 pH 8.2 moiety, JC-1 moiety, mStrawberry moiety, MitoTracker Red moiety, MitoTracker Red, MeOH moiety, X-Rhod-1 Ca2+ moiety, Alexa 568 moiety, 5-ROX pH 7.0 moiety, 5-ROX (5-Carboxy-X-rhodamine, triethylammonium salt) moiety, BO-PRO-3-DNA moiety, BOPRO-3 moiety, BOBO-3-DNA moiety, Ethidium Bromide moiety, ReAsH moiety, Calcium Crimson moiety, Calcium Crimson Ca2+ moiety, mRFP moiety, mCherry moiety, HcRed moiety, DyLight 594 moiety, Ethidium homodimer-1-DNA moiety, Ethidiumhomodimer moiety, Propidium Iodide moiety, SYPRO Ruby moiety, Propidium Iodide-DNA moiety, Alexa 594 moiety, BODIPY TR-X, SE moiety, BODIPY TR-X, MeOH moiety, BODIPY TR-X phallacidin pH 7.0 moiety, Alexa Fluor 610 R-phycoerythrin streptavidin pH 7.2 moiety, YO-PRO-3-DNA moiety, Di-8 ANEPPS moiety, Di-8-ANEPPS-lipid moiety, YOYO-3-DNA moiety, Nile Red-lipid moiety, Nile Red moiety, DyLight 633 moiety, mPlum moiety, TO-PRO-3-DNA moiety, DDAO pH 9.0 moiety, Fura Red high Ca moiety, Allophycocyanin pH 7.5 moiety, APC (allophycocyanin) moiety, Nile Blue, EtOH moiety, TOTO-3-DNA moiety, Cy 5 moiety, BODIPY 650/665-X, MeOH moiety, Alexa Fluor 647 R-phycoerythrin streptavidin pH 7.2 moiety, DyLight 649 moiety, Alexa 647 moiety, Fura Red Ca2+ moiety, Atto 647 moiety, Fura Red, low Ca moiety, Carboxynaphthofluorescein pH 10.0 moiety, Alexa 660 moiety, Cy 5.5 moiety, Alexa 680 moiety, DyLight 680 moiety, Alexa 700 moiety, FM 4-64, 2% CHAPS moiety, or FM 4-64 moiety. In embodiments, the dectable moiety is a moiety of 1,1-Diethyl-4,4-carbocyanine iodide, 1,2-Diphenylacetylene, 1,4-Diphenylbutadiene, 1,4-Diphenylbutadiyne, 1,6-Diphenylhexatriene, 1,6-Diphenylhexatriene, 1-anilinonaphthalene-8-sulfonic acid, 2,7-Dichlorofluorescein, 2,5-DIPHENYLOXAZOLE, 2-Di-1-ASP, 2-dodecylresorufin, 2-Methylbenzoxazole, 3,3-Diethylthiadicarbocyanine iodide, 4-Dimethylamino-4-Nitrostilbene, 5(6)-Carboxyfluorescein, 5(6)-Carboxynaphtofluorescein, 5(6)-Carboxytetramethylrhodamine B, 5-(and -6)-carboxy-2',7'-dichlorofluorescein, 5-(and -6)-carboxy-2,7-dichlorofluorescein, 5-(N-hexadecanoyl)aminoeosin, 5-(N-hexadecanoyl)aminoeosin, 5-chloromethylfluorescein, 5-FAM, 5-ROX, 5-TAMRA, 5-TAMRA, 6,8-difluoro-7-hydroxy-4-methylcoumarin, 6,8-difluoro-7-hydroxy-4-methylcoumarin, 6-carboxyrhodamine 6G, 6-HEX, 6-JOE, 6-JOE, 6-TET, 7-aminoactinomycin D, 7-Benzylamino-4-Nitrobenz-2-Oxa-1,3-Diazole, 7-Methoxycoumarin-4-Acetic Acid, 8-Benzyloxy-5,7-diphenylquinoline, 8-Benzyloxy-5,7-diphenylquinoline, 9,10-Bis(Phenylethynyl) Anthracene, 9,10-Diphenylanthracene, 9-METHYLCARBAZOLE, $(CS)_2Ir(\mu-Cl)_2Ir(CS)_2$, AAA, Acridine Orange, Acridine Orange, Acridine Yellow, Acridine Yellow, Adams Apple Red 680, Adirondack Green 520, Alexa Fluor 350, Alexa Fluor 405, Alexa Fluor 430, Alexa Fluor 430, Alexa Fluor 480, Alexa Fluor 488, Alexa Fluor 488, Alexa Fluor 488 hydrazide, Alexa Fluor 500, Alexa Fluor 514, Alexa Fluor 532, Alexa Fluor 546, Alexa Fluor 546, Alexa Fluor 555, Alexa Fluor 555, Alexa Fluor 568, Alexa Fluor 594, Alexa Fluor 594, Alexa Fluor 594, Alexa Fluor 610, Alexa Fluor 610-R-PE, Alexa Fluor 633, Alexa Fluor 635, Alexa Fluor 647, Alexa Fluor 647, Alexa Fluor 647-R-PE, Alexa Fluor 660, Alexa Fluor 680, Alexa Fluor 680-APC, Alexa Fluor 680-R-PE, Alexa Fluor 700, Alexa Fluor 750, Alexa Fluor 790, Allophycocyanin, AmCyanl, Aminomethylcoumarin, Amplex Gold (product), Amplex Red Reagent, Amplex UltraRed, Anthracene, APC, APC-Seta-750, AsRed2, ATTO 390, ATTO 425, ATTO 430LS, ATTO 465, ATTO 488, ATTO 490LS, ATTO 495, ATTO 514, ATTO 520, ATTO 532, ATTO 550, ATTO 565, ATTO 590, ATTO 594, ATTO 610, ATTO 620, ATTO 633, ATTO 635, ATTO 647, ATTO 647N, ATTO 655, ATTO 665, ATTO 680, ATTO 700, ATTO 725, ATTO 740, ATTO Oxal2, ATTO Rho3B, ATTO Rho6G, ATTO Rho 11, ATTO Rhol2, ATTO Rhol3, ATTO Rhol4, ATTO Rhol01, ATTO Thiol2, Auramine O, Azami Green, Azami Green monomeric, B-phycoerythrin, BCECF, BCECF, Bex1, Biphenyl, Birch Yellow 580, Blue-green algae, BO-PRO-1, BO-PRO-3, BOBO-1, BOBO-3, BODIPY 630 650-X, BODIPY 650/665-X, BODIPY FL, BODIPY FL, BODIPY R6G, BODIPY TMR-X, BODIPY TR-X, BODIPY TR-X Ph 7.0, BODIPY TR-X phallacidin, BODIPY-DiMe, BODIPY-Phenyl, BODIPY-TMSCC, C3-Indocyanine, C3-Indocyanine, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, C545T, C-Phycocyanin, Calcein, Calcein red-orange, Calcium Crimson, Calcium Green-1, Calcium Orange, Calcofluor white 2MR, Carboxy SNARF-1 pH 6.0, Carboxy SNARF-1 pH 9.0, Carboxynaphthofluorescein, Cascade Blue, Cascade Yellow, Catskill Green 540, CBQCA, CellMask Orange, CellTrace BODIPY TR methyl ester, CellTrace calcein violet, CellTrace™ Far Red, CellTracker Blue, CellTracker Red CMTPX, CellTracker Violet BMQC, CF405M, CF405S, CF488A, CF543, CF555, CFP, CFSE, CF™ 350, CF™ 485, Chlorophyll A, Chlorophyll B, Chromeo 488, Chromeo 494, Chromeo 505, Chromeo 546, Chromeo 642, Citrine, Citrine, ClOH butoxy aza-BODIPY, ClOH C12 aza-BODIPY, CM-H2DCFDA, Coumarin 1, Coumarin 6, Coumarin 6, Coumarin 30, Coumarin 314, Coumarin 334, Coumarin 343, Coumarine 545T, Cresyl Violet Perchlorate, CryptoLight CF1, CryptoLight CF2, CryptoLight CF3, CryptoLight CF4, CryptoLight CF5, CryptoLight CF6, Crystal Violet, Cumarin153, Cy2, Cy3, Cy3, Cy3.5, Cy3B, Cy3B, Cy3Cy5 ET, Cy5, Cy5, Cy5.5, Cy7, Cyanine3 NHS ester, Cyanine5 carboxylic acid, Cyanine5 NHS ester, Cyclotella meneghiniana Kutzing, CypHer5, CypHer5 pH 9.15, CyQUANT GR, CyTrak Orange, Dabcyl SE, DAF-FM, DAMC (Weiss), dansyl cadaverine, Dansyl Glycine (Dioxane), DAPI, DAPI, DAPI, DAPI, DAPI (DMSO), DAPI ($H_2O$), Dapoxyl (2-aminoethyl)sulfonamide, DCI, DCM, DCM, DCM (acetonitrile), DCM (MeOH), DDAO, Deep Purple, di-8-ANEPPS, DiA, Dichlorotris(1,10-phenanthroline) ruthenium(II), DiClOH C12 aza-BODIPY, DiClOHbutoxy aza-BODIPY, DiD, DiI, DiIC18(3), DiO, DiR, Diversa Cyan-FP, Diversa Green-FP, DM-NERF pH 4.0, DOCI, Doxorubicin, DPP pH-Probe 590-7.5, DPP pH- Probe 590-9.0, DPP pH-Probe 590-11.0, DPP pH-Probe 590-11.0, Dragon Green, DRAQ5, DsRed, DsRed, DsRed, DsRed-Express, DsRed-Express2, DsRed-Express T1, dTomato, DY-350XL, DY-480, DY-480XL MegaStokes, DY-485, DY-485XL MegaStokes, DY-490, DY-490XL MegaStokes, DY-500, DY-500XL MegaStokes, DY-520, DY-520XL MegaStokes, DY-547, DY-549P1, DY-549P1, DY-554, DY-555, DY-557, DY-557, DY-590, DY-590, DY-615, DY-630, DY-631, DY-633, DY-635, DY-636, DY-647, DY-649P1, DY-649P1, DY-650, DY-651, DY-656, DY-673, DY-675, DY-676, DY-680, DY-681, DY-700, DY-701, DY-730, DY-731, DY-750, DY-751, DY-776, DY-782, Dye-28, Dye-33, Dye-45, Dye-304, Dye-1041, DyLight 488, DyLight 549, DyLight 594, DyLight 633, DyLight 649, DyLight 680, E2-Crimson, E2-Orange, E2-Red/Green, EBFP, ECF, ECFP, ECL Plus, eGFP, ELF 97, Emerald, Envy Green, Eosin, Eosin Y, epicocconone, EqFP611, Erythrosin-5-isothiocyanate, Ethidium bromide, ethidium homodimer-1, Ethyl Eosin, Ethyl Eosin, Ethyl Nile Blue A, Ethyl-p-Dimethylaminobenzoate, Ethyl-p-Dimethylaminobenzoate, Eu203 nanoparticles, Eu (Soini), Eu(tta) 3DEADIT, EvaGreen, EVOblue-30, EYFP, FAD, FITC, FITC, FlAsH (Adams), Flash Red EX, FlAsH-CCPGCC, FlAsH-CCXXCC, Fluo-3, Fluo-4, Fluo-5F, Fluorescein, Fluorescein 0.1 NaOH, Fluorescein-Dibase, fluoro-emerald, Fluorol 5G, FluoSpheres blue, FluoSpheres crimson, FluoSpheres dark red, FluoSpheres orange, FluoSpheres red, FluoSpheres yellow-green, FM4-64 in CTC, FM4-64 in SDS, FM 1-43, FM 4-64, Fort Orange 600, Fura Red, Fura Red Ca free, fura-2, Fura-2 Ca free, Gadodiamide, Gd-Dtpa-Bma, Gadodiamide, Gd-Dtpa-Bma, GelGreen™, Ge1Red™, H9-40, HcRedl, Hemo Red 720, HiLyte Fluor 488, HiLyte Fluor 555, HiLyte Fluor 647, HiLyte Fluor 680, HiLyte Fluor 750, HiLyte Plus 555, HiLyte Plus 647, HiLyte Plus 750, HmGFP, Hoechst 33258, Hoechst 33342, Hoechst-33258, Hoechst-33258, Hops Yellow 560, HPTS, HPTS, HPTS, HPTS, HPTS, indo-1, Indo-1 Ca free, Ir(Cn)$_2$(acac), Ir(Cs)$_2$(acac), IR-775 chloride, IR-806, Ir-OEP—CO-Cl, IRDye® 650 Alkyne, IRDye® 650 Azide, IRDye® 650 Carboxylate, IRDye® 650 DBCO, IRDye® 650 Maleimide, IRDye® 650 NHS Ester, IRDye® 680LT Carboxylate, IRDye® 680LT Maleimide, IRDye® 680LT NHS Ester, IRDye® 680RD Alkyne, IRDye® 680RD Azide, IRDye® 680RD Carboxylate, IRDye® 680RD DBCO, IRDye® 680RD Maleimide, IRDye® 680RD NHS Ester, IRDye® 700 phosphoramidite, IRDye® 700DX, IRDye® 700DX, IRDye® 700DX Carboxylate, IRDye® 700DX NHS Ester, IRDye® 750 Carboxylate, IRDye® 750 Maleimide, IRDye® 750 NHS Ester, IRDye® 800 phosphoramidite, IRDye® 800CW, IRDye® 800CW Alkyne, IRDye® 800CW Azide, IRDye® 800CW Carboxylate, IRDye® 800CW DBCO, IRDye® 800CW Maleimide, IRDye® 800CW NHS Ester, IRDye® 800RS, IRDye® 800RS Carboxylate, IRDye® 800RS NHS Ester, IRDye® QC-1 Carboxylate, IRDye® QC-1 NHS Ester, *Isochrysis galbana*—Parke, JC-1, JC-1, JOJO-1, Jonamac Red Evitag T2, Kaede Green, Kaede Red, kusabira orange, Lake Placid 490, LDS 751, Lissamine Rhodamine (Weiss), LOLO-1, lucifer yellow CH, Lucifer Yellow CH, lucifer yellow CH, Lucifer Yellow CH Dilitium salt, Lumio Green, Lumio Red, Lumogen F Orange, Lumogen Red F300, Lumogen Red F300, LysoSensor Blue DND-192, LysoSensor Green DND-153, LysoSensor Green DND-153, LysoSensor Yellow/Blue DND-160 pH 3, LysoSensor YellowBlue DND-160, LysoTracker Blue DND-22, LysoTracker Blue DND-22, LysoTracker Green DND-26, LysoTracker Red DND-99, LysoTracker Yellow HCK-123, Macoun Red Evitag T2, Macrolex Fluorescence Red G, Macrolex Fluorescence Yellow 1OGN, Macrolex Fluorescence Yellow 1OGN, Magnesium Green, Magnesium Octaethylporphyrin, Magnesium Orange, Magnesium Phthalocyanine, Magnesium Phthalocyanine, Magnesium Tetramesitylporphyrin, Magnesium Tetraphenylporphyrin, malachite green isothiocyanate, Maple Red-Orange 620, Marina Blue, mBanana, mBBr, mCherry, Merocyanine 540, Methyl green, Methyl green, Methyl green, Methylene Blue, Methylene Blue, mHoney-Dew, MitoTracker Deep Red 633, MitoTracker Green FM, MitoTracker Orange CMTMRos, MitoTracker Red CMXRos, monobromobimane, Monochlorobimane, Monoraphidium, mOrange, mOrange2, mPlum, mRaspberry, mRFP, mRFP1, mRFP1.2 (Wang), mStrawberry (Shaner), mTangerine (Shaner), N,N-Bis(2,4,6-trimethylphenyl)-3,4:9,10-perylenebis(dicarboximide), NADH, Naphthalene, Naphthalene, Naphthofluorescein, Naphthofluorescein, NBD-X, NeuroTrace 500525, Nilblau perchlorate, nile blue, Nile Blue, Nile Blue (EtOH), nile red, Nile Red, Nile Red, Nile red, Nileblue A, NIR1, NIR2, NIR3, NIR4, NIR820, Octaethylporphyrin, OH butoxy aza-BODIPY, OHC12 aza-BODIPY, Orange Fluorescent Protein, Oregon Green 488, Oregon Green 488 DUPE, Oregon Green 514, Oxazin1, Oxazin 750, Oxazine 1, Oxazine 170, P4-3, P-Quaterphenyl, P-Terphenyl, PA-GFP (post-activation), PA-GFP (pre-activation), Pacific Orange, Palladium (II) meso-tetraphenyl-tetrabenzoporphyrin, PdOEPK, PdTFPP, PerCP-Cy5.5, Perylene, Perylene, Perylene bisimide pH-Probe 550-5.0, Perylene bisimide pH-Probe 550-5.5, Perylene bisimide pH-Probe 550-6.5, Perylene Green pH-Probe 720-5.5, Perylene Green Tag pH-Probe 720-6.0, Perylene Orange pH-Probe 550-2.0, Perylene Orange Tag 550, Perylene Red pH-Probe 600-5.5, Perylenediimid, Perylne Green pH-Probe 740-5.5, Phenol, Phenylalanine, pHrodo, succinimidyl ester, Phthalocyanine, PicoGreen dsDNA quantitation reagent, Pinacyanol-Iodide, Piroxicam, Platinum(II) tetraphenyltetrabenzoporphyrin, Plum Purple, PO—PRO-1, PO—PRO-3, POPO-1, POPO-3, POPOP, Porphin, PPO, Proflavin, PromoFluor-350, PromoFluor-405, PromoFluor-415, PromoFluor-488, PromoFluor-488 Premium, PromoFluor-488LSS, PromoFluor-500LSS, PromoFluor-505, PromoFluor-510LSS, PromoFluor-514LSS, PromoFluor-520LSS, PromoFluor-532, PromoFluor-546, PromoFluor-555, PromoFluor-590, PromoFluor-610, PromoFluor-633, PromoFluor-647, PromoFluor-670, PromoFluor-680, PromoFluor-700, PromoFluor-750, PromoFluor-770, PromoFluor-780, PromoFluor-840, propidium iodide, Protoporphyrin IX, PTIR475/UF, PTIR545/UF, PtOEP, PtOEPK, PtTFPP, Pyrene, QD525, QD565, QD585, QD605, QD655, QD705, QD800, QD903, QD PbS 950, QDot 525, QDot 545, QDot 565, Qdot 585, Qdot 605, Qdot 625, Qdot 655, Qdot 705, Qdot 800, QpyMe2, QSY 7, QSY 7, QSY 9, QSY 21, QSY 35, quinine, Quinine Sulfate, Quinine sulfate, R-phycoerythrin, R-phycoerythrin, ReAsH-CCPGCC, ReAsH-CCXXCC, Red Beads (Weiss), Redmond Red, Resorufin, resorufin, rhod-2, Rhodamin 700 perchlorate, rhodamine, Rhodamine 6G, Rhodamine 6G, Rhodamine 101, rhodamine 110, Rhodamine 123, rhodamine 123, Rhodamine B, Rhodamine B, Rhodamine Green, Rhodamine pH-Probe 585-7.0, Rhodamine pH-Probe 585-7.5, Rhodamine phalloidin, Rhodamine Red-X, Rhodamine Red-X, Rhodamine Tag pH-Probe 585-7.0, Rhodol Green, Riboflavin, Rose Bengal, Sapphire, SBFI, SBFI Zero Na, *Scenedesmus* sp., SensiLight PBXL-1, SensiLight PBXL-3, Seta 633-NHS, Seta-633-NHS, SeTau-380-NHS, SeTau-647-NHS, Snake-Eye Red 900, SNIR1, SNIR2, SNIR3, SNIR4, Sodium Green, Solophenyl flavine 7GFE 500, Spectrum Aqua, Spectrum Blue, Spectrum FRed, Spectrum Gold, Spectrum Green, Spectrum Orange, Spectrum Red, Squarylium dye III, Stains All, Stilben derivate, Stilbene, Styryl8 perchlorate, Sulfo-Cyanine3 carboxylic acid, Sulfo-Cyanine3 carboxylic acid, Sulfo-Cyanine3 NHS ester, Sulfo-Cyanine5 carboxylic acid, Sulforhodamine 101, sulforhodamine 101, Sulforhodamine B, Sulforhodamine G, Suncoast Yellow, SuperGlo BFP, SuperGlo GFP, Surf Green EX, SYBR Gold nucleic acid gel stain, SYBR Green I, SYPRO Ruby, SYTO 9, SYTO 11, SYTO 13, SYTO 16, SYTO 17, SYTO 45, SYTO 59, SYTO 60, SYTO 61, SYTO 62, SYTO 82, SYTO RNASelect, SYTO RNASelect, SYTOX Blue, SYTOX Green, SYTOX Orange, SYTOX Red, T-Sapphire, Tb (Soini), tCO, tdTomato, Terrylen, Terrylendiimid, testdye, Tetra-t-Butylazaporphine, Tetra-t-Butylnaphthalocyanine, Tetracen, Tetrakis(o-Aminophenyl)Porphyrin, Tetramesitylporphyrin, Tetramethylrhodamine, tetramethylrhodamine, Tetraphenylporphyrin, Tetraphenylporphyrin, Texas Red, Texas Red DUPE, Texas Red-X, ThiolTracker Violet, Thionin acetate, TMRE, TO-PRO-1, TO-PRO-3, Toluene, Topaz (Tsienl998), TOTO-1, TOTO-3, Tris(2,2-Bipyridyl)Ruthenium(II) chloride, Tri s(4,4-diphenyl-2,2-bipyridine) ruthenium(II) chloride, Tris(4,7-diphenyl-1,10-phenanthroline) ruthenium(II) TMS, TRITC (Weiss), TRITC Dextran (Weiss), Tryptophan, Tyrosine, Vex1, Vybrant DyeCycle Green stain, Vybrant DyeCycle Orange stain, Vybrant DyeCycle Violet stain, WEGFP (post-activation), WellRED D2, WellRED D3, WellRED D4, WtGFP, WtGFP (Tsienl998), X-rhod-1, Yakima Yellow, YFP, YO-PRO-1, YO-PRO-3, YOYO-1, YoYo-1, YoYo-1 dsDNA, YoYo-1 ssDNA, YOYO-3, Zinc Octaethylporphyrin, Zinc Phthalocyanine, Zinc Tetramesitylporphyrin, Zinc Tetraphenylporphyrin, ZsGreenl, or ZsYellowl. In embodiments, $R^4$ is a monovalent moiety of a compound described within this paragraph.

In embodiments, the detectable moiety is a moiety of a derivative of one of the detectable moieties described immediately above, wherein the derivative differs from one of the detectable moieties immediately above by a modification resulting from the conjugation of the detectable moiety to a compound described herein.

In embodiments, the detectable label is a fluorescent dye. In embodiments, the detectable label is a fluorescent dye capable of exchanging energy with another fluorescent dye (e.g., fluorescence resonance energy transfer (FRET) chromophores).

The term "cyanine" or "cyanine moiety" as described herein refers to a detectable moiety containing two nitrogen groups separated by a polymethine chain. In embodiments, the cyanine moiety has 3 methine structures (i.e., cyanine 3 or Cy3). In embodiments, the cyanine moiety has 5 methine structures (i.e., cyanine 5 or Cy5). In embodiments, the cyanine moiety has 7 methine structures (i.e., cyanine 7 or Cy7).

Descriptions of compounds (e.g., nucleotide analogues) of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

As used herein, the term "salt" refers to acid or base salts of the compounds described herein. Thus, the compounds of the present invention may exist as salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. In embodiments, compounds may be presented with a positive charge, and it is understood an appropriate counter-ion (e.g., chloride ion, fluoride ion, or acetate ion) may also be present, though not explicitly shown. Likewise, for compounds having a negative charge (e.g., 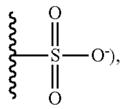

it is understood an appropriate counter-ion (e.g., a proton, sodium ion, potassium ion, or ammonium ion) may also be present, though not explicitly shown. The protonation state of the compound (e.g., a compound described herein) depends on the local environment (i.e., the pH of the environment), therefore, in embodiments, the compound may be described as having a moiety in a protonated state (e.g., 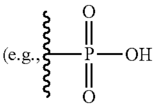 or

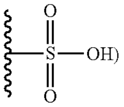

or an ionic state (e.g., 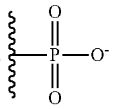 or

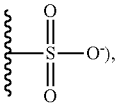

and it is understood these are interchangeable. In embodiments, the counter-ion is represented by the symbol M (e.g., $M^+$ or $M^-$). The neutral forms of the compounds are preferably regenerated by contacting the salt with a base or acid and isolating the parent compound in the conventional manner. The parent form of the compound may differ from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Hybridize" shall mean the annealing of one single-stranded nucleic acid (such as a primer) to another nucleic acid based on the well-understood principle of sequence complementarity. In an embodiment the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. Those skilled in the art understand how to estimate and adjust the stringency of hybridization conditions such that sequences having at least a desired level of complementarity will stably hybridize, while those having lower complementarity will not. As used herein, the term "stringent condition" refers to condition(s) under which a polynucleotide probe or primer will hybridize preferentially to its target sequence, and to a lesser extent to, or not at all to, other sequences. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex which comprises a double-stranded portion of nucleic acid.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated, however, that the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

An "effective amount" is an amount sufficient for a compound to accomplish a stated purpose relative to the absence of the compound (e.g., achieve the effect for which it is administered). An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Nucleic acid" refers to nucleotides (e.g., deoxyribonucleotides or ribonucleotides) and polymers thereof in either single-, double- or multiple-stranded form, or complements thereof, or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. Nucleic acids and polynucleotides are polymers of any length, including longer lengths, e.g., 200, 300, 500, 1000, 2000, 3000, 5000, 7000, 10,000, etc. In certain embodiments the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see, Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. A residue of a nucleic acid, as referred to herein, is a monomer of the nucleic acid (e.g., a nucleotide). The term "nucleoside" refers, in the usual and customary sense, to a glycosylamine including a nucleobase and a five-carbon sugar (ribose or deoxyribose). Non-limiting examples of nucleosides include cytidine, uridine, adenosine, guanosine, thymidine and inosine. Nucleosides may be modified at the base and/or the sugar. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g., polynucleotides contemplated herein include any types of RNA, e.g., mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like. A "nucleic acid moiety" as used herein is a monovalent form of a nucleic acid. In embodiments, the nucleic acid moiety is attached to the 3' or 5' position of a nucleotide or nucleoside.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

As used herein, the term "template polynucleotide" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s). In the context of selective sequencing, "target polynucleotide (s)" refers to the subset of polynucleotide(s) to be sequenced from within a starting population of polynucleotides.

"Nucleotide," as used herein, refers to a nucleoside-5'-phosphate (e.g., polyphosphate) compound, or a structural analog thereof, which can be incorporated (e.g., partially incorporated as a nucleoside-5'-monophosphate or derivative thereof) by a nucleic acid polymerase to extend a growing nucleic acid chain (such as a primer). Nucleotides may comprise bases such as adenine (A), cytosine (C), guanine (G), thymine (T), uracil (U), or analogues thereof, and may comprise 1, 2, 3, 4, 5, 6, 7, 8, or more phosphates in the phosphate group. Nucleotides may be modified at one or more of the base, sugar, or phosphate group. A nucleotide may have a label or tag attached (a "labeled nucleotide" or "tagged nucleotide"). In an embodiment, the nucleotide is a deoxyribonucleotide. In another embodiment, the nucleotide is a ribonucleotide. In embodiments, nucleotides comprise 3 phosphate groups (e.g., a triphosphate group).

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphorothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g., phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

In embodiments, "nucleotide analogue," "nucleotide analog," or "nucleotide derivative" shall mean an analogue of adenine (A), cytosine (C), guanine (G), thymine (T), or uracil (U) (that is, an analogue or derivative of a nucleotide comprising the base A, G, C, T or U), comprising a phosphate group, which may be recognized by DNA or RNA polymerase (whichever is applicable) and may be incorporated into a strand of DNA or RNA (whichever is appropriate). Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the —OH group at the 3-position of deoxyribose. Nucleotide analogues and DNA polymerase-based DNA sequencing are also described in U.S. Pat. No. 6,664,079, which is incorporated herein by reference in its entirety for all purposes.

A "nucleoside" is structurally similar to a nucleotide, but is missing the phosphate moieties. An example of a nucleoside analogue would be one in which the label is linked to the base and there is no phosphate group attached to the sugar molecule. "Nucleoside," as used herein, refers to a glycosyl compound consisting of a nucleobase and a 5-membered ring sugar (e.g., either ribose or deoxyribose). Nucleosides may comprise bases such as adenine (A), cytosine (C), guanine (G), thymine (T), uracil (U), or analogues thereof. Nucleosides may be modified at the base and/or and the sugar. In an embodiment, the nucleoside is a deoxyribonucleoside. In another embodiment, the nucleoside is a ribonucleoside.

The terms "bioconjugate group," "bioconjugate reactive moiety," and "bioconjugate reactive group" refer to a chemical moiety which participates in a reaction to form a bioconjugate linker (e.g., covalent linker). Non-limiting examples of bioconjugate groups include —$NH_2$, —COOH, —$COOCH_3$, —N-hydroxysuccinimide, -maleimide,

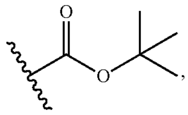
, or

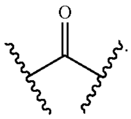
.

In embodiments, the bioconjugate reactive group may be protected (e.g., with a protecting group). Additional examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |

-continued

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or streptavidin to form a avidin-biotin complex or streptavidin-biotin complex.

The term "monophosphate" is used in accordance with its ordinary meaning in the arts and refers to a moiety having the formula:

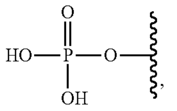

or ionized forms thereof. The term "polyphosphate" refers to at least two phosphate groups, having the formula:

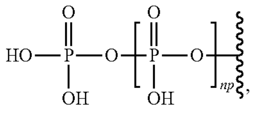

or ionized forms thereof, wherein np is an integer of 1 or greater. In embodiments, np is an integer from 1 to 5. In embodiments, np is an integer from 1 to 2. In embodiments, np is 2. The term "diphosphate" is used in accordance with its ordinary meaning in the arts and refers to a moiety having the formula:

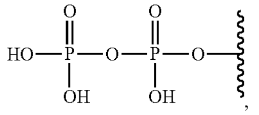 [SMILES: *OP(=O)(O)OP(=O)(O)O]

or ionized forms thereof. The term "triphosphate" is used in accordance with its ordinary meaning in the arts and refers to a moiety having the formula:

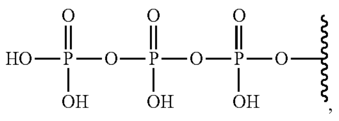 [SMILES: *OP(=O)(O)OP(=O)(O)OP(=O)(O)O]

or ionized forms thereof. In embodiments, a polyphosphate is a diphosphate. In embodiments, a polyphosphate is a triphosphate.

The term "nucleobase" or "base" as used herein refers to a purine or pyrimidine compound, or a derivative thereof, that may be a constituent of nucleic acid (i.e., DNA or RNA, or a derivative thereof). In embodiments, the nucleobase is a divalent purine or pyrimidine, or derivative thereof. In embodiments, the nucleobase is a monovalent purine or pyrimidine, or derivative thereof. In embodiments, the base is a derivative of a naturally occurring DNA or RNA base (e.g., a base analogue). In embodiments, the base is a hybridizing base. In embodiments the base hybridizes to a complementary base. In embodiments, the base is capable of forming at least one hydrogen bond with a complementary base (e.g., adenine hydrogen bonds with thymine, adenine hydrogen bonds with uracil, guanine pairs with cytosine). Non-limiting examples of a base includes cytosine or a derivative thereof (e.g., cytosine analogue), guanine or a derivative thereof (e.g., guanine analogue), adenine or a derivative thereof (e.g., adenine analogue), thymine or a derivative thereof (e.g., thymine analogue), uracil or a derivative thereof (e.g., uracil analogue), hypoxanthine or a derivative thereof (e.g., hypoxanthine analogue), xanthine or a derivative thereof (e.g., xanthine analogue), 7-methylguanine or a derivative thereof (e.g., 7-methylguanine analogue), deaza-adenine or a derivative thereof (e.g., deaza-adenine analogue), deaza-guanine or a derivative thereof (e.g., deaza-guanine), deaza-hypoxanthine or a derivative thereof, 5,6-dihydrouracil or a derivative thereof (e.g., 5,6-dihydrouracil analogue), 5-methylcytosine or a derivative thereof (e.g., 5-methylcytosine analogue), or 5-hydroxymethylcytosine or a derivative thereof (e.g., 5-hydroxymethylcytosine analogue) moieties. In embodiments, the base is adenine, guanine, uracil, cytosine, thymine, hypoxanthine, xanthine, theobromine, caffeine, uric acid, or isoguanine, which may be optionally substituted or modified. In embodiments, the base is adenine, guanine, hypoxanthine, xanthine, theobromine, caffeine, uric acid, or isoguanine, which may be optionally substituted or modified.

As used herein, the term "complementary" or "substantially complementary" refers to the hybridization, base pairing, or the formation of a duplex between nucleotides or nucleic acids. For example, complementarity exists between the two strands of a double-stranded DNA molecule or between an oligonucleotide primer and a primer binding site on a single-stranded nucleic acid when a nucleotide (e.g., RNA or DNA) or a sequence of nucleotides is capable of base pairing with a respective cognate nucleotide or cognate sequence of nucleotides. As described herein and commonly known in the art the complementary (matching) nucleotide of adenosine (A) is thymidine (T) and the complementary (matching) nucleotide of guanosine (G) is cytosine (C). Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. "Duplex" means at least two oligonucleotides and/or polynucleotides that are fully or partially complementary undergo Watson-Crick type base pairing among all or most of their nucleotides so that a stable complex is formed.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin or loop structure, with or without an overhang) or portions of separate polynucleotides. In embodiments, one or both sequences in a pair of complementary sequences form portions of longer polynucleotides, which may or may not include additional regions of complementarity.

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. In embodiments, a cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). In embodiments, a cleavable linker is a self-immolative linker, a trivalent linker, or a linker capable of dendritic amplication of signal, or a self-immolative dendrimer containing linker (e.g., all as described in US 2007/0009980, US 2006/0003383, and US 2009/0047699, which are incorporated by reference in their entirety for any purpose). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is sodium dithionite ($Na_2S_2O_4$), weak acid, hydrazine ($N_2H_4$), Pd(0), or light-irradiation (e.g., ultraviolet radiation). In embodiments, cleaving includes removing. A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include a modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group(s). In embodiments, the scissile site includes at least one uracil nucleobase. In embodiments, a uracil nucleobase can be cleaved with a uracil DNA glycosylase (UDG) or Formamidopyrimidine DNA Glycosylase Fpg. In embodiments, the scissile linkage site includes a sequence-specific nicking site having a nucleotide sequence that is recognized and nicked by a nicking endonuclease enzyme or a uracil DNA glycosylase. The term "self-immolative" referring to a linker is used in accordance with its well understood meaning in Chemistry and Biology as used in US 2007/0009980, US 2006/0003383, and US 2009/0047699, which are incorporated by reference in their entirety for any purpose. In embodiments "self-immolative" referring to a linker refers to a linker that is capable of additional cleavage following initial cleavage by an external stimuli. The term dendrimer is used in accordance with its well understood meaning in Chemistry. In embodiments, the term "self-immolative dendrimer" is used as described in US 2007/0009980, US 2006/0003383, and US 2009/0047699, which are incorporated by reference in their entirety for any purpose and in embodiments refers to a dendrimer that is capable of releasing all of its tail units through a self-immolative fragmentation following initial cleavage by an external stimulus.

A "photocleavable linker" (e.g., including or consisting of an o-nitrobenzyl group) refers to a linker which is capable of being split in response to photo-irradiation (e.g., ultraviolet radiation). An acid-cleavable linker refers to a linker which is capable of being split in response to a change in the pH (e.g., increased acidity). A base-cleavable linker refers to a linker which is capable of being split in response to a change in the pH (e.g., decreased acidity). An oxidant-cleavable linker refers to a linker which is capable of being split in response to the presence of an oxidizing agent. A reductant-cleavable linker refers to a linker which is capable of being split in response to the presence of a reducing agent (e.g., tris(3-hydroxypropyl)phosphine). In embodiments, the cleavable linker is a dialkylketal linker (Binaulda S., et al., *Chem. Commun.,* 2013, 49, 2082-2102; Shenoi R. A., et al., *J. Am. Chem. Soc.,* 2012, 134, 14945-14957), an azo linker (Rathod, K. M., et al., *Chem. Sci. Tran.,* 2013, 2, 25-28; Leriche G., et al., *Eur. J. Org. Chem.,* 2010, 23, 4360-64), an allyl linker, a cyanoethyl linker, a 1-(4,4-dimethyl-2,6-dioxocyclohex-1-ylidene)ethyl linker, or a nitrobenzyl linker.

The term "orthogonally cleavable linker" or "orthogonal cleavable linker" as used herein refer to a cleavable linker that is cleaved by a first cleaving agent (e.g., enzyme, nucleophilic/basic reagent, reducing agent, photo-irradiation, electrophilic/acidic reagent, organometallic and metal reagent, oxidizing reagent) in a mixture of two or more different cleaving agents and is not cleaved by any other different cleaving agent in the mixture of two or more cleaving agents. For example, two different cleavable linkers are both orthogonal cleavable linkers when a mixture of the two different cleavable linkers are reacted with two different cleaving agents and each cleavable linker is cleaved by only one of the cleaving agents and not the other cleaving agent and the agent that cleaves each cleavable linker is different. In embodiments, an orthogonally is a cleavable linker that following cleavage the two separated entities (e.g., fluorescent dye, bioconjugate reactive group) do not further react and form a new orthogonally cleavable linker.

The term "orthogonal detectable label" or "orthogonal detectable moiety" as used herein refer to a detectable label (e.g., fluorescent dye or detectable dye) that is capable of being detected and identified (e.g., by use of a detection means (e.g., emission wavelength, physical characteristic measurement)) in a mixture or a panel (collection of separate samples) of two or more different detectable labels. For example, two different detectable labels that are fluorescent dyes are both orthogonal detectable labels when a panel of the two different fluorescent dyes is subjected to a wavelength of light that is absorbed by one fluorescent dye but not the other and results in emission of light from the fluorescent dye that absorbed the light but not the other fluorescent dye. Orthogonal detectable labels may be separately identified by different absorbance or emission intensities of the orthogonal detectable labels compared to each other and not only be the absolute presence of absence of a signal. An example of a set of four orthogonal detectable labels is the set of Rox-Labeled Tetrazine, Alexa488-Labeled SHA, Cy5-Labeled Streptavidin, and R6G-Labeled Dibenzocyclooctyne.

The term "polymerase-compatible cleavable moiety" or "reversible terminator" as used herein refers to a cleavable moiety which does not interfere with a function of a polymerase (e.g., DNA polymerase, modified DNA polymerase, in incorporating the nucleotide, to which the polymerase-compatible cleavable moiety is attached, to the 3' end of the newly formed nucleotide strand). Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible cleavable moiety does not decrease the function of a polymerase relative to the absence of the polymerase-compatible cleavable moiety. In embodiments, the polymerase-compatible cleavable moiety does not negatively affect DNA polymerase recognition. In embodiments, the polymerase-compatible cleavable moiety does not negatively affect (e.g., limit) the read length of the DNA polymerase. Additional examples of a polymerase-compatible cleavable moiety may be found in U.S. Pat. No. 6,664,079, Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides & Nucleic Acids* 29:879-895, which are incorporated herein by reference in their entirety for all purposes. In embodiments, a polymerase-compatible cleavable moiety includes an azido moiety or a dithiol linking moiety. In embodiments, the polymerase-compatible cleavable moiety is $—NH_2$, —CN, $—CH_3$, $C_2$-$C_6$ allyl (e.g., $—CH_2—CH{=}CH_2$), methoxyalkyl (e.g., $—CH_2—O—CH_3$), or $—CH_2N_3$. In embodiments, the polymerase-compatible cleavable moiety comprises a disulfide moiety. In embodiments, a polymerase-compatible cleavable moiety is a cleavable moiety on a nucleotide, nucleobase, nucleoside, or nucleic acid that does not interfere with a function of a polymerase (e.g., DNA polymerase, modified DNA polymerase).

The term "polymerase-compatible moiety" as used herein refers a moiety which does not interfere with the function of a polymerase (e.g., DNA polymerase, modified DNA polymerase) in incorporating the nucleotide to which the polymerase-compatible moiety is attached to the 3' end of the newly formed nucleotide strand. The polymerase-compatible moiety does, however, interfere with the polymerase function by preventing the addition of another nucleotide to the 3' oxygen of the nucleotide to which the polymerase-compatible moiety is attached. Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible moiety does not decrease the function of a polymerase relative to the absence of the polymerase-compatible moiety. In embodiments, the polymerase-compatible moiety does not negatively affect DNA polymerase recognition. In embodiments, the polymerase-compatible moiety does not negatively affect (e.g., limit) the read length of the DNA polymerase. Additional examples of a polymerase-compatible moiety may be found in U.S. Pat. No. 6,664,079, Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides & Nucleic Acids* 29:879-895, which are incorporated herein by reference in their entirety for all purposes. In embodiments, a polymerase-compatible moiety includes hydrogen, $—N_3$, —CN, or halogen. In embodiments, a polymerase-compatible moiety is a moiety on a nucleotide, nucleobase, nucleoside, or nucleic acid that does not interfere with the function of a polymerase (e.g., DNA polymerase, modified DNA polymerase).

"Polymerase," as used herein, refers to any natural or non-naturally occurring enzyme or other catalyst that is capable of catalyzing a polymerization reaction, such as the polymerization of nucleotide monomers to form a nucleic acid polymer. Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9° N polymerase or a variant thereof, *E. Coli* DNA polymerase I, Bacteriophage T4 DNA polymerase, Sequenase, Taq DNA polymerase, DNA polymerase from *Bacillus stearothermophilus*, Bst 2.0 DNA polymerase, 9° N polymerase, 9° N polymerase (exo-)A485L/Y409V, Phi29 DNA Polymerase ($\varphi^{29}$ DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or Therminator™ IX DNA Polymerase. In embodiments, the polymerase is a protein polymerase.

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol τ DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g. Therminator γ, 9° N polymerase (exo-), Therminator II, Therminator III, or Therminator IX). In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044).

As used herein, the term "thermophilic nucleic acid polymerase" refers to a family of DNA polymerases (e.g., 9° N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. PNAS. 1996; 93(11):5281-5285). A thermophilic nucleic acid polymerase is a member of the family B DNA polymerases. Site-directed mutagenesis of the 3'-5' exo motif I (Asp-Ile-Glu or DIE) to AIA, AIE, EIE, EID or DIA yielded polymerase with no detectable 3' exonuclease activity. Mutation to Asp-Ile-Asp (DID) resulted in reduction of 3'-5' exonuclease specific activity to <1% of wild type, while maintaining other properties of the polymerase including its high strand displacement activity. The sequence AIA (D141A, E143A) was chosen for reducing exonuclease. Subsequent mutagenesis of key amino acids results in an increased ability of the enzyme to incorporate dideoxynucleotides, ribonucleotides and acyclonucleotides (e.g., Therminator II enzyme from New England Biolabs with D141A/E143A/Y409V/A485L mutations); 3'-amino-dNTPs, 3'-azido-dNTPs and other 3'-modified nucleotides (e.g., NEB Therminator III DNA Polymerase with D141A/E143A/L408S/Y409A/P410V mutations, NEB Therminator IX DNA polymerase), or γ-phosphate labeled nucleotides (e.g., Therminator γ: D141A/E143A/W355A/L408W/R460A/Q461S/K464E/D480V/R484W/A485L). Typically, these enzymes do not have 5'-3' exonuclease activity. Additional information about thermophilic nucleic acid polymerases may be found in (Southworth M W, et al. PNAS. 1996; 93(11):5281-5285; Bergen K, et al. ChemBioChem. 2013; 14(9):1058-1062; Kumar S, et al. Scientific Reports. 2012; 2:684; Fuller C W, et al. 2016; 113(19):5233-5238; Guo J, et al. Proceedings of the National Academy of Sciences of the United States of America. 2008; 105(27):9145-9150), which are incorporated herein in their entirety for all purposes.

As used herein, the term "exonuclease activity" is used in accordance with its ordinary meaning in the art, and refers to the removal of a nucleotide from a nucleic acid by an enzyme (e.g. DNA polymerase, a lambda exonuclease, Exo I, Exo III, T5, Exo V, Exo VII or the like). For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

As used herein, the terms "polynucleotide primer" and "primer" refers to any polynucleotide molecule that may hybridize to a polynucleotide template, be bound by a polymerase, and be extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The phrase "stringent hybridization conditions" refers to conditions under which a primer will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

The term "polymer" refers to a molecule including repeating subunits (e.g., polymerized monomers). For example, polymeric molecules may be based upon polyethylene glycol (PEG), tetraethylene glycol (TEG), polyvinylpyrrolidone (PVP), poly(xylene), or poly(p-xylylene). The term "polymerizable monomer" is used in accordance with its meaning in the art of polymer chemistry and refers to a compound that may covalently bind chemically to other monomer molecules (such as other polymerizable monomers that are the same or different) to form a polymer.

"Solid substrate" shall mean any suitable medium present in the solid phase to which a nucleic acid or an agent may be affixed. Non-limiting examples include chips, beads and columns. The solid substrate can be non-porous or porous. Exemplary solid substrates include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides, etc.), nylon, ceramics, resins, Zeonor, silica or silica-based materials including silicon and modified silicon, carbon, metals, inorganic glasses, optical fiber bundles, and polymers. In embodiments, the solid substrate for have at least one surface located within a flow cell. The solid substrate, or regions thereof, can be substantially flat. The solid substrate can have surface features such as wells, pits, channels, ridges, raised regions, pegs, posts or the like. The term solid substrate is encompassing of a substrate (e.g., a flow cell) having a surface comprising a polymer coating covalently attached thereto. In embodiments, the solid substrate is a flow cell. The term "flowcell" or "flow cell" as used herein refers to a chamber including a solid surface across which one or more fluid reagents can be flowed. Examples of flowcells and related fluidic systems and detection platforms that can be readily used in the methods of the present disclosure are described, for example, in Bentley et al., Nature 456:53-59 (2008).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., *Current Protocols in Molecular Biology*, ed. Ausubel, et al., supra.

Where a range of values is provided herein, it is understood that each intervening value, to the tenth of the unit (if appropriate) of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

While various embodiments of the invention are shown and described herein, it will be understood by those skilled in the art that such embodiments are provided by way of example only. Numerous variations, changes, and substitutes may occur to those skilled in the art without departing from the invention. It should be understood that various alternatives to the embodiments of the invention described herein may be employed.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In embodiments the protecting group is an amine protecting group. Non-limiting examples of amine protecting groups include carbobenzyloxy (Cbz), tert-butyloxycarbonyl (BOC), 9-Fluorenylmethyloxycarbonyl (FMOC), acetyl, benzoyl, benzyl, carbamate, p-methoxybenzyl ether (PMB), and tosyl (Ts). In embodiments, the protecting group is a nucleoside protecting group. In embodiments, the protecting group is a 5'-O-nucleoside protecting group.

The term "5'-nucleoside protecting group" as used herein refers to a moiety covalently bound to a heteroatom (e.g., O) on the 5' position of sugar to prevent reactivity of the heteroatom during one or more chemical reactions performed prior to removal of the protecting group. Typically a protecting group is bound to a heteroatom (e.g., O) during a part of a multipart synthesis wherein it is not desired to have the heteroatom react (e.g., during a chemical reduction) with the reagent. Following protection the protecting group may be removed by any appropriate means (e.g., by modulating the pH). Non-limiting examples of 5'-O-nucleoside protecting groups include silyl ethers (e.g., tert-butyl-diphenylsilyl (TBDPS), or primary and secondary tert-butyldimethylsilyl (TBDMS)) or trityl (e.g., 4,4'-dimethoxytrityl (DMT)). In embodiments, $R^1$ includes a protecting group found in *Green's Protective Groups in Organic Chemistry*, Wiley, Fourth edition, 2007, Peter G.M. Wuts and Theodora W. Greene, and *Current Protocols in Nucleic Acid Chemistry* (2000) 2.3.1-2.3.34, John Wiley & Sons, Inc. which is incorporated herein by reference in its entirety for all purposes.

The term "deprotect" or "deprotecting" is used in accordance with its ordinary meaning in organic chemistry and refers a process or chemical reaction that remove a protecting group, which is covalently bound to a heteroatom, heterocycloalkyl, or heteroaryl, to recover reactivity of the heteroatom, heterocycloalkyl, or heteroaryl for subsequent chemical reactions or metabolic pathway. The "deprotecting agent" or "deprotecting reagent" is used in accordance with its ordinary meaning in organic chemistry and refers to a molecule used for deprotecting. In embodiments, the deprotecting agent is an acid or a base. In embodiments, the deprotecting agent includes alpha-hydroxy amines (amino alcohol), primary amines and secondary amines. In embodiments, the deprotecting agent is ammonium salt (e.g., ammonium hydroxide, ammonium hydrogen sulfate, ceric ammonium nitrate, or ammonium fluoride). In embodiments, the deprotecting agent is concentrated ammonium hydroxide. The terms "5'-nucleoside protecting group" and "5'-O-nucleoside protecting group" are used interchangeably herein.

The term "reaction vessel" is used in accordance with its ordinary meaning in chemistry or chemical engineering, and refers to a container having an inner volume in which a reaction takes place. In embodiments, the reaction vessel may be designed to provide suitable reaction conditions such as reaction volume, reaction temperature or pressure, and stirring or agitation, which may be adjusted to ensure that the reaction proceeds with a desired, sufficient or highest efficiency for producing a product from the chemical reaction. In embodiments, the reaction vessel is a container for liquid, gas or solid. In embodiments, the reaction vessel may include an inlet, an outlet, a reservoir and the like. In embodiments, the reaction vessel is connected to a pump (e.g., vacuum pump), a controller (e.g., CPU), or a monitoring device (e.g., UV detector or spectrophotometer). In embodiments, the reaction vessel is a flow cell. In embodiments, the reaction vessel is within a sequencing device.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or $—CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., packaging, buffers, written instructions for performing a method, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

As used herein, the terms "sequencing", "sequence determination", "determining a nucleotide sequence", and the like include determination of a partial or complete sequence information, including the identification, ordering, or locations of the nucleotides that comprise the polynucleotide being sequenced, and inclusive of the physical processes for generating such sequence information. That is, the term includes sequence comparisons, consensus sequence determination, contig assembly, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide. In some embodiments, a sequencing process described herein comprises contacting a template and an annealed primer with a suitable polymerase under conditions suitable for polymerase extension and/or sequencing. The sequencing methods are preferably carried out with the target polynucleotide arrayed on a solid substrate. Multiple target polynucleotides can be immobilized on the solid support through linker molecules, or can be attached to particles, e.g., microspheres, which can also be attached to a solid substrate. In embodiments, the solid substrate is in the form of a chip, a bead, a well, a capillary tube, a slide, a wafer, a filter, a fiber, a porous media, or a column. In embodiments, the solid substrate is gold, quartz, silica, plastic, glass, diamond, silver, metal, or polypropylene. In embodiments, the solid substrate is porous.

As used herein, the term "extension" or "elongation" is used in accordance with its plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) polynucleotide strand.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode sequence and a template nucleotide sequence. In embodiments, a sequencing read includes reading a template nucleotide sequence. In embodiments, a sequencing read includes reading a barcode and not a template nucleotide sequence.

The term "azidolating reagent" is used in accordance with its plain ordinary meaning in the arts and refers to a substance (e.g., a compound or solution) which participates in chemical reaction and results in the formation of an alkoxy azide moiety (e.g.,)

(e.g., 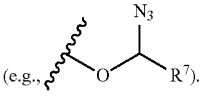).

For example, trialkylailyl azides (e.g., trimethylsilyl azide) is a known azidolating reagent (see for example, Omura et al Chemistry Letters Vol. 36, No. 4 (2007) or Franzini and Kool, J. Am. Chem. Soc. Vol. 131, No. 44, 2009, each of which is incorporated herein by reference). In embodiments, the azidolating reagent is an alkyl tin azide (e.g., $Bu_3$—$SnN_3$ or azidotrimethyltin(IV)), Diphenyl phosphoryl azide (DPPA), sulfonyl azides (e.g., toluenesulfonyl azide), azidoadamantane, azido ethyl acetate (AEA), tetrabutylammonium azide ($Bu_4N^+N_3^-$), or hydrazinium azide. In embodiments, the azidolating reagent is an azide containing salt (e.g., sodium azide, litium azide, or potassium azide). In embodiments, the azidolating reagent is tetrabutylammonium azide. In embodiments, the azidolating reagent is trimethylsilyl azide (TMSN3), benzyl azide, diphenyl phosphoryl azide, azidoadamantane, azidotrimethyltin(IV), or toluenesulfonyl azide.

II. Compositions & Kits

In an aspect is provided a compound having the formula:

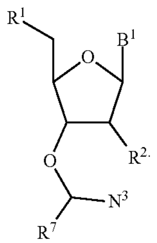

(I)

$B^1$ is a nucleobase. $R^1$ is a polyphosphate moiety, 5'-O-nucleoside protecting group, monophosphate moiety, nucleic acid moiety, hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCH_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a polymerase-compatible cleavable moiety. $R^7$ is substituted or unsubstituted cycloalkyl, substituted or unsubstituted heterocycloalkyl, substituted or unsubstituted aryl, or substituted or unsubstituted heteroaryl.

In embodiments, the compounds of Formula I are referred to as nucleotides or nucleotide analogues. In embodiments, the compounds of Formula I include a nucleotide portion and a 3'-O-reversible terminator. For example, the nucleotide portion is

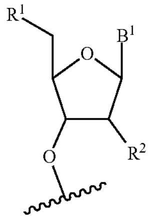

and the 3'-O-reversible terminator portion is

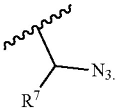

In embodiments, $R^1$ is —OH, a 5'-O-nucleoside protecting group, monophosphate moiety, polyphosphate moiety, or nucleic acid moiety. In embodiments, $R^1$ is a triphosphate moiety. In embodiments, $R^1$ is —OH. In embodiments, $R^1$ is a 5'-O-nucleoside protecting group. In embodiments, $R^1$ is a nucleic acid moiety. In embodiments, $R^1$ is independently a monophosphate moiety or a derivative thereof (e.g., including a phosphoramidate moiety, phosphorothioate moiety, phosphorodithioate moiety, or O-methylphosphoroamidite moiety), polyphosphate moiety or derivative thereof (e.g., including a phosphoramidate, phosphorothioate, phosphorodithioate, or O-methylphosphoroamidite), or nucleic acid moiety or derivative thereof (e.g., including a phosphoramidate, phosphorothioate, phosphorodithioate, or O-methylphosphoroamidite).

In embodiments, $R^1$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-O-nucleoside protecting group, monophosphate moiety, polyphosphate moiety, or nucleic acid moiety. In embodiments, $R^1$ is a monophosphate moiety including a phosphodiester derivative. In embodiments, $R^1$ is a polyphosphate moiety including a phosphodiester derivative. In embodiments, $R^1$ is a nucleic acid moiety including a phosphodiester derivative. In embodiments, $R^1$ is a phosphoramidate moiety. In embodiments, $R^1$ is a polyphosphate moiety including a phosphoramidate. In embodiments, $R^1$ is a nucleic acid moiety including a phosphoramidate. In embodiments, $R^1$ is a phosphorothioate moiety. In embodiments, $R^1$ is a polyphosphate moiety including a phosphorothioate. In embodiments, $R^1$ is a nucleic acid moiety including a phosphorothioate. In embodiments, $R^1$ is a phosphorodithioate moiety. In embodiments, $R^1$ is a polyphosphate moiety including a phosphorodithioate. In embodiments, $R^1$ is a nucleic acid moiety including a phosphorodithioate. In embodiments, $R^1$ is an O-methylphosphoroamidite moiety. In embodiments, $R^1$ is a polyphosphate moiety including an O-methylphosphoroamidite. In embodiments, $R^1$ is a nucleic acid moiety including an O-methylphosphoroamidite. In embodiments, $R^1$ is a nucleic acid moiety including a nucleotide analog. In embodiments, $R^1$ is a nucleic acid moiety including a plurality of optionally different nucleotide analogs.

In embodiments, $R^1$ is a monophosphate moiety. In embodiments, $R^1$ is a polyphosphate moiety. In embodiments, $R^1$ is a nucleic acid moiety. In embodiments, $R^1$ has the formula:

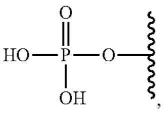
, or ionized forms thereof. In embodiments, $R^1$ has the formula

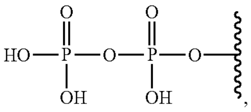 [SMILES: *OP(=O)(O)OP(=O)(O)O]
, or ionized forms thereof. In embodiments, $R^1$ has the formula

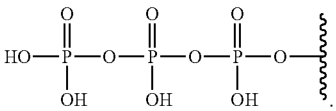 [SMILES: *OP(=O)(O)OP(=O)(O)OP(=O)(O)O]
.

or ionized forms thereof. In embodiments, $R^1$ has the formula:

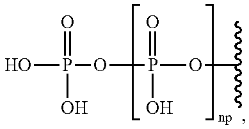
, or ionized forms thereof, wherein np is an integer of 1 or greater. In embodiments, np is an integer from 1 to 5. In embodiments, np is 1. In embodiments, np is 2.

In embodiments, $R^1$ is a 5'-O-nucleoside protecting group, for example a 5'-O-nucleoside protecting group known in the art include those described in Seliger H. Curr. Protoc Nucleic Acid Chem. 2001; Chapter 2 or K. Seio et al, Nucleic Acids Research Supplement 2, 27-28 (2002); both of which are incorporated by reference for all purposes. Non-limiting examples of 5'-O-nucleoside protecting groups include 2,2,2-Trichloroethyl carbonate (Troc), 2-Methoxyethoxymethyl ether (MEM), 2-Naphthylmethyl ether (Nap), 4-Methoxybenzyl ether (PMB), Acetate (Ac), Benzoate (Bz), Benzyl ether (Bn), Benzyloxymethyl acetal (BOM), Ethoxyethyl acetal (EE), Methoxymethyl acetal (MOM), Methoxypropyl acetal (MOP), Methyl ether, Tetrahydropyranyl acetal (THP), Triethylsilyl ether (TES), Triisopropylsilyl ether (TIPS), Trimethylsilyl ether (TMS), tert-Butyldimethylsilyl ether (TBS, TBDMS), or tert-Butyldiphenylsilyl ether (TBDPS). In embodiments, $R^1$ is

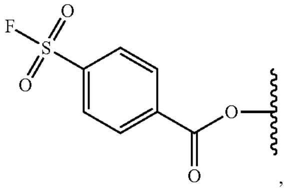
,

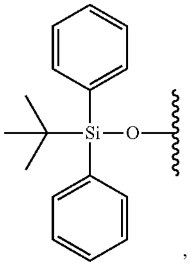
,

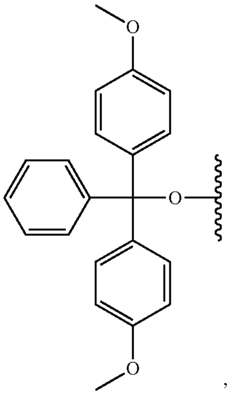
,

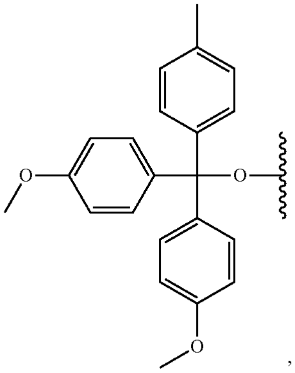
, or

-continued

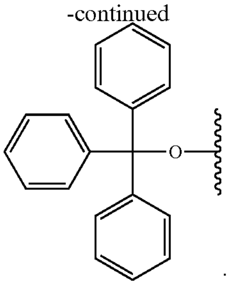

In embodiments, $R^1$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_2NH_2$, —$NHNH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted (e.g., substituted with a substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkyl (e.g., 2 to 8, 2 to 6, 4 to 6, 2 to 3, or 4 to 5 membered), substituted (e.g., substituted with a substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkyl (e.g., 3 to 8, 3 to 6, 4 to 6, 4 to 5, or 5 to 6 membered), substituted (e.g., substituted with a substituent group, size-limited substituent group, or lower substituent group) or unsubstituted aryl (e.g., $C_6$-$C_{10}$ or phenyl), or substituted (e.g., substituted with a substituent group, size-limited substituent group, or lower substituent group) or unsubstituted heteroaryl (e.g., 5 to 10 membered, 5 to 9 membered, or 5 to 6 membered), or a 5'-O-nucleoside protecting group; or $R^1$ is a monophosphate moiety, polyphosphate moiety, or nucleic acid moiety. In embodiments, $R^1$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_2NH_2$, —$NHNH_2$, —$NHC(O)NHNH_2$, —NHC(O) $NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted (e.g., substituted with a substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkyl (e.g., 2 to 8, 2 to 6, 4 to 6, 2 to 3, or 4 to 5 membered), substituted (e.g., substituted with a substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkyl (e.g., 3 to 8, 3 to 6, 4 to 6, 4 to 5, or 5 to 6 membered), substituted (e.g., substituted with a substituent group, size-limited substituent group, or lower substituent group) or unsubstituted aryl (e.g., $C_6$-$C_{10}$ or phenyl), or substituted (e.g., substituted with a substituent group, size-limited substituent group, or lower substituent group) or unsubstituted heteroaryl (e.g., 5 to 10 membered, 5 to 9 membered, or 5 to 6 membered). In embodiments, $R^1$ is a 5'-O-nucleoside protecting group. In embodiments, $R^1$ is a monophosphate moiety, polyphosphate moiety, or nucleic acid moiety. In embodiments, $R^1$ is a monophosphate moiety. In embodiments, $R^1$ is a polyphosphate moiety. In embodiments, $R^1$ is a nucleic acid moiety. In embodiments, $R^1$ is hydrogen. In embodiments, $R^1$ is a triphosphate moiety. In embodiments, $R^1$ is —OH.

In embodiments, a substituted $R^1$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group. In embodiments, when $R^1$ is substituted, it is substituted with 1 to 10 substituent groups. In embodiments, when $R^1$ is substituted, it is substituted with 1 to 10 size-limited substituent groups. In embodiments, when $R^1$ is substituted, it is substituted with 1 to 10 lower substituent groups. In embodiments, when $R^1$ is substituted, it is substituted with 1 to 5 substituent groups. In embodiments, when $R^1$ is substituted, it is substituted with 1 to 5 size-limited substituent groups. In embodiments, when $R^1$ is substituted, it is substituted with 1 to 5 lower substituent groups. In embodiments, when $R^1$ is substituted, it is substituted with a substituent group. In embodiments, when $R^1$ is substituted, it is substituted with a size-limited substituent group. In embodiments, when $R^1$ is substituted, it is substituted with a lower substituent group.

In embodiments, $R^1$ is —OH, a 5'-O-nucleoside protecting group, monophosphate moiety, polyphosphate moiety, or nucleic acid moiety. In embodiments, $R^1$ is a triphosphate moiety.

In embodiments, $R^2$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC (O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety. In embodiments, $R^2$ is hydrogen. In embodiments, $R^2$ is —OH. In embodiments, $R^2$ is an —O-polymerase-compatible cleavable moiety, wherein the —O— is attached to the 2' position of the ribose sugar of a nucleotide and a polymerase-compatible cleavable moiety is as described herein.

In embodiments, $R^2$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{2A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2A}$-substituted or unsubstituted heteroalkyl (e.g., 2 to 20, 8 to 20, 2 to 10, 2 to 8, 2 to 6, or 2 to 4 membered), $R^{2A}$-substituted or unsubstituted cycloalkyl (e.g., $C_3$-$C_8$, $C_3$-$C_6$, or $C_5$-$C_6$), $R^{2A}$-substituted or unsubstituted heterocycloalkyl (e.g., 3 to 8, 3 to 6, or 5 to 6 membered), $R^{2A}$-substituted or unsubstituted aryl (e.g., $C_6$-$C_{10}$, $C_{10}$, or phenyl), or $R^{2A}$-substituted or unsubstituted heteroaryl (e.g., 5 to 10, 5 to 9, or 5 to 6 membered). In embodiments, $R^2$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered); or a polymerase-compatible cleavable moiety.

$R^{2A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H$—, —SCN, —$ONO_2$, $R^{2B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2B}$-substituted or unsubstituted heteroalkyl (e.g., 2 to 20, 8 to 20, 2 to 10, 2 to 8, 2 to 6, or 2 to 4 membered), $R^{2B}$-substituted or unsubstituted cycloalkyl (e.g., $C_3$-$C_8$, $C_3$-$C_6$, or $C_5$-$C_6$), $R^{2B}$-substituted or unsubstituted heterocycloalkyl (e.g., 3 to 8, 3 to 6, or 5 to 6 membered), $R^{2B}$-substituted or unsubstituted aryl (e.g., $C_6$-$C_{10}$, $C_{10}$, or phenyl), or $R^{2B}$-substituted or unsubstituted heteroaryl (e.g., 5 to 10, 5 to 9, or 5 to 6 membered), or a polymerase-compatible cleavable moiety. In embodiments, $R^{2A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3$*, —$SO_3^-$, —$OPO_3H$—, —SCN, —$ONO_2$, $R^{2B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2B}$-substituted or unsubstituted heteroalkyl (e.g., 2 to 20, 8 to 20, 2 to 10, 2 to 8, 2 to 6, or 2 to 4 membered), $R^{2B}$-substituted or unsubstituted cycloalkyl (e.g., $C_3$-$C_8$, $C_3$-$C_6$, or $C_5$-$C_6$), $R^{2B}$-substituted or unsubstituted heterocycloalkyl (e.g., 3 to 8, 3 to 6, or 5 to 6 membered), $R^{2B}$-substituted or unsubstituted aryl (e.g., $C_6$-$C_{10}$, $C_{10}$, or phenyl), or $R^{2B}$_substituted or unsubstituted heteroaryl (e.g., 5 to 10, 5 to 9, or 5 to 6 membered). In embodiments, $R^{2A}$ is independently a polymerase-compatible cleavable moiety.

$R^{2B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H$, —SCN, —$ONO_2$, $R^{2C}$ -substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2C}$-substituted or unsubstituted heteroalkyl (e.g., 2 to 20, 8 to 20, 2 to 10, 2 to 8, 2 to 6, or 2 to 4 membered), $R^{2C}$-substituted or unsubstituted cycloalkyl (e.g., $C_3$-$C_8$, $C_3$-$C_6$, or $C_5$-$C_6$), $R^{2C}$-substituted or unsubstituted heterocycloalkyl (e.g., 3 to 8, 3 to 6, or 5 to 6 membered), $R^{2C}$-substituted or unsubstituted aryl (e.g., $C_6$-$C_{10}$, $C_{10}$, or phenyl), or $R^{2C}$-substituted or unsubstituted heteroaryl (e.g., 5 to 10, 5 to 9, or 5 to 6 membered).

$R^{2C}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H$—, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^2$ is hydrogen. In embodiments, $R^2$ is —OH. In embodiments, $R^2$ is —O-polymerase-compatible cleavable moiety. In embodiments, the —O-polymerase-compatible cleavable moiety is:

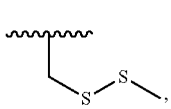, 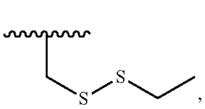,

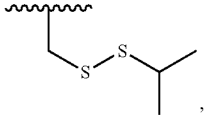, 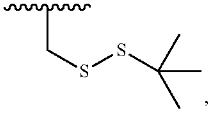,

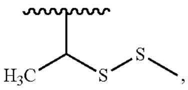, 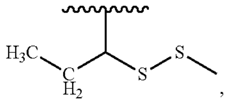,

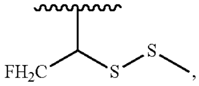, 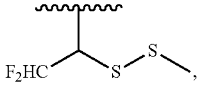,

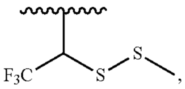, 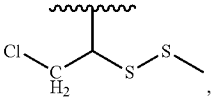,

-continued
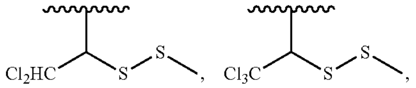
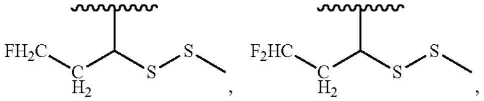
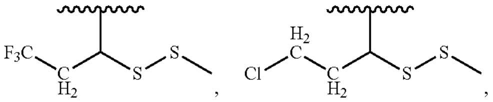
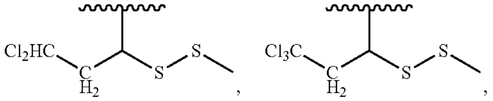
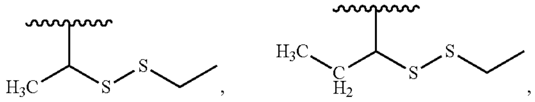
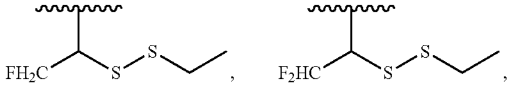
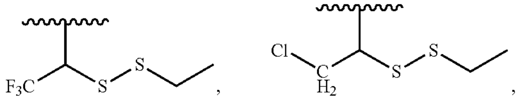
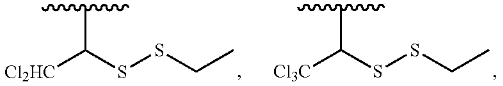
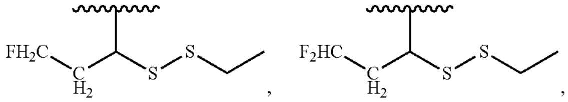
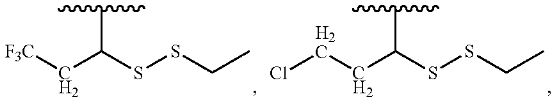
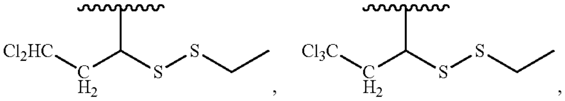
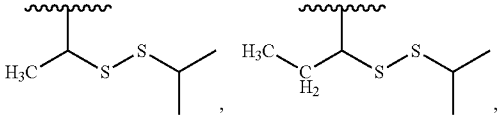
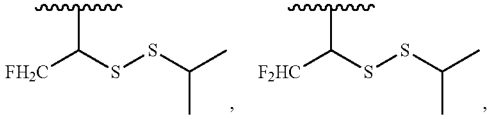
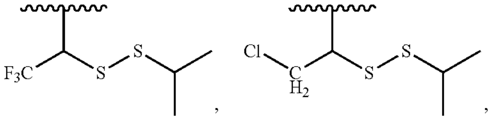
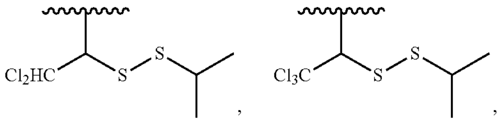
-continued
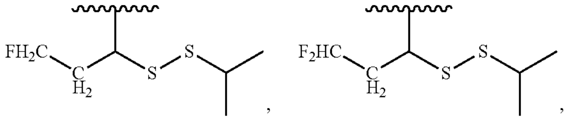
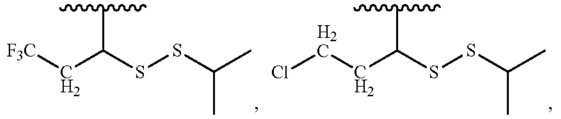
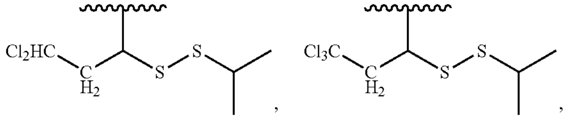
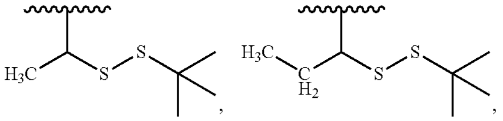
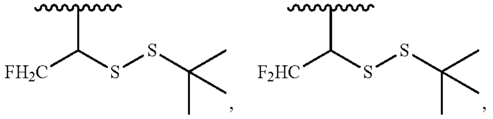
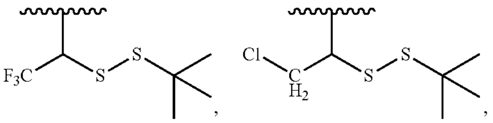
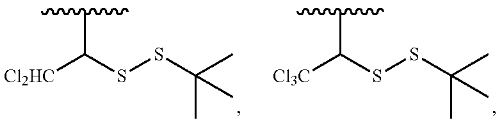
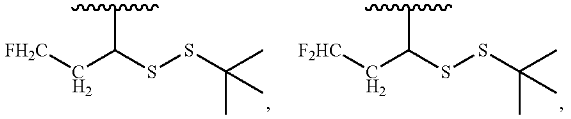
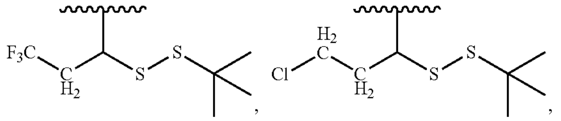
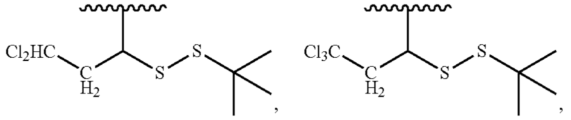
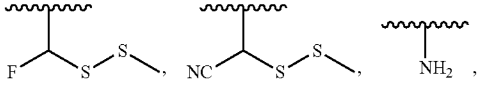
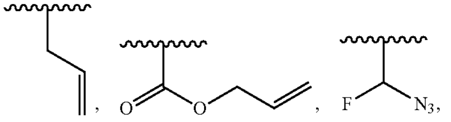
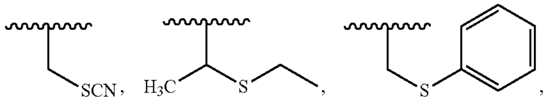
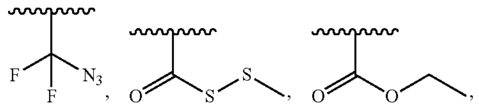
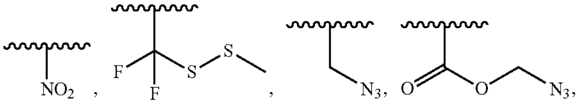

-continued

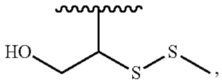,
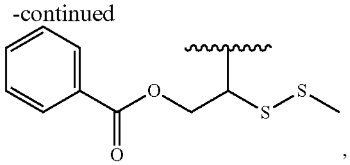,
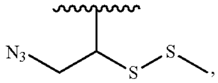,
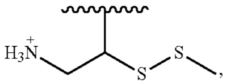,
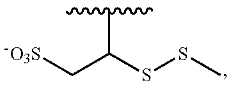,
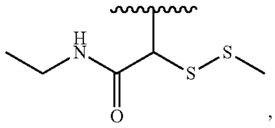,
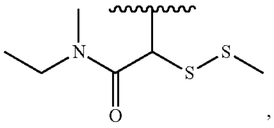,
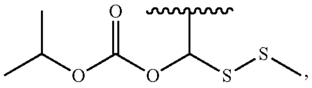,
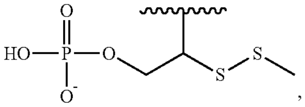,
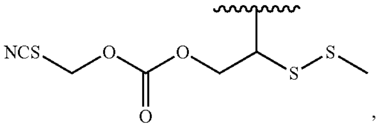,
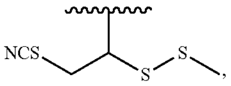,
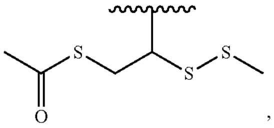,
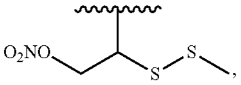,
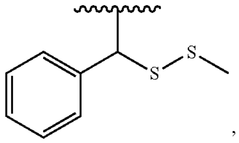, or
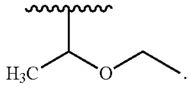.

In embodiments, the -polymerase-compatible cleavable moiety is:

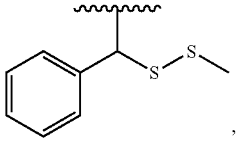,
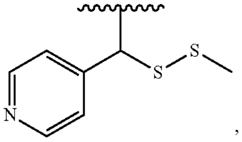,
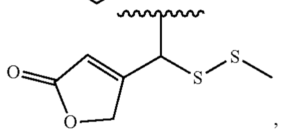, or

-continued

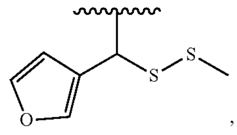,

In embodiments, $B^1$ is a cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof. In embodiments, $B^1$ is

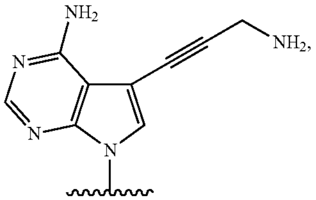
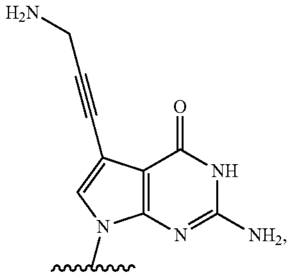
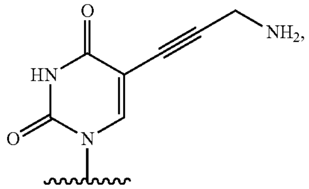
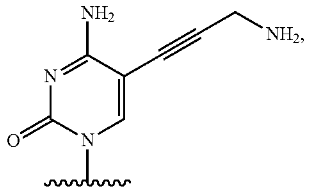
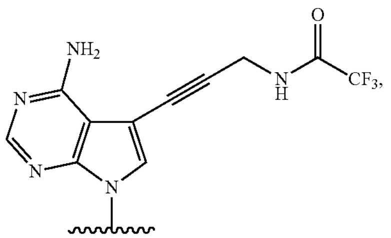

-continued

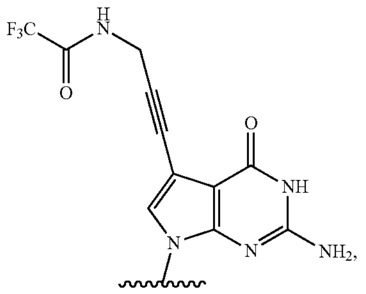

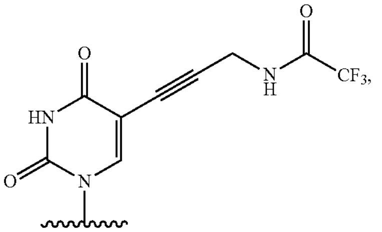

or

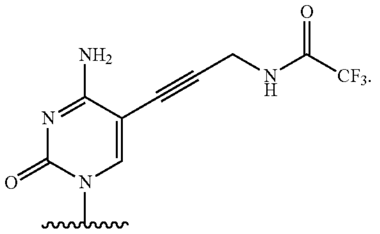

In embodiments, $B^1$ is

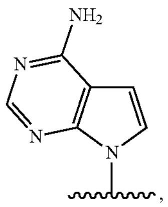

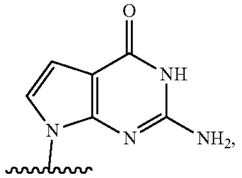

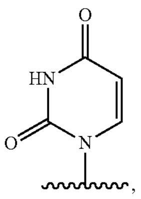

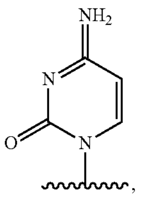

-continued

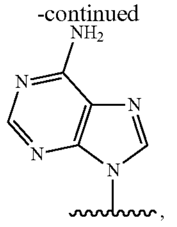

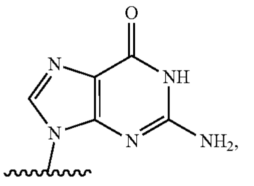

or

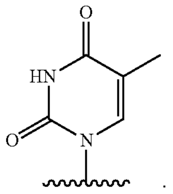

In embodiments, $B^1$ is a monovalent nucleobase, or a derivative thereof. In embodiments, $B^1$ is a monovalent cytosine or a derivative thereof, monovalent guanine or a derivative thereof, monovalent adenine or a derivative thereof, monovalent thymine or a derivative thereof, monovalent uracil or a derivative thereof, monovalent hypoxanthine or a derivative thereof, monovalent xanthine or a derivative thereof, monovalent 7-methylguanine or a derivative thereof, monovalent 5,6-dihydrouracil or a derivative thereof, monovalent 5-methylcytosine or a derivative thereof, or monovalent 5-hydroxymethylcytosine or a derivative thereof. In embodiments, $B^1$ is a monovalent cytosine or a derivative thereof. In embodiments, $B^1$ is a monovalent guanine or a derivative thereof. In embodiments, $B^1$ is a monovalent adenine or a derivative thereof. In embodiments, $B^1$ is a monovalent thymine or a derivative thereof. In embodiments, $B^1$ is a monovalent uracil or a derivative thereof. In embodiments, $B^1$ is a monovalent hypoxanthine or a derivative thereof. In embodiments, $B^1$ is a monovalent xanthine or a derivative thereof. In embodiments, $B^1$ is a monovalent 7-methylguanine or a derivative thereof. In embodiments, $B^1$ is a monovalent 5,6-dihydrouracil or a derivative thereof. In embodiments, $B^1$ is a monovalent 5-methylcytosine or a derivative thereof. In embodiments, $B^1$ is a monovalent 5-hydroxymethylcytosine or a derivative thereof. In embodiments, $B^1$ is a monovalent cytosine. In embodiments, $B^1$ is a monovalent guanine. In embodiments, $B^1$ is a monovalent adenine. In embodiments, $B^1$ is a monovalent thymine. In embodiments, $B^1$ is a monovalent uracil. In embodiments, $B^1$ is a monovalent hypoxanthine. In embodiments, $B^1$ is a monovalent xanthine. In embodiments, $B^1$ is a monovalent 7-methylguanine. In embodiments, $B^1$ is a monovalent 5,6-dihydrouracil. In embodiments, $B^1$ is a monovalent 5-methylcytosine. In embodiments, $B^1$ is a monovalent 5-hydroxymethylcytosine.

In embodiments, $B^1$ is,
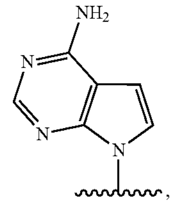,
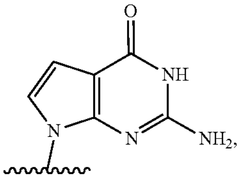,
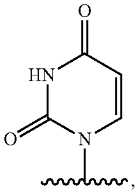,
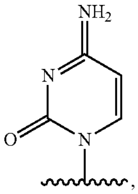,
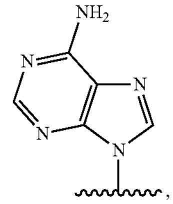,
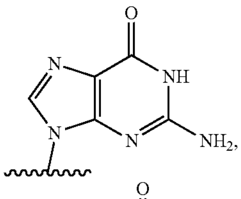, or
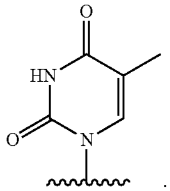.
In embodiments, $B^1$ is
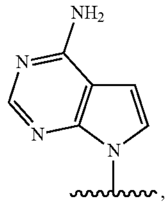,
-continued
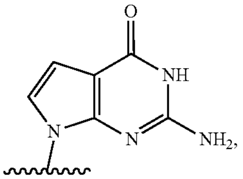,
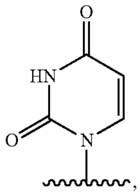, or
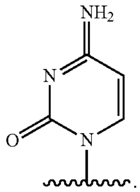.
In embodiments, $B^1$ is
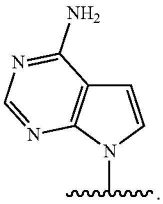 [SMILES: *n1ccc2c(N)ncnc21].
In embodiments, $B^1$ is
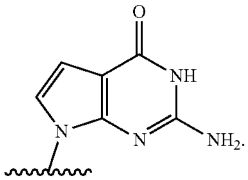 [SMILES: *n1ccc2c(=O)[nH]c(N)nc21].
In embodiments, $B^1$ is
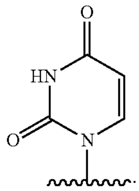.

In embodiments, $B^1$ is
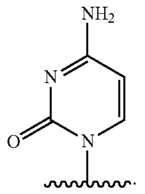
In embodiments, $B^1$ is
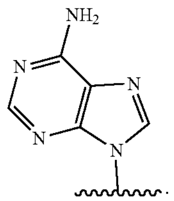 [SMILES: *n1cnc2c(N)ncnc21]
In embodiments, $B^1$ is
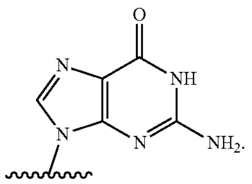 [SMILES: *n1cnc2c(=O)[nH]c(N)nc21]
In embodiments, $B^1$ is
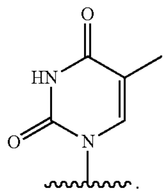 [SMILES: *n1cc(C)c(=O)[nH]c1=O]
In embodiments, $B^1$ is
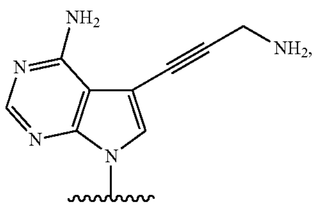
-continued
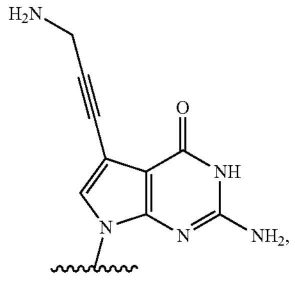
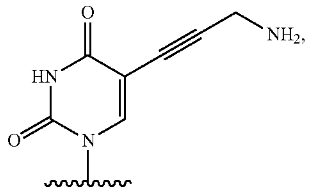
or
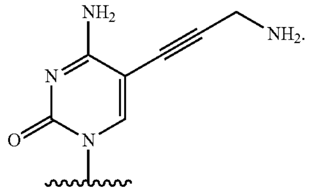
In embodiments, $B^1$ is
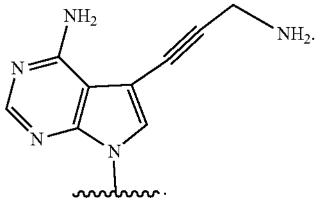 [SMILES: *n1cc(C#CCN)c2c(N)ncnc21]
In embodiments, $B^1$ is
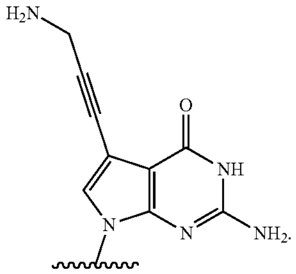 [SMILES: *n1cc(C#CCN)c2c(=O)[nH]c(N)nc21]
In embodiments, $B^1$ is
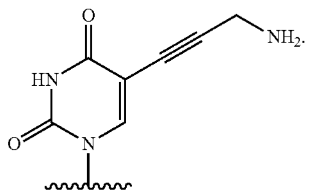 [SMILES: *n1cc(C#CCN)c(=O)[nH]c1=O]

In embodiments, $B^1$ is
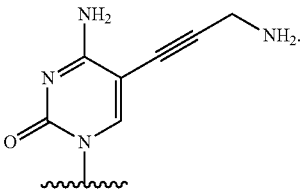
In embodiments, $B^1$ is
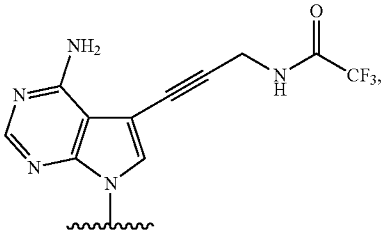
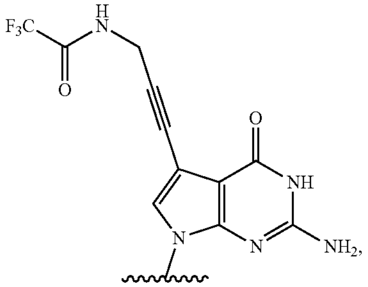
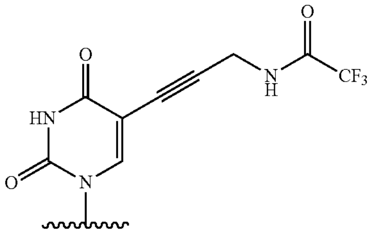
, or
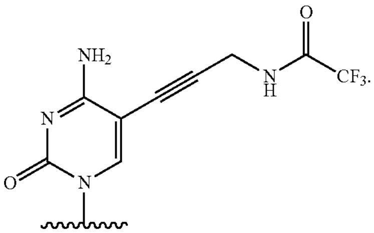
In embodiments, $B^1$ is
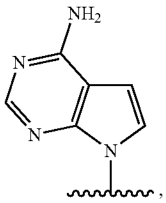
-continued
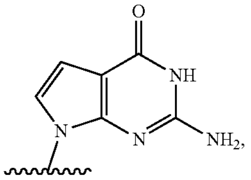
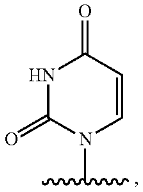
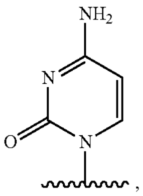
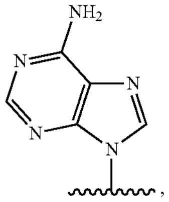
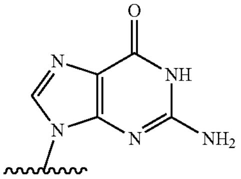
, or
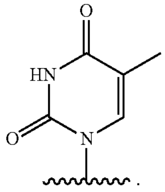
In embodiments, $B^1$ is
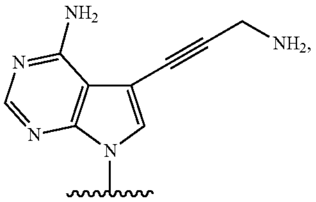

-continued

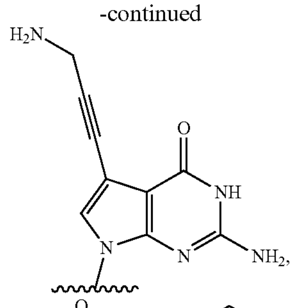

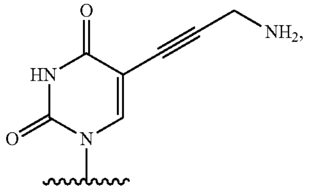

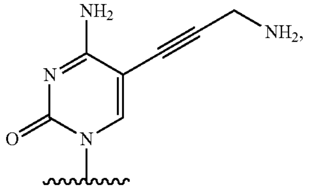 [SMILES: *n1cc(C#CCN)c(N)nc1=O]

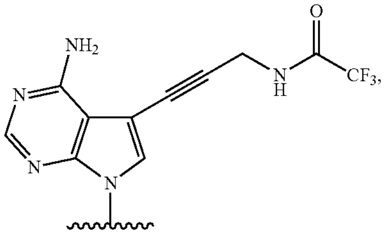

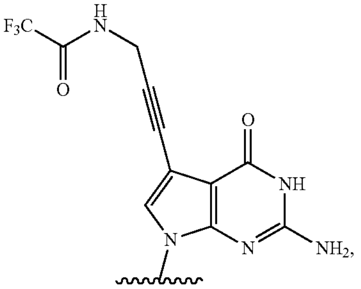

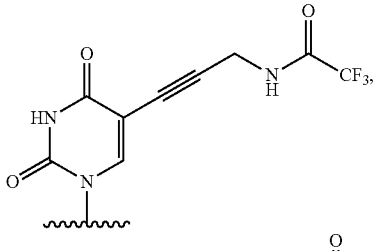

or

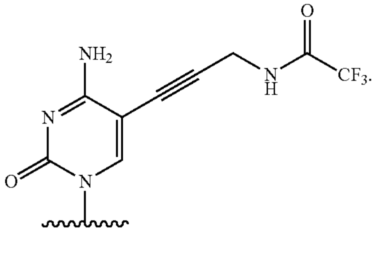

In embodiments, B[1] includes a substituted or unsubstituted propargyl amine moiety, which may further include S—S linker, fluorophores or protecting group. In embodiments, the propargyl amine moiety may further include at least one or more fluorophores. In embodiments, the propargyl amine moiety may further be linked via a linker (e.g., an S—S linker) to at least one or more fluorophores. In embodiments, the propargyl amine moiety may further include at least one or more protecting groups. In embodiments, the propargyl amine moiety may further be linked to a S—S-containing linker or an azido (e.g., —$N_3$) containing linker, which may be connected to at least one or more protecting groups. In embodiments, B[1] is a divalent nucleobase. In embodiments, B[1] is

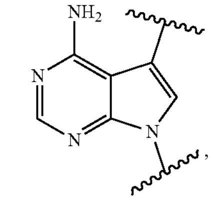

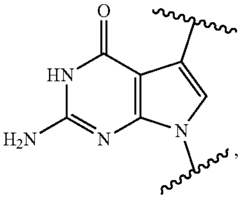

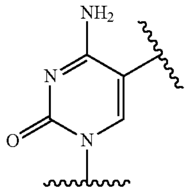

, or

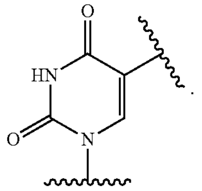

In embodiments, B is

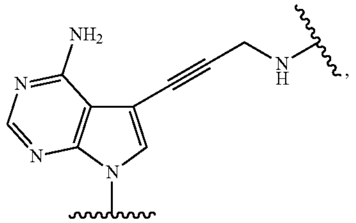

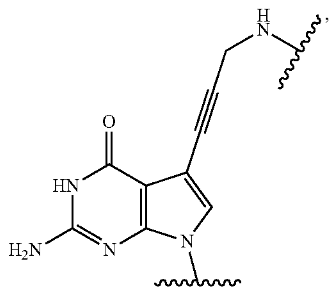

-continued

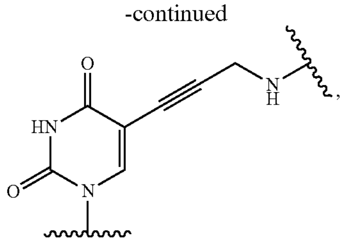

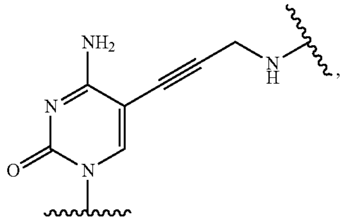

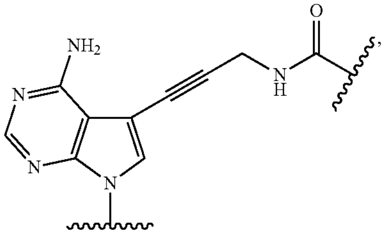

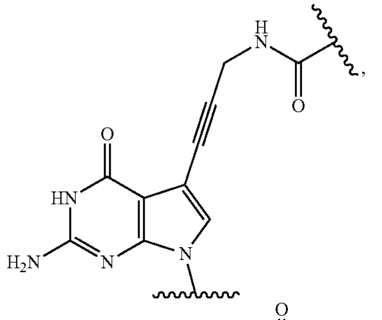

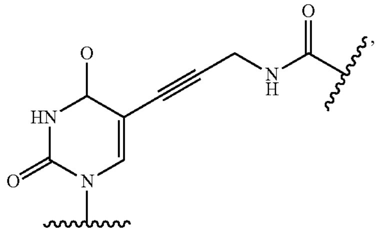

or

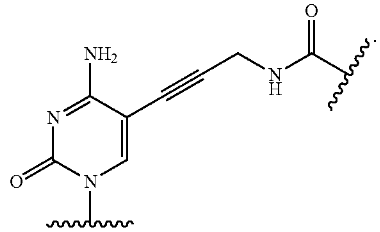 [SMILES: *C(=O)NCC#Cc1cn(*)c(=O)nc1N]

In embodiments, $B^1$ is —B-$L^{100}$-$R^4$. B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof. $L^{100}$ is a divalent linker; and $R^4$ is a detectable moiety.

In embodiments, B is

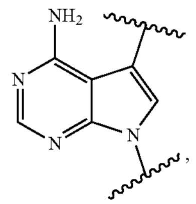

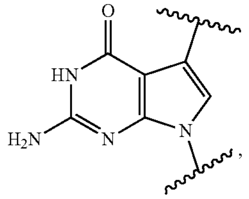

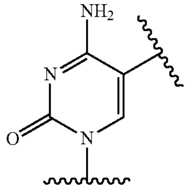

, or

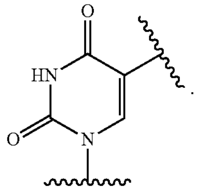

In embodiments, B is

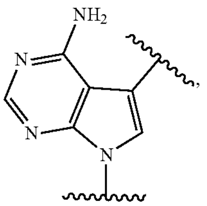

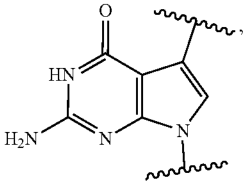

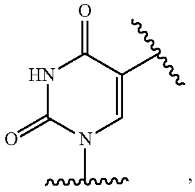

, or

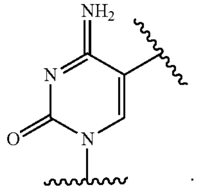

.

In embodiments, B is
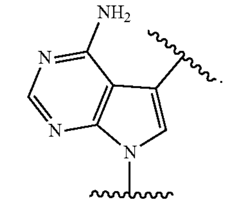 [SMILES: *c1cn(*)c2ncnc(N)c12]
In embodiments, B is
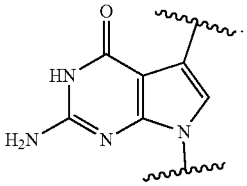 [SMILES: *c1cn(*)c2nc(N)[nH]c(=O)c12]
In embodiments, B is
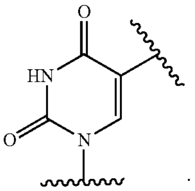 [SMILES: *c1cn(*)c(=O)[nH]c1=O]
In embodiments, B is
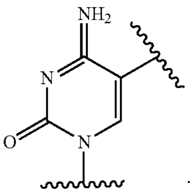
In embodiments, B is
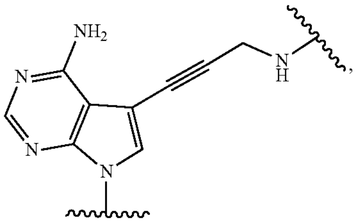
-continued
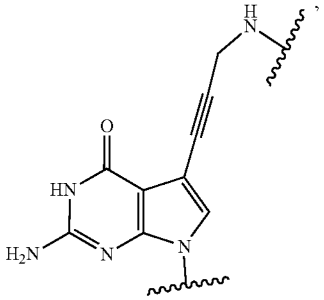
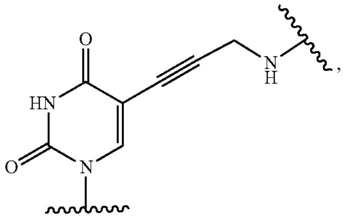
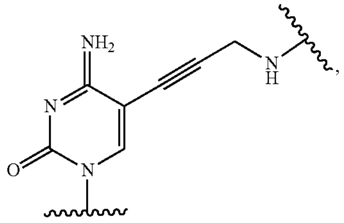
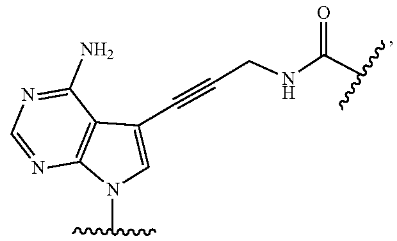
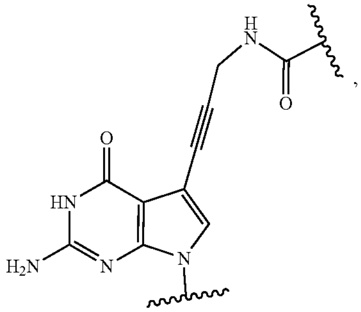
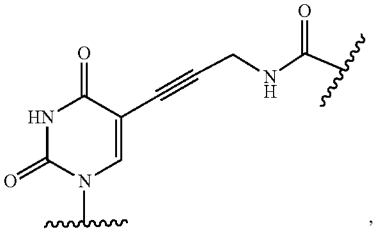
, or -continued

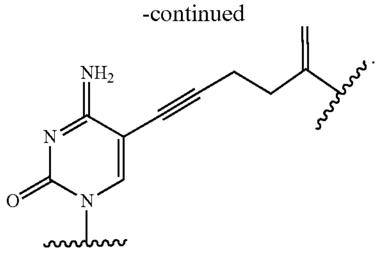

In embodiments, B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof. In embodiments, B is a divalent cytosine or a derivative thereof. In embodiments, B is a divalent guanine or a derivative thereof. In embodiments, B is a divalent adenine or a derivative thereof. In embodiments, B is a divalent thymine or a derivative thereof. In embodiments, B is a divalent uracil or a derivative thereof. In embodiments, B is a divalent hypoxanthine or a derivative thereof. In embodiments, B is a divalent xanthine or a derivative thereof. In embodiments, B is a divalent 7-methylguanine or a derivative thereof. In embodiments, B is a divalent 5,6-dihydrouracil or a derivative thereof. In embodiments, B is a divalent 5-methylcytosine or a derivative thereof. In embodiments, B is a divalent 5-hydroxymethylcytosine or a derivative thereof. In embodiments, B is a divalent cytosine. In embodiments, B is a divalent guanine. In embodiments, B is a divalent adenine. In embodiments, B is a divalent thymine. In embodiments, B is a divalent uracil. In embodiments, B is a divalent hypoxanthine. In embodiments, B is a divalent xanthine. In embodiments, B is a divalent 7-methylguanine. In embodiments, B is a divalent 5,6-dihydrouracil. In embodiments, B is a divalent 5-methylcytosine. In embodiments, B is a divalent 5-hydroxymethylcytosine.

In embodiments, $R^7$ is substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^7$ is substituted or unsubstituted cycloalkyl (e.g., $C_3$-$C_8$, $C_3$-$C_6$, $C_4$-$C_6$, or $C_5$-$C_6$). In embodiments, $R^7$ is substituted cycloalkyl (e.g., $C_3$-$C_8$, $C_3$-$C_6$, $C_4$-$C_6$, or $C_5$-$C_6$). In embodiments, $R^7$ is an unsubstituted cycloalkyl (e.g., $C_3$-$C_8$, $C_3$-$C_6$, $C_4$-$C_6$, or $C_5$-$C_6$). In embodiments, $R^7$ is substituted or unsubstituted heterocycloalkyl (e.g., 3 to 8 membered, 3 to 6 membered, 4 to 6 membered, 4 to 5 membered, or 5 to 6 membered). In embodiments, $R^7$ is substituted heterocycloalkyl (e.g., 3 to 8 membered, 3 to 6 membered, 4 to 6 membered, 4 to 5 membered, or 5 to 6 membered). In embodiments, $R^7$ is an unsubstituted heterocycloalkyl (e.g., 3 to 8 membered, 3 to 6 membered, 4 to 6 membered, 4 to 5 membered, or 5 to 6 membered).

In embodiments, $R^7$ is unsubstituted cycloalkyl (e.g., $C_3$-$C_8$, $C_3$-$C_6$, $C_4$-$C_6$, or $C_5$-$C_6$). In embodiments, $R^7$ is unsubstituted $C_3$-$C_8$ cycloalkyl. In embodiments, $R^7$ is unsubstituted $C_3$-$C_6$ cycloalkyl. In embodiments, $R^7$ is unsubstituted $C_4$-$C_6$ cycloalkyl. In embodiments, $R^7$ is unsubstituted $C_5$-$C_6$ cycloalkyl. In embodiments, $R^7$ is unsubstituted cyclopropyl. In embodiments, $R^7$ is unsubstituted cyclobutyl. In embodiments, $R^7$ is unsubstituted cyclopentyl. In embodiments, $R^7$ is unsubstituted cyclohexyl. In embodiments, $R^7$ is unsubstituted cycloheptyl. In embodiments, $R^7$ is unsubstituted cyclooctyl.

In embodiments, $R^7$ is substituted cycloalkyl (e.g., $C_3$-$C_8$, $C_3$-$C_6$, $C_4$-$C_6$, or $C_5$-$C_6$). In embodiments, $R^7$ is substituted $C_3$-$C_8$ cycloalkyl. In embodiments, $R^7$ is substituted $C_3$-$C_6$ cycloalkyl. In embodiments, $R^7$ is substituted $C_4$-$C_6$ cycloalkyl. In embodiments, $R^7$ is substituted $C_5$-$C_6$ cycloalkyl. In embodiments, $R^7$ is substituted cyclopropyl. In embodiments, $R^7$ is substituted cyclobutyl. In embodiments, $R^7$ is substituted cyclopentyl. In embodiments, $R^7$ is substituted cyclohexyl. In embodiments, $R^7$ is substituted cycloheptyl. In embodiments, $R^7$ is substituted cyclooctyl.

In embodiments, $R^7$ is substituted or unsubstituted heterocycloalkyl (e.g., 3 to 8 membered, 3 to 6 membered, 4 to 6 membered, 4 to 5 membered, or 5 to 6 membered). In embodiments, $R^7$ is substituted heterocycloalkyl (e.g., 3 to 8 membered, 3 to 6 membered, 4 to 6 membered, 4 to 5 membered, or 5 to 6 membered). In embodiments, $R^7$ is an unsubstituted heterocycloalkyl (e.g., 3 to 8 membered, 3 to 6 membered, 4 to 6 membered, 4 to 5 membered, or 5 to 6 membered).

In embodiments, $R^7$ is unsubstituted 3 to 8 membered heterocycloalkyl. In embodiments, $R^7$ is unsubstituted 3 to 6 membered heterocycloalkyl. In embodiments, $R^7$ is unsubstituted 4 to 6 membered heterocycloalkyl. In embodiments, $R^7$ is unsubstituted 4 to 5 membered heterocycloalkyl. In embodiments, $R^7$ is unsubstituted 5 to 6 membered heterocycloalkyl. In embodiments, $R^7$ is a substituted 3 to 8 membered heterocycloalkyl. In embodiments, $R^7$ is a substituted 3 to 6 membered heterocycloalkyl. In embodiments, $R^7$ is a substituted 4 to 6 membered heterocycloalkyl. In embodiments, $R^7$ is a substituted 4 to 5 membered heterocycloalkyl. In embodiments, $R^7$ is a substituted 5 to 6 membered heterocycloalkyl.

In embodiments, $R^7$ is substituted or unsubstituted aryl (e.g., $C_6$-$C_{10}$, $C_{10}$, or phenyl). In embodiments, $R^7$ is substituted aryl (e.g., $C_6$-$C_{10}$, $C_{10}$, or phenyl). In embodiments, $R^7$ is unsubstituted aryl (e.g., $C_6$-$C_{10}$, $C_{10}$, or phenyl). In embodiments, $R^7$ is unsubstituted phenyl. In embodiments, $R^7$ is substituted or unsubstituted heteroaryl (e.g., 5 to 10, 5 to 9, or 5 to 6 membered). In embodiments, $R^7$ is substituted heteroaryl (e.g., 5 to 10, 5 to 9, or 5 to 6 membered). In embodiments, $R^7$ is unsubstituted heteroaryl (e.g., 5 to 10, 5 to 9, or 5 to 6 membered). In embodiments, $R^7$ is a substituted or unsubstituted 5 membered heteroaryl. In embodiments, $R^7$ is a substituted or unsubstituted 6 membered heteroaryl. In embodiments, $R^7$ is a substituted or unsubstituted 7 membered heteroaryl. In embodiments, $R^7$ is an unsubstituted 5 membered heteroaryl. In embodiments, $R^7$ is an unsubstituted 6 membered heteroaryl. In embodiments, $R^7$ is an unsubstituted 7 membered heteroaryl.

In embodiments, $R^7$ is $R^{7A}$-substituted or unsubstituted aryl (e.g., $C_6$-$C_{10}$, $C_{10}$, or phenyl), or $R^{7A}$-substituted or unsubstituted heteroaryl (e.g., 5 to 10, 5 to 9, or 5 to 6 membered). $R^{7A}$ is independently oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, —$OCHF_2$, —$OCH_2Cl$, —$OCH_2Br$, —$OCH_2I$, —$OCH_2F$, —$N_3$, —$SF_5$, —$OPO_3H$, $R^{7B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{7B}$-substituted or unsubstituted heteroalkyl (e.g., 2 to 20, 8 to 20, 2 to 10, 2 to 8, 2 to 6, or 2 to 4 membered), $R^{7B}$-substituted or unsubstituted cycloalkyl (e.g., $C_3$-$C_8$, $C_3$-$C_6$, or $C_5$-$C_6$), $R^{7B}$-substituted or unsubstituted heterocycloalkyl (e.g., 3 to 8, 3 to 6, or 5 to 6 membered), $R^{7B}$-substituted or unsubstituted aryl (e.g., $C_6$-$C_{10}$, $C_{10}$, or phenyl), or $R^{7B}$-substituted or unsubstituted heteroaryl (e.g., 5 to 10, 5 to 9, or 5 to 6 membered). In embodiments, $R^{7A}$ is independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, or —$OPO_3H$. $R^{7B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{7C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{7C}$-substituted or unsubstituted heteroalkyl (e.g., 2 to 20, 8 to 20, 2 to 10, 2 to 8, 2 to 6, or 2 to 4 membered), $R^{7C}$-substituted or unsubstituted cycloalkyl (e.g., $C_3$-$C_8$, $C_3$-$C_6$, or $C_5$-$C_6$), $R^{7C}$-substituted or unsubstituted heterocycloalkyl (e.g., 3 to 8, 3 to 6, or 5 to 6 membered), $R^{7C}$-substituted or unsubstituted aryl (e.g., $C_6$-$C_{10}$, $C_{10}$, or phenyl), or $R^{7C}$-substituted or unsubstituted heteroaryl (e.g., 5 to 10, 5 to 9, or 5 to 6 membered). $R^{7C}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^7$ is $R^{7A}$-substituted cycloalkyl (e.g., $C_3$-$C_8$, $C_3$-$C_6$, $C_4$-$C_6$, or $C_5$-$C_6$). In embodiments, $R^7$ is $R^{7A}$-substituted heterocycloalkyl (e.g., 3 to 8 membered, 3 to 6 membered, 4 to 6 membered, 4 to 5 membered, or 5 to 6 membered). In embodiments, $R^{7A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$OPO_3H$, $R^{7B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{7B}$-substituted or unsubstituted heteroalkyl (e.g., 2 to 20, 8 to 20, 2 to 10, 2 to 8, 2 to 6, or 2 to 4 membered), $R^{7B}$-substituted or unsubstituted cycloalkyl (e.g., $C_3$-$C_8$, $C_3$-$C_6$, or $C_5$-$C_6$), $R^{7B}$-substituted or unsubstituted heterocycloalkyl (e.g., 3 to 8, 3 to 6, or 5 to 6 membered), $R^{7B}$-substituted or unsubstituted aryl (e.g., $C_6$-$C_{10}$, $C_{10}$, or phenyl), or $R^{7B}$-substituted or unsubstituted heteroaryl (e.g., 5 to 10, 5 to 9, or 5 to 6 membered).

In embodiments, $R^7$ is $R^{7A}$-substituted cycloalkyl (e.g., $C_3$-$C_8$, $C_3$-$C_6$, $C_4$-$C_6$, or $C_5$-$C_6$). In embodiments, $R^7$ is $R^{7A}$-substituted $C_3$-$C_8$ cycloalkyl. In embodiments, $R^7$ is $R^{7A}$-substituted $C_3$-$C_6$ cycloalkyl. In embodiments, $R^7$ is $R^{7A}$-substituted $C_4$-$C_6$ cycloalkyl. In embodiments, $R^7$ is $R^{7A}$-substituted $C_5$-$C_6$ cycloalkyl. In embodiments, $R^7$ is $R^{7A}$-substituted cyclopropyl. In embodiments, $R^7$ is $R^{7A}$-substituted cyclobutyl. In embodiments, $R^7$ is $R^{7A}$-substituted cyclopentyl. In embodiments, $R^7$ is $R^{7A}$-substituted cyclohexyl. In embodiments, $R^7$ is $R^{7A}$-substituted cycloheptyl. In embodiments, $R^7$ is $R^{7A}$-substituted cyclooctyl.

Two adjacent $R^{7A}$ substituents may optionally be joined to form a substituted or unsubstituted cycloalkyl, substituted or unsubstituted heterocycloalkyl, substituted or unsubstituted aryl, or substituted or unsubstituted heteroaryl. Two adjacent $R^{7A}$ substituents may optionally be joined to form a $R^{7B}$-substituted or unsubstituted cycloalkyl, $R^{7B}$-substituted or unsubstituted heterocycloalkyl, $R^{7B}$-substituted or unsubstituted aryl, or $R^{7B}$-substituted or unsubstituted heteroaryl. Two adjacent $R^{7A}$ substituents may optionally be joined to form a $R^{7B}$-substituted cycloalkyl, $R^{7B}$-substituted heterocycloalkyl, $R^{7B}$-substituted aryl, or $R^{7B}$-substituted heteroaryl. Two adjacent $R^{7A}$ substituents may optionally be joined to form an unsubstituted cycloalkyl, unsubstituted heterocycloalkyl, unsubstituted aryl, or unsubstituted heteroaryl.

In embodiments, $R^7$ is

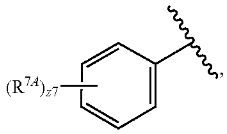

wherein $R^{7A}$ is as described herein and z7 is an integer from 0 to 5. In embodiments, $R^7$ is

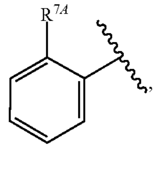

wherein $R^{7A}$ is as described herein. In embodiments, $R^7$ is

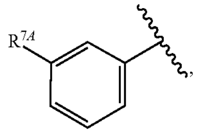

wherein $R^{7A}$ is as described herein. In embodiments, $R^7$ is

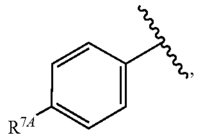

wherein $R^{7A}$ is as described herein. In embodiments, $R^{7A}$ is —CN, —$NO_2$, —$CF_3$, —$N_3$, —$NH_2$, —OMe, —OH, —F, —Cl, or —$CH_3$. In embodiments, $R^{7A}$ is —$N_3$, —$NH_2$, —OMe, —OH, —F, —Cl, or —$CH_3$. In embodiments, $R^7$ is

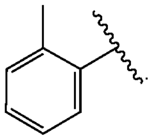 [SMILES: *c1ccccc1C]

In embodiments, $R^7$ is

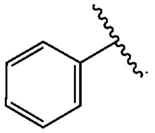 [SMILES: *c1ccccc1]

In embodiments, $R^7$ is

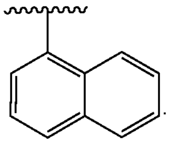

In embodiments, $R^7$ is

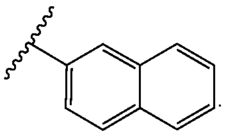 [SMILES: *c1ccc2ccccc2c1]

In embodiments, $R^7$ is

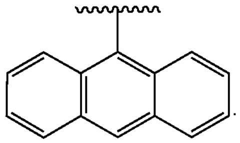 [SMILES: *c1c2ccccc2cc2ccccc12]

In embodiments, $R^7$ is

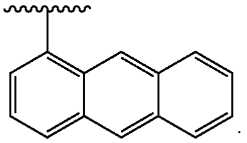 [SMILES: *c1cccc2cc3ccccc3cc12]

In embodiments $R^7$ is

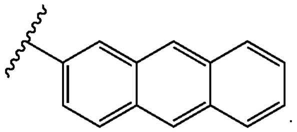 [SMILES: *c1ccc2cc3ccccc3cc2c1]

In embodiments, $R^7$ is

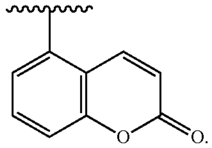 [SMILES: *c1cccc2oc(=O)ccc12]

In embodiments, $R^7$ is

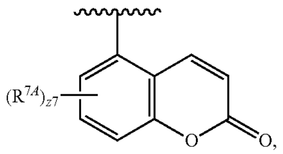

wherein z7 and $R^{7A}$ are as described herein. In embodiments, z7 is 4. In embodiments, z7 is 3. In embodiments, z7 is 2. In embodiments, z7 is 1. In embodiments, $R^7$ is

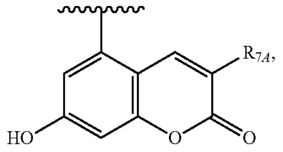

wherein $R^{7A}$ is as described herein. In embodiments, $R^7$ is

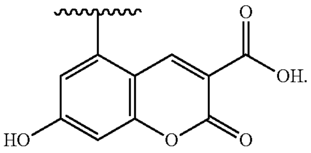 [SMILES: *c1cc(O)cc2oc(=O)c(C(=O)O)cc12]

In embodiments, $R^7$ is
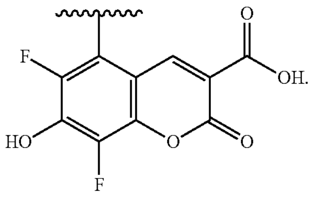 [SMILES: *c1c(F)c(O)c(F)c2oc(=O)c(C(=O)O)cc12]
In embodiments, $R^7$ is
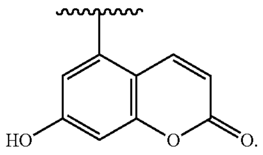 [SMILES: *c1cc(O)cc2oc(=O)ccc12]
In embodiments, $R^7$ is
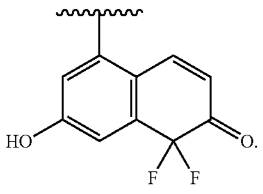 [SMILES: *c1cc(O)cc2c1C=CC(=O)C2(F)F]
In embodiments, $R^7$ is
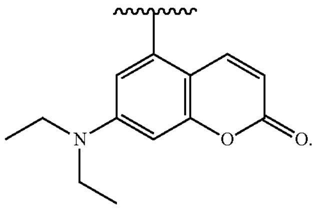 [SMILES: *c1cc(N(CC)CC)cc2oc(=O)ccc12]
In embodiments, $R^7$ is
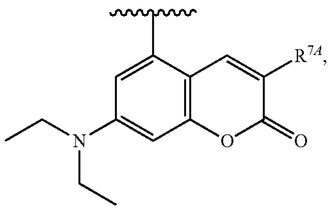
wherein $R^{7A}$ is as described herein.
In embodiments, $R^7$ is
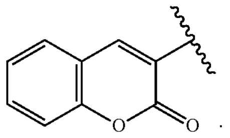 [SMILES: *c1cc2ccccc2oc1=O]
In embodiments, $R^7$ is
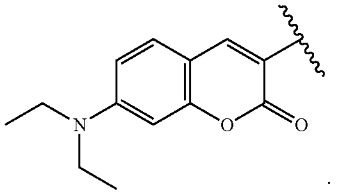 [SMILES: *c1cc2ccc(N(CC)CC)cc2oc1=O]
In embodiments, $R^7$ is
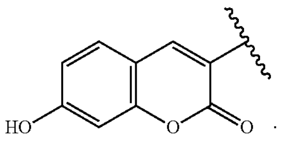 [SMILES: *c1cc2ccc(O)cc2oc1=O]
In embodiments, $R^7$ is
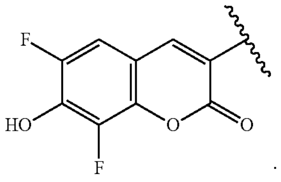 [SMILES: *c1cc2cc(F)c(O)c(F)c2oc1=O]
In embodiments, $R^7$ is
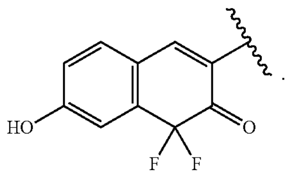 [SMILES: *C1=Cc2ccc(O)cc2C(F)(F)C1=O]
In embodiments, $R^7$ is
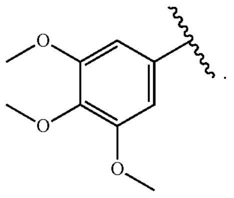 [SMILES: *c1cc(OC)c(OC)c(OC)c1]

In embodiments, $R^7$ is
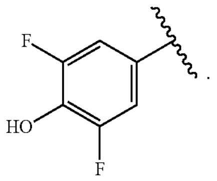
In embodiments, $R^7$ is a moiety depicted in Table 2.
In embodiments, $R^7$ is
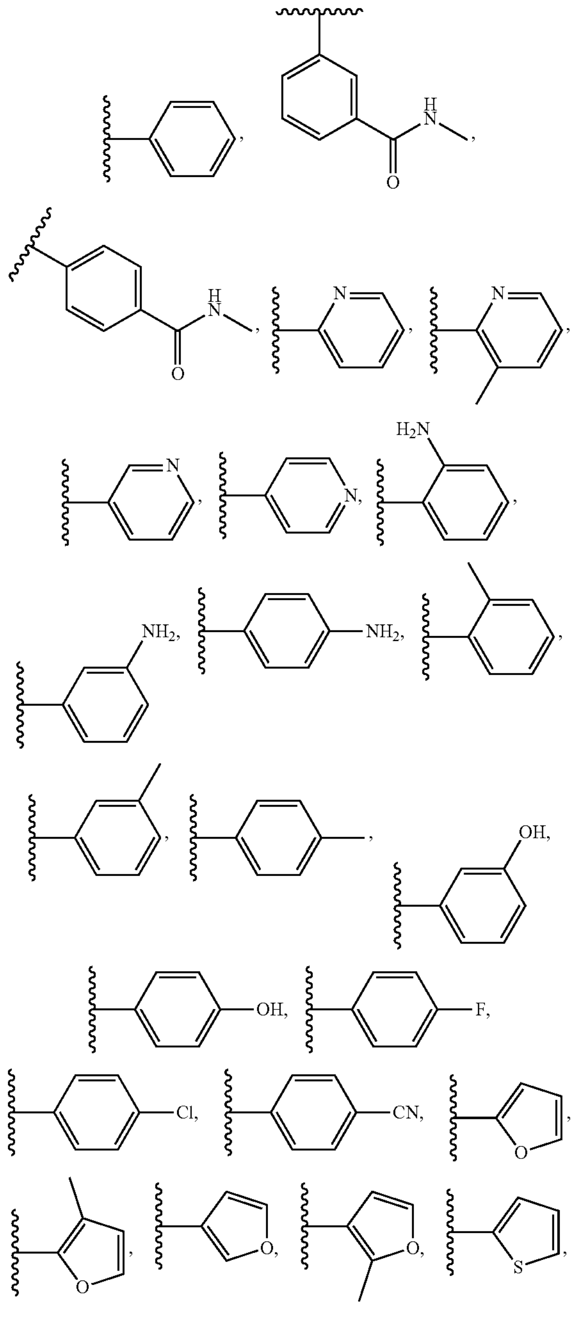
-continued
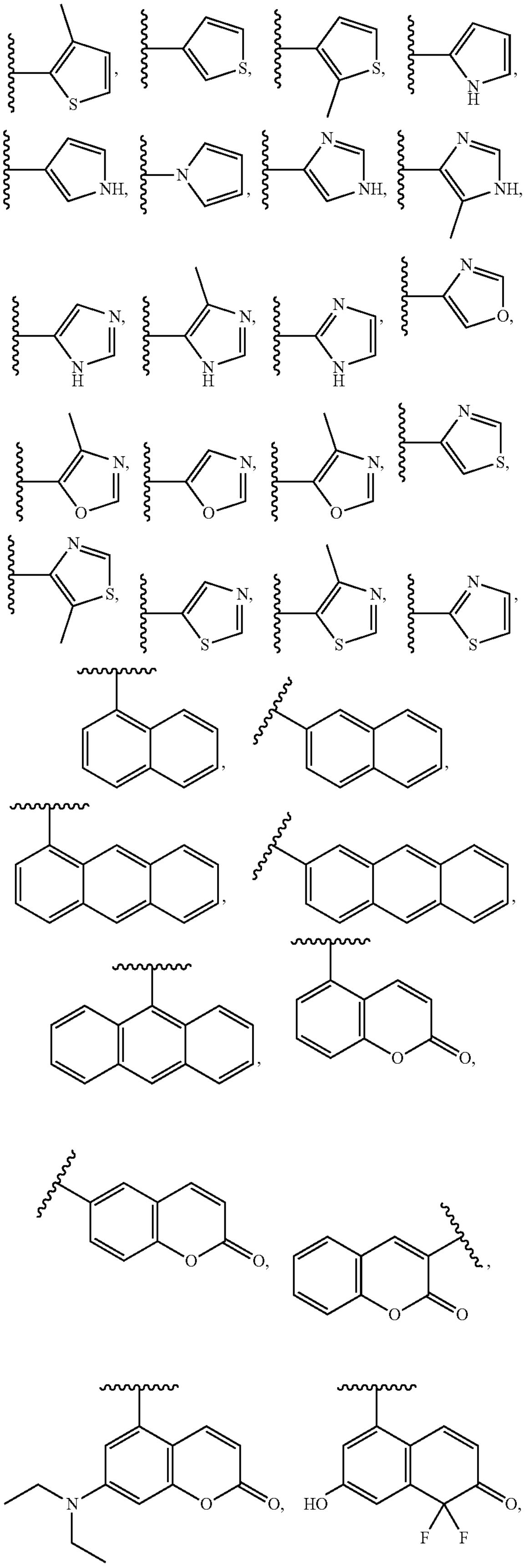

-continued
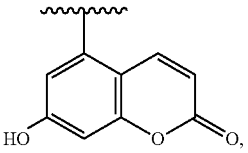
or
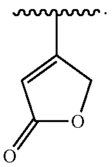
In embodiments, $R^7$ is
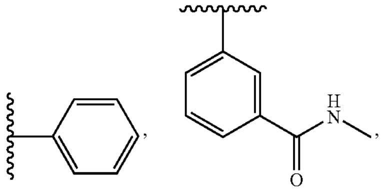
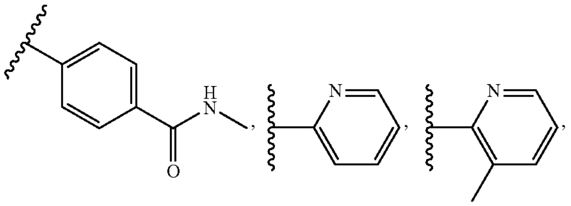
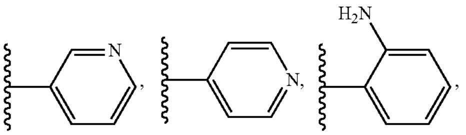
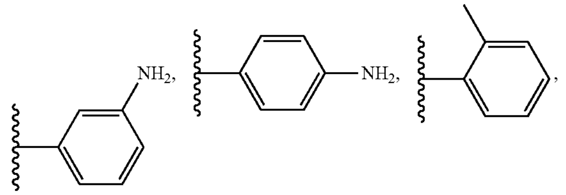
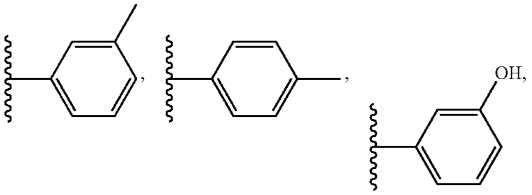
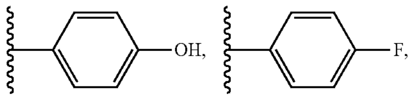
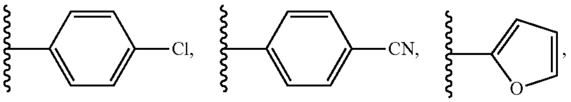
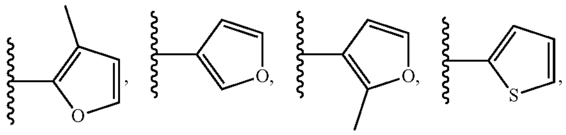
-continued
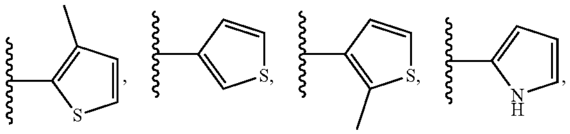
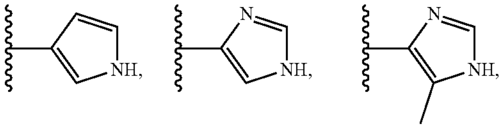
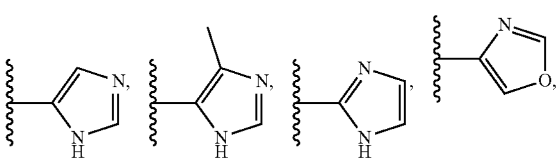
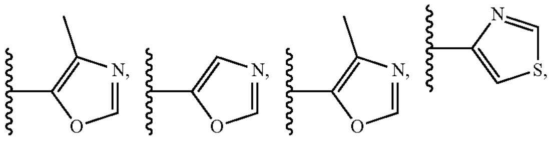
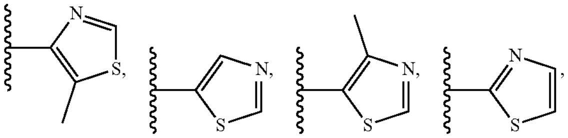
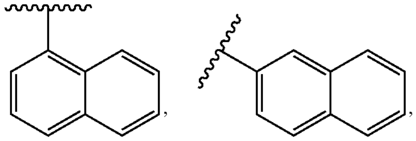
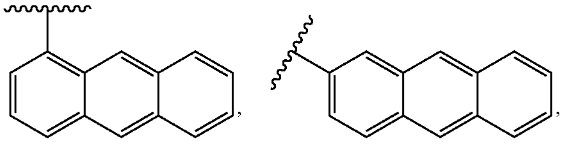
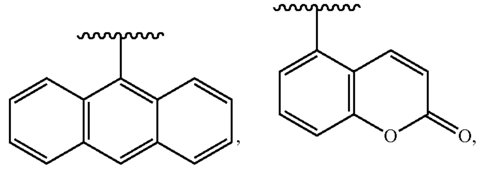
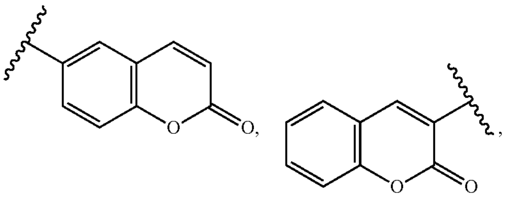
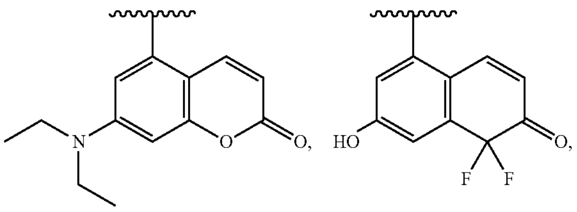

-continued
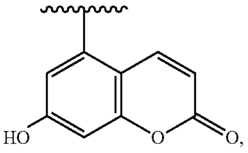
or
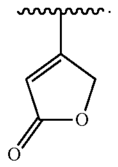
In embodiments, $R^7$ is
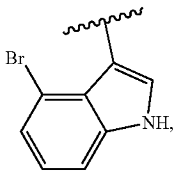
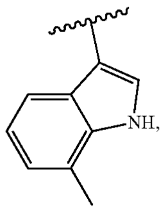
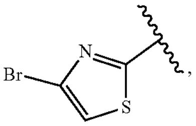
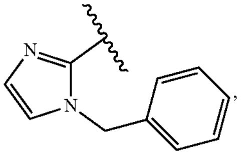
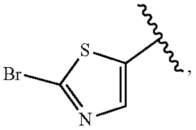
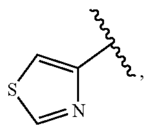
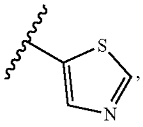
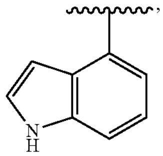
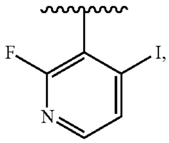
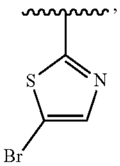
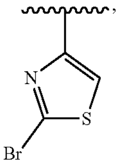
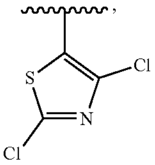
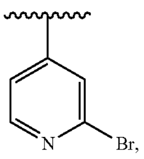
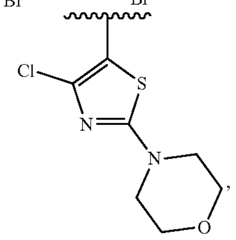
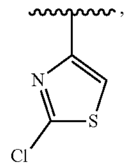
-continued
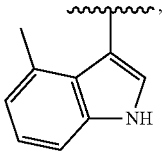
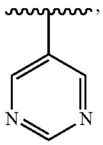
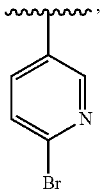
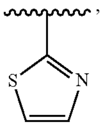
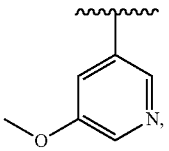
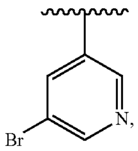
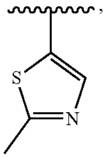
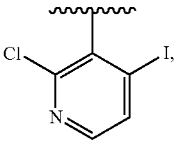
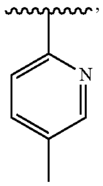
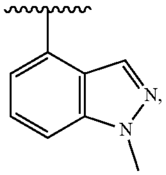
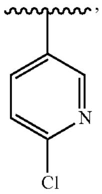
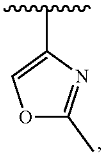
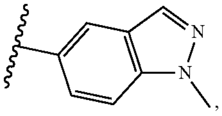
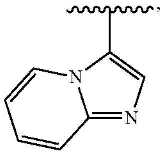
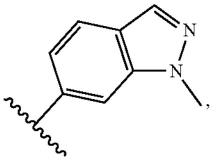
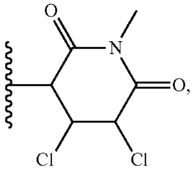
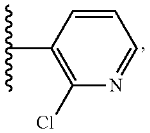
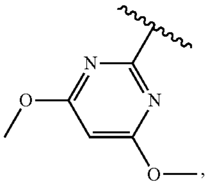
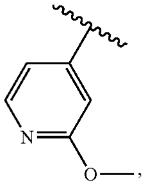
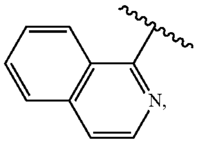
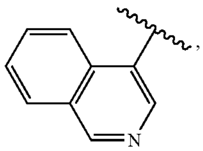
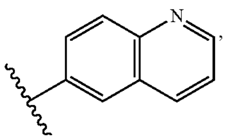

-continued
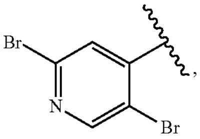, 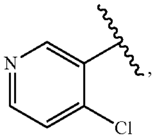, 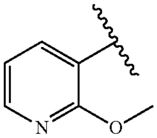,
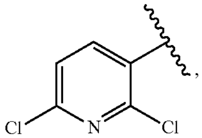, or 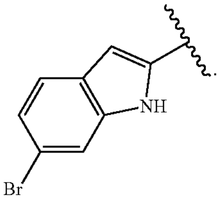
In embodiments, $R^7$ is
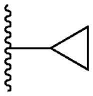, 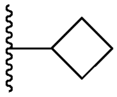, 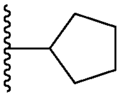,
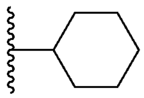, 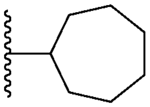, or 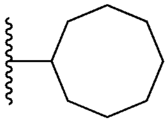.
In embodiments, $R^7$ is
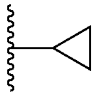.
In embodiments, $R^7$ is
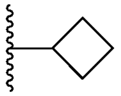.
In embodiments, $R^7$ is
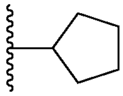.
In embodiments, $R^7$ is
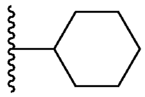.
In embodiments, $R^7$ is
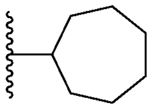.
In embodiments, $R^7$ is
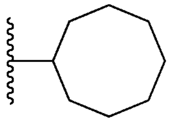.
In embodiments, $R^7$ is
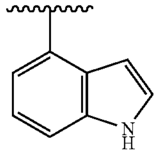.
In embodiments, $R^7$ is
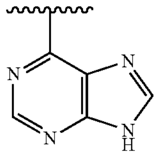.
In embodiments, $R^7$ is
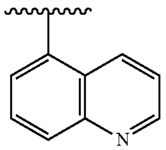.
In embodiments, $R^7$ is
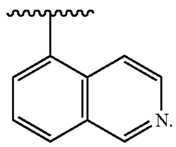 [SMILES: *c1cccc2cnccc12]
In embodiments, $R^7$ is
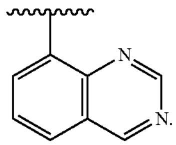 [SMILES: *c1cccc2cncnc12]

In embodiments, $R^7$ is

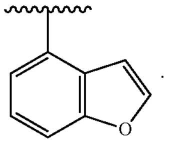 [SMILES: *c1cccc2occc12]

In embodiments, $R^7$ is

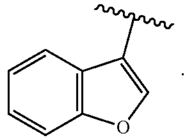 [SMILES: *c1coc2ccccc12]

In embodiments, $R^7$ is

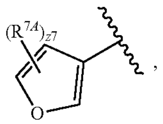

wherein $R^{7A}$ and z7 are as described herein. In embodiments, $R^7$ is

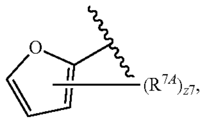

wherein $R^{7A}$ and z7 are as described herein. In embodiments, $R^7$ is

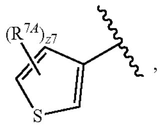

wherein $R^{7A}$ and z7 are as described herein. In embodiments, $R^7$ is

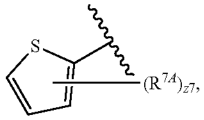

wherein $R^{7A}$ and z7 are as described herein. In embodiments, $R^7$ is

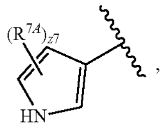

wherein $R^{7A}$ and z7 are as described herein. In embodiments, $R^7$ is

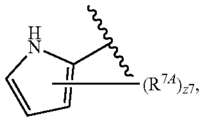

wherein $R^{7A}$ and z7 are as described herein. In embodiments, $R^7$ is

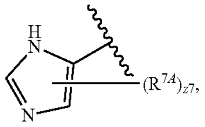

wherein $R^{7A}$ and z7 are as described herein. In embodiments, $R^7$ is

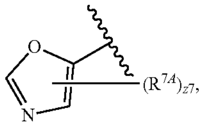

wherein $R^{7A}$ and z7 are as described herein. In embodiments, $R^7$ is

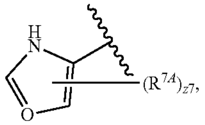

wherein $R^{7A}$ and z7 are as described herein. In embodiments, $R^7$ is

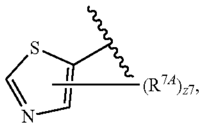

wherein $R^{7A}$ and z7 are as described herein. In embodiments, $R^7$ is

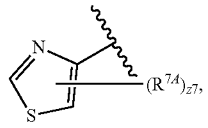

wherein $R^{7A}$ and z7 are as described herein. In embodiments, z7 is an integer from 0 to 2. In embodiments, $R^7$ is

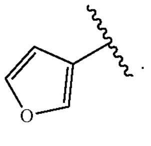 [SMILES: *c1ccoc1]

In embodiments, $R^7$ is

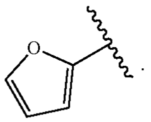 [SMILES: *c1ccco1]

In embodiments, $R^7$ is

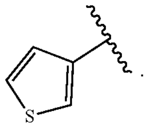 [SMILES: *c1ccsc1]

In embodiments, $R^7$ is

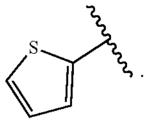 [SMILES: *c1cccs1]

In embodiments, $R^7$ is

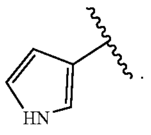 [SMILES: *c1cc[nH]c1]

In embodiments, $R^7$ is

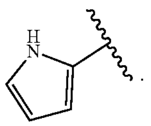

In embodiments, $R^7$ is

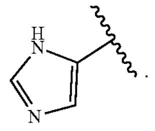

In embodiments, $R^7$ is

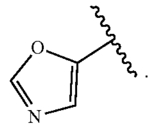

In embodiments, $R^7$ is

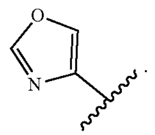 [SMILES: *c1cocn1]

In embodiments $R^7$ is

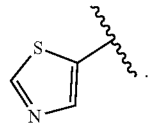

In embodiments, $R^7$ is

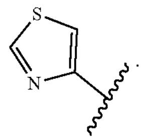 [SMILES: *c1cscn1]

In embodiments, $R^7$ is

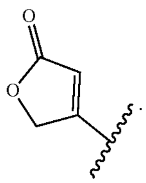 [SMILES: *C1=CC(=O)OC1]

In embodiments, $R^7$ is

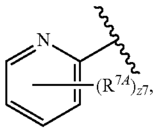

wherein $R^{7A}$ and z7 are as described herein. In embodiments, $R^7$ is

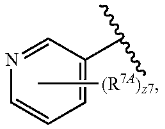

wherein $R^{7A}$ and z7 are as described herein. In embodiments, $R^7$ is

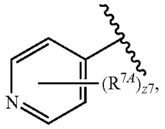

wherein $R^{7A}$ and z7 are as described herein. In embodiments, $R^7$ is

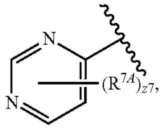

wherein $R^{7A}$ and z7 are as described herein. In embodiments, $R^7$ is

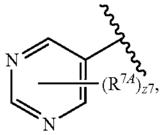

wherein $R^{7A}$ and z7 are as described herein. In embodiments, $R^7$ is

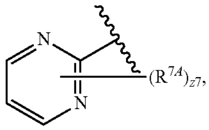

wherein $R^{7A}$ and z7 are as described herein. In embodiments, $R^7$ is

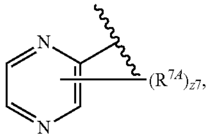

wherein $R^{7A}$ and z7 are as described herein. In embodiments, $R^7$ is

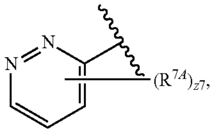

wherein $R^{7A}$ and z7 are as described herein. In embodiments, $R^7$ is

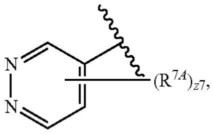

wherein $R^{7A}$ and z7 are as described herein. In embodiments, $R^7$ is

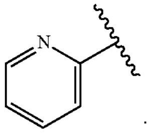 [SMILES: *c1ccccn1]

.

In embodiments, $R^7$ is

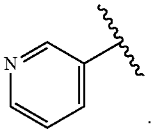 [SMILES: *c1cccnc1]

.

In embodiments, $R^7$ is

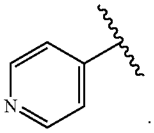 [SMILES: *c1ccncc1]

.

In embodiments, $R^7$ is

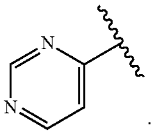 [SMILES: *c1ccncn1]

.

In embodiments $R^7$ is

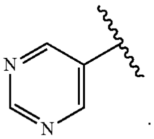

.

In embodiments, $R^7$ is
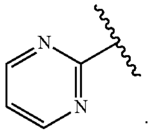 [SMILES: *c1ncccn1]
.
In embodiments, $R^7$ is
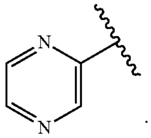 [SMILES: *c1cnccn1]
.
In embodiments, $R^7$ is
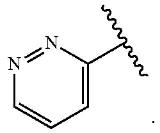 [SMILES: *c1cccnn1]
.
In embodiments, $R^7$ is
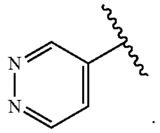 [SMILES: *c1ccnnc1]
.
In embodiments, $R^7$ is
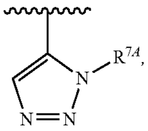
wherein $R^{7A}$ is as described herein. In embodiments, $R^7$ is
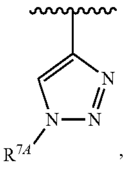
,
wherein $R^{7A}$ is as described herein.
In embodiments, $R^7$ is
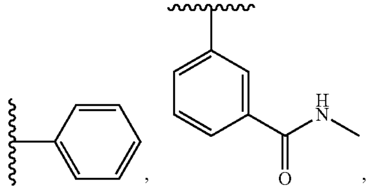
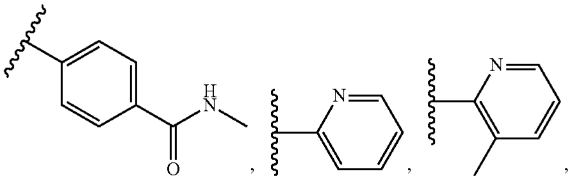
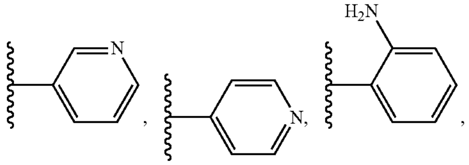
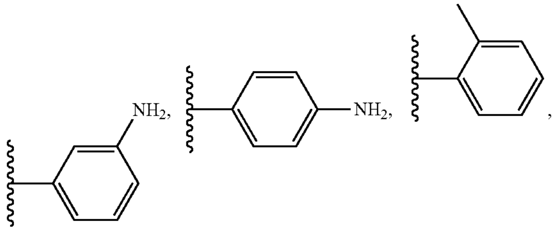
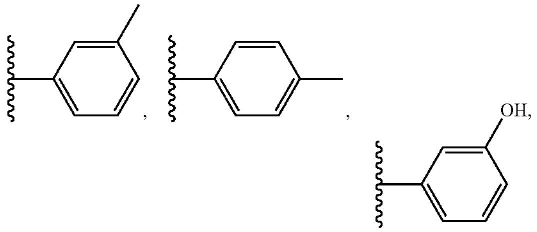
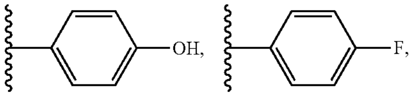
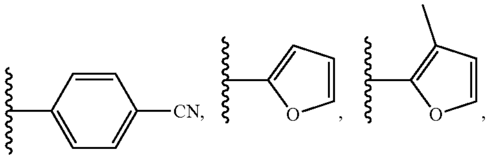
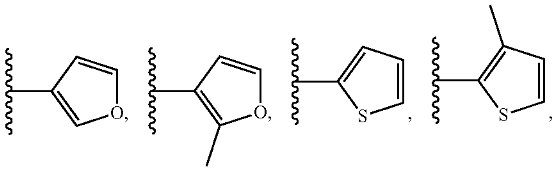
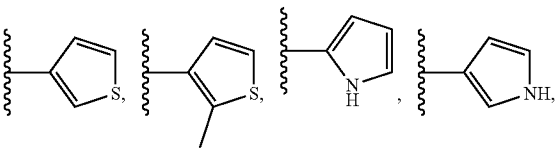

-continued
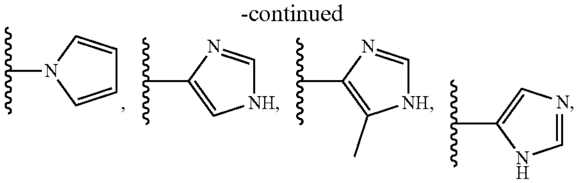
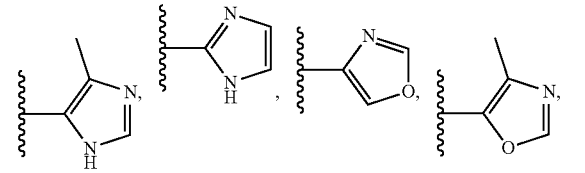
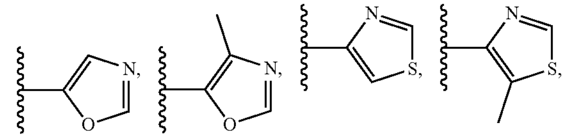
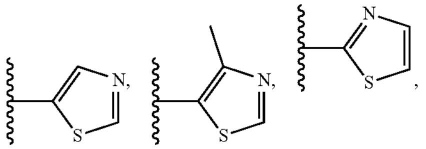
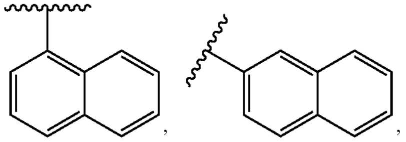
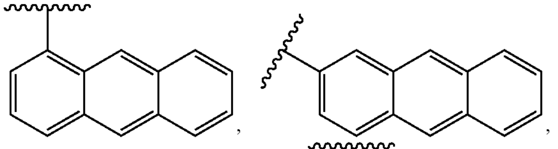
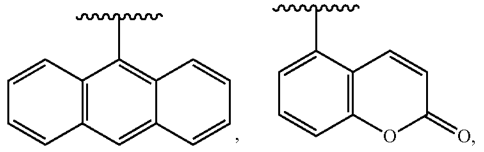
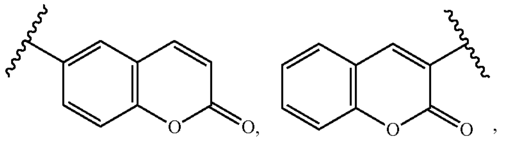
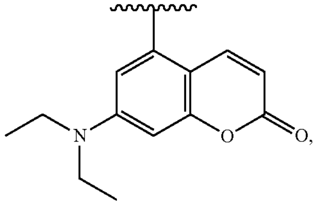
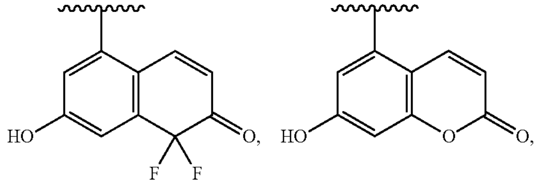
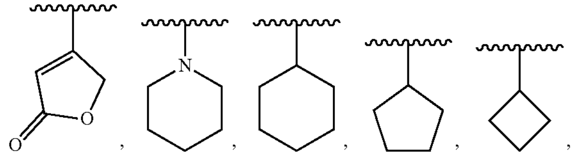
-continued
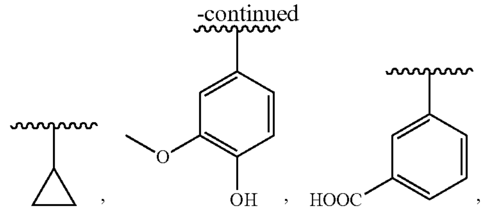
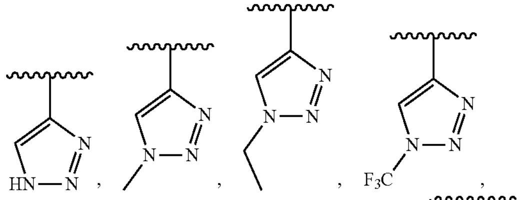
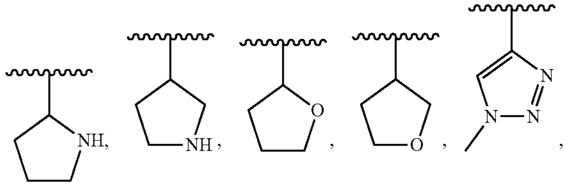
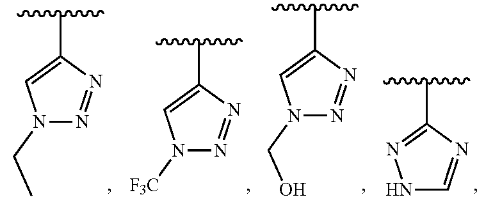
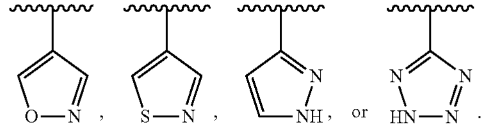
In embodiments, $R^7$ is
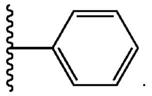
In embodiments, $R^7$ is
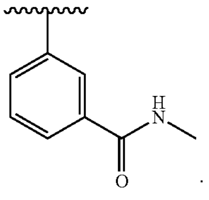 [SMILES: *c1cccc(C(=O)NC)c1]
In embodiments, $R^7$ is
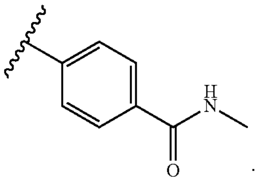 [SMILES: *c1ccc(C(=O)NC)cc1]

In embodiments, $R^7$ is
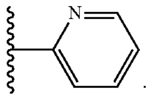 [SMILES: *c1ccccn1]
In embodiments, $R^7$ is
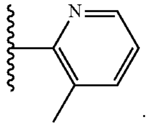 [SMILES: *c1ncccc1C]
In embodiments, $R^7$ is
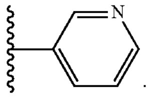
In embodiments, $R^7$ is
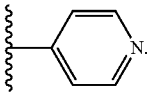 [SMILES: *c1ccncc1]
In embodiments, $R^7$ is
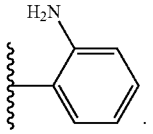
In embodiments, $R^7$ is
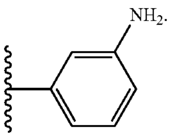 [SMILES: *c1cccc(N)c1]
In embodiments, $R^7$ is
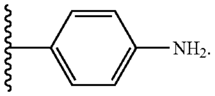 [SMILES: *c1ccc(N)cc1]
In embodiments, $R^7$ is
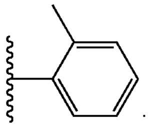
In embodiments, $R^7$ is
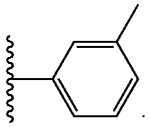 [SMILES: *c1cccc(C)c1]
In embodiments, $R^7$ is
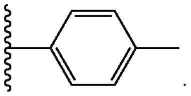 [SMILES: *c1ccc(C)cc1]
In embodiments, $R^7$ is
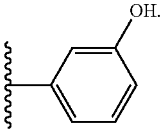 [SMILES: *c1cccc(O)c1]
In embodiments, $R^7$ is
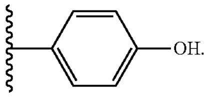 [SMILES: *c1ccc(O)cc1]
In embodiments, $R^7$ is
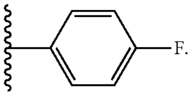
In embodiments, $R^7$ is
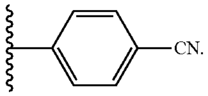 [SMILES: *c1ccc(C#N)cc1]

In embodiments, $R^7$ is
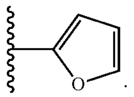
In embodiments, $R^7$ is
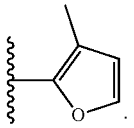
In embodiments, $R^7$ is
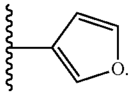 [SMILES: *c1ccoc1]
In embodiments, $R^7$ is
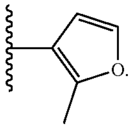 [SMILES: *c1ccoc1C]
In embodiments, $R^7$ is
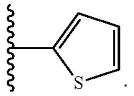
In embodiments, $R^7$ is
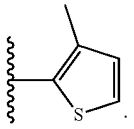
In embodiments, $R^7$ is
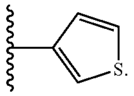
In embodiments, $R^7$ is
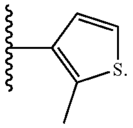
In embodiments, $R^7$ is
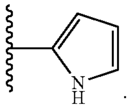
In embodiments, $R^7$ is
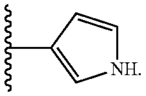 [SMILES: *c1cc[nH]c1]
In embodiments, $R^7$ is
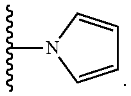
In embodiments, $R^7$ is
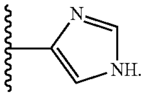
In embodiments, $R^7$ is
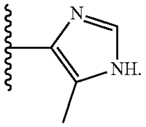 [SMILES: *c1nc[nH]c1C]
In embodiments, $R^7$ is
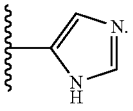
In embodiments, $R^7$ is
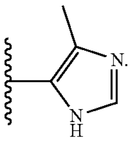

In embodiments, $R^7$ is
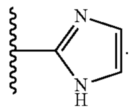
In embodiments, $R^7$ is
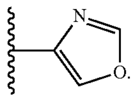
In embodiments, $R^7$ is
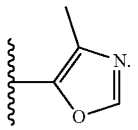
In embodiments, $R^7$ is
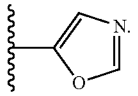
In embodiments, $R^7$ is
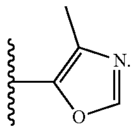 [SMILES: *c1ocnc1C]
In embodiments, $R^7$ is
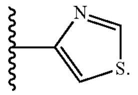
In embodiments, $R^7$ is
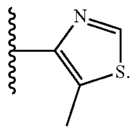
In embodiments, $R^7$ is
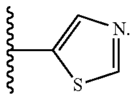
In embodiments, $R^7$ is
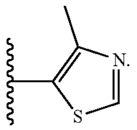 [SMILES: *c1scnc1C]
In embodiments, $R^7$ is
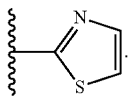
In embodiments, $R^7$ is
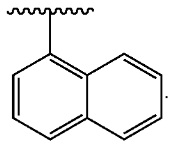 [SMILES: *c1cccc2ccccc12]
In embodiments, $R^7$ is
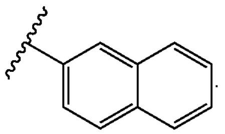 [SMILES: *c1ccc2ccccc2c1]
In embodiments, $R^7$ is
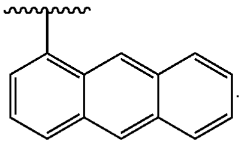 [SMILES: *c1cccc2cc3ccccc3cc12]
In embodiments, $R^7$ is
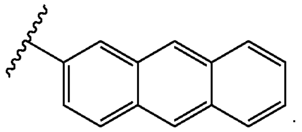 [SMILES: *c1ccc2cc3ccccc3cc2c1]

In embodiments, $R^7$ is
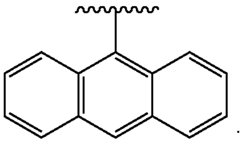 [SMILES: *c1c2ccccc2cc2ccccc12]
In embodiments, $R^7$ is
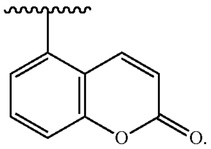 [SMILES: *c1cccc2oc(=O)ccc12]
In embodiments, $R^7$ is
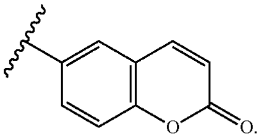 [SMILES: *c1ccc2oc(=O)ccc2c1]
In embodiments, $R^7$ is
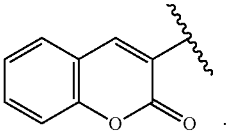 [SMILES: *c1cc2ccccc2oc1=O]
In embodiments, $R^7$ is
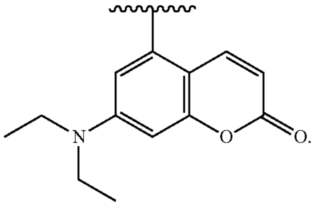 [SMILES: *c1cc(N(CC)CC)cc2oc(=O)ccc12]
In embodiments, $R^7$ is
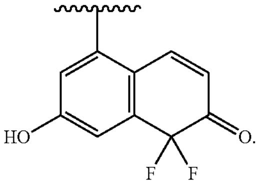 [SMILES: *c1cc(O)cc2c1C=CC(=O)C2(F)F]
In embodiments, $R^7$ is
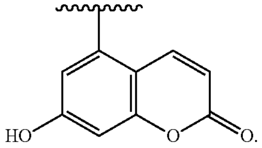 [SMILES: *c1cc(O)cc2oc(=O)ccc12]
In embodiments, $R^7$ is
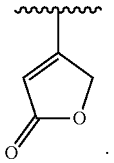
In embodiments, $R^7$ is
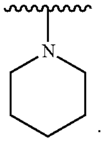
In embodiments, $R^7$ is
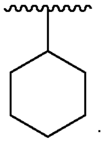 [SMILES: *C1CCCCC1]
In embodiments, $R^7$ is
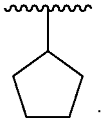
In embodiments, $R^7$ is
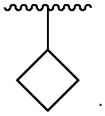 [SMILES: *C1CCC1]
In embodiments, $R^7$ is
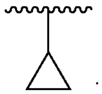 [SMILES: *C1CC1]

In embodiments, $R^7$ is
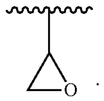 [SMILES: *C1CO1]
In embodiments, $R^7$ is
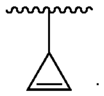 [SMILES: *C1C=C1]
In embodiments, $R^7$ is
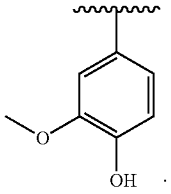 [SMILES: *c1ccc(O)c(OC)c1]
In embodiments, $R^7$ is
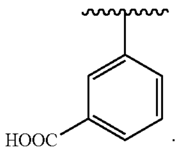 [SMILES: *c1cccc(C(=O)O)c1]
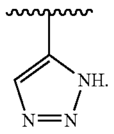 [SMILES: *c1cnn[nH]1]
In embodiments, $R^7$ is
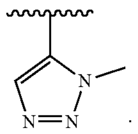 [SMILES: *c1cnnn1C]
In embodiments, $R^7$ is
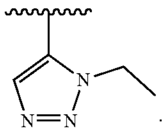
In embodiments, $R^7$ is
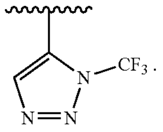 [SMILES: *c1cnnn1C(F)(F)F]
In embodiments, $R^7$ is
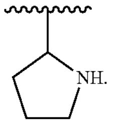 [SMILES: *C1CCCN1]
In embodiments, $R^7$ is
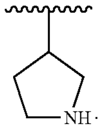
In embodiments, $R^7$ is
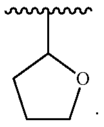 [SMILES: *C1CCCO1]
In embodiments, $R^7$ is
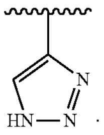
In embodiments, $R^7$ is
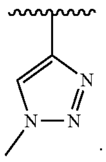 [SMILES: *c1cn(C)nn1]
In embodiments, $R^7$ is
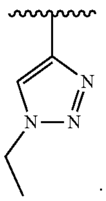

In embodiments, $R^7$ is
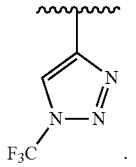
.
In embodiments, $R^7$ is
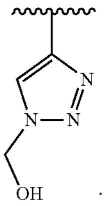 [SMILES: *c1cn(CO)nn1]
.
In embodiments, $R^7$ is
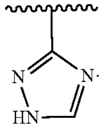
In embodiments, $R^7$ is
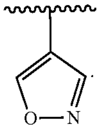 [SMILES: *c1cnoc1]
In embodiments, $R^7$ is
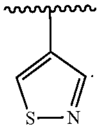 [SMILES: *c1cnsc1]
In embodiments, $R^7$ is
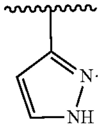
In embodiments, $R^7$ is
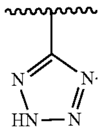
In embodiments, $R^7$ is
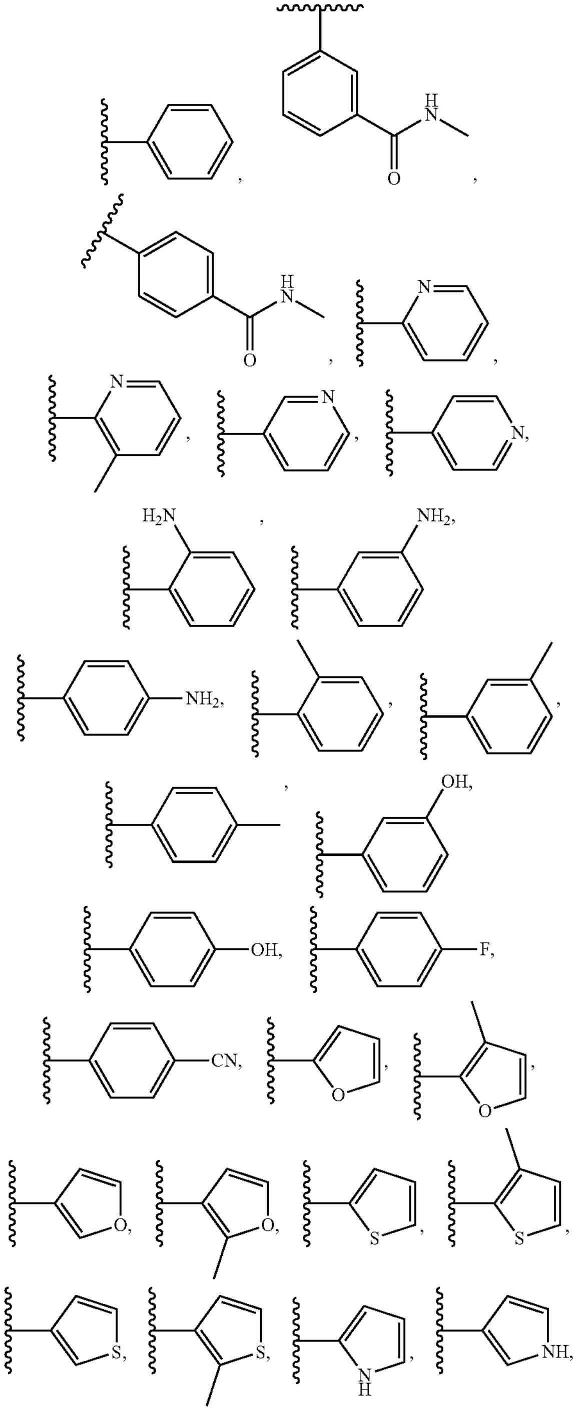

-continued

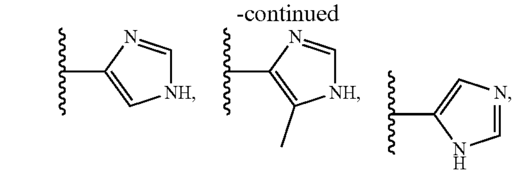

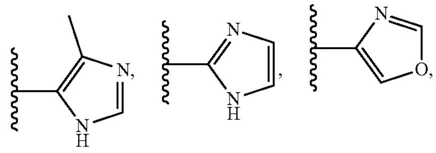

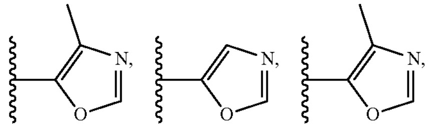

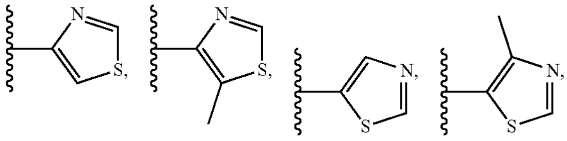

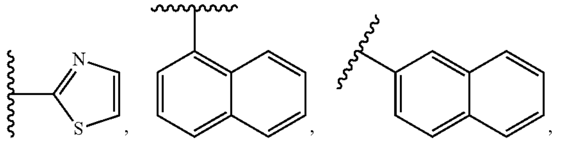

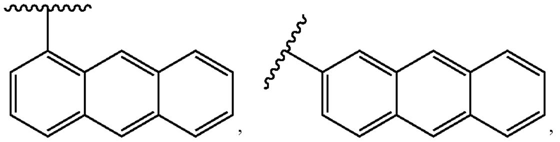

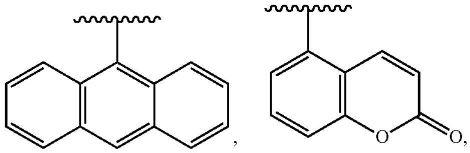

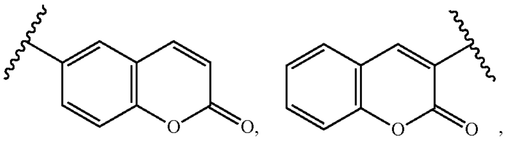

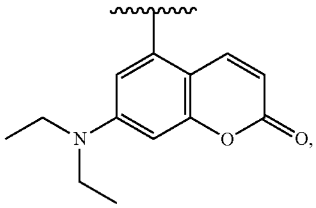

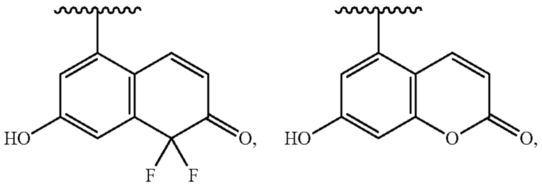

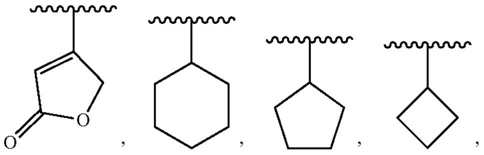

-continued

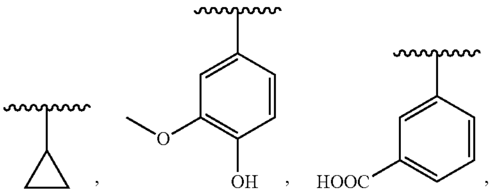

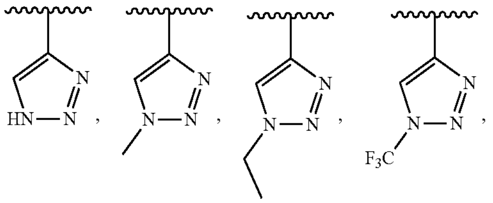

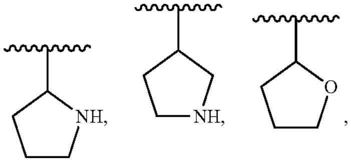

or

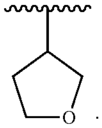

In embodiments, $R^7$ is

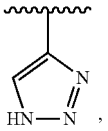

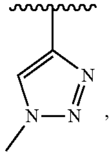

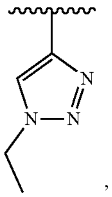

or

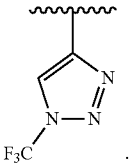

In embodiments, $R^7$ is substituted or unsubstituted aryl. In embodiments, $R^7$ is substituted or unsubstituted heteroaryl. In embodiments, $R^7$ is substituted or unsubstituted cycloalkyl, or substituted or unsubstituted heterocycloalkyl. In embodiments, $R^7$ is substituted or unsubstituted 5 to 6 membered heteroaryl. In embodiments, $R^7$ is,

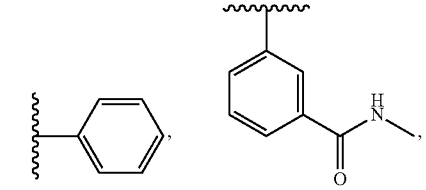
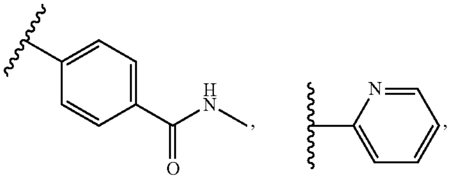
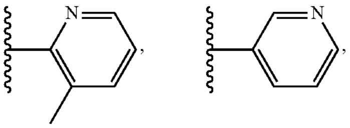
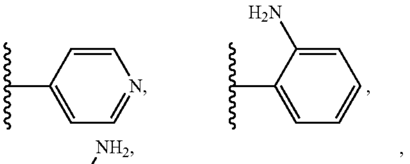
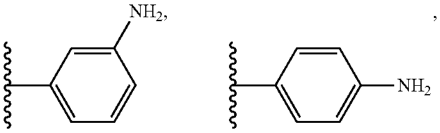
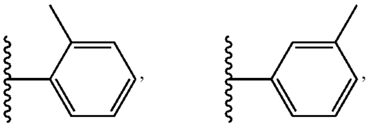
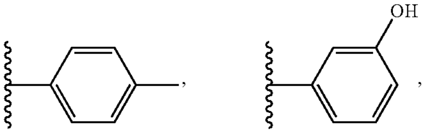
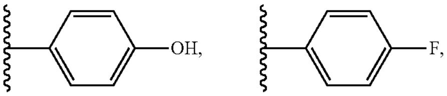
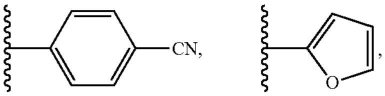
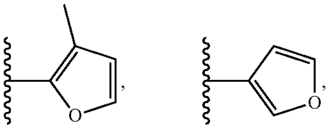
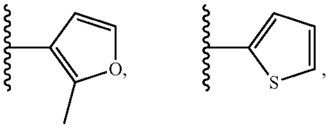
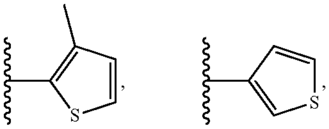
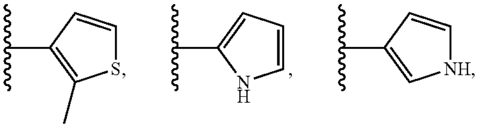
-continued
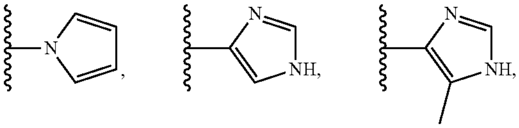
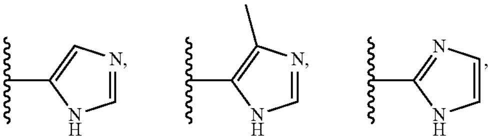
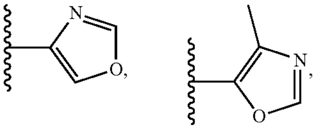
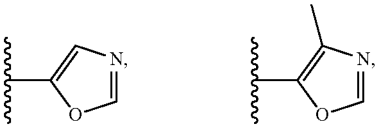
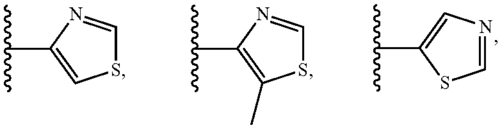
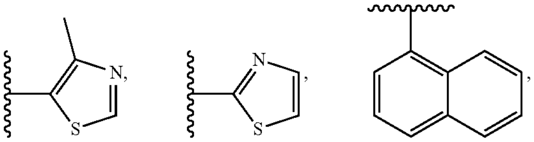
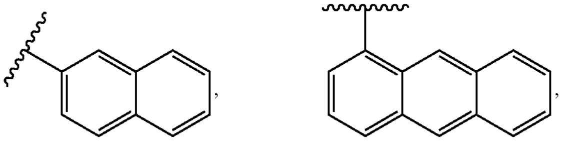
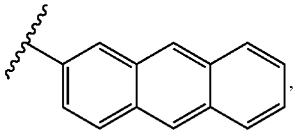
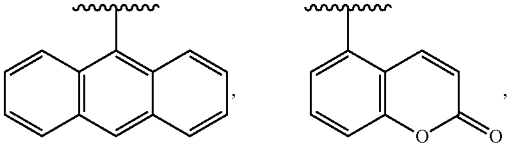
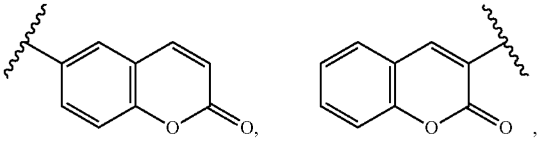
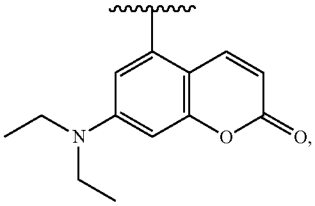

-continued

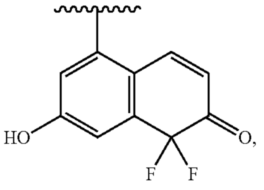

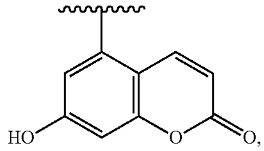 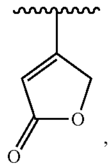

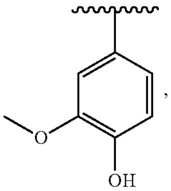 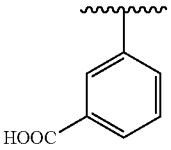 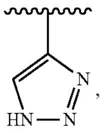

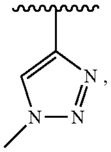 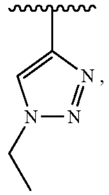 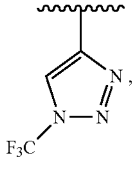

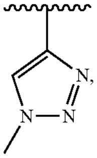 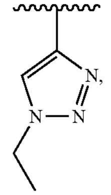 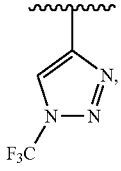

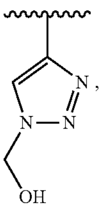 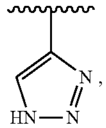 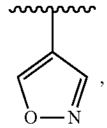

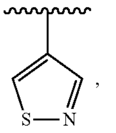 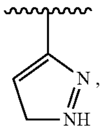 or 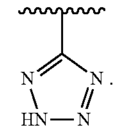

In embodiments, $L^{100}$ is a divalent linker including

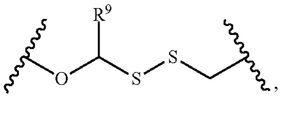 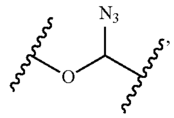

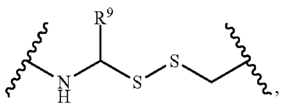

-continued

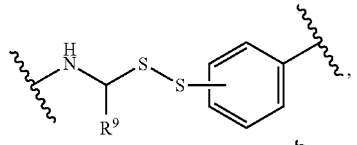

(e.g. 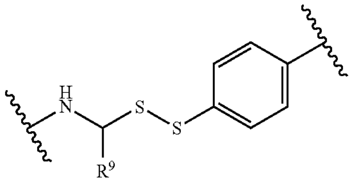), or

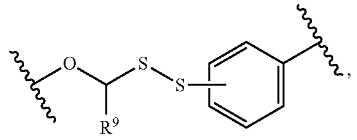

(e.g. 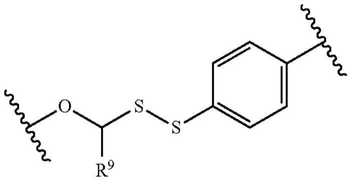).

$R^9$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$ is a moiety represented by $R^7$. In embodiments, $R^9$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NIC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered).

In embodiments, $R^9$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{10}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{10}$-substituted or unsubstituted heteroalkyl (e.g., 2 to 20, 8 to 20, 2 to 10, 2 to 8, 2 to 6, or 2 to 4 membered), $R^{10}$-substituted or unsubstituted cycloalkyl (e.g., $C_3$-$C_8$, $C_3$-$C_6$, or $C_5$-$C_6$), $R^{10}$-substituted or unsubstituted heterocycloalkyl (e.g., 3 to 8, 3 to 6, or 5 to 6 membered), $R^{10}$-substituted or unsubstituted aryl (e.g., $C_6$-$C_{10}$, $C_{10}$, or phenyl), or $R^{10}$-substituted or unsubstituted heteroaryl (e.g., 5 to 10, 5 to 9, or 5 to 6 membered). In embodiments, $R^9$ is $R^{10}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{10}$-substituted or unsubstituted heteroalkyl (e.g., 2 to 20, 8 to 20, 2 to 10, 2 to 8, 2 to 6, or 2 to 4 membered), $R^{10}$-substituted or unsubstituted cycloalkyl (e.g., $C_3$-$C_8$, $C_3$-$C_6$, or $C_5$-$C_6$), $R^{10}$-substituted or unsubstituted heterocycloalkyl (e.g., 3 to 8, 3 to 6, or 5 to 6 membered), $R^{10}$-substituted or unsubstituted aryl (e.g., $C_6$-$C_{10}$, $C_{10}$, or phenyl), or $R^{10}$-substituted or unsubstituted heteroaryl (e.g., 5 to 10, 5 to 9, or 5 to 6 membered). In embodiments, $R^9$ is unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^9$ is unsubstituted alkyl (e.g., $C_1$-$C_{20}$, $C_{10}$-$C_{20}$, $C_1$-$C_8$, $C_1$-$C_6$, or $C_1$-$C_4$). In embodiments, $R^9$ is unsubstituted $C_1$-$C_6$ alkyl. In embodiments, $R^9$ is unsubstituted $C_1$-$C_4$ alkyl. In embodiments, $R^9$ is unsubstituted methyl. In embodiments, $R^9$ is unsubstituted ethyl. In embodiments, $R^9$ is unsubstituted propyl. In embodiments, $R^9$ is unsubstituted tert-butyl. In embodiments, $R^9$ is unsubstituted $C_3$-$C_8$ cycloalkyl. In embodiments, $R^9$ is unsubstituted $C_3$-$C_6$ cycloalkyl. In embodiments, $R^9$ is unsubstituted $C_3$ cycloalkyl. In embodiments, $R^9$ is unsubstituted $C_5$-$C_6$ cycloalkyl. In embodiments, $R^9$ is unsubstituted 3 to 8 membered heterocycloalkyl. In embodiments, $R^9$ is unsubstituted 3 to 6 membered heterocycloalkyl. In embodiments, $R^9$ is unsubstituted 5 to 6 membered heterocycloalkyl. In embodiments, $R^9$ is unsubstituted phenyl. In embodiments, $R^9$ is unsubstituted 5 to 6 membered heteroaryl. In embodiments, $R^9$ is unsubstituted 5 membered heteroaryl. In embodiments, $R^9$ is unsubstituted 6 membered heteroaryl. In embodiments, $R^9$ is

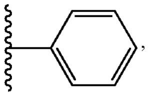,
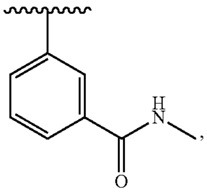,

-continued

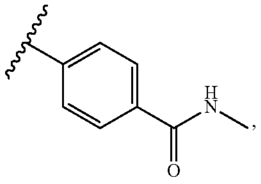,
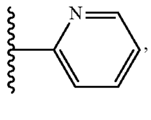,
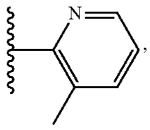,

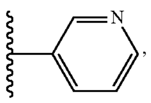,
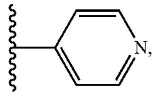,
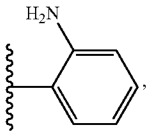,

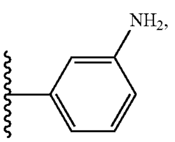,
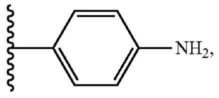,
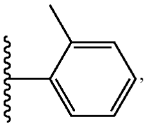,

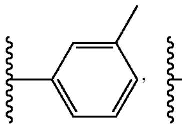,
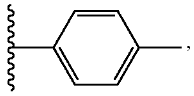,
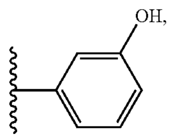,

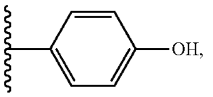,
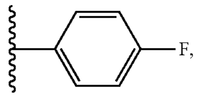,

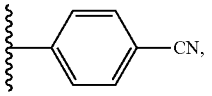,
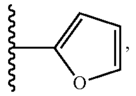,
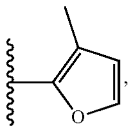,

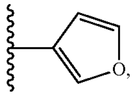,
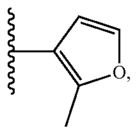,
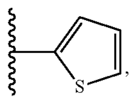,
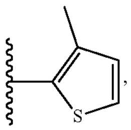,

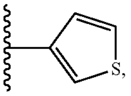,
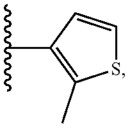,
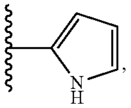,
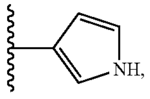,

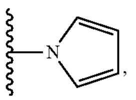,
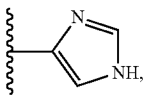,
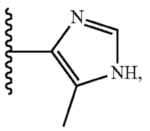,

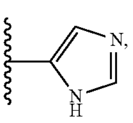,
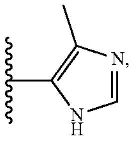,
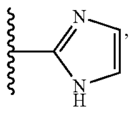,
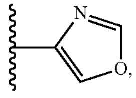,

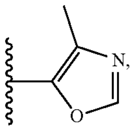,
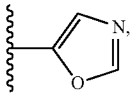,
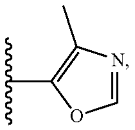,
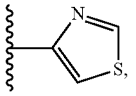,

-continued

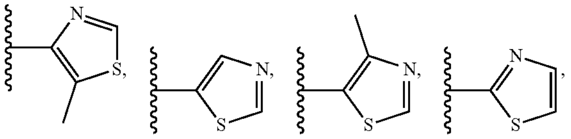

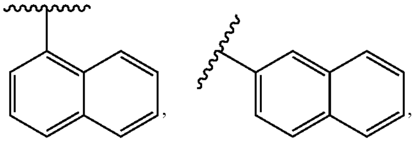

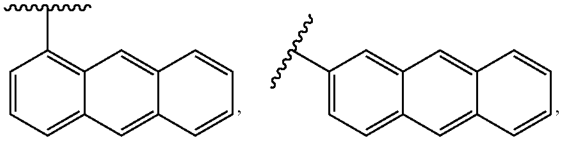

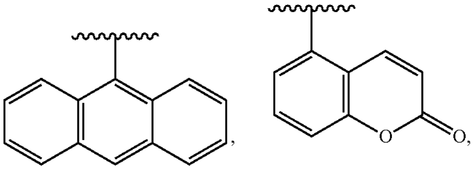

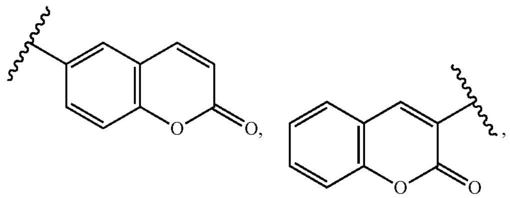

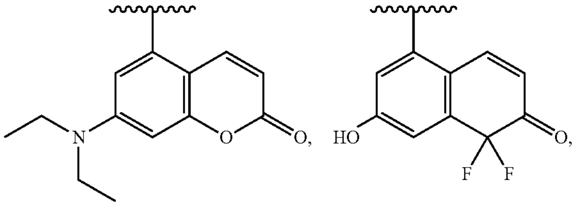

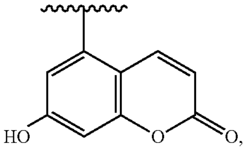

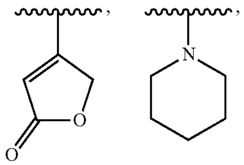

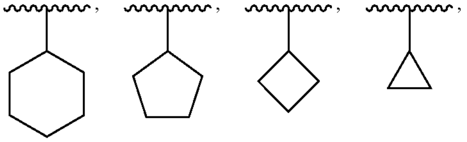

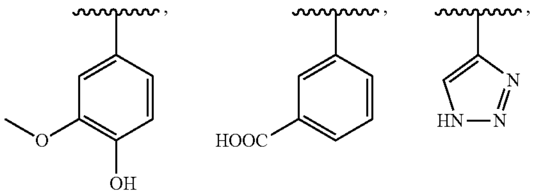

-continued

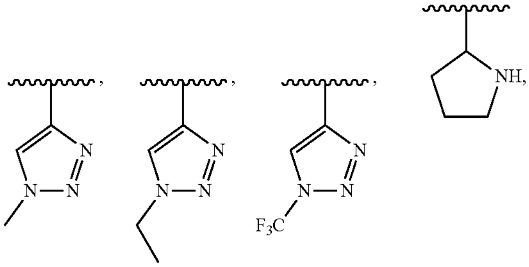

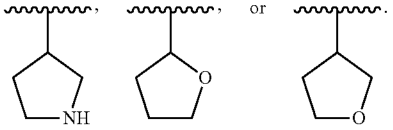

$R^{10}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$—$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In $N_3$ embodiments, $L^{100}$ is a divalent linker comprising

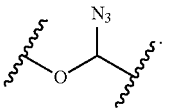

In embodiments, $L^{100}$ is a divalent linker including

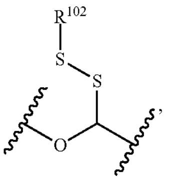

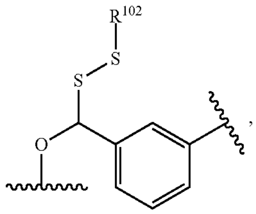

or

-continued

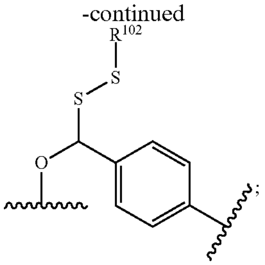

wherein $R^{102}$ is substituted or unsubstituted alkyl.

In embodiments, $R^{102}$ is $R^{102B}$-substituted alkyl. $R^{102B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{102}$ is unsubstituted $C_1$-$C_4$ alkyl. In embodiments, $R^{102}$ is unsubstituted $C_1$ alkyl. In embodiments, $R^{102}$ is unsubstituted $C_2$ alkyl. In embodiments, $R^{102}$ is unsubstituted $C_3$ alkyl. In embodiments, $R^{102}$ is unsubstituted $C_4$ alkyl.

In embodiments, $L^{100}$ is -$L^{101}$-$L^{102}$-$L^{103}$-$L^{104}$-$L^{105}$-. $L^{101}$, $L^{102}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, —N═N—, —SS—, substituted or unsubstituted alkylene (e.g., —CH(OH)— or —$C(CH_2)$—), substituted or unsubstituted heteroalkylene, substituted or unsubstituted cycloalkylene, substituted or unsubstituted heterocycloalkylene, substituted or unsubstituted arylene, or substituted or unsubstituted heteroarylene, a bioconjugate linker, a cleavable linker, a self-immolative linker, a linker capable of dendritic amplification of signal (e.g., capable of increasing fluorescence by releasing fluorophores from the remainder of the linker), a trivalent linker, or a self-immolative dendrimer linker (e.g., capable of increasing fluorescence by releasing fluorophores from the remainder of the linker). In embodiments, $L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{101}$, $L^{102}$, $L^{103}$, $L^{104}$, and $L^{105}$ independently includes PEG. In embodiments, $L^{101}$, $L^{102}$, $L^{103}$, $L^{104}$, and $L^{105}$ independently includes

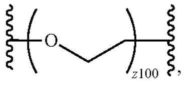

wherein z100 is an integer from 1 to 8. In embodiments, z100 is 1. In embodiments, z100 is 2. In embodiments, z100 is 3. In embodiments, z100 is 4. In embodiments, z100 is 5. In embodiments, z100 is 6. In embodiments, z100 is 7. In embodiments, z100 is 8. In embodiments, z100 is 2 to 8. In embodiments, z100 is 4 to 6.

In embodiments, $L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{101}$, $L^{102}$, $L^{103}$, $L^{104}$, and/or $L^{105}$ are independently a bond, —NH—, —S—, —O—, —C(O)—, —C(O)O—, —OC(O)—, —CH(OH)—, —NHC(O)—, —C(O)NH—, —NHC(O)NH—, —NHC(NH)NH—, —C(S)—, or —$C(CH_2)$—.

In embodiments, $L^{100}$ is

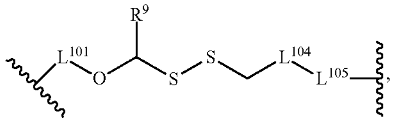

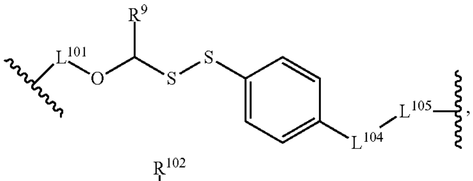

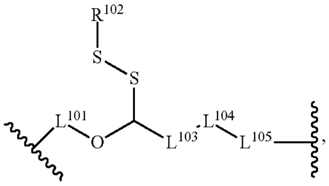

or

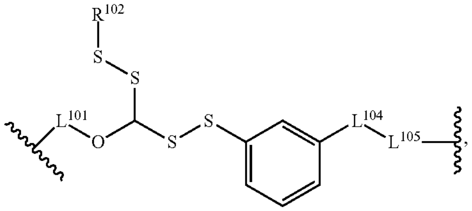

wherein $L^{101}$, $L^{103}$, $L^{104}$, $L^{105}$, $R^9$, and $R^{102}$ are as described herein. In embodiments $L^{100}$ is

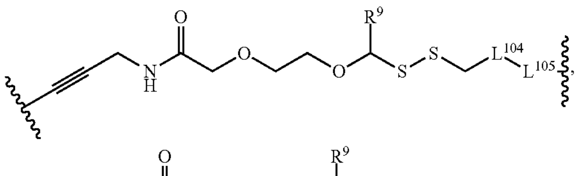

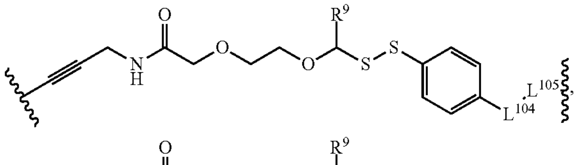

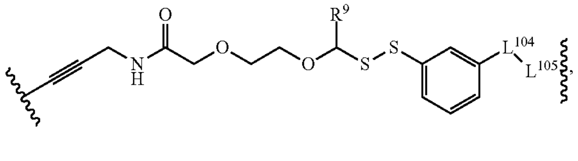

-continued

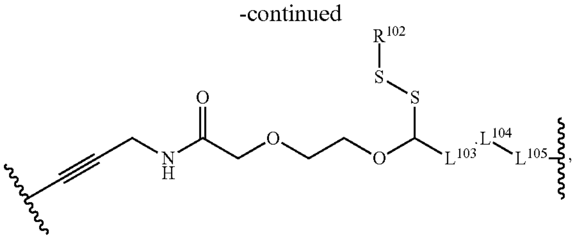

,

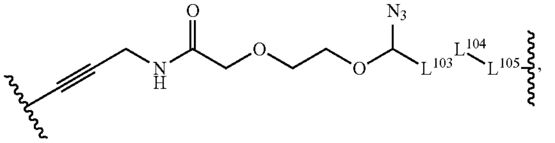

or

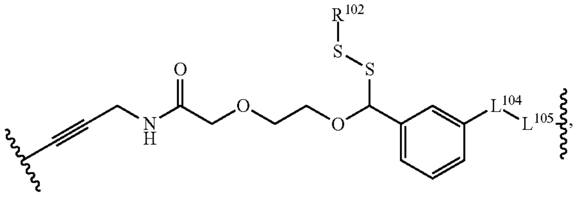

, wherein $L^{103}$, $L^{104}$, $L^{105}$, $R^9$, and $R^{102}$ are as described herein.

In embodiments, $L^{101}$ is a substituted or unsubstituted $C_1$-$C_4$ alkylene or substituted or unsubstituted 8 to 20 membered heteroalkylene; $L^{103}$ is a bond or substituted or unsubstituted 2 to 10 membered heteroalkylene; $L^{104}$ is a bond, substituted or unsubstituted 4 to 18 membered heteroalkylene, or substituted or unsubstituted phenylene; $L^{105}$ is a bond or substituted or unsubstituted 4 to 18 membered heteroalkylene; and $R^{102}$ is unsubstituted $C_1$-$C_4$ alkyl. In embodiments, $L^{101}$ is a substituted or unsubstituted $C_1$-$C_4$ alkylene or substituted or unsubstituted 8 to 20 membered heteroalkylene. In embodiments, $L^{103}$ is a bond or substituted or unsubstituted 2 to 10 membered heteroalkylene. In embodiments, $L^{104}$ is a bond, substituted or unsubstituted 4 to 18 membered heteroalkylene, or substituted or unsubstituted phenylene. In embodiments, $L^{105}$ is a bond or substituted or unsubstituted 4 to 18 membered heteroalkylene.

In embodiments, $L^{101}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{101}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, $R^{101}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{101}$-substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), $R^{101}$-substituted or unsubstituted cycloalkylene (e.g., $C_3$-$C_8$, $C_3$-$C_6$, or $C_5$-$C_6$), $R^{101}$-substituted or unsubstituted heterocycloalkylene (e.g., 3 to 8, 3 to 6, or 5 to 6 membered), $R^{101}$-substituted or unsubstituted arylene (e.g., $C_6$-$C_{10}$, $C_{10}$, or phenylene), or $R^{101}$-substituted or unsubstituted heteroarylene (e.g., 5 to 10, 5 to 9, or 5 to 6 membered).

$R^{101}$ is independently oxo, halogen, $—CCl_3$, $—CBr_3$, $—CF_3$, $—CI_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—N_3$, $R^{101A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{101A}$-substituted or unsubstituted heteroalkyl (e.g., 2 to 20, 8 to 20, 2 to 10, 2 to 8, 2 to 6, or 2 to 4 membered), $R^{101A}$-substituted or unsubstituted cycloalkyl (e.g., $C_3$-$C_8$, $C_3$-$C_6$, or $C_5$-$C_6$), $R^{101A}$-substituted or unsubstituted heterocycloalkyl (e.g., 3 to 8, 3 to 6, or 5 to 6 membered), $R^{101A}$-substituted or unsubstituted aryl (e.g., $C_6$-$C_{10}$, $C_{10}$, or phenyl), or $R^{101A}$-substituted or unsubstituted heteroaryl (e.g., 5 to 10, 5 to 9, or 5 to 6 membered).

$R^{101A}$ is independently oxo, halogen, $—CCl_3$, $—CBr_3$, $—CF_3$, $—CI_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—N_3$, $R^{101B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{101B}$-substituted or unsubstituted heteroalkyl (e.g., 2 to 20, 8 to 20, 2 to 10, 2 to 8, 2 to 6, or 2 to 4 membered), $R^{101B}$-substituted or unsubstituted cycloalkyl (e.g., $C_3$-$C_8$, $C_3$-$C_6$, or $C_5$-$C_6$), $R^{101B}$-substituted or unsubstituted heterocycloalkyl (e.g., 3 to 8, 3 to 6, or 5 to 6 membered), $R^{101B}$-substituted or unsubstituted aryl (e.g., $C_6$-$C_{10}$, $C_{10}$, or phenyl), or $R^{101B}$-substituted or unsubstituted heteroaryl (e.g., 5 to 10, 5 to 9, or 5 to 6 membered).

$R^{101B}$ is independently oxo, halogen, $—CCl_3$, $—CBr_3$, $—CF_3$, $—CI_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{102}$ is a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{102}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, —SS—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered). In embodiments, $L^{102}$ is $R^{102}$-substituted or unsubstituted $C_1$-$C_{20}$ alkylene. In embodiments, $L^{102}$ is $R^{102}$-substituted or unsubstituted 2 to 20 membered heteroalkylene. In embodiments, $L^{102}$ is $R^{102}$-substituted or unsubstituted $C_3$-$C_8$ cycloalkylene. In embodiments, $L^{102}$ is $R^{102}$-substituted or unsubstituted 3 to 8 membered heterocycloalkylene. In embodiments, $L^{102}$ is $R^{102}$-substituted or unsubstituted $C_6$-$C_{10}$ arylene. In embodiments, $L^{102}$ is $R^{102}$-substituted or unsubstituted phenylene. In embodiments, $L^{102}$ is $R^{102}$-substituted or unsubstituted 5 to 10 membered heteroarylene.

$R^{102}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{102B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{102B}$-substituted or unsubstituted heteroalkyl (e.g., 2 to 20, 8 to 20, 2 to 10, 2 to 8, 2 to 6, or 2 to 4 membered), $R^{102B}$-substituted or unsubstituted cycloalkyl (e.g., $C_3$-$C_8$, $C_3$-$C_6$, or $C_5$-$C_6$), $R^{102B}$-substituted or unsubstituted heterocycloalkyl (e.g., 3 to 8, 3 to 6, or 5 to 6 membered), $R^{102B}$-substituted or unsubstituted aryl (e.g., $C_6$-$C_{10}$, $C_{10}$, or phenyl), or $R^{102B}$-substituted or unsubstituted heteroaryl (e.g., 5 to 10, 5 to 9, or 5 to 6 membered).

In embodiments, $L^{103}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, —N=N—, —SS—, $R^{103}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{103}$-substituted or unsubstituted heteroalkylene (e.g., 2 to 20 membered, 8 to 20 membered, 5 to 16 membered, 2 to 10, 2 to 8, 2 to 6, or 2 to 4 membered), $R^{103}$-substituted or unsubstituted cycloalkylene (e.g., $C_3$-$C_8$, $C_3$-$C_6$, or $C_5$-$C_6$), $R^{103}$-substituted or unsubstituted heterocycloalkylene (e.g., 3 to 8, 3 to 6, or 5 to 6 membered), $R^{103}$-substituted or unsubstituted arylene (e.g., $C_6$-$C_{10}$, $C_{10}$, or phenylene), or $R^{103}$-substituted or unsubstituted heteroarylene (e.g., 5 to 10, 5 to 9, or 5 to 6 membered). In embodiments, $L^{103}$ is $R^{103}$-substituted or unsubstituted $C_1$-$C_{20}$ alkylene. In embodiments, $L^{103}$ is $R^{103}$-substituted or unsubstituted 2 to 20 membered heteroalkylene. In embodiments, $L^{103}$ is $R^{103}$-substituted or unsubstituted 5 to 16 membered heteroalkylene. In embodiments, $L^{103}$ is $R^{103}$-substituted or unsubstituted 2 to 10 membered heteroalkylene. In embodiments, $L^{103}$ is $R^{103}$-substituted or unsubstituted $C_3$-$C_8$ cycloalkylene. In embodiments, $L^{103}$ is $R^{103}$-substituted or unsubstituted 3 to 8 membered heterocycloalkylene. In embodiments, $L^{103}$ is $R^{103}$-substituted or unsubstituted $C_6$-$C_{10}$ arylene. In embodiments, $L^{103}$ is $R^{103}$-substituted or unsubstituted 5 to 10 membered heteroarylene.

$R^{103}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{103A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{103A}$-substituted or unsubstituted heteroalkyl (e.g., 2 to 20, 8 to 20, 2 to 10, 2 to 8, 2 to 6, or 2 to 4 membered), $R^{103A}$-substituted or unsubstituted cycloalkyl (e.g., $C_3$-$C_8$, $C_3$-$C_6$, or $C_5$-$C_6$), $R^{103A}$-substituted or unsubstituted heterocycloalkyl (e.g., 3 to 8, 3 to 6, or 5 to 6 membered), $R^{103A}$-substituted or unsubstituted aryl (e.g., $C_6$-$C_{10}$, $C_{10}$, or phenyl), or $R^{103A}$-substituted or unsubstituted heteroaryl (e.g., 5 to 10, 5 to 9, or 5 to 6 membered).

$R^{103A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{103B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{103B}$-substituted or unsubstituted heteroalkyl (e.g., 2 to 20, 8 to 20, 2 to 10, 2 to 8, 2 to 6, or 2 to 4 membered), $R^{103B}$-substituted or unsubstituted cycloalkyl (e.g., $C_3$-$C_8$, $C_3$-$C_6$, or $C_5$-$C_6$), $R^{103B}$-substituted or unsubstituted heterocycloalkyl (e.g., 3 to 8, 3 to 6, or 5 to 6 membered), $R^{103B}$-substituted or unsubstituted aryl (e.g., $C_6$-$C_{10}$, $C_{10}$, or phenyl), or $R^{103B}$-substituted or unsubstituted heteroaryl (e.g., 5 to 10, 5 to 9, or 5 to 6 membered).

$R^{103B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{104}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, $R^{104}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{104}$-substituted or unsubstituted heteroalkylene (e.g., 2 to 20 membered, 8 to 20 membered, 5 to 16 membered, 2 to 10, 2 to 8, 2 to 6, or 2 to 4 membered), $R^{104}$-substituted or unsubstituted cycloalkylene (e.g., $C_3$-$C_8$, $C_3$-$C_6$, or $C_5$-$C_6$), $R^{104}$-substituted or unsubstituted heterocycloalkylene (e.g., 3 to 8, 3 to 6, or 5 to 6 membered), $R^{104}$-substituted or unsubstituted arylene (e.g., $C_6$-$C_{10}$, $C_{10}$, or phenylene), or $R^{104}$-substituted or unsubstituted heteroarylene (e.g., 5 to 10, 5 to 9, or 5 to 6 membered).

$R^{104}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{104A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{104A}$-substituted or unsubstituted heteroalkyl (e.g., 2 to 20, 8 to 20, 2 to 10, 2 to 8, 2 to 6, or 2 to 4 membered), $R^{104A}$-substituted or unsubstituted cycloalkyl (e.g., $C_3$-$C_8$, $C_3$-$C_6$, or $C_5$-$C_6$), $R^{104A}$-substituted or unsubstituted heterocycloalkyl (e.g., 3 to 8, 3 to 6, or 5 to 6 membered), $R^{104A}$-substituted or unsubstituted aryl (e.g., $C_6$-$C_{10}$, $C_{10}$, or phenyl), or $R^{104A}$-substituted or unsubstituted heteroaryl (e.g., 5 to 10, 5 to 9, or 5 to 6 membered).

$R^{104A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{104B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{104B}$-substituted or unsubstituted heteroalkyl (e.g., 2 to 20, 8 to 20, 2 to 10, 2 to 8, 2 to 6, or 2 to 4 membered), $R^{104B}$-substituted or unsubstituted cycloalkyl (e.g., $C_3$-$C_8$, $C_3$-$C_6$, or $C_5$-$C_6$), $R^{104B}$-substituted or unsubstituted heterocycloalkyl (e.g., 3 to 8, 3 to 6, or 5 to 6 membered), $R^{104B}$-substituted or unsubstituted aryl (e.g., $C_6$-$C_{10}$, $C_{10}$, or phenyl), or $R^{104B}$-substituted or unsubstituted heteroaryl (e.g., 5 to 10, 5 to 9, or 5 to 6 membered).

$R^{104B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{105}$ is a bond, —NH—, —$NR^{105}$—, —S—, —O—, —C(O)—, —C(O)O—, —OC(O)—, —NHC(O)—, —C(O)NH—, —NHC(O)NH—, —NHC(NH)NH—, —C(S)—, $R^{105}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{105}$-substituted or unsubstituted heteroalkylene (e.g., 2 to 20 membered, 8 to 20 membered, 5 to 16 membered, 2 to 10, 2 to 8, 2 to 6, or 2 to 4 membered), $R^{105}$-substituted or unsubstituted cycloalkylene (e.g., $C_3$-$C_8$, $C_3$-$C_6$, or $C_5$-$C_6$), $R^{105}$-substituted or unsubstituted heterocycloalkylene (e.g., 3 to 8, 3 to 6, or 5 to 6 membered), $R^{105}$-substituted or unsubstituted arylene (e.g., $C_6$-$C_{10}$, $C_{10}$, or phenylene), or $R^{10}$ 5-substituted or unsubstituted heteroarylene (e.g., 5 to 10, 5 to 9, or 5 to 6 membered).

$R^{105}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{105A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{105A}$-substituted or unsubstituted heteroalkyl (e.g., 2 to 20, 8 to 20, 2 to 10, 2 to 8, 2 to 6, or 2 to 4 membered), $R^{105A}$-substituted or unsubstituted cycloalkyl (e.g., $C_3$-$C_8$, $C_3$-$C_6$, or $C_5$-$C_6$), $R^{105A}$-substituted or unsubstituted heterocycloalkyl (e.g., 3 to 8, 3 to 6, or 5 to 6 membered), $R^{105A}$-substituted or unsubstituted aryl (e.g., $C_6$-$C_{10}$, $C_{10}$, or phenyl), or $R^{105A}$-substituted or unsubstituted heteroaryl (e.g., 5 to 10, 5 to 9, or 5 to 6 membered).

$R^{105A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{105B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{105B}$-substituted or unsubstituted heteroalkyl (e.g., 2 to 20, 8 to 20, 2 to 10, 2 to 8, 2 to 6, or 2 to 4 membered), $R^{105B}$-substituted or unsubstituted cycloalkyl (e.g., $C_3$-$C_8$, $C_3$-$C_6$, or $C_5$-$C_6$), $R^{105B}$-substituted or unsubstituted heterocycloalkyl (e.g., 3 to 8, 3 to 6, or 5 to 6 membered), $R^{105B}$-substituted or unsubstituted aryl (e.g., $C_6$-$C_{10}$, $C_{10}$, or phenyl), or $R^{105B}$-substituted or unsubstituted heteroaryl (e.g., 5 to 10, 5 to 9, or 5 to 6 membered).

$R^{105B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{10}$ 1, $L^{103}$, $L^{104}$, and $L^{105}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$ is a substituted or unsubstituted $C_1$-$C_4$ alkylene or substituted or unsubstituted 8 to 20 membered heteroalkylene; $L^{103}$ is a bond or substituted or unsubstituted 2 to 10 membered heteroalkylene; $L^{104}$ is a bond, substituted or unsubstituted 4 to 18 membered heteroalkylene, or substituted or unsubstituted phenylene; $L^{105}$ is a bond or substituted or unsubstituted 4 to 18 membered heteroalkylene.

In embodiments, $L^{101}$, $L^{10}$3, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{104}$ is unsubstituted phenylene.

In embodiments, $L^{101}$ is a substituted or unsubstituted $C_1$-$C_4$ alkylene or substituted or unsubstituted 8 to 20 membered heteroalkylene. In embodiments, $L^{103}$ is a bond or substituted or unsubstituted 2 to 10 membered heteroalkylene. In embodiments, $L^{104}$ is an unsubstituted phenylene. In embodiments, $L^{105}$ is a bond or substituted or unsubstituted 4 to 18 membered heteroalkylene.

In embodiments, $L^{101}$ is

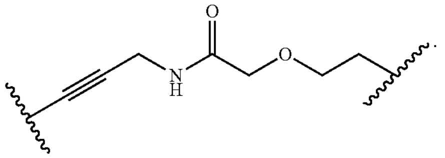

In embodiments, $L^{101}$ is

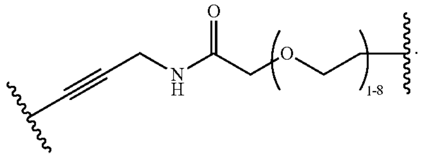

In embodiments, $^{L}$ is

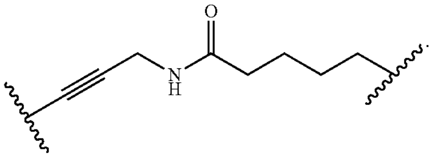

In embodiments, $L^{101}$ is

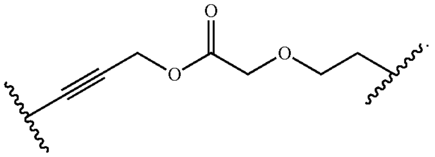

In embodiments, $L^{101}$ is

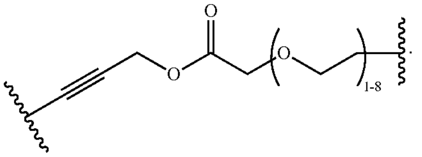

In embodiments, $L^{101}$ is

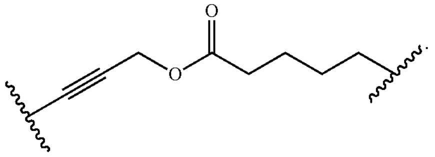

In embodiments, $L^{101}$ is

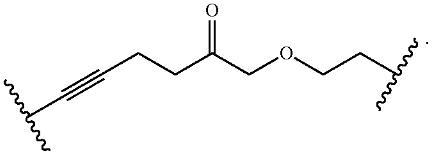 [SMILES: *C#CCCC(=O)COCC*]

In embodiments, $L^{101}$ is

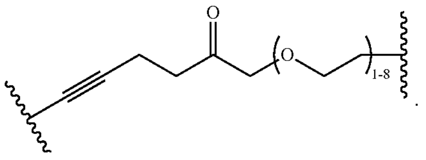

In embodiments, $L^{101}$ is

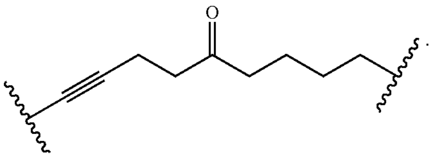 [SMILES: *C#CCCC(=O)CCCC*]

In embodiments, $L^{102}$ is —OCH($R^9$)SS— and $L^{103}$ is —$CH_2$—; wherein $R^9$ is as described herein. In embodiments, $L^{102}$ is —OCH($R^9$)SS— and $L^{103}$ is unsubstituted phenylene; wherein $R^9$ is as described herein. In embodiments, $L^{102}$ is —OCH(SS$R^{102}$)—; wherein $R^{102}$ is as described herein. In embodiments, $L^{102}$ is —OCH (SS$R^{102}$)— and $L^{103}$ is unsubstituted phenylene; wherein $R^{102}$ is as described herein. In embodiments, $L^{102}$ is —OCH ($N_3$)—.

In embodiments, the compound has the formula:

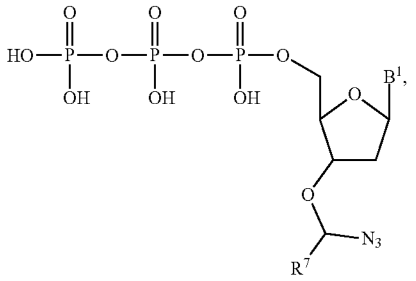

wherein $B^1$ and $R^7$ are as described herein. In embodiments, $R^7$ is substituted or unsubstituted aryl. In embodiments, $R^7$ is

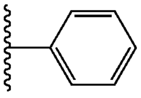 , 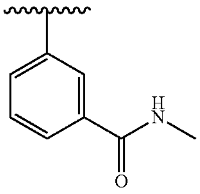 ,

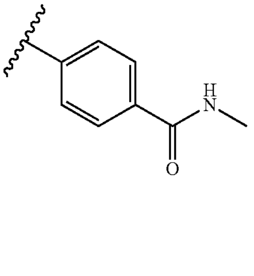 , 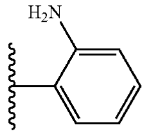 ,

-continued
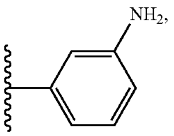
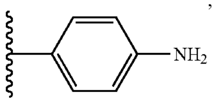
,
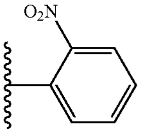
,
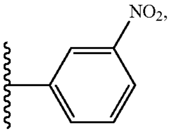
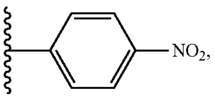
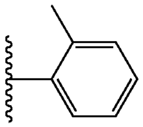
,
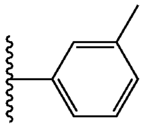
,
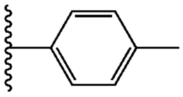
,
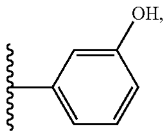
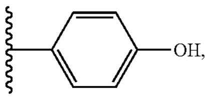
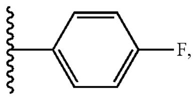
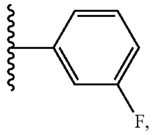
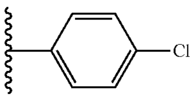
,
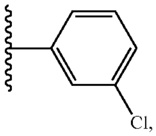
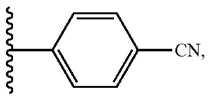
or
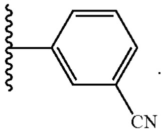
.
In embodiments, the compound has the formula:
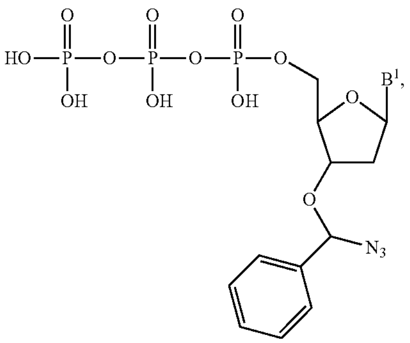
-continued
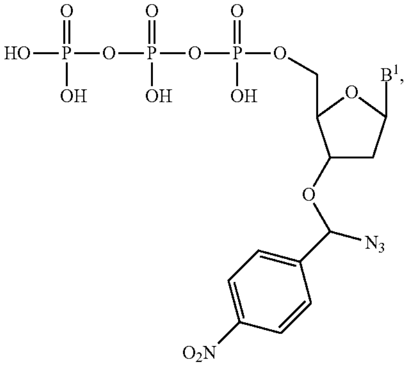
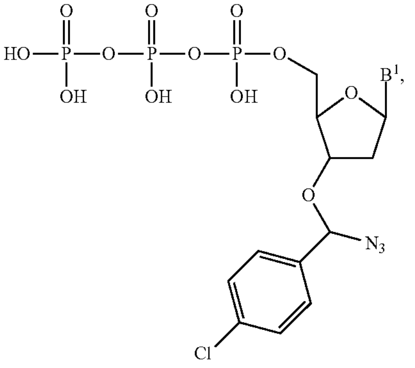
or
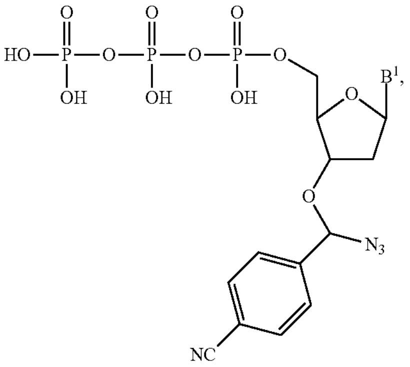
wherein $B^1$ is as described herein. In embodiments, the compound has the formula:
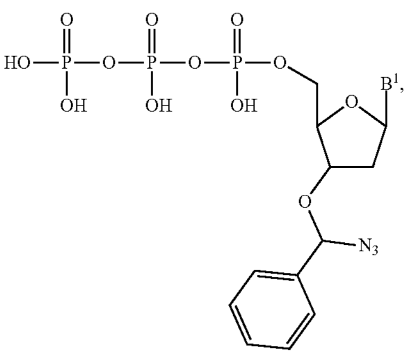
wherein $B^1$ is as described herein. In embodiments, the compound has the formula:

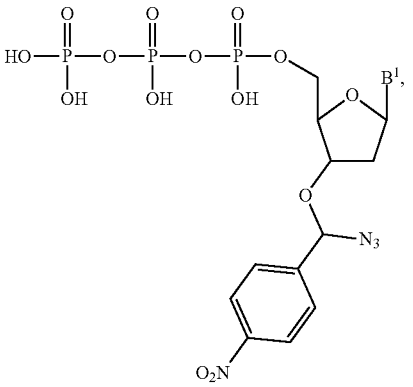

wherein $B^1$ is as described herein. In embodiments, the compound has the formula:

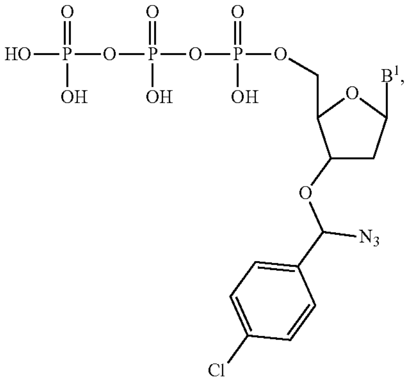

wherein $B^1$ is as described herein. In embodiments, the compound has the formula:

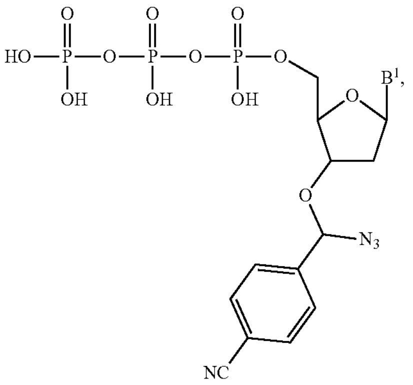

wherein $B^1$ is as described herein.

In embodiments, the compound has the formula:

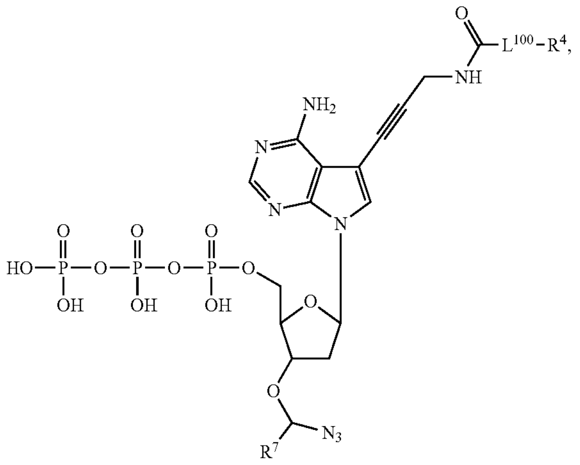

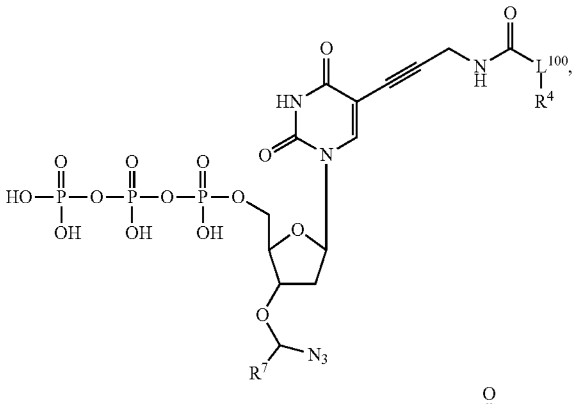

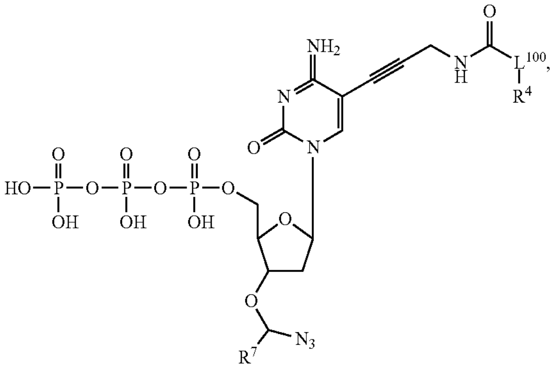

or

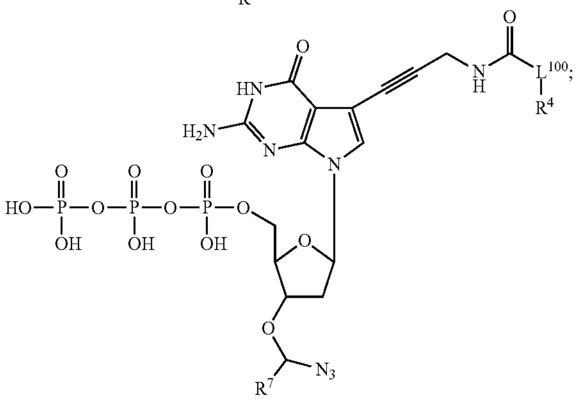

wherein $R^7$ is as described herein; $L^{100}$ is a cleavable linker; and $R^4$ is a detectable moiety. In embodiments, $L^{100}$ is

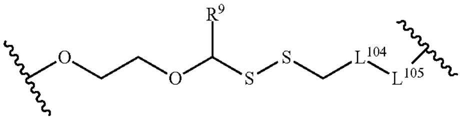

,

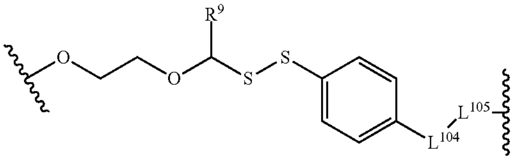

,

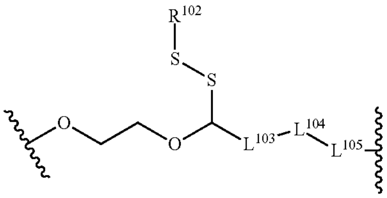

,

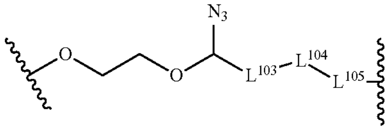

, or

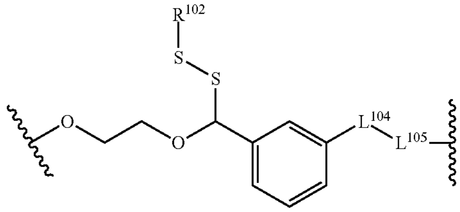

, wherein $R^9$, $L^{104}$, $L^{105}$, and $R^{102}$ are as described herein.

In embodiments, $R^4$ is a detectable moiety. In embodiments, $R^4$ is a fluorescent dye moiety. In embodiments, $R^4$ is a detectable moiety described herein (e.g., Table 1). In embodiments, $R^4$ is a detectable moiety described in Table 1.

TABLE 1

Detectable moieties to be used in selected embodiments.

| Nucleoside/nucleotide abbreviation | Dye name | λmax (nm) |
|---|---|---|
| dC | Atto 532 | 532 |
| dC | Atto Rho 6G | 535 |
| dC | R6G | 534 |
| dC | Tet | 521 |
| dT | Atto Rho 11 | 572 |
| dT | Atto 565 | 564 |
| dT | Alexa Fluor 568 | 578 |
| dT | dTamra | 578 |
| dA | Alexa Fluor 647 | 650 |
| dA | Atto 647N | 644 |
| dA | Janelia Fluor 646 | 646 |
| dG | Alexa Fluor 680 | 682 |
| dG | Alexa Fluor 700 | 696 |
| dG | CF680R | 680 |

In embodiments, $R^4$ is

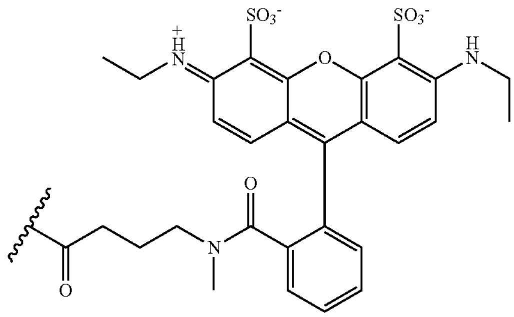

,

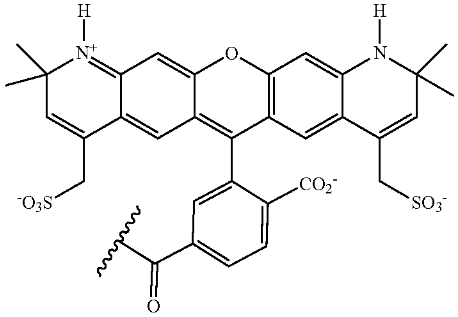

,

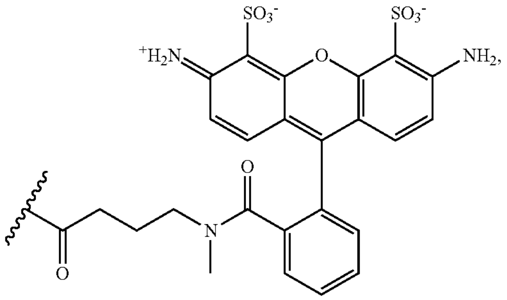

or

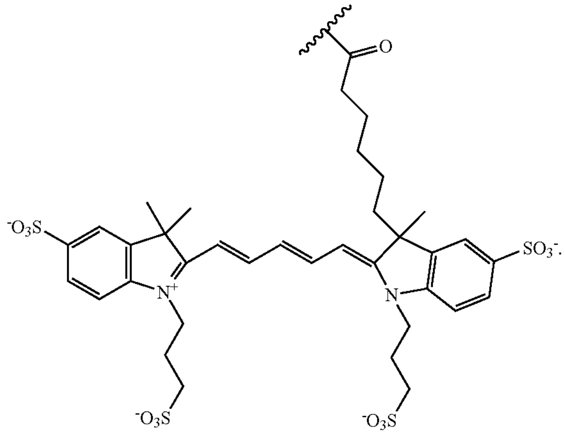

In embodiments, $L^{100}$ is
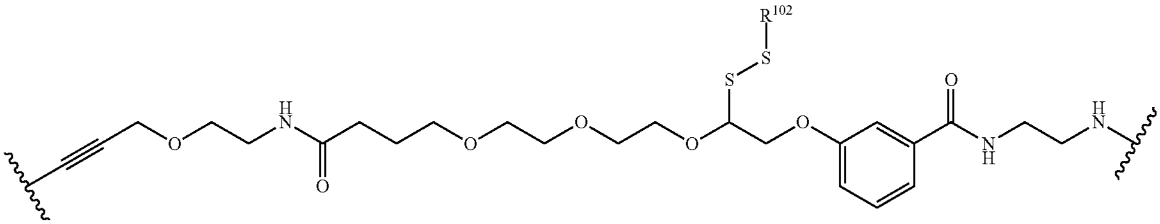
,
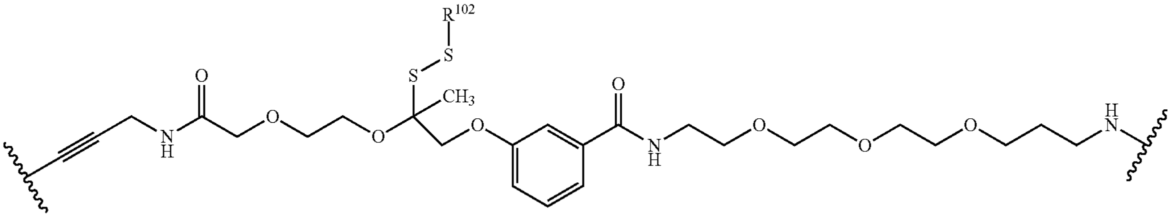
,
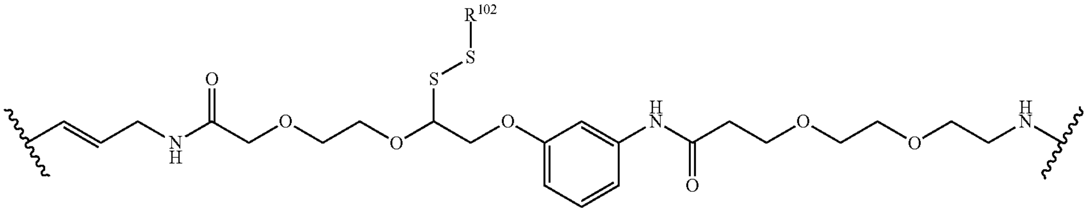
,
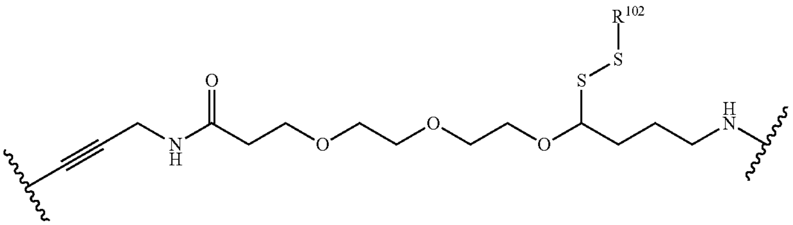
,
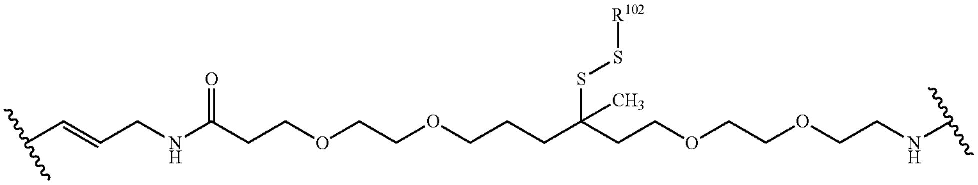
,
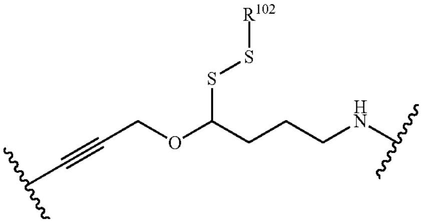
,
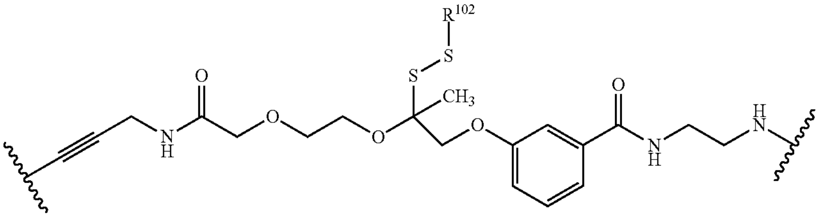
, or -continued
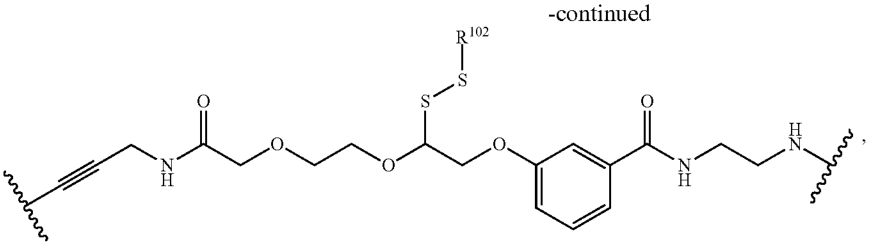
wherein $R^{102}$ is as described herein. In embodiments, $L^{100}$ is
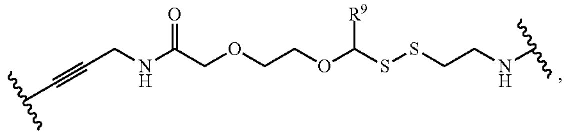
wherein $R^9$ is as described herein. In embodiments, $L^{100}$ is a
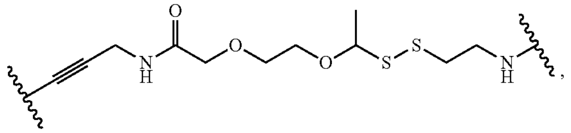
-continued
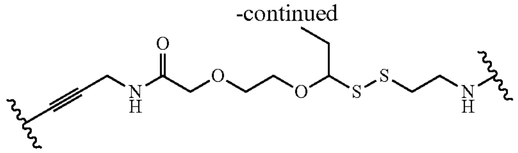
or
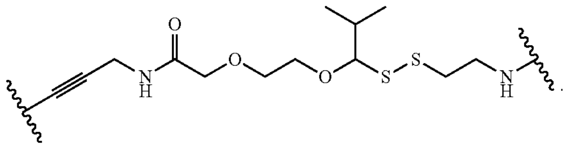
In embodiments $L^{100}$ is
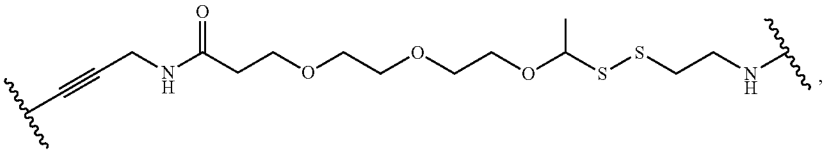
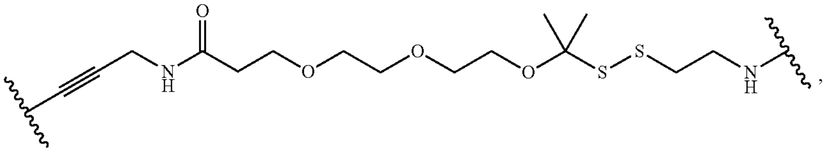
or
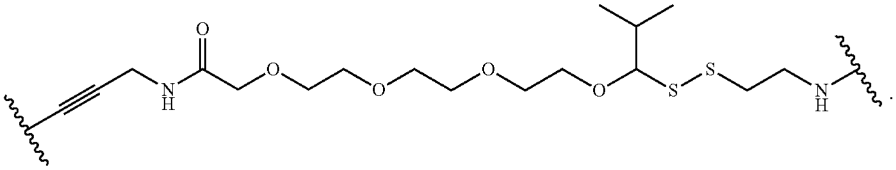
In embodiments, $L^{100}$ is
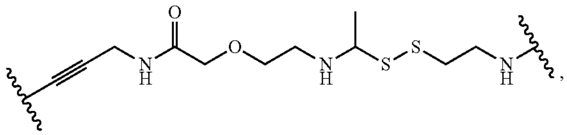

-continued
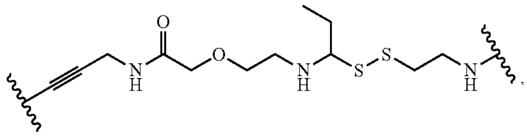
or
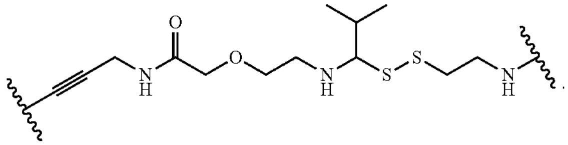
-continued
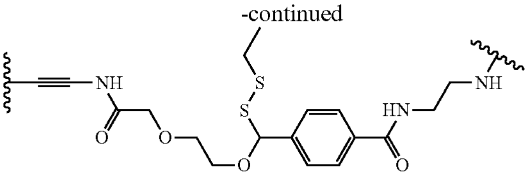
or
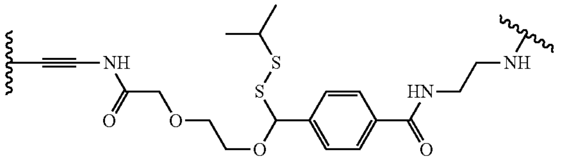
In embodiments, $L^{100}$ is
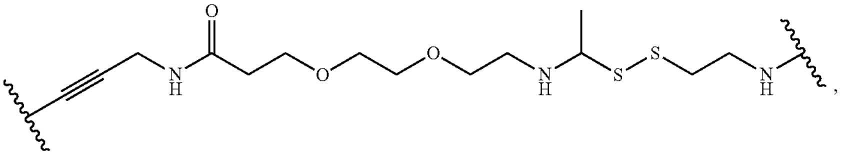
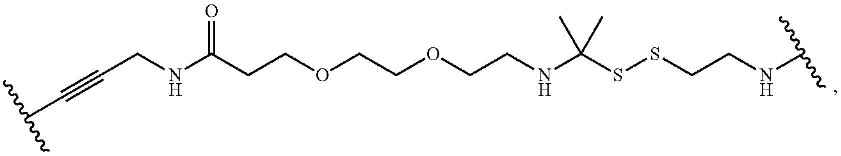
or
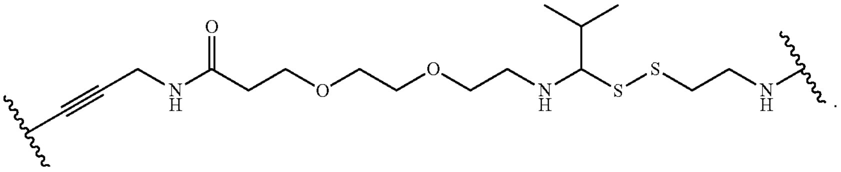
In embodiments, $L^{100}$ is
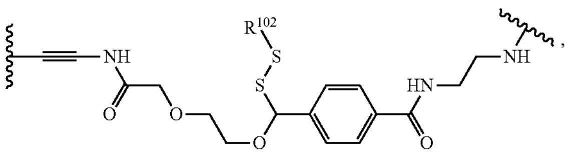
wherein $R^{102}$ is as described herein. In embodiments, $L^{100}$ is
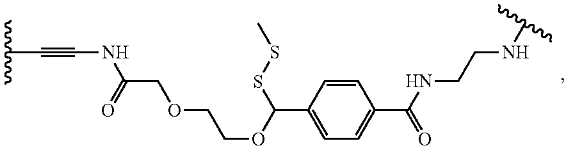
In embodiments, $L^{100}$ is
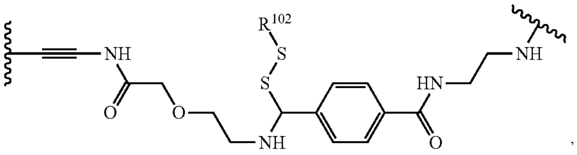
wherein $R^{102}$ is as described herein. In embodiments, $L^{100}$ is
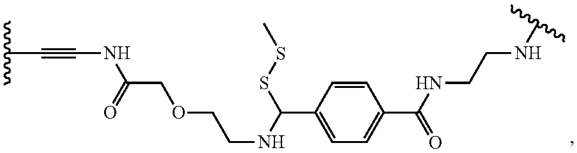
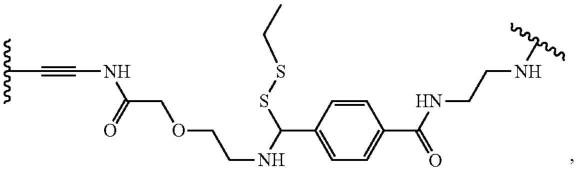

-continued or

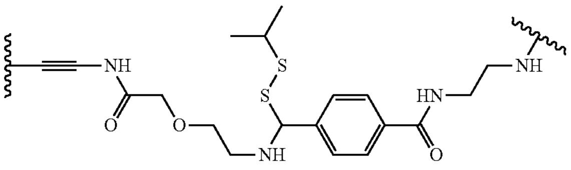

.

In embodiments $L^{100}$ is

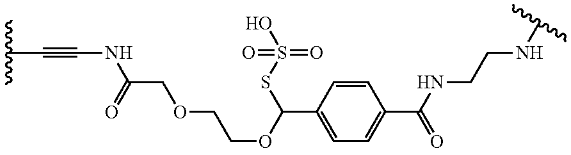

.

In embodiments, $L^{100}$

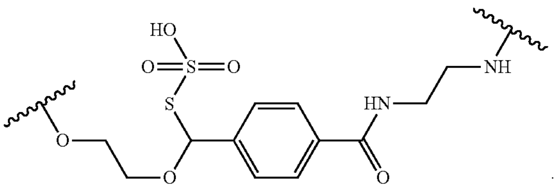 [SMILES: *NCCNC(=O)c1ccc(C(OCCO*)SS(=O)(=O)O)cc1]

.

Methods for cleaving the disulfide bond of —S—$SO_3H$ bonds are known in the art, see for example Meguro et al. Tetrahedron Letters 61 (2020) 152198, which is incorporated herein by reference in its entirety. In embodiments, the cleaving agent is aqueous sodium sulfide ($Na_2S$). In embodiments, the cleaving agent is TCEP or THPP.

In embodiments, $L^{100}$ is

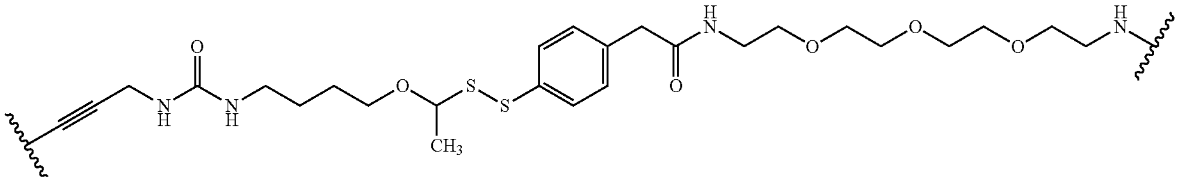

,

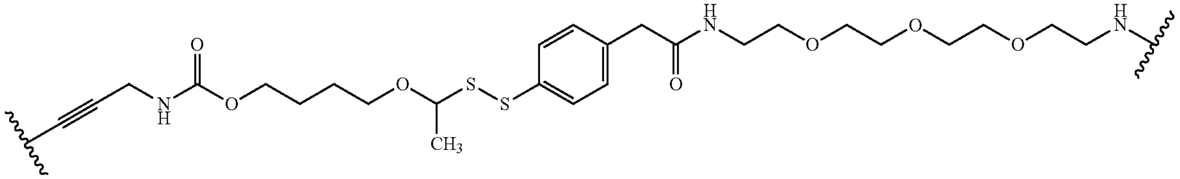

,

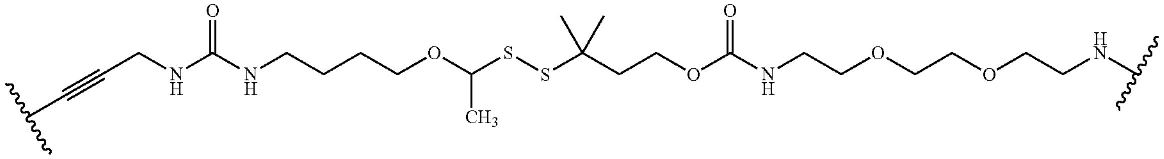

,

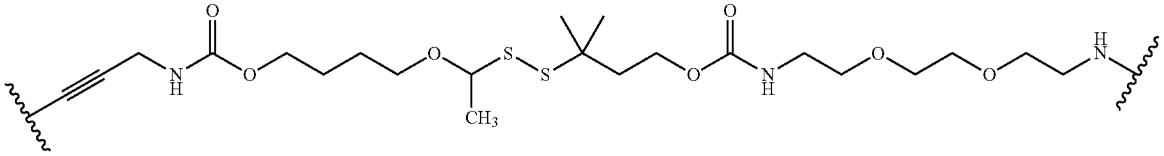

,

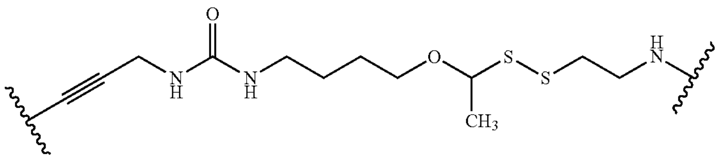

,

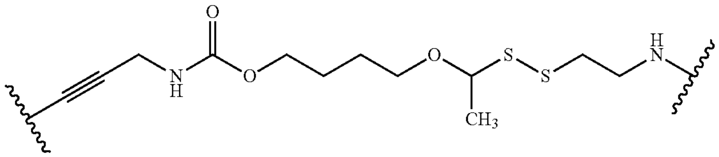

,

-continued

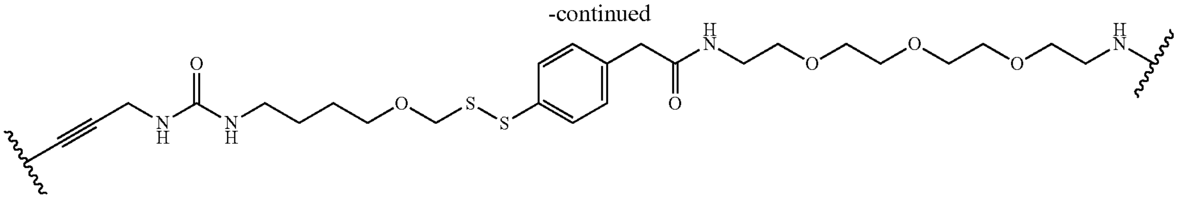

,

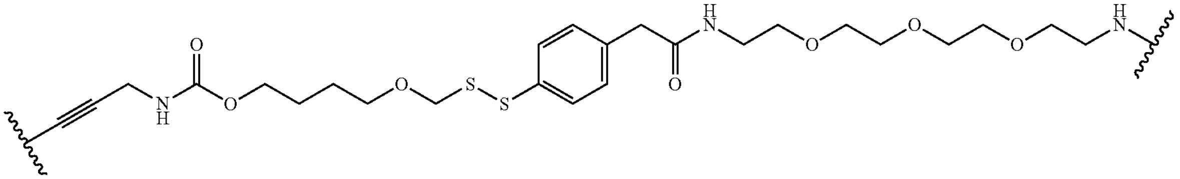

,

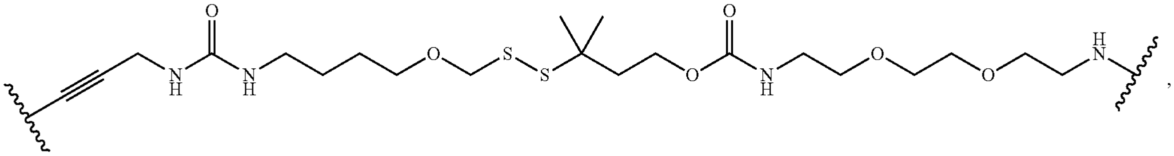

,

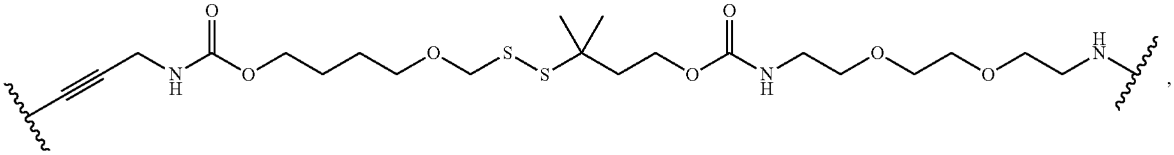

,

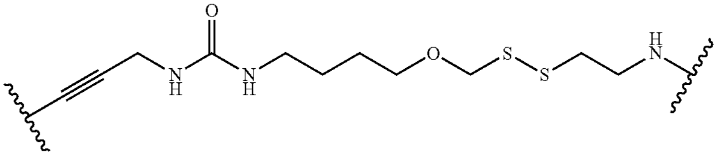

,

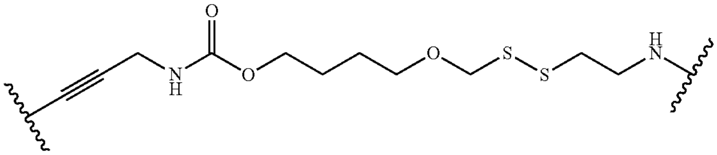

, or

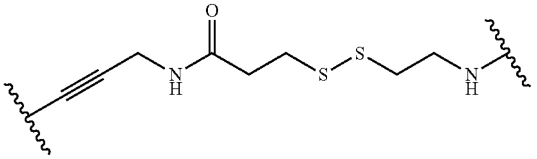

.

In an aspect is provided a compound having the formula:

(II)

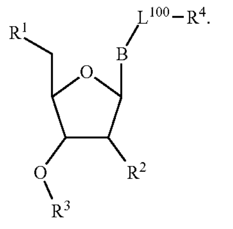

is a divalent nucleobase. $R^1$ is a polyphosphate moiety, 5'-O-nucleotide protecting group, monophosphate moiety, nucleic acid moiety, hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC(O) $NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety. $R^3$ is a polymerase-compatible cleavable moiety. $R^4$ is a detectable moiety. $L^{100}$ is a divalent linker including

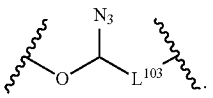

$L^{103}$ substituted or unsubstituted cycloalkylene, substituted or unsubstituted heterocycloalkylene, substituted or unsubstituted arylene, substituted or unsubstituted heteroarylene. In embodiments, $L^{100}$ is $-L^{101}-OCH(N_3)-L^{103}-L^{104}-L^{105}-$; $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, the compound has the formula:

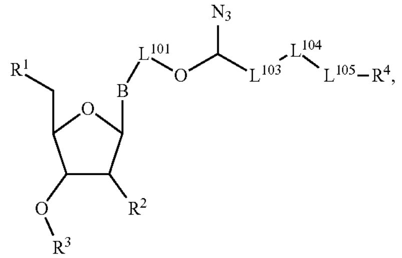

wherein $R^1$, $R^3$, $R^4$, $L^{101}$, $L^{103}$, $L^{104}$, and $L^{105}$ are as described herein.

In embodiments, $R^1$ is —OH, a 5'-O-nucleoside protecting group, monophosphate moiety, polyphosphate moiety, or nucleic acid moiety. In embodiments, $R^1$ is a triphosphate moiety. In embodiments, the polymerase-compatible cleavable moiety is -(substituted or unsubstituted alkylene)-SS-(unsubstituted alkyl).

In embodiments, the polymerase-compatible cleavable moiety is

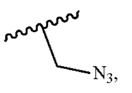 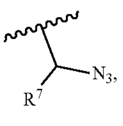 or 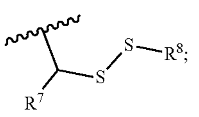

wherein $R^7$ is substituted or unsubstituted cycloalkyl, substituted or unsubstituted heterocycloalkyl, substituted or unsubstituted aryl, substituted or unsubstituted heteroaryl; and $R^8$ is unsubstituted $C_1$-$C_6$ alkyl. In embodiments, the polymerase-compatible cleavable moiety is

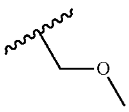, 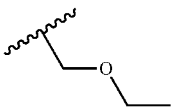,

-continued

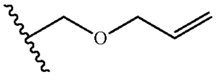, 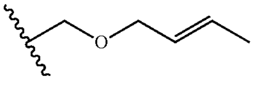,

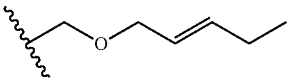, 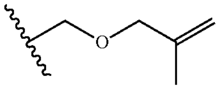,

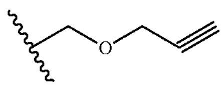, 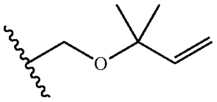,

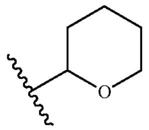, or 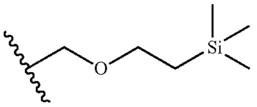

In embodiments, the polymerase-compatible cleavable moiety is

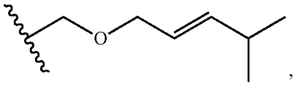, 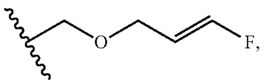

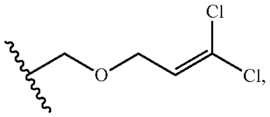 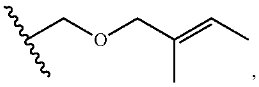, or

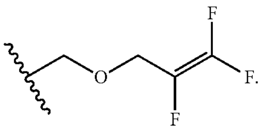

In embodiments, $R^8$ is unsubstituted $C_1$-$C_6$ or $C_1$-$C_4$ alkyl. In embodiments, $R^8$ is unsubstituted $C_1$-$C_4$ alkyl. In embodiments, $R^8$ is unsubstituted $C_1$-$C_6$ alkyl. In embodiments, $R^8$ is unsubstituted methyl. In embodiments, $R^8$ is unsubstituted $C_2$ alkyl. In embodiments, $R^8$ is unsubstituted $C_3$ alkyl. In embodiments, $R^8$ is unsubstituted $C_4$ alkyl. In embodiments, $R^8$ is unsubstituted $C_5$ alkyl. In embodiments, $R^8$ is unsubstituted $C_6$ alkyl.

In embodiments, $R^8$ is unsubstituted $C_1$-$C_6$ or $C_1$-$C_4$ saturated alkyl. In embodiments, $R^8$ is unsubstituted $C_1$-$C_4$ saturated alkyl. In embodiments, $R^8$ is unsubstituted $C_1$-$C_6$ saturated alkyl. In embodiments, $R^8$ is unsubstituted methyl. In embodiments, $R^8$ is unsubstituted $C_2$ saturated alkyl. In embodiments, $R^8$ is unsubstituted $C_3$ saturated alkyl. In embodiments, $R^8$ is unsubstituted $C_4$ saturated alkyl. In embodiments, $R^8$ is unsubstituted $C_5$ saturated alkyl. In embodiments, $R^8$ is unsubstituted $C_6$ saturated alkyl.

In embodiments, the polymerase-compatible cleavable moiety is independently:

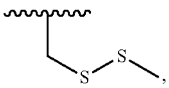, 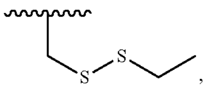,

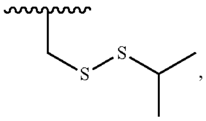, 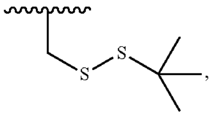,

-continued
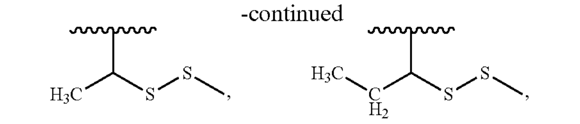
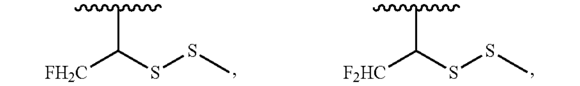
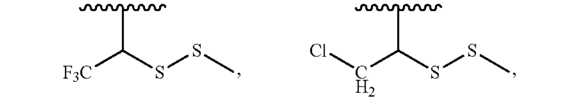
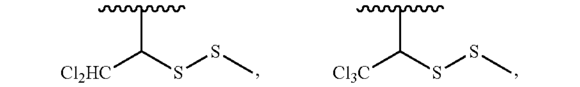
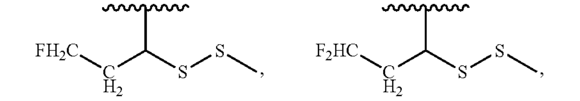
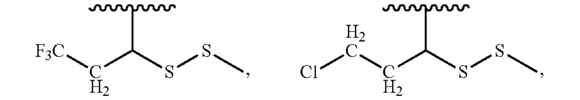
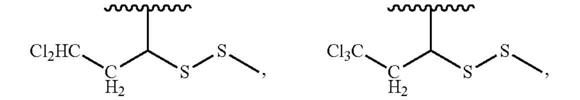
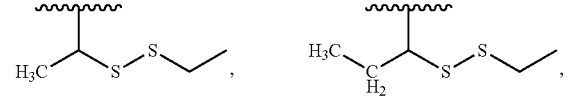
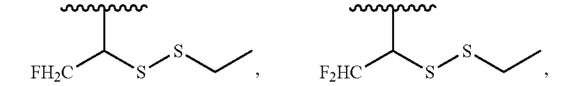
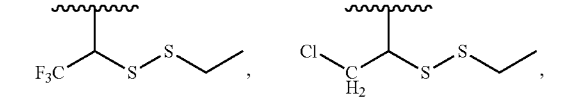
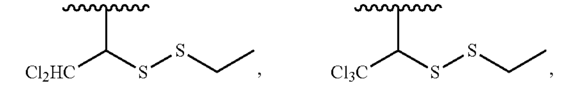
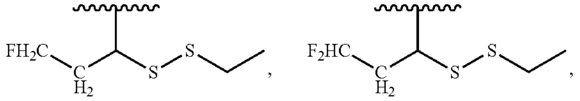
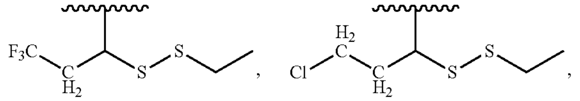
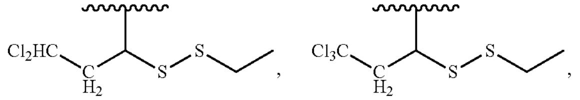
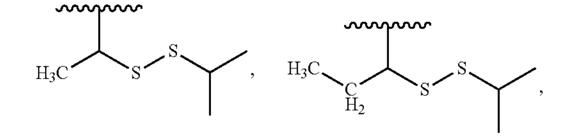
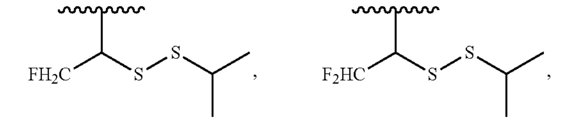
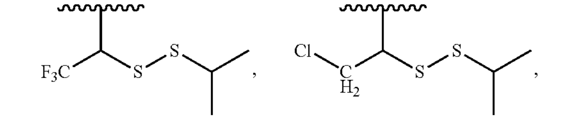
-continued
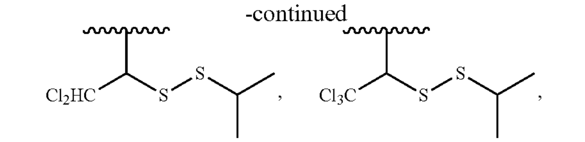
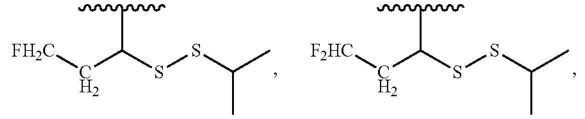
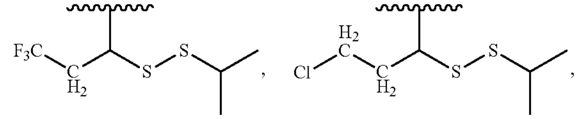
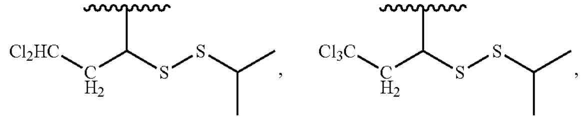
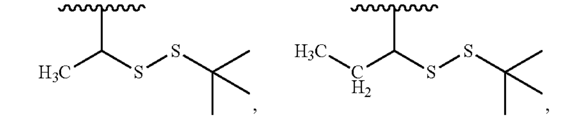
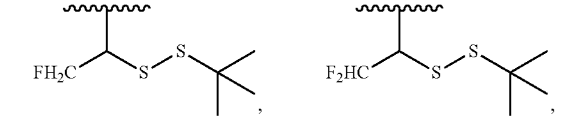
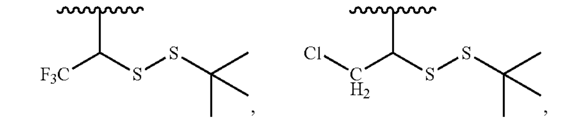
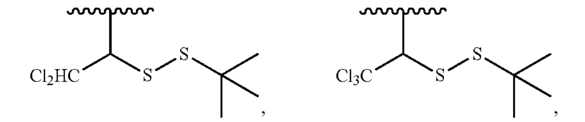
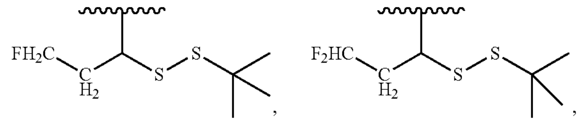
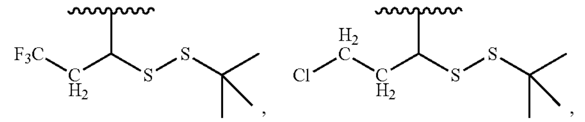
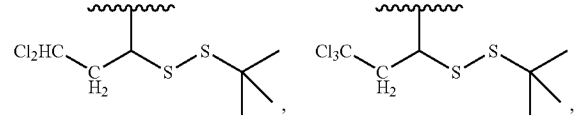
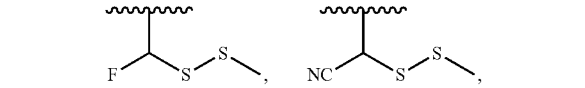
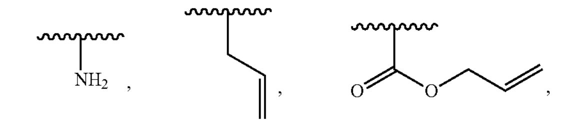
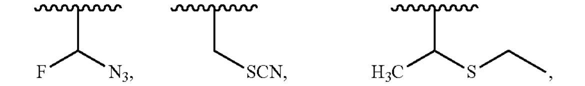
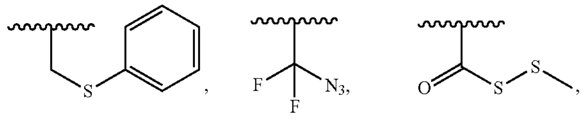

-continued

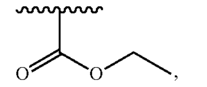, 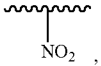, 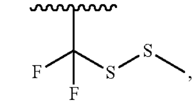,

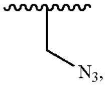, 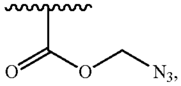, 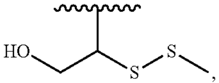,

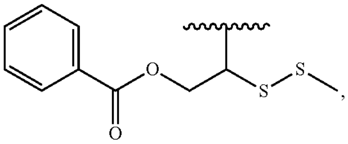,

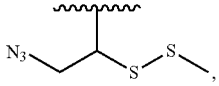, 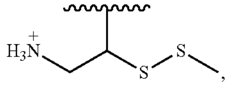,

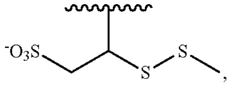, 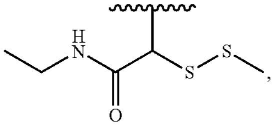,

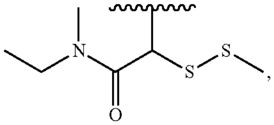,

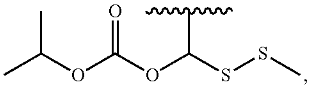,

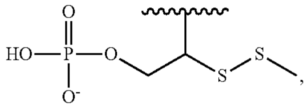,

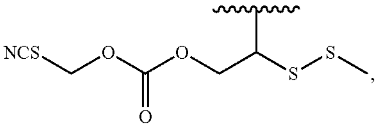,

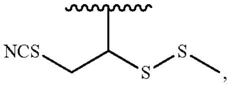,

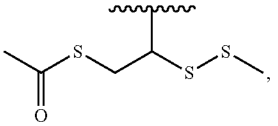, or

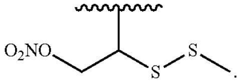.

In an aspect is provided a nucleic acid polymerase complex, wherein the nucleic acid polymerase is bound (e.g., non-covalently bound) to a compound described herein, including embodiments. In embodiments, the nucleic acid polymerase is bound to a primer.

In embodiments, the nucleic acid polymerase is a Taq polymerase, Therminator γ, 9°N polymerase (exo-), Therminator II, Therminator III, or Therminator IX. In embodiments, the nucleic acid polymerase is Therminator γ. In embodiments, the nucleic acid polymerase is 9°N polymerase (exo-). In embodiments, the nucleic acid polymerase is Therminator II. In embodiments, the nucleic acid polymerase is Therminator III. In embodiments, the nucleic acid polymerase is Therminator IX. In embodiments, the nucleic acid polymerase is a Taq polymerase. In embodiments, the nucleic acid polymerase is a nucleic acid polymerase. In embodiments, the nucleic acid polymerase is 9°N and mutants thereof. In embodiments, the nucleic acid polymerase is Phi29 and mutants thereof. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044).

In embodiments, the 3' moiety of a compound described herein is chemically cleaved faster than a control nucleotide. In embodiments, the 3' moiety of a compound described herein is chemically cleaved faster than a nucleotide with a 3'-$OCH_2SSCH_3$ moiety under identical cleavage conditions (e.g., same reaction time, same reaction temperature, and/or the same reducing agent). In embodiments, the 3' moiety of a compound described herein is chemically cleaved faster than a nucleotide with a 3'-$OCH_2N_3$ moiety under identical cleavage conditions (e.g., same reaction time, same reaction temperature, and/or the same reducing agent).

In embodiments, chemical cleavage of a compound described herein (e.g., in an aspect or embodiment) is at least 1.1-fold (e.g., 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000, 10000, or 100000-fold) faster than chemical cleavage of an identical compound wherein the 3'-$OCH(R^7)SSCH_3$ is replaced with a 3'-$OCH_2SSCH_3$ or 3'-$OCH_2N_3$(e.g., under identical cleavage conditions).

In embodiments, chemical cleavage of a compound (e.g., cleavage of the 3' moiety of a compound described herein or cleavage of an SS bond in a 3' moiety of a compound described herein) described herein (e.g., in an aspect or embodiment) includes contacting the compound with a reducing agent (e.g., tris(hydroxypropyl)phosphine (THPP), tris-(2-carboxyethyl)phosphine (TCEP), tris(hydroxymethyl)phosphine (THMP), or tris(hydroxyethyl)phosphine (THEP), DTT, dithiobutylamine (DTBA)). In embodiments, chemical cleavage of a compound (e.g., cleavage of the 3' moiety of a compound described herein or cleavage of an SS bond in a 3' moiety of a compound described herein) described herein (e.g., in an aspect or embodiment) includes contacting the compound with THPP (e.g., about 10 mM THPP, or at least 1 mM THPP). In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at less than about 65° C. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at less than 65° C. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at about 45-65° C. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at 45-65° C. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., or 65° C. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at about 55° C. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at a temperature of at least 55° C. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at about pH 9.5. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at about pH 9.5. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at pH 9.5. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed using 0.1, 0.2, 0.3, 0.4, 0.5, 0.6, 0.7, 0.8, 0.9, or 1.0 mM of THPP. In embodiments, the chemical cleavage is performed using less than 1.0 mM THPP. In embodiments, the chemical cleavage is performed using about 1.0 mM THPP. In embodiments, the chemical cleavage is performed using about 0.05 to about 1.0 mM THPP. In embodiments, the chemical cleavage is performed using about 1.0 to about 5.0 mM THPP. In embodiments, the chemical cleavage is performed using about 10 mM THPP. In embodiments, the chemical cleavage is performed using 1.0 mM THPP. In embodiments, the chemical cleavage is performed using about 0.05 to 1.0 mM THPP. In embodiments, the chemical cleavage is performed using 1.0 to about 5.0 mM THPP. In embodiments, the chemical cleavage is performed using 10 mM THPP.

In embodiments, the compounds described herein provide superior stability in solution during storage, or reagent handling during sequencing applications, compared to the same compounds that have 3'-OH reversible terminating groups disclosed in the prior art, such as for example the 3'-O-azidomethyl reversible terminator.

In an aspect is provided a kit. Some embodiments disclosed herein relate to kits including a labeled nucleoside or nucleotide (e.g., a compound as described herein) including a linker between the fluorophore and the nucleoside or nucleotide, wherein the linker is a linker as described herein. In embodiments, the kit includes a compound described herein. In embodiments, the kit includes a plurality of compounds described herein. In embodiments, the kit includes labeled nucleotides including differently labeled nucleotides (e.g., compounds described herein). In embodiments, the kit further includes instructions for use thereof. In embodiments, kits described herein include a polymerase. In embodiments, the polymerase is a DNA polymerase. In embodiments, the DNA polymerase is a thermophilic nucleic acid polymerase. In embodiments, the DNA polymerase is a modified archaeal DNA polymerase. In embodiments, the kit includes a sequencing solution. In embodiments, the sequencing solution include labeled nucleotides including differently labeled nucleotides, wherein the label (or lack thereof) identifies the type of nucleotide. For example, each adenine nucleotide, or analog thereof; a thymine nucleotide; a cytosine nucleotide, or analog thereof, and a guanine nucleotide, or analog thereof may be labeled with a different fluorescent label.

In embodiments, the sequencing solution includes a buffer solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, Tricine, HEPES, TES, MOPS, MOPSO and PIPES. In embodiments, the buffer includes ethanolamine (EA), tris(hydroxymethyl)aminomethane (Tris), glycine, a carbonate salt, a phosphate salt, a borate salt, 2-dimethyalaminomethanol (DMEA), 2-diethyalaminomethanol (DEEA), N,N,N',N'-tetramethylethylenediamine (TEMED), and N,N,N',N'-tetraethylethylenediamine (TEEDA), or a combination thereof. Additionally, other buffer agents that can be used in enzyme reactions, hybridization reactions, and detection reactions are well known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid. In some embodiments, a concentration can be more than about 1 μM, more than about 2 μM, more than about 5 μM, more than about 10 μM, more than about 25 μM, more than about 50 μM, more than about 75 μM, more than about 100 μM, more than about 200 μM, more than about 300 μM, more than about 400 μM, more than about 500 μM, more than about 750 μM, more than about 1 mM, more than about 2 mM, more than about 5 mM, more than about 10 mM, more than about 20 mM, more than about 30 mM, more than about 40 mM, more than about 50 mM, more than about 60 mM, more than about 70 mM, more than about 80 mM, more than about 90 mM, more than about 100 mM, more than about 150 mM, more than about 200 mM, more than about 250 mM, more than about 300 mM, more than about 350 mM, more than about 400 mM, more than about 450 mM, more than about 500 mM, more than about 550 mM, more than about 600 mM, more than about 650 mM, more than about 700 mM, more than about 750 mM, more than about 800 mM, more than about 850 mM, more than about 900 mM, more than about 950 mM or more than about 1 M.

III. Methods

In an aspect is provided a method for sequencing a nucleic acid, including: (i) incorporating in series with a nucleic acid polymerase, (e.g., within a reaction vessel) one of four different compounds (e.g., nucleotide analogues) into a primer to create an extension strand, wherein the primer is hybridized to the nucleic acid and wherein each of the four different compounds comprises a unique detectable label; and (ii) detecting the unique detectable label of each incorporated compound, so as to thereby identify each incorporated compound in the extension strand, thereby sequencing the nucleic acid; wherein each of the four different compounds is independently a compound as described herein, including embodiments.

In embodiments, the compounds are described herein. In embodiments, the four different four different compounds are labeled nucleotide analogues as described herein (e.g., four different compounds described herein each including a different nucleobase and a different label (e.g., fluorescent dye moiety)). In embodiments, the four different labeled nucleotide analogues are four different compounds described herein (e.g., four different compounds described herein each including a different nucleobase). In embodiments, the four different labeled nucleotide analogues are four different compounds described herein (e.g., four different compounds described herein each including a different label (e.g., fluorescent dye moiety)).

In embodiments, the method further including, after each of the incorporating steps, adding to the reaction vessel four different unlabeled nucleotide analogues, wherein each of the four different unlabeled nucleotide analogues are of the structure as described herein, including embodiments, wherein in the first of the four different unlabeled nucleotide analogues, B is a thymidine or uridine hybridizing base; in the second of the four different unlabeled nucleotide analogues, B is an adenosine hybridizing base; in the third of the four different unlabeled nucleotide analogues, B is a guanosine hybridizing base; and in the fourth of the four different unlabeled nucleotide analogues, B is a cytosine hybridizing base.

In an aspect is provided a method for sequencing a nucleic acid, including (i) incorporating in series with a nucleic acid polymerase, within a reaction vessel, one of four different compounds into a primer to create an extension strand, wherein the primer is hybridized to the nucleic acid and wherein each of the four different compounds includes a unique detectable label; (ii) detecting the unique detectable label of each incorporated compound, so as to thereby identify each incorporated compound in the extension strand, thereby sequencing the nucleic acid; wherein each of the four different compounds is independently a compound as described herein, including embodiments. In embodiments, the compound includes at least one of the following: cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, 7-methylguanine or a derivative thereof, 5,6-dihydrouracil or a derivative thereof, 5-methylcytosine or a derivative thereof, and 5-hydroxymethylcytosine or a derivative thereof. In embodiments, the compound includes at least one of the following: cytosine or a derivative thereof, guanine or a derivative thereof, adenine or a derivative thereof, thymine or a derivative thereof, and uracil or a derivative thereof. In embodiments, the compound includes at least one of the following: cytosine or a derivative thereof, guanine or a derivative thereof, adenine or a derivative thereof, and thymine or a derivative thereof. In embodiments, the compound includes at least one of the following: cytosine or a derivative thereof, guanine or a derivative thereof, adenine or a derivative thereof, and uracil or a derivative thereof. In embodiments, the method further includes, after incorporating, contacting the compound with a cleaving agent. In embodiments, the method includes incorporating a first nucleotide including a 3'-O-reversible terminator (e.g., 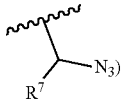)

and a first detectable label; detecting the first detectable label; and removing the 3'-O-reversible terminator from the first nucleotide to generate a nucleotide including a 3'-OH. In embodiments, the method includes generating one or more sequencing reads.

In embodiments, the nucleic acid to be sequenced is DNA or RNA, or a hybrid molecule comprised of deoxynucleotides and ribonucleotides. In embodiments, the nucleic acid to be sequenced is attached to a solid substrate via any suitable linkage method known in the art, e.g., using covalent linkage. In embodiments, the nucleic acid is attached directly to a solid substrate. In embodiments, the surface of the solid support includes a polymer that provides the attachment points for the nucleic acid.

In embodiments, the nucleic acid is within a cluster. The terms "cluster" and "colony" are used interchangeably throughout this application and refer to a discrete site on a solid support comprised of a plurality of immobilized nucleic acid strands. The term "clustered array" refers to an array formed from such clusters or colonies. In this context the term "array" is not to be understood as requiring an ordered arrangement of clusters. The term "array" is used in accordance with its ordinary meaning in the art, and refers to a population of different molecules that are attached to one or more solid-phase substrates such that the different molecules can be differentiated from each other according to their relative location. An array can include different molecules that are each located at different addressable features on a solid-phase substrate. The molecules of the array can be nucleic acid primers, nucleic acid probes, nucleic acid templates or nucleic acid enzymes such as polymerases or ligases. Arrays useful in the invention can have densities that ranges from about 2 different features to many millions, billions or higher. The density of an array can be from 2 to as many as a billion or more different features per square cm. For example an array can have at least about 100 features/$cm^2$, at least about 1,000 features/$cm^2$, at least about 10,000 features/$cm^2$, at least about 100,000 features/$cm^2$, at least about 10,000,000 features/$cm^2$, at least about 100,000,000 features/$cm^2$, at least about 1,000,000,000 features/$cm^2$, at least about 2,000,000,000 features/$cm^2$ or higher. In embodiments, the arrays have features at any of a variety of densities including, for example, at least about 10 features/$cm^2$, 100 features/$cm^2$, 500 features/$cm^2$, 1,000 features/$cm^2$, 5,000 features/$cm^2$, 10,000 features/$cm^2$, 50,000 features/$cm^2$, 100,000 features/$cm^2$, 1,000,000 features/$cm^2$, 5,000,000 features/$cm^2$, or higher.

In another aspect is provided a method of incorporating a compound into a primer, the method including combining a polymerase, a primer hybridized to nucleic acid template and the compound within a reaction vessel and allowing the polymerase to incorporate the compound into the primer thereby forming an extended primer, wherein the compound is a compound as described herein, including embodiments.

In embodiments, incorporating a compound into a primer refers to the 5' phosphate joining in phosphodiester linkage to the 3'-OH group of a second (modified or unmodified) nucleotide, which may itself form part of a longer polynucleotide chain.

In embodiments, the method further including, after the incorporating, cleaving the linker (e.g., $L^{100}$) with a cleaving reagent (e.g., tris(hydroxypropyl)phosphine (THPP)). In embodiments, the cleaving reagent is an acid, base, oxidizing agent, reducing agent, Pd(0), tris-(2-carboxyethyl)phosphine, dilute nitrous acid, fluoride, tris(3-hydroxypropyl) phosphine), sodium dithionite ($Na_2S_2O_4$), or hydrazine ($N_2H_4$). In embodiments, the cleaving reagent is in a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer. In embodiments, the method includes contacting the compound (e.g., a compound described herein) with a reducing agent. In embodiments, the method further including, after the incorporating, cleaving the linker at about 55° C. In embodiments, the method further including, after the incorporating, cleaving the linker at about 55° C. to about 80° C. In embodiments, the method further including, after the incorporating, cleaving the linker at about 60° C. to about 70° C. In embodiments, the method further including, after the incorporating, cleaving the linker at about 65° C. to about 75° C. In embodiments, the method further including, after the incorporating, cleaving the linker at about 65° C. In embodiments, the method further including, after the incorporating, cleaving the linker at about 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or about 80° C. In embodiments, the method further including, after the incorporating, cleaving the linker at a pH at about 8.0 to 11.0. In embodiments, the pH is 9.0 to 11.0. In embodiments, the pH is 9.5. In embodiments, the pH is 10.0. In embodiments, the pH is 8.0, 8.5, 9.0, 9.5, 10.0, 10.5, or 11.0. In embodiments, the pH is from 9.0 to 11.0, and the temperature is from about 60° C. to about 70° C.

In embodiments, the cleaving reagent cleaves both the linker and the polymerase-compatible cleavable moiety simultaneously.

In embodiments, the nucleic acid polymerase is a Taq polymerase, Therminator γ, 9° N polymerase (exo-), Therminator II, Therminator III, or Therminator IX. In embodiments, the thermophilic nucleic acid polymerase is Therminator γ. In embodiments, the thermophilic nucleic acid polymerase is 9° N polymerase (exo-). In embodiments, the thermophilic nucleic acid polymerase is Therminator II. In embodiments, the thermophilic nucleic acid polymerase is Therminator III. In embodiments, the thermophilic nucleic acid polymerase is Therminator IX. In embodiments, the thermophilic nucleic acid polymerase is a Taq polymerase. In embodiments, the nucleic acid polymerase is a thermophilic nucleic acid polymerase. In embodiments, the nucleic acid polymerase is 9°N and mutants thereof. In embodiments, the nucleic acid polymerase is Phi29 and mutants thereof. In embodiments, the polymerase is a non-thermophilic nucleic acid polymerase.

In an aspect is provided a method of determining the sequence of a target single-stranded polynucleotide. In embodiments, the method includes incorporating a compound as described herein, (e.g., a compound of Formula I or Formula II) into an oligonucleotide strand complementary to at least a portion of the target polynucleotide strand; and detecting the identity of the compound incorporated into the oligonucleotide strand. In embodiments, the compound includes a 3'-O-polymerase-compatible cleavable moiety as described herein and a detectable label. In embodiments, the method further includes chemically removing the detectable label and the 3'-O-polymerase-compatible cleavable moiety from the compound incorporated into the oligonucleotide strand. In embodiments, the 3'-O-polymerase-compatible cleavable moiety and the detectable label of the incorporated compound are removed prior to introducing the next complementary compound. In embodiments, the 3'-O-polymerase-compatible cleavable moiety and the detectable label are removed in a single step of chemical reaction. In embodiments, the sequential incorporation described herein is performed at least 50 times, at least 100 times, at least 150 times, at least 200 times, at least 250 times, at least 300 times, at least 350 times, at least 400 times, at least 450 times, or at least 500 times. In embodiments, the sequential incorporation is performed 80 to 200 times. In embodiments, the sequential incorporation is performed 100 to 200 times. In embodiments, the sequential incorporation is performed 120 to 250 times.

In embodiments, chemical cleavage of a compound (e.g., cleavage of a polymerase-compatible cleavable moiety or cleavage of a linker of a compound described herein) described herein (e.g., in an aspect or embodiment) includes contacting the compound with a reducing agent. In embodiments, chemical cleavage of a (e.g., cleavage of a polymerase-compatible cleavable moiety or cleavage of a linker of a compound described herein) described herein (e.g., in an aspect or embodiment) includes contacting the compound with THPP (e.g., about 10 mM THPP, at least 10 mM THPP). In embodiments, chemical cleavage of a compound (e.g., cleavage of a polymerase-compatible cleavable moiety or cleavage of a linker of a compound described herein) described herein (e.g., in an aspect or embodiment) is performed at about 55 degrees Celsius. In embodiments, chemical cleavage of a compound (e.g., cleavage of a polymerase-compatible cleavable moiety or cleavage of a linker of a compound described herein) described herein (e.g., in an aspect or embodiment) is performed at a temperature of at least 55 degrees Celsius. In embodiments, chemical cleavage of a compound (e.g., cleavage of a polymerase-compatible cleavable moiety or cleavage of a linker of a compound described herein) described herein (e.g., in an aspect or embodiment) is performed at about pH 9.5 to 10.0. In embodiments, chemical cleavage of a compound (e.g., cleavage of a polymerase-compatible cleavable moiety or cleavage of a linker of a compound described herein) described herein (e.g., in an aspect or embodiment) is performed at a pH from 9.5 to 10.0. In embodiments, chemical cleavage of a compound (e.g., cleavage of a polymerase-compatible cleavable moiety or cleavage of a linker of a compound described herein) described herein (e.g., in an aspect or embodiment) is performed at pH 9.5.

In another aspect is provided a method of preparing or synthesizing a compound of Formula (I)

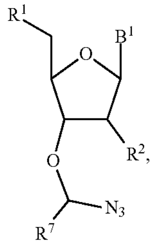
(I)

the method including mixing compound (A), compound (B), and an azidolating reagent together in a reaction vessel, wherein compound (A) has the formula:

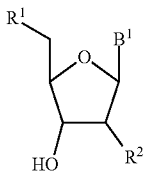
(A)

and compound (B) has the formula:

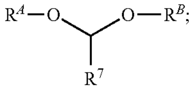
(B)

wherein $B^1$, $R^1$, $R^2$ and $R^7$ are as described herein. $R^A$ and $R^B$ are independently hydrogen, substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered).

In an aspect is provided a method of preparing or synthesizing a compound of Formula (I)

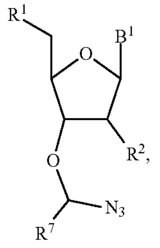
(I)

the method including mixing compound (A) and an azidolating reagent together in a reaction vessel, wherein compound (A) has the formula:

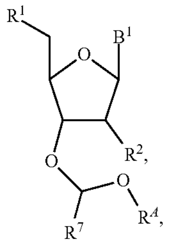
(A)

wherein $B^1$, $R^1$, $R^2$, and $R^7$ are as described herein. $R^A$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^A$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect is provided a method of preparing or synthesizing a compound of Formula (I)

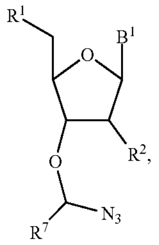
(I)

the method including mixing compound (C), compound (D), and an azidolating reagent together in a reaction vessel, wherein compound (C) has the formula:

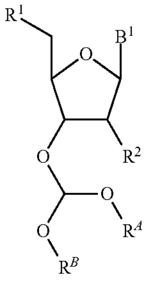
(C)

and compound (B) has the formula:

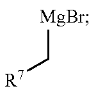
(D)

wherein $B^1$, $R^1$, $R^2$, and $R^7$ are as described herein. $R^A$ and $R^B$ are independently hydrogen, substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered). In embodiments, the azidolating reagent is trimethylsilyl azide (TMSN3).

In embodiments, a substituted $R^A$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^A$ is substituted with a plurality of groups selected from substituent groups, size-limited substituent groups, and lower substituent groups; each substituent group, size-limited substituent group, and/or lower substituent group may optionally be different. In embodiments, when $R^A$ is substituted, it is substituted with at least one substituent group. In embodiments, when $R^A$ is substituted, it is substituted with at least one size-limited substituent group. In embodiments, when $R^A$ is substituted, it is substituted with at least one lower substituent group.

In embodiments, a substituted $R^B$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^B$ is substituted with a plurality of groups selected from substituent groups, size-limited substituent groups, and lower substituent groups; each substituent group, size-limited substituent group, and/or lower substituent group may optionally be different. In embodiments, when $R^B$ is substituted, it is substituted with at least one substituent group. In embodiments, when $R^B$ is substituted, it is substituted with at least one size-limited substituent group. In embodiments, when $R^B$ is substituted, it is substituted with at least one lower substituent group.

In embodiments, the method includes mixing a substituted or unsubstituted pyridine in the reaction vessel. In embodiments, the method includes mixing lutidine or collidine in the reaction vessel. In embodiments, the method includes mixing 2,3-Lutidine (2,3-dimethylpyridine), 2,4-Lutidine (2,4-dimethylpyridine), 2,5-Lutidine (2,5-dimethylpyridine), 2,6-Lutidine (2,6-dimethylpyridine), 3,4-Lutidine (3,4-dimethylpyridine), or 3,5-Lutidine (3,5-dimethylpyridine) in the reaction vessel. In embodiments, the method includes mixing 2,3,4-Collidine (2,3,4-trimethylpyridine), 2,3,5-Collidine (2,3,5-trimethylpyridine), 2,3,6-Collidine (2,3,6-trimethylpyridine), 2,4,5-Collidine (2,4,5-trimethylpyridine), 2,4,6-Collidine (2,4,6-trimethylpyridine), or 3,4,5-Collidine (3,4,5-trimethylpyridine) in the reaction vessel. In embodiments, the method includes mixing 4-N,N-dimethylaminopyridine in the reaction vessel.

In embodiments, $R^1$ is a 5'-O-nucleoside protecting group, for example a 5'-O-nucleoside protecting group known in the art include those described in Seliger H. Curr. Protoc Nucleic Acid Chem. 2001; Chapter 2 or K. Seio et al, Nucleic Acids Research Supplement 2, 27-28 (2002); both of which are incorporated by reference for all purposes. Non-limiting examples of 5'-O-nucleoside protecting groups include 2,2,2-Trichloroethyl carbonate (Troc), 2-Methoxyethoxymethyl ether (MEM), 2-Naphthylmethyl ether (Nap), 4-Methoxybenzyl ether (PMB), Acetate (Ac), Benzoate (Bz), Benzyl ether (Bn), Benzyloxymethyl acetal (BOM), Ethoxyethyl acetal (EE), Methoxymethyl acetal (MOM), Methoxypropyl acetal (MOP), Methyl ether, Tetrahydropyranyl acetal (THP), Triethylsilyl ether (TES), Triisopropylsilyl ether (TIPS), Trimethylsilyl ether (TMS), tert-Butyldimethylsilyl ether (TBS, TBDMS), or tert-Butyldiphenylsilyl ether (TBDPS). In embodiments, $R^1$ is

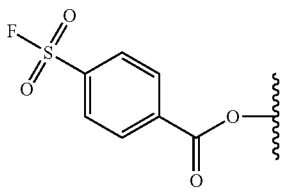
,
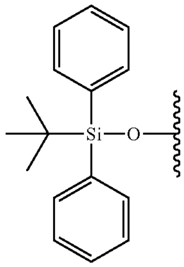
,
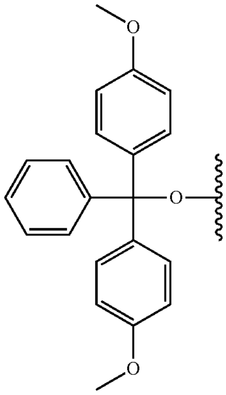
,
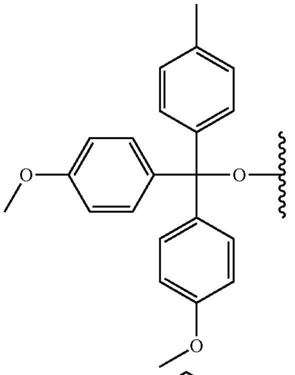
, or
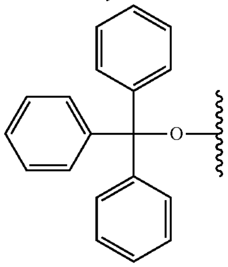
.

In embodiments, the protecting group is removed by contacting the compound with a deprotecting agent. In embodiments, the deprotecting reagent is tetra-n-butylammonium fluoride (TBAF). In embodiments, the deprotecting reagent is tetra-n-butylammonium fluoride (TBAF) and tetrahydrofuran (THF). In embodiments, the deprotecting reagent includes $K_2CO_2$ or $Na_2CO_3$. In embodiments, the deprotecting reagent includes $K_2CO_2$ or $Na_2CO_3$ in methanol. In embodiments, the deprotecting reagent includes $K_2CO_2$ or Na2CO3 in methanol and water. In embodiments, the deprotecting reagent includes LiOH. In embodiments, the deprotecting reagent includes LiOH and THF. In embodiments, the deprotecting reagent includes LiOH, methanol, in methanol. In embodiments, the deprotecting reagent includes LiOH, methanol, in methanol and water. In embodiments, the deprotecting reagent includes $NH_3$. In embodiments, the deprotecting reagent includes NH3 in methanol. In embodiments, the deprotecting reagent includes methylamine. In embodiments, the deprotecting reagent includes methylamine in methanol. In embodiments, the deprotecting reagent includes tert-butylamine. In embodiments, the deprotecting reagent includes tert-butylamine in methanol. In embodiments, the deprotecting reagent includes tert-butylamine.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1. Novel Modified Nucleotides

In the context of nucleic acid sequencing, the use of nucleotides bearing a 3' reversible terminator (RT) (also referred to herein as a polymerase-compatible cleavable moiety) allows successive nucleotides to be incorporated into a polynucleotide chain in a controlled manner. The DNA template for a sequencing reaction will typically comprise a double-stranded region having a free 3' hydroxyl group which serves as a primer or initiation point for the addition of further nucleotides in the sequencing reaction. The region of the DNA template to be sequenced will overhang this free 3' hydroxyl group on the complementary strand. The primer bearing the free 3' hydroxyl group may be added as a separate component (e.g., a short oligonucleotide) which hybridizes to a region of the template to be sequenced. Following the addition of a single nucleotide to the DNA template, the presence of the 3' reversible terminator prevents incorporation of a further nucleotide into the polynucleotide chain. While the addition of subsequent nucleotides is prevented, the identity of the incorporated nucleotide is detected (e.g., exciting a unique detectable label that is linked to the incorporated nucleotide). The reversible terminator is then removed (and optionally the cleavable linker is removed simultaneously), leaving a free 3' hydroxyl group for addition of the next nucleotide. The sequencing cycle can then continue with the incorporation of the next blocked, labeled nucleotide.

Sequencing by synthesis of nucleic acids ideally requires the controlled (i.e., one at a time), yet rapid, incorporation of the correct complementary nucleotide opposite the oligonucleotide being sequenced. This allows for accurate sequencing by adding nucleotides in multiple cycles as each nucleotide residue is sequenced one at a time, thus preventing an uncontrolled series of incorporations occurring. Nucleotides bearing a 3' RT have been described in the literature, see for example U.S. Pat. No. 6,664,079 or Ju J. et al. (2006) Proc Natl Acad. Sci USA 103(52):19635-19640, however despite the recent advances only a few solutions have been presented, most of which cause other problems, including inefficient or incomplete incorporation by the polymerase, inefficient or incomplete cleavage of the removable group, or harsh conditions needed for the cleaving step causing spurious problems with the remainder of the assay and/or fidelity of the target sequence.

There are limitations on types of reversible terminators that can be added onto a nucleotide and still be suitable. The reversible terminator should prevent additional nucleotide molecules from being added to the polynucleotide while simultaneously being easily removable from the sugar moiety without causing damage to the polynucleotide or sequencing enzyme (e.g., DNA polymerase or reverse transcriptase). Ideal reversible terminators therefore possess long term stability, can be efficiently incorporated by the sequencing enzyme, can prevent secondary or further nucleotide incorporation, and have the ability to be removed under mild conditions that do not cause damage to any sequencing component (e.g., nucleotides, primers, enzymes, polymers, etc.) preferably under aqueous conditions. Developing a truly reversible set of nucleotide RTs and cleavable linkers that are stable and cleave rapidly has been a goal for many years.

An important property of a reversible terminator on a nucleotide is that it can be rapidly cleaved under conditions that do not adversely affect the DNA. Removal of a reversible terminator to form the 3'-OH requires contacting reversible terminator with a reducing agent (e.g., tris(2-carboxyethyl)phosphine (TCEP)), followed by conversion to a hydroxide (see scheme 1). The complete reaction may be considered as four separate reactions, as depicted in FIG. 1A. Briefly, the 3' oxygen, i.e., wherein the oxygen is attached to the 3' position of the deoxyribose, is protected with an R-substituted methylene azide, wherein R is as described herein (e.g., as $R^7$). A phosphine-containing reducing agent (e.g., tris(2-carboxyethyl)phosphine (TCEP)), depicted as $P(R')_3$, contacts the reversible terminator to generate $N_2$ and a phosphine imide (rxn1). The resulting phoshine imide hydrolyzes to form an amine (rxn2), which further evolves to an acetal releasing ammonia (rxn3). Finally, the acetal hydrolyzes to form an aldehyde and a 3' OH on the nucleotide (rxn4). Thermodynamic analysis of each of the individual reactions (i.e., rxn1, rxn2, rxn3, rxn4 described in FIG. 1A) aids in determining the cleavage rate. Described herein, two of the subreactions, rxn3 and rxn4, were discovered to advantageously cleave faster by including a resonance-stabilizing moiety (e.g., a cyclic moiety, such as an aromatic or heteroaromatic moiety) at the methylene (i.e., $R^7$).

Scheme 1. A generalized overview of the cleavage process of an incorporated modified nucleotide to produce a 3′-OH and an aldehyde. In the scheme, B is a nucleobase (e.g., A, T, G, C), and $R^7$ is as described herein.

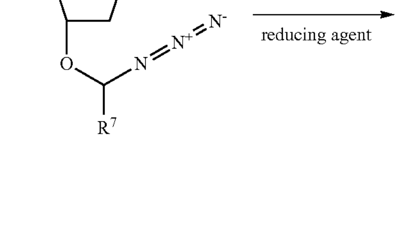

-continued

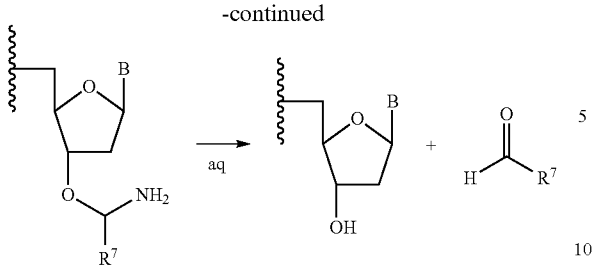

Figure 1B:
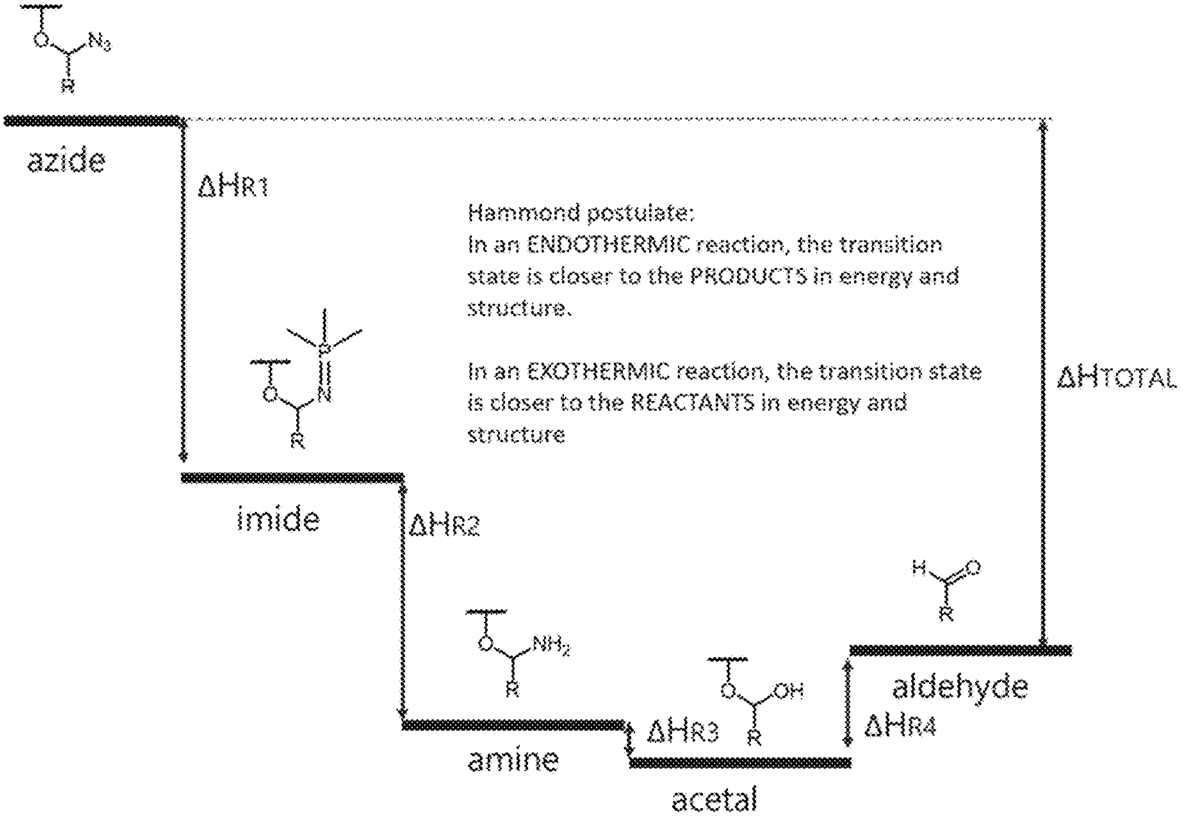

The kinetics of a reaction depend on the activation energy, i.e., the difference between the energy of the reactants and the transition state. However, transition states have only a transitory existence and are difficult, if not impossible, to observe, isolate, and quantify. A generalization to predicting reaction rates is provided in the Hammond Postulate, which proposes the activation energy of the rate determining step is inversely proportional to the stability of the transition state. In an endothermic reaction the transition state structure is closer to the structure of the products, and so it follows that a more stable product reflects a more stable transition state and has a lower activation energy. Simple thermodynamics provides the enthalpy changes of the reaction, ΔH, as a measure of the thermodynamic stability. The enthalpy change is calculated as the difference in the enthalpy of the products and reactants, $\Delta H=\Delta H_{products}-\Delta H_{reactants}$. Additionally, enthalpy is additive over the entire reaction, that is the total summation of the enthalpy of the subreactions, $\Delta H_{rxn\ TOTAL}=\Delta H_{rxn1}+\Delta H_{rxn2}+\Delta H_{rxn3}+\Delta H_{rxn4}$, see FIG. 1B.

Using ΔH as a corollary for the reaction rate, it is possible to predict which reversible terminators will cleave rapidly under suitable conditions. Gas phase calculations were performed using hybrid Density Functional Theory (B3LYP) with a large basis set (Valence triple-zeta with two sets of polarization functions) to determine the optimized structure and internal energy of the reactants and the products to derive a $\Delta H_{rxn}$ for a variety of compounds, see Table 2.

Experimental evidence supports using ΔH as a proxy for the reaction rate. For example, the half-life of RT having the structure

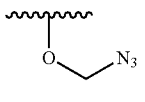

(referred to as an azidomethyl, or RT #1), was 20.4 minutes, compared to 8.9 minutes and 2.9 minutes for RT #2 and RT #5, respectively, (see for example, US 2016/0002721, which is incorporated herein by reference for all purposes). The relative enthalpy of the reaction, ΔΔH, defined as $\Delta\Delta H_{rxn\ TOTAL}=(\Delta H_{rxn\ TOTAL})_{RT\ \#}-(\Delta H_{rxn\ TOTAL})_{RT\ \#1}$, supports using the enthalpy as a corollary to the reaction rate.

| | RT#1 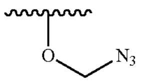 | RT#2 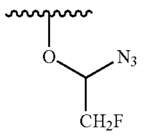 | RT#5 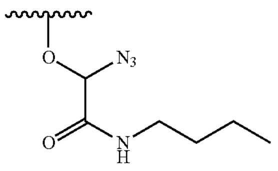 |
|---|---|---|---|
| Half-life (min) | 20.4 | 8.9 | 2.9 |
| ΔΔH (kcal/mol) | 0.0 | −3.4 | −5.2 |

Figure 4:
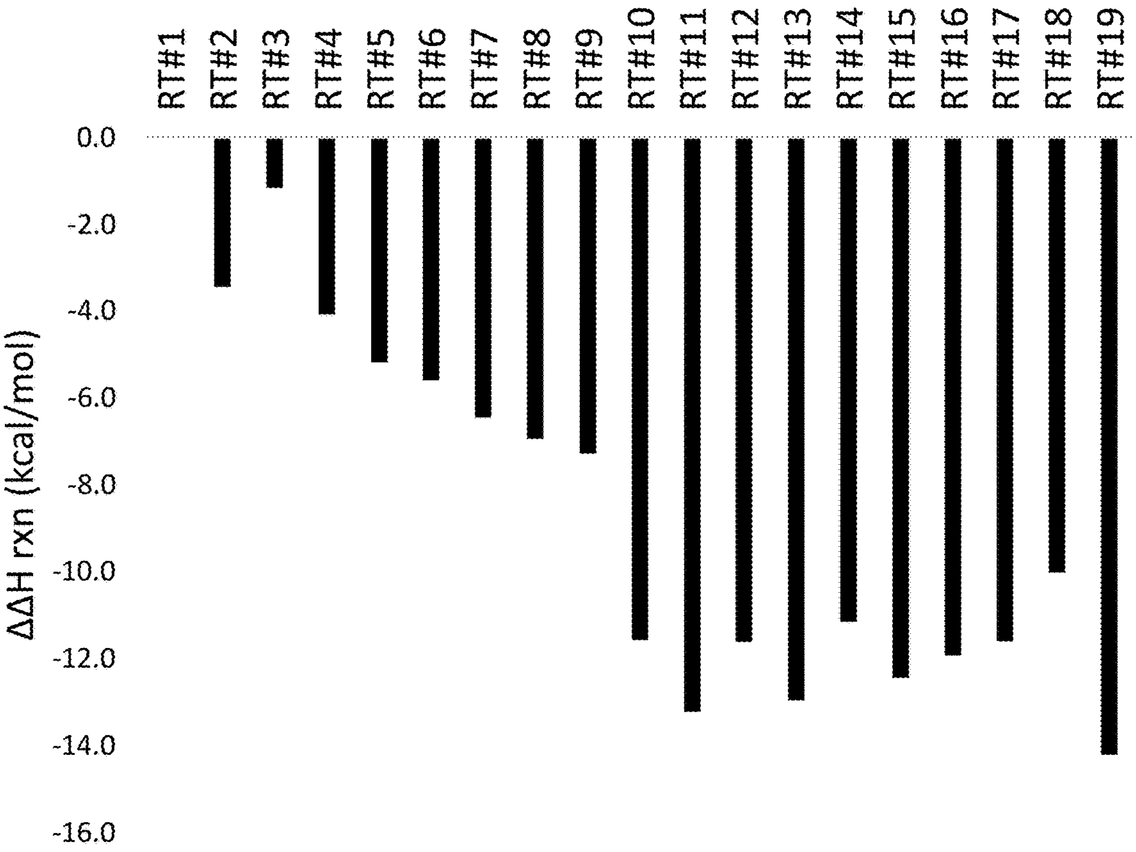
FIG. 4. Reporting the relative change in enthalpy, relative to RT #1, for a variety of reversible terminators. The relative change in enthalpy for the overall reaction is surprisingly decreased by including cyclic moieties, and in particular aromatic moieties (i.e., RT #10-RT #19) compared to non-cyclic moieties (i.e., RT #1-RT #7). Reducing the energetic burden on the system, i.e., reducing the enthalpy, corresponds to faster cleavage rates.
Figure 5:
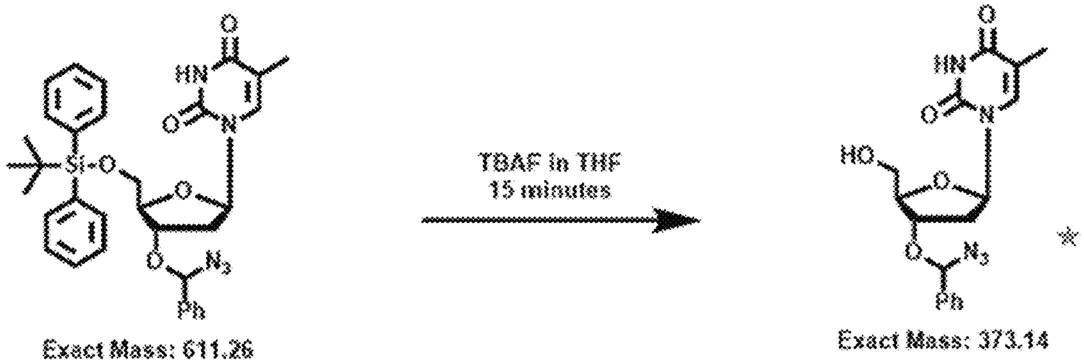
FIG. 5. LC-MS confirmation of a nucleoside analogue described herein.
Figure 5:
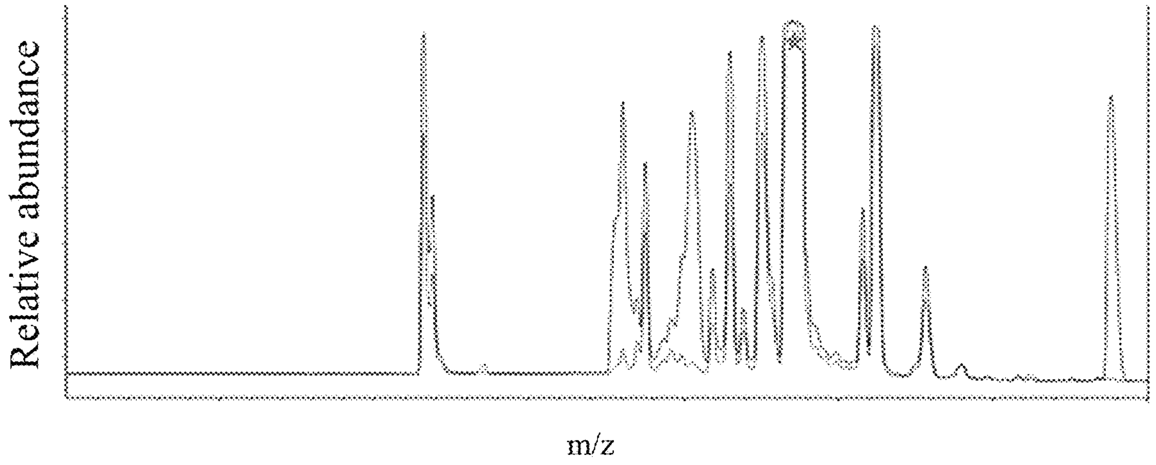

The thermodynamic analysis was extended to determine the change in enthalpy for each reaction (i.e., rxn1, rxn2, rxn3, and rxn4), FIGS. 3A-3D, and the relative change in enthalpy, Table 2 and FIG. 4, for a variety of substituents. A significant improvement in the storage and cleavage rates may be realized by including resonance-stabilizing moiety (e.g., a cyclic moiety, such as an aromatic or heteroaromatic moiety) as described herein.

TABLE 2

Calculated enthalpies for each subreaction, rxn1, rxn2, rxn3, and rxn4, including the total enthalpy relative to RT#1.

| $R^7$ (of Formula I) | Internal Ref No. | $\Delta\Delta H_{rnx1}$ (kcal/mol) | $\Delta\Delta H_{rnx2}$ (kcal/mol) | $\Delta\Delta H_{rnx3}$ (kcal/mol) | $\Delta\Delta H_{rnx4}$ (kcal/mol) | $\Delta\Delta H_{TOTAL}$ (kcal/mol) |
|---|---|---|---|---|---|---|
| 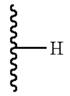 | RT #1 | 0.0 | 0.0 | 0.0 | 0.0 | 0.0 |
| 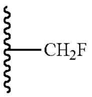 | RT #2 | 0.2 | 1.0 | −0.5 | −4.2 | −3.4 |

TABLE 2-continued

Calculated enthalpies for each subreaction, rxn1, rxn2, rxn3, and rxn4, including the total enthalpy relative to RT#1.

| $R^7$ (of Formula I) | Internal Ref No. | $\Delta\Delta H_{rnx1}$ (kcal/mol) | $\Delta\Delta H_{rnx2}$ (kcal/mol) | $\Delta\Delta H_{rnx3}$ (kcal/mol) | $\Delta\Delta H_{rnx4}$ (kcal/mol) | $\Delta\Delta H_{TOTAL}$ (kcal/mol) |
|---|---|---|---|---|---|---|
| 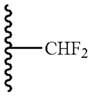 | RT #3 | −2.2 | 2.8 | −0.3 | −1.4 | −1.2 |
| 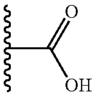 | RT #4 | −7.0 | 7.6 | −0.1 | −4.7 | −4.1 |
| 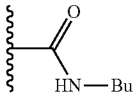 | RT #5 | −1.9 | 3.0 | 0.3 | −6.5 | −5.2 |
| 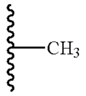 | RT #6 | 2.0 | −0.5 | 0.7 | −7.8 | −5.6 |
| 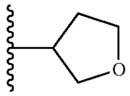 | RT #7 | 1.8 | −1.8 | −1.2 | −5.2 | −6.4 |
| 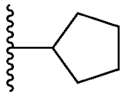 | RT #8 | 3.6 | −2.6 | −1.7 | −6.2 | −6.9 |
| 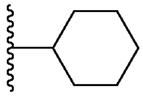 [SMILES: *C1CCCCC1] | RT #9 | −2.4 | −2.6 | −1.9 | −0.4 | −7.3 |
| 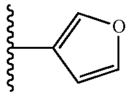 | RT #10 | 3.0 | −3.2 | −0.9 | −10.5 | −11.6 |
| 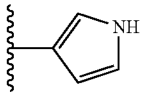 | RT #11 | 2.6 | −1.8 | −1.5 | −12.5 | −13.2 |
| 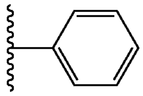 [SMILES: *c1ccccc1] | RT #12 | 0.8 | −0.3 | −1.5 | −10.6 | −11.6 |
| 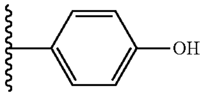 [SMILES: *c1ccc(O)cc1] | RT #13 | 1.5 | −0.7 | −1.6 | −12.1 | −13.0 |
| 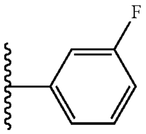 [SMILES: *c1cccc(F)c1] | RT #14 | 0.0 | 0.0 | −1.3 | −9.8 | −11.1 |
| 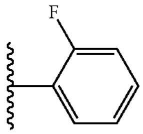 [SMILES: *c1ccccc1F] | RT #15 | −1.2 | 0.0 | −1.4 | −9.9 | −12.4 |

TABLE 2-continued

Calculated enthalpies for each subreaction, rxn1, rxn2, rxn3, and rxn4, including the total enthalpy relative to RT#1.

| $R^7$ (of Formula I) | Internal Ref No. | $\Delta\Delta H_{rxn1}$ (kcal/mol) | $\Delta\Delta H_{rxn2}$ (kcal/mol) | $\Delta\Delta H_{rxn3}$ (kcal/mol) | $\Delta\Delta H_{rxn4}$ (kcal/mol) | $\Delta\Delta H_{TOTAL}$ (kcal/mol) |
|---|---|---|---|---|---|---|
| 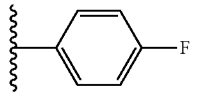 | RT #16 | 0.5 | −0.3 | −1.3 | −10.7 | −11.9 |
| 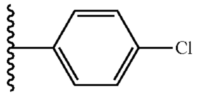 [SMILES: *c1ccc(Cl)cc1] | RT #17 | 0.1 | −0.2 | −1.2 | −10.3 | −11.6 |
| 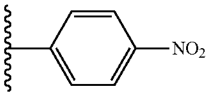 | RT #18 | −1.6 | 0.6 | −0.7 | −8.3 | −10.0 |
| 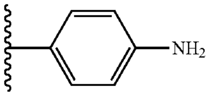 | RT #19 | 1.4 | 0.0 | −1.9 | −13.7 | −14.2 |
| 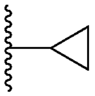 [SMILES: *C1CC1] | RT #20 | −1.3 | 0.4 | −0.8 | −8.7 | −10.4 |
| 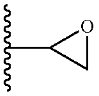 | RT #21 | 2.8 | −1.5 | −1.8 | −9.3 | −9.7 |
| 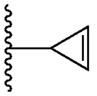 [SMILES: *C1C=C1] | RT #22 | −0.5 | −0.7 | −1.0 | −3.8 | −6.0 |

Figure 2A:
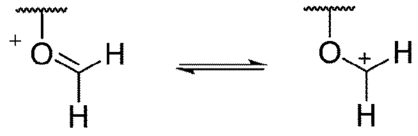
FIGS. 2A-2B shows the related resonance structures for different intermediates and products. Comparing RT #1 to RT #12, the greater number of resonant structures is a reflection of the greater electron delocalization, which lowers the potential energy of the carbocation (FIG. 2A) and the aldehyde (FIG. 2B), thereby stabilizing the molecule.
Figure 2A:
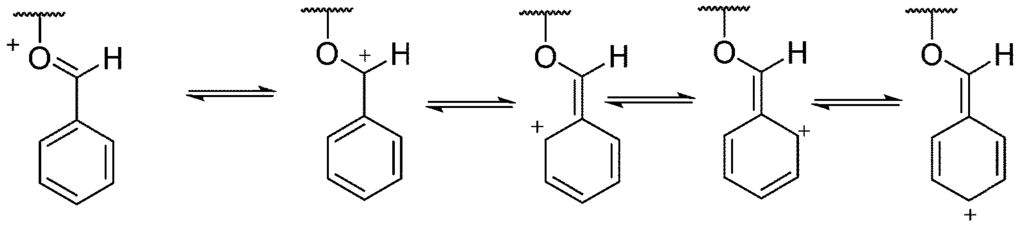

The thermodynamic stability of the intermediate compounds (e.g., the phosphine imide, amine, or acetal compounds described in FIG. 1A) influences the overall cleavage rate. For example, depicted in rxn3, the reaction yields an amine (see, for example rnx3 of FIG. 1A). A detailed look at the rxn3 mechanism, provided in Scheme 2, suggests the formation of a carbocation intermediate. Replacing one of the hydrogen atoms with a resonance-stabilizing moiety (e.g., a cyclic moiety, such as an aromatic or heteroaromatic moiety) provides additional resonant stabilizing structures, as depicted in FIG. 2A, resulting in a more stable intermediate thus permitting faster cleavage. The calculated change in enthalpy, shown in FIG. 3C for rxn3, supports this understanding wherein cyclic moieties (i.e., RT #8-RT #19) generally are more exothermic than non-cyclic moieties (i.e., RT #1-RT #7).

Scheme 2. A detailed analysis of the rxn3 and rxn4 mechanisms highlighting the formation of the carbocation and terminal aldehyde.

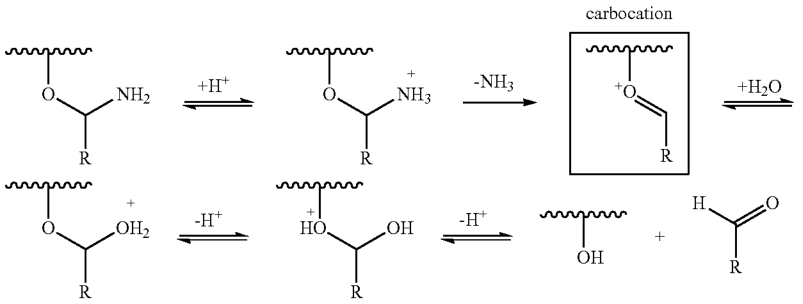

Figure 2B:
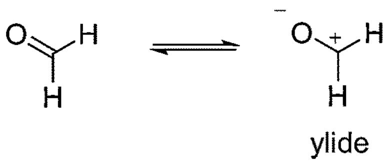
Figure 2B:
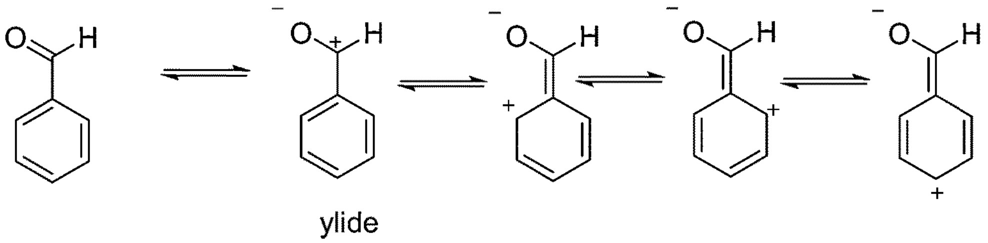
Figure 3A:
FIGS. 3A-3D reports the calculated enthalpy for the first reaction (rxnl.
Figure 3B:
Figure 3C:
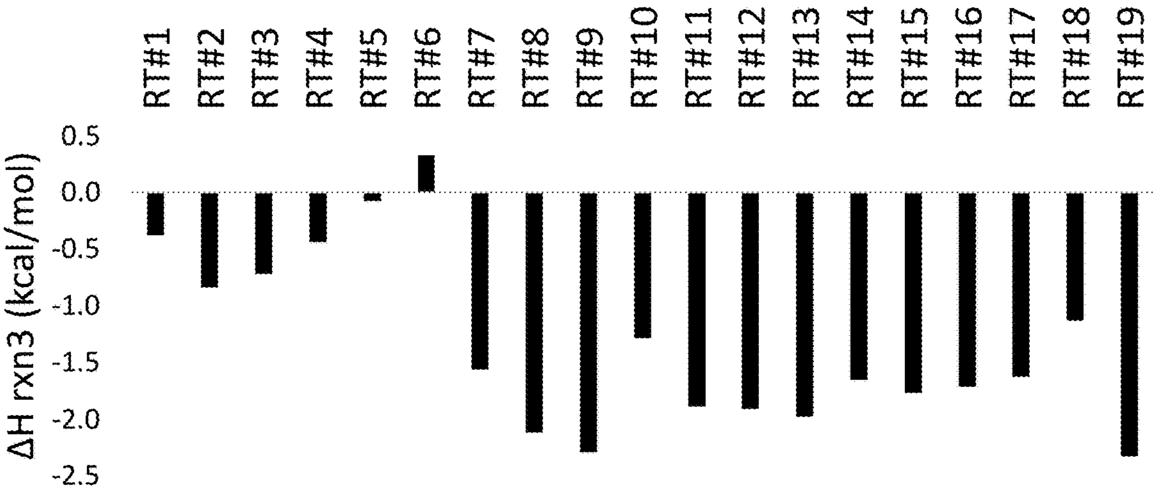
Figure 3D:
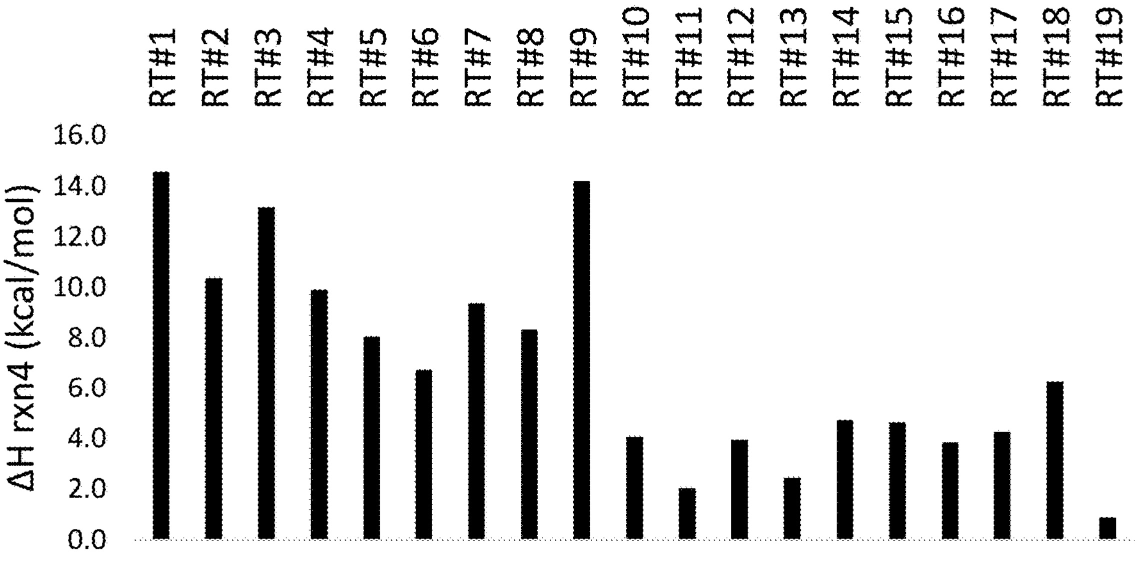

Additionally, the stability of the resultant aldehyde influences the cleavage rate of the acetal. For example, rxn4 results in the formation of formaldehyde. Formaldehydes are reactive and prone to polymerization and oxidation and due to the lack of steric and resonance stabilization afforded to the sp2 carbon by the hydrogens. In accordance with the Hammond Postulate, for an endothermic reaction, the transition state is geometrically more similar to the aldehyde (see for example March's Advanced Organic Chemistry, 6th Ed., Wiley, 2007, Michael B. Smith and Jerry March, Chapter 6 Methods of determining mechanisms, page 308). Conceptualizing the aldehyde with all available resonance geometries (see FIG. 2B) suggests a stable ylide structure that is geometrically similar to the resultant aldehyde will be more thermodynamically favored. The calculated change in enthalpy, shown in FIG. 3DC for rxn4, supports this understanding wherein cyclic moieties, and in particular aromatic moieties (i.e., RT #10-RT #19) generally are less endothermic than non-cyclic moieties (i.e., RT #1-RT #7).

Due to the lack of steric and resonance stabilization afforded to the sp2 carbon by the hydrogens in RT #1, the relative change in enthalpy for the overall reaction is surprisingly decreased by including resonant stabilizing moieties; see for example FIG. 4. Reducing the energetic burden on the system, i.e., reducing the enthalpy, corresponds to faster cleavage rates. Therefore, increasing the resonance stabilization to the sp2 carbon by including a resonance-stabilizing moiety (e.g., a cyclic moiety, such as an aromatic or heteroaromatic moiety) involves only a small reorganization of the molecular structures and thus permits faster cleavage.

The nucleotides described herein can be incorporated by the polymerase enzyme used in SBS chemistry at a similar rate to control nucleotides (e.g., nucleotides disclosed in U.S. Pat. Nos. 10,738,072 and 11,174,281, which are hereby incorporated by reference). For example, using an enzyme that includes optimized mutations for the control nucleotides, the average incorporation halftime for a nucleotide including RT #18 was 47+/−3 seconds when both isomers of RT #18 were present, and 17+/3 seconds for one of the isomers. The incorporation halftime is about 10 seconds greater than the control, and further mutational optimization of the incorporation binding pocket of the enzyme to accommodate nucleotides as described herein can further enhance the incorporation rate. The cleavage kinetics are similarly increased relative to a control. The cleavage kinetics of azidomethyl nucleotides (i.e., wherein the 3' oxygen of the nucleotide is bound to an azidomethyl moiety

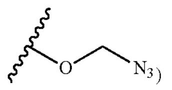 [SMILES: *OCN=[N+]=[N-]]

may be enhanced by substituting the bridging methylene between the 3' oxygen and the azido moiety. The average halftime for cleaving an azidomethyl bearing nucleotide is about 40 seconds at 65° C. using 1 mM of cleaving agent (i.e., THPP or TCEP). In contrast, the average halftime for cleaving a nucleotide described herein (RT #18) is 10 seconds at 55° C. and 0.25 mM cleaving agent. Modifying the reaction conditions (e.g., elevating the temperature to 65° C., increasing the pH, increasing the amount of cleaving agent) results in faster cleavage. Thus, it was a surprise that lowering the temperature and reducing the concentration of the cleaving agent still resulted in significantly faster cleavage.

Example 2. Chemical Synthesis of Modified Nucleotides

Included in Scheme 3 is a generalized overview for synthesizing a modified nucleotide as described herein. Introducing the resonance-stabilizing moiety (e.g., cyclic moiety such as an aromatic or heteroaromatic moiety) in the reversible terminator is achieved by introducing a functionalized acetal. The acetal may be formed via an aldehyde conversion reaction using mild conditions, as depicted in Scheme 4, and reported in Grabowski et al *Org. Biomol. Chem.,* 2018, 16, 3114.

Scheme 3. A generalized synthetic protocol for producing a nucleotide as described herein, wherein $R^7$ is as described herein. Optionally, an oxidizing agent (e.g., tert-butyl hydroperoxide) is added during the final purification step to prevent premature deblocking.

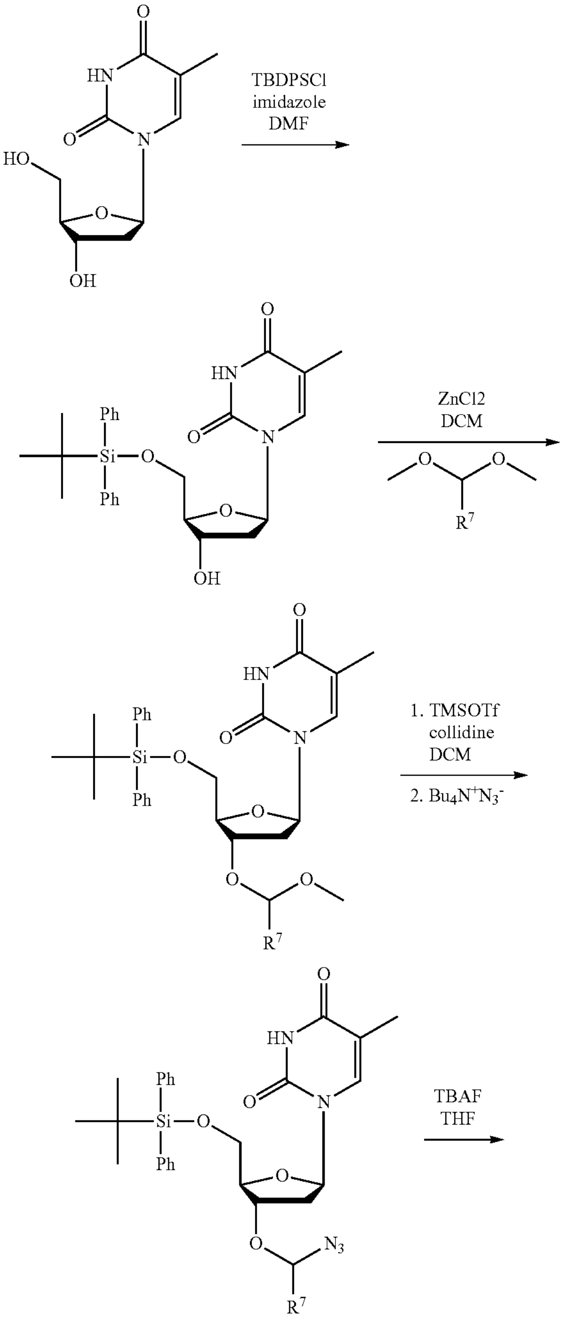

-continued

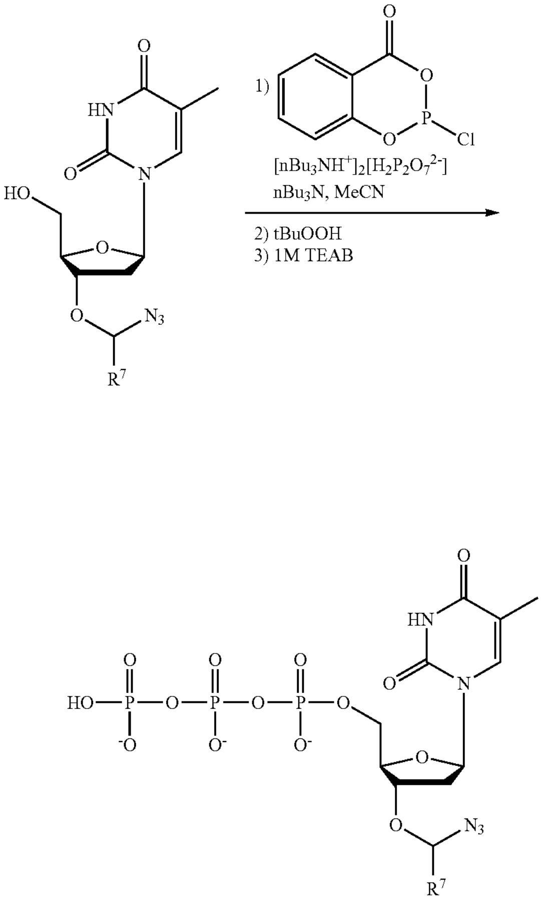

Scheme 4. Synthetic protocols for the synthesis of acetals used in Scheme 3, wherein $R^7$ is as described herein. Both reactions can be modified to generate the desired $R^7$-substituted acetals from the corresponding aldehyde starting material.

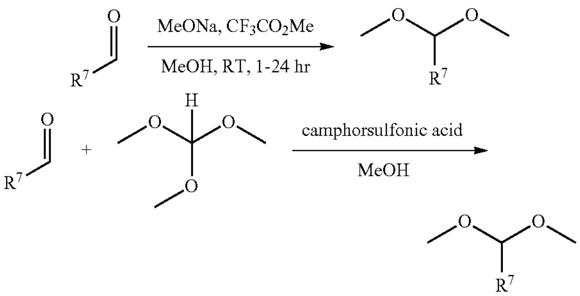

Alternatively, the starting nucleoside may include a protected propargyl amine connected to the nucleobase, as shown in Scheme 4. Nucleosides containing a protected propargyl amine off the base may be used as the input nucleoside in Scheme 4, following a similar protocol to produce a reversible terminator containing nucleotide with a protected propargyl amine off the base. The protecting group is then removed by exposing the nucleoside containing a protected propargyl amine off the base to concentrated ammonium hydroxide.

Scheme 5. Synthetic protocol for generating an input nucleoside containing a propargyl amine on the base

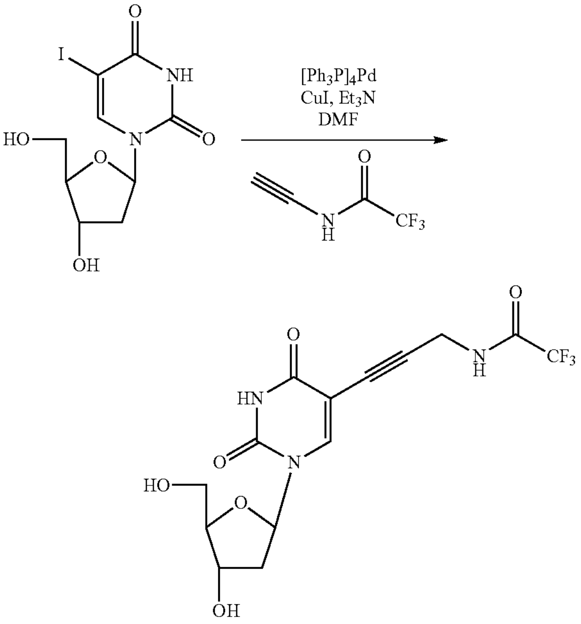

Scheme 6. Synthetic protocol for generating compound comprising a CN-substituted $R^7$.

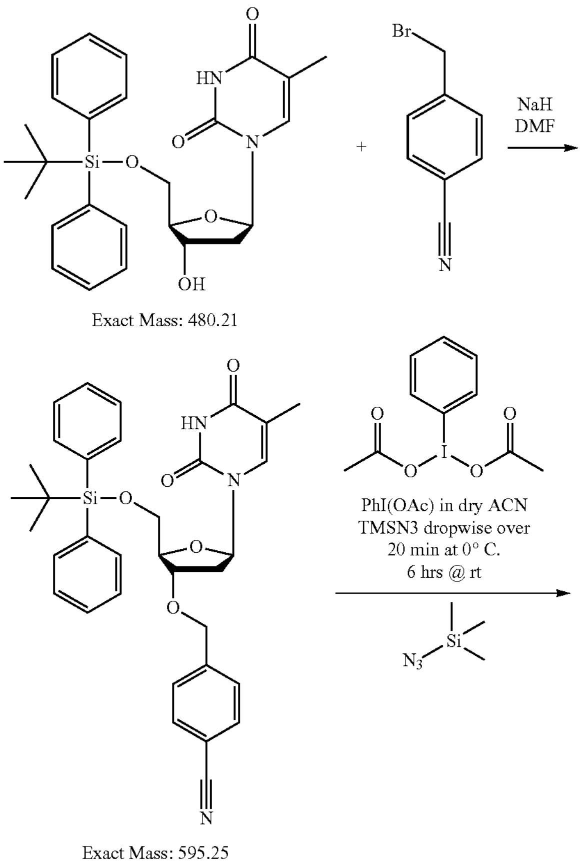

-continued

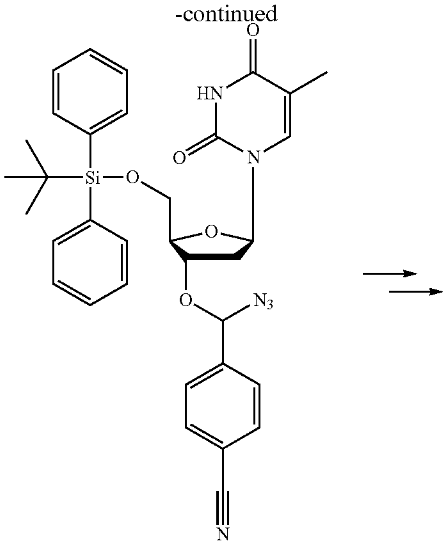

Exact Mass: 636.25

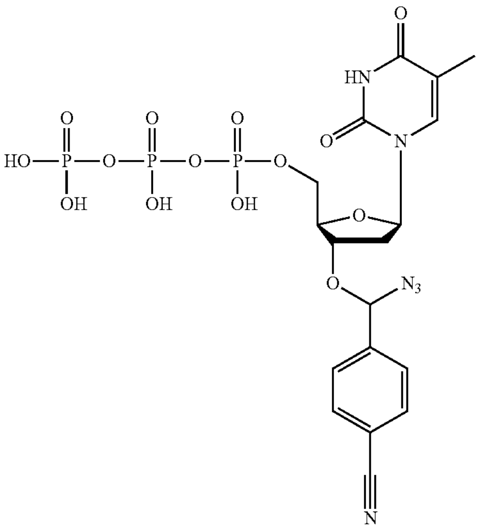

Exact Mass: 638.03

As shown in Scheme 7, to a mixture of 5'-O-TBDPS protected thymidine (2.4 g, 5 mmol) and 4-chlorobenzaldehyde (9.4 g, 50 mmol) was added a solution of zinc chloride (12.5 mL, 2.0 M in 2-methyl tetrahydrofuran) at room temperature. The reaction mixture was allowed to react at room temperature for five hours before being quenched with saturated $NaHCO_3$. After five hours, the reaction mixture was quenched with sodium bicarbonate solution. The reaction mixture was diluted with methylene chloride then the organic layer was separated, concentrated, and purified by Biotage (Hexanes/EtOAc) to yield 1.9 g (60%) pure desired product and confirmed via LCMS.

Scheme 7. Synthetic protocol for generating compound comprising a thymidine acetal. This may be combined with the protocols described in Scheme 3.

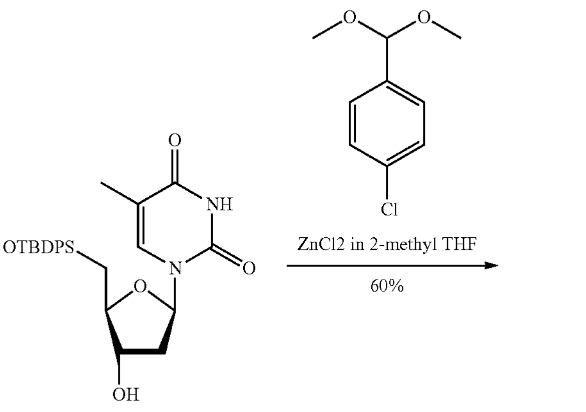

Exact Mass: 480.21

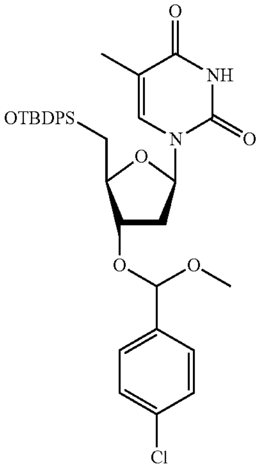

Exact Mass: 634.23

Scheme 8. A generalized synthetic protocol for producing a nucleotide as described herein. Optionally, an oxidizing agent (e.g., tert-butyl hydroperoxide, tBuOOH) is added during the final purification step to prevent premature deblocking.

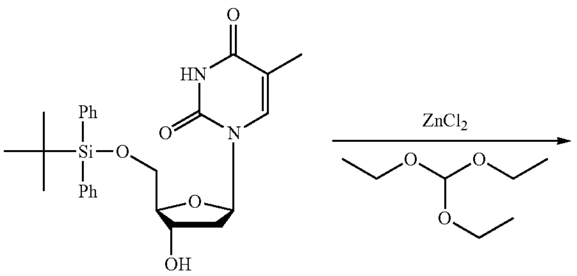

-continued
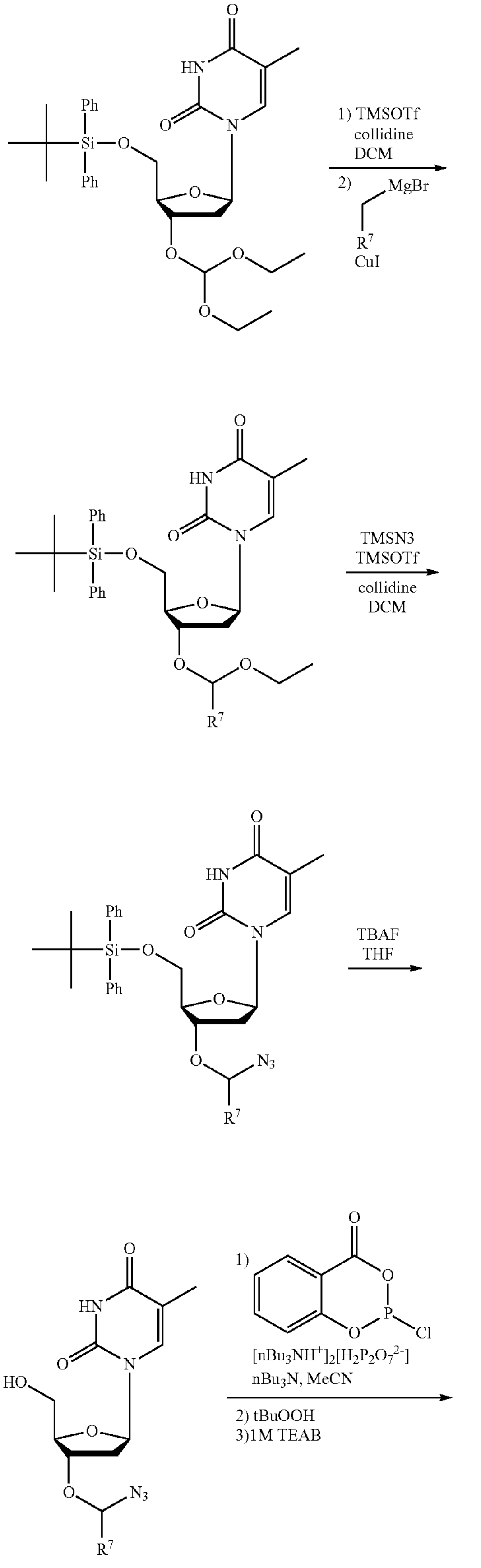
-continued
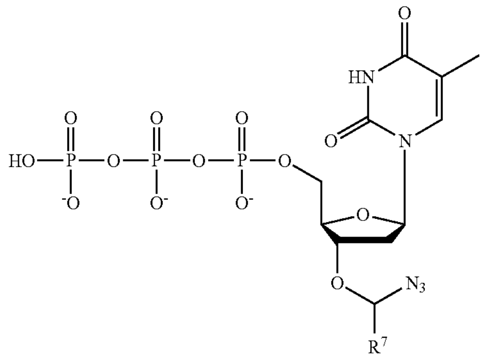
Scheme 9. A synthetic protocol for producing a nucleotide as described herein. LCMS confirmation of the cycloproyl azide nuceloside was confirmed at 337.14 Da.
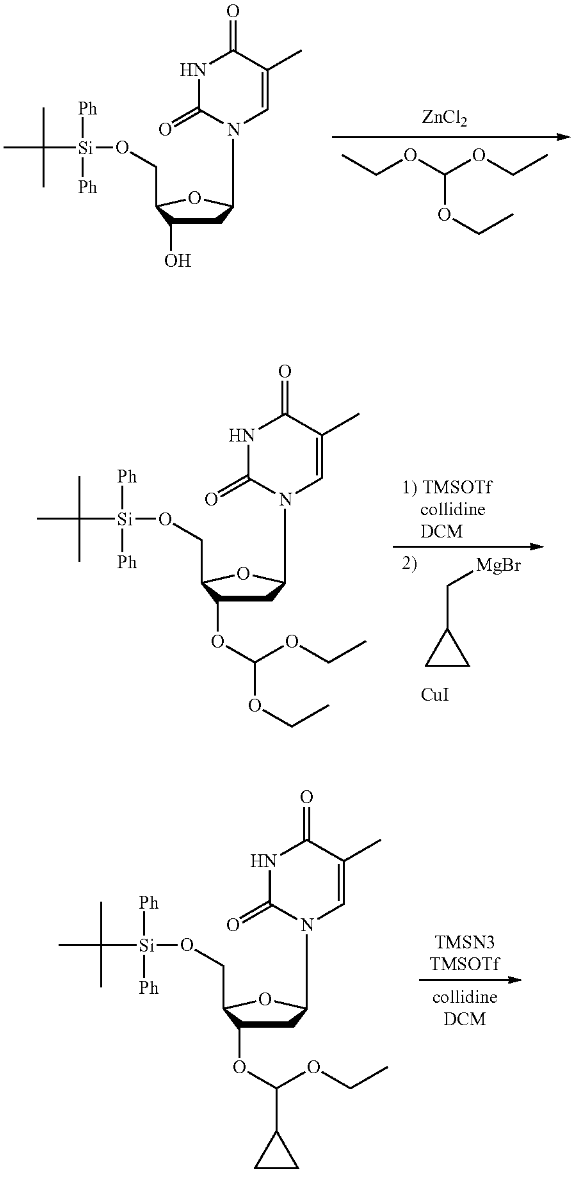

-continued

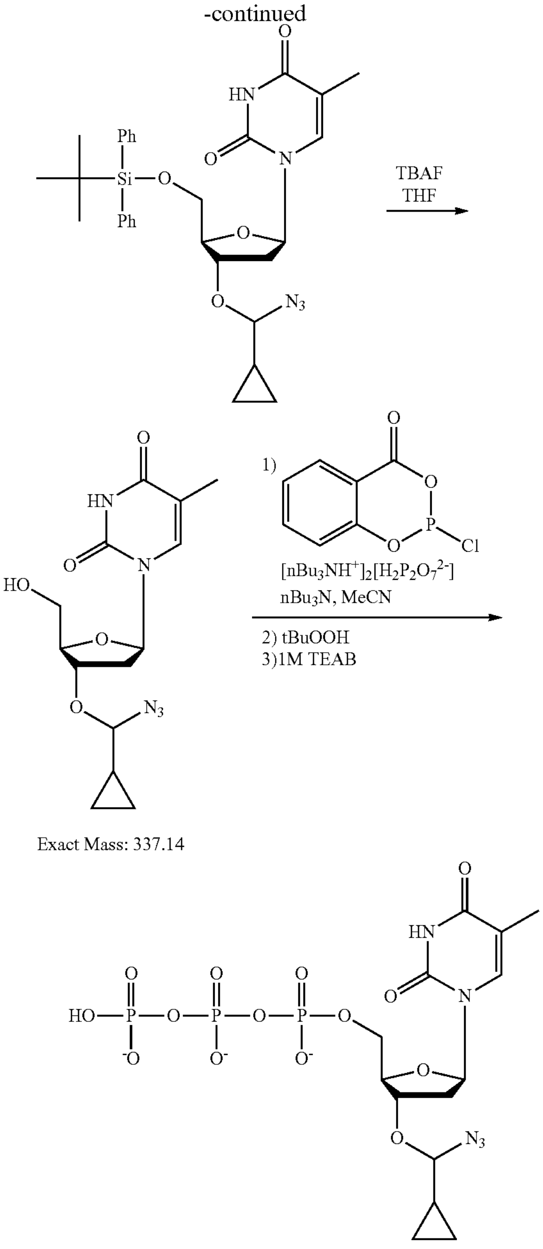

Example 3. Scarless Sequencing

Typical modified nucleotides were designed based on the rationale that each of the nucleotides is modified by attaching a unique cleavable fluorophore to the specific location of the base and capping the 3'-OH group with a small reversible-terminating moiety so they are still recognized by DNA polymerase as substrates. A potential disadvantage of this approach is the production of a small molecular "scar" (e.g., a propargylamine or a modified propargylamino moiety) at the nucleotide base after cleavage of the fluorescent dye from the incorporated nucleotide in the polymerase reaction. The growing DNA chain accumulates these scars through each successive round of SBS. In embodiments described herein, some compounds include a cyclic moiety (e.g., substituted or unsubstituted cycloalkyl, heterocycloalkyl, aryl, or heteroaryl) off the 3'-oxygen position (i.e., $R^7$ of Formula I) permitting the compounds to be "scarless" nucleotide reversible terminators (NRT) for DNA sequencing by synthesis (SBS). In embodiments, the base of the scarless nucleotides is a monovalent base. The 3' attached reporter indicated by the symbol $R^7$, may be fluorescent (e.g., a coumarin or coumarin derivative; non-limiting examples of coumarin derivatives are provided in Matikonda et al. Chem. Sci., 2020,11, 7302-7307, which is incorporated herein by reference). Such novel NRTs may be employed in a set for use in SBS, wherein each NRT is 3'-O reversibly blocked and is labeled with a fluorescent dye that has a unique fluorescence emission corresponding to the type of base of each nucleotide (e.g., a separate emission for A, T, G, and C respectively), thereby installing dual functions (serving as both a reversible blocker and a cleavable fluorescence reporter) to the 3'-O-modified nucleotide analogues. During SBS, after a nucleotide is incorporated, and the fluorescent reporter imaged, the 3'-O-dye will be cleaved with a cleaving agent (cleaving agents may include THPP or TCEP) to generate a 3'-OH group that is ready for subsequent extension reactions. Many fluorescent dye species (several of which are identified herein) are suitable for polymerase incorporation when attached to the 3'-O of these nucleotide analogues.

In embodiments, $R^7$ is a coumarin dye or a derivative thereof. In embodiments, $R^7$ is

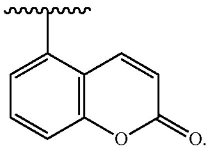 [SMILES: *c1cccc2oc(=O)ccc12]

In embodiments, $R^7$ is

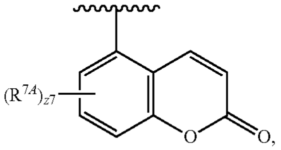

wherein $R^{7A}$ is as described herein, and z7 is an integer from 0 to 5. In embodiments, $R^7$ is

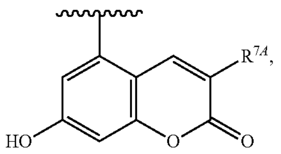

wherein $R^{7A}$ is as described herein. In embodiments, $R^7$ is

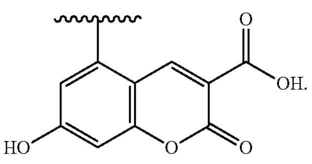 [SMILES: *c1cc(O)cc2oc(=O)c(C(=O)O)cc12]

In embodiments, $R^7$ is

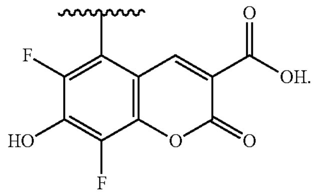 [SMILES: *c1c(F)c(O)c(F)c2oc(=O)c(C(=O)O)cc12]

In embodiments, $R^7$ is

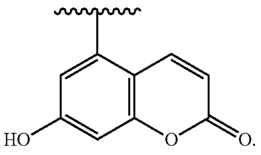 [SMILES: *c1cc(O)cc2oc(=O)ccc12]

In embodiments, $R^7$ is

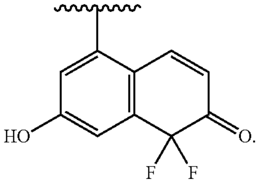 [SMILES: *c1cc(O)cc2c1C=CC(=O)C2(F)F]

In embodiments, $R^7$ is

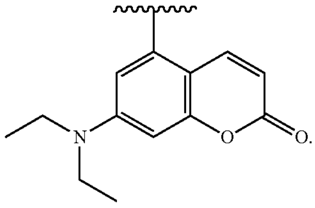 [SMILES: *c1cc(N(CC)CC)cc2oc(=O)ccc12]

In embodiments, $R^7$ is

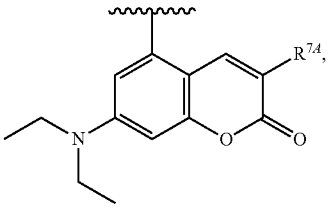

wherein $R^{7A}$ is as described herein. In embodiments, $R^7$ is In embodiments, $R^7$ is

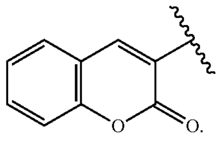 [SMILES: *c1cc2ccccc2oc1=O]

In embodiments, $R^7$ is

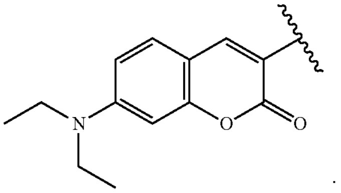 [SMILES: *c1cc2ccc(N(CC)CC)cc2oc1=O]

In embodiments, $R^7$ is

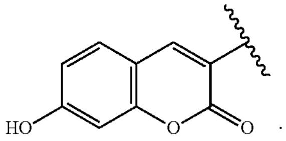 [SMILES: *c1cc2ccc(O)cc2oc1=O]

In embodiments, $R^7$ is

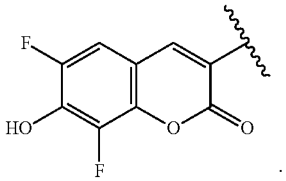 [SMILES: *c1cc2cc(F)c(O)c(F)c2oc1=O]

In embodiments, $R^7$ is

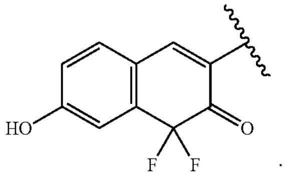 [SMILES: *C1=Cc2ccc(O)cc2C(F)(F)C1=O]

EMBODIMENTS

The present disclosure provides the following additional illustrative embodiments.

Embodiment P-1. A compound having the formula:

(I)

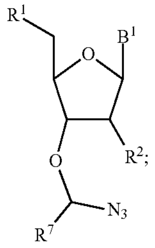

wherein $B^1$ is a nucleobase; $R^1$ is a polyphosphate moiety, 5'-O-nucleoside protecting group, monophosphate moiety, nucleic acid moiety, hydrogen, halogen, $—CCl_3$, $—CBr_3$, $—CF_3$, $—CI_3$, $—CHCl_2$, $—CHBr_2$, $—CHF_2$, $—CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a polymerase-compatible cleavable moiety; and $R^7$ is substituted or unsubstituted cycloalkyl, substituted or unsubstituted heterocycloalkyl, substituted or unsubstituted aryl, or substituted or unsubstituted heteroaryl.

Embodiment P-2. The compound of embodiment P-1, wherein $R^2$ is hydrogen.

Embodiment P-3. The compound of any one of embodiments P-1 to P-2, wherein $R^1$ is —OH, a 5'-O-nucleoside protecting group, monophosphate moiety, polyphosphate moiety, or nucleic acid moiety.

Embodiment P-4. The compound of any one of embodiments P-1 to P-2, wherein $R^1$ is a triphosphate moiety.

Embodiment P-5. The compound of any one of embodiments P-1 to P-4, wherein $B^1$ is a cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

Embodiment P-6. The compound of any one of embodiments P-1 to P-4, wherein $B^1$ is

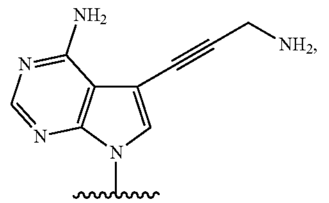

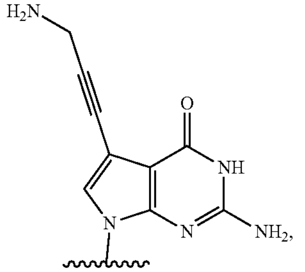

-continued

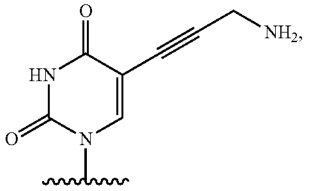

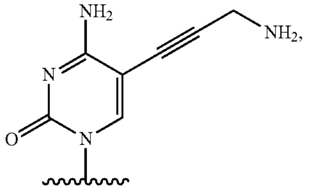

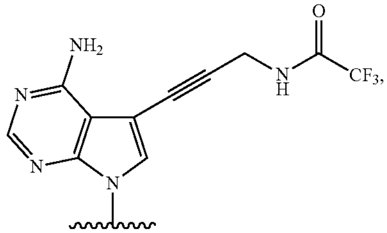

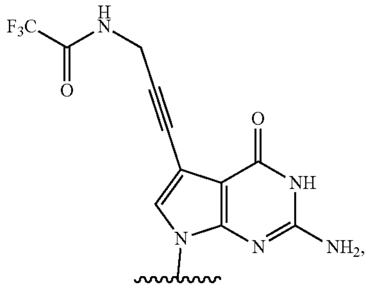

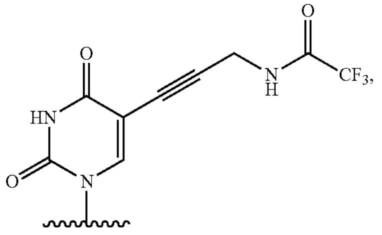

or

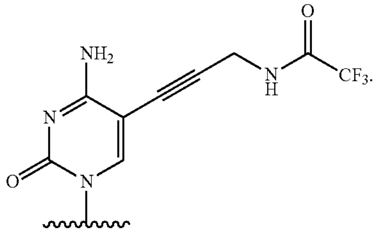

Embodiment P-7. The compound of any one of embodiments P-1 to P-4, wherein B is

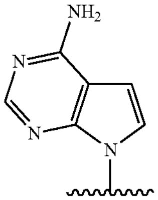

,

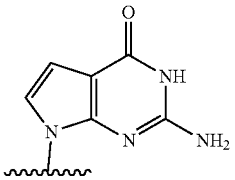

,

-continued

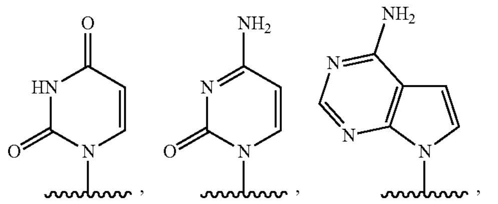

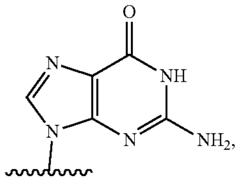

or

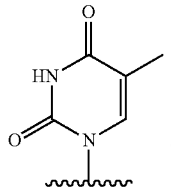

.

Embodiment P-8. The compound of any one of embodiments P-1 to P-4, wherein B is —B-$L^{100}$-$R^4$; B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof, $L^{100}$ is a divalent linker; and $R^4$ is a detectable moiety.

Embodiment P-9. The compound of embodiment P-8, wherein $L^{100}$ is a divalent linker comprising

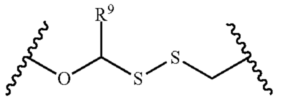

or

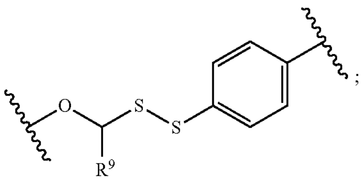

;

wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P-10. The compound of embodiment P-8, wherein $L^{100}$ is a divalent linker comprising

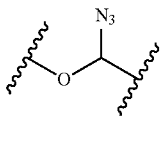

.

Embodiment P-11. The compound of embodiment P-8, wherein $L^{100}$ is a divalent linker comprising

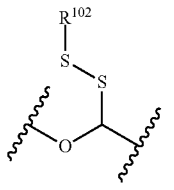

or

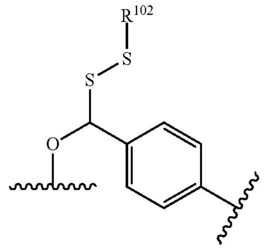

;

wherein $R^{102}$ is substituted or unsubstituted alkyl.

Embodiment P-12. The compound of embodiment P-8, wherein $L^{100}$ is -$L^{101}$-$L^{102}$-$L^{103}$-$L^{104}$-$L^{105}$-; $L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment P-13. The compound of embodiment P-12, wherein $L^{100}$ is

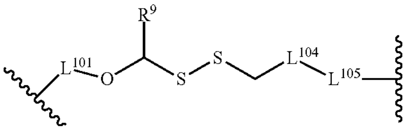

,

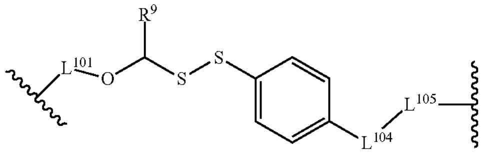

,

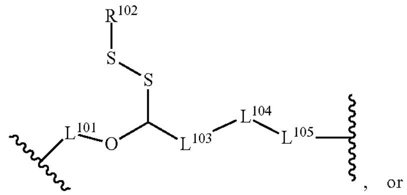

, or

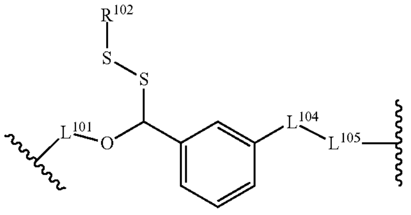

;

wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{102}$ is substituted or unsubstituted alkyl.

Embodiment P-14. The compound of embodiment P-12, wherein $L^{100}$ is

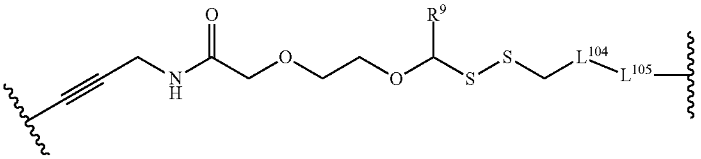

,

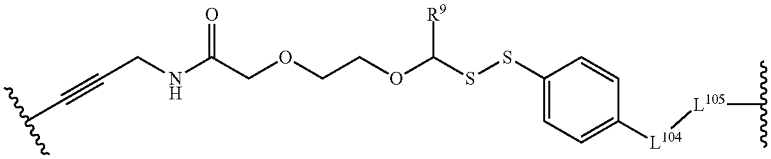

,

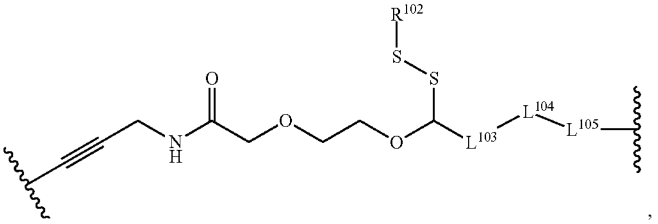

, or

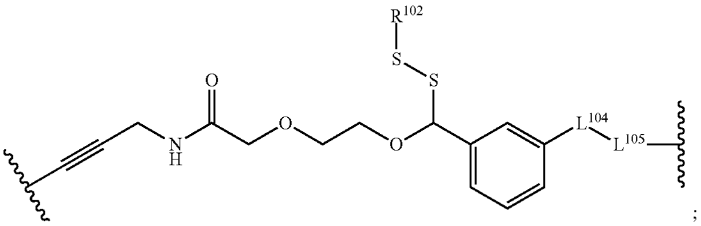

;

wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{102}$ is substituted or unsubstituted alkyl.

Embodiment P-15. The compound of any one of embodiments P-1 to P-14, wherein $R^7$ is substituted or unsubstituted aryl.

Embodiment P-16. The compound of any one of embodiments P-1 to P-14, wherein $R^7$ is substituted or unsubstituted heteroaryl.

Embodiment P-17. The compound of any one of embodiments P-1 to P-14, wherein $R^7$ is substituted or unsubstituted cycloalkyl, or substituted or unsubstituted heterocycloalkyl.

Embodiment P-18. The compound of any one of embodiments P-1 to P-14, wherein $R^7$ is unsubstituted cycloalkyl.

Embodiment P-19. The compound of any one of embodiments P-1 to P-14, wherein $R^7$ is substituted or unsubstituted 5 to 6 membered heteroaryl.

Embodiment P-20. The compound of any one of embodiments P-1 to P-14, wherein $R^7$

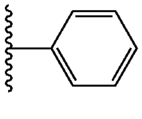

,

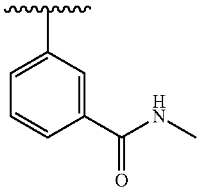

,

-continued

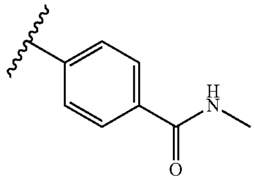

,

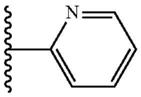

,

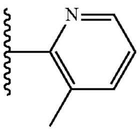

,

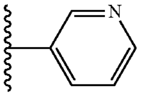

,

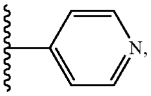

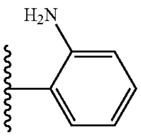

,

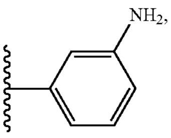

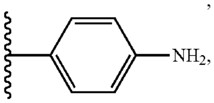

,

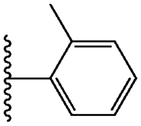

,

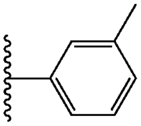

,

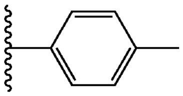

,

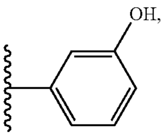

,

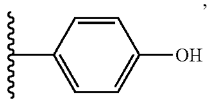

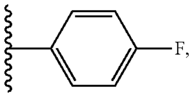

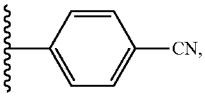

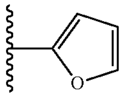

,

-continued
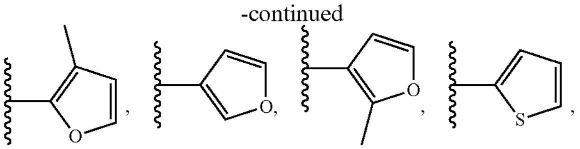
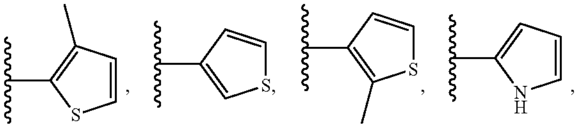
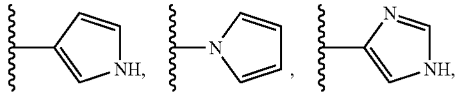
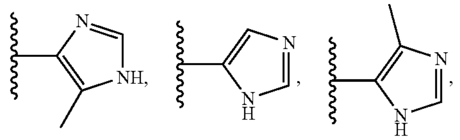
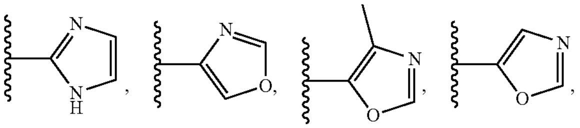
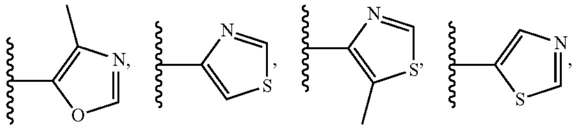
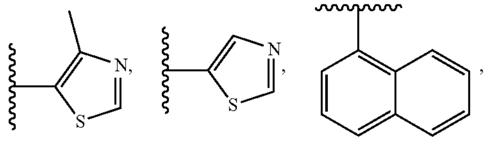
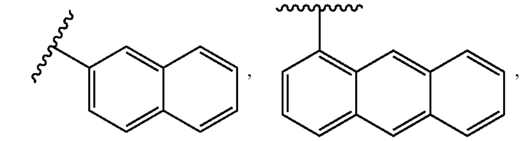
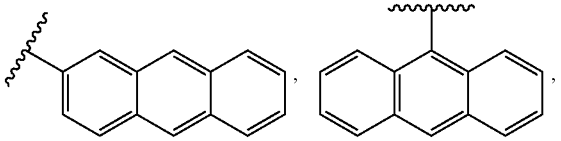
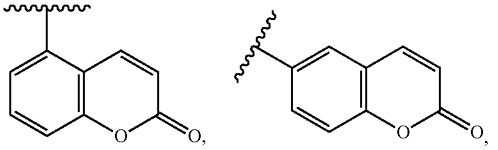
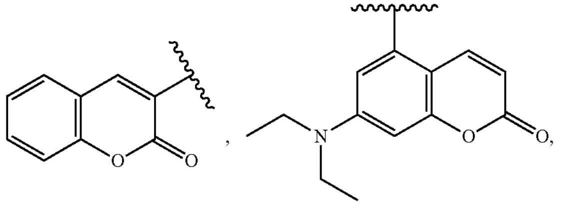
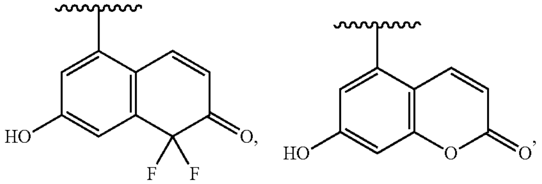
-continued
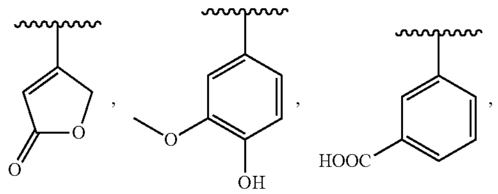
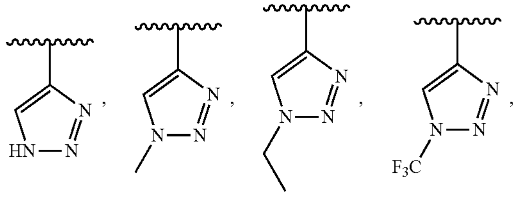
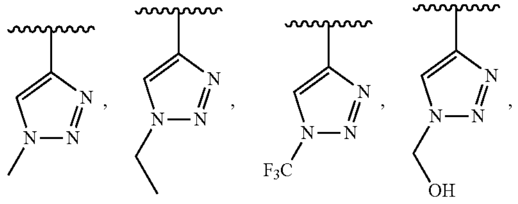
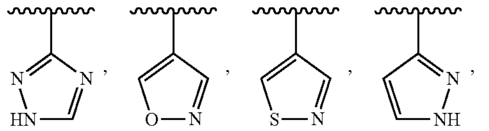
or
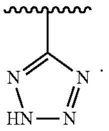
Embodiment P-21. The compound of embodiment P-1, having the formula:
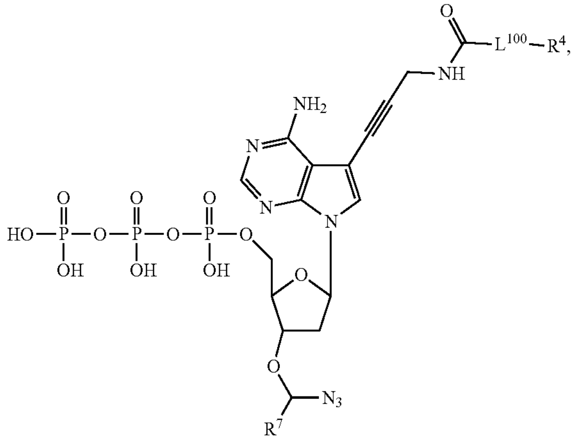

-continued

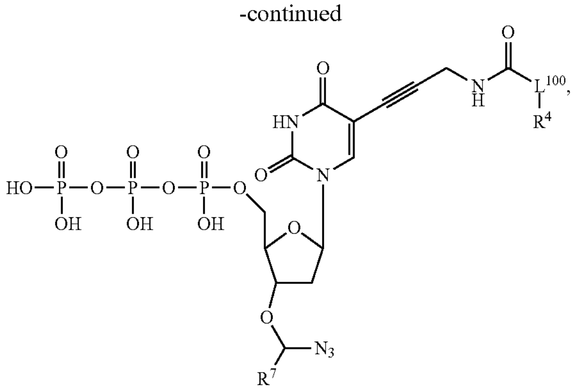

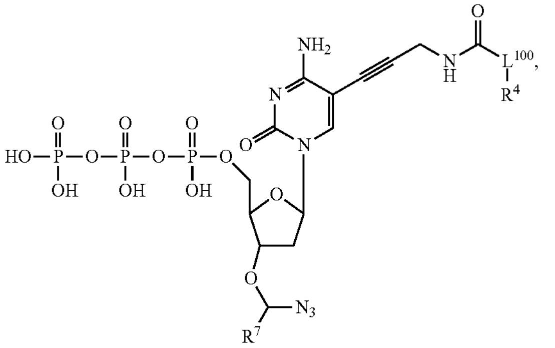

or

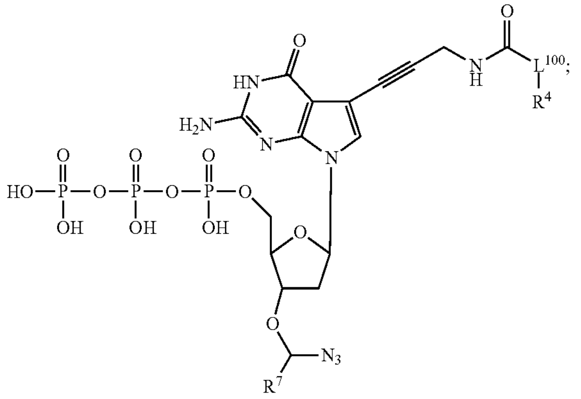

wherein $L^{100}$ is a cleavable linker; and $R^4$ is a detectable moiety.

Embodiment P-22. A compound having the formula:

(II)

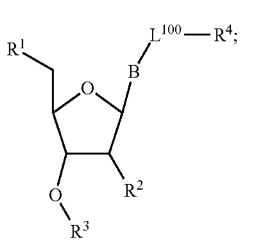

wherein B is a divalent nucleobase; $R^1$ is a polyphosphate moiety, 5'-O-nucleoside protecting group, monophosphate moiety, nucleic acid moiety, hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety; $R^3$ is a polymerase-compatible cleavable moiety; $R^4$ is a detectable moiety; $L^{100}$ is a divalent linker comprising

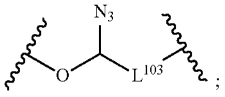

;

and $L^{103}$ is substituted or unsubstituted cycloalkylene, substituted or unsubstituted heterocycloalkylene, substituted or unsubstituted arylene, substituted or unsubstituted heteroarylene.

Embodiment P-23. The compound of embodiment P-22, wherein $L^{100}$ is $-L^{101}-OCH(N_3)-L^{103}-L^{104}-L^{105}-$; $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment P-24. The compound of embodiment P-23, having the formula:

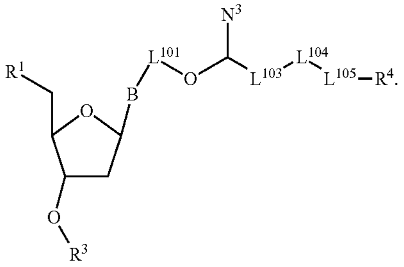

Embodiment P-25. The compound of any one of embodiments P-22 to P-24, wherein $R^1$ is —OH, a 5'-O-nucleoside protecting group, monophosphate moiety, polyphosphate moiety, or nucleic acid moiety.

Embodiment P-26. The compound of any one of embodiments P-22 to P-24, wherein $R^1$ is a triphosphate moiety.

Embodiment P-27. The compound of any one of embodiments P-22 to P-26, wherein the polymerase-compatible cleavable moiety is independently -(substituted or unsubstituted alkylene)-SS-(unsubstituted alkyl).

Embodiment P-28. The compound of any one of embodiments P-22 to P-26, wherein the polymerase-compatible cleavable moiety is

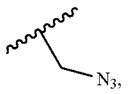
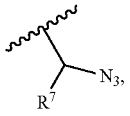
or
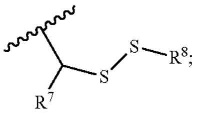

wherein $R^7$ is substituted or unsubstituted cycloalkyl, substituted or unsubstituted heterocycloalkyl, substituted or unsubstituted aryl, substituted or unsubstituted heteroaryl; and $R^8$ is unsubstituted $C_1$-$C_6$ alkyl.

Embodiment P-29. The compound of any one of embodiments P-22 to P-26, wherein the polymerase-compatible cleavable moiety is independently:

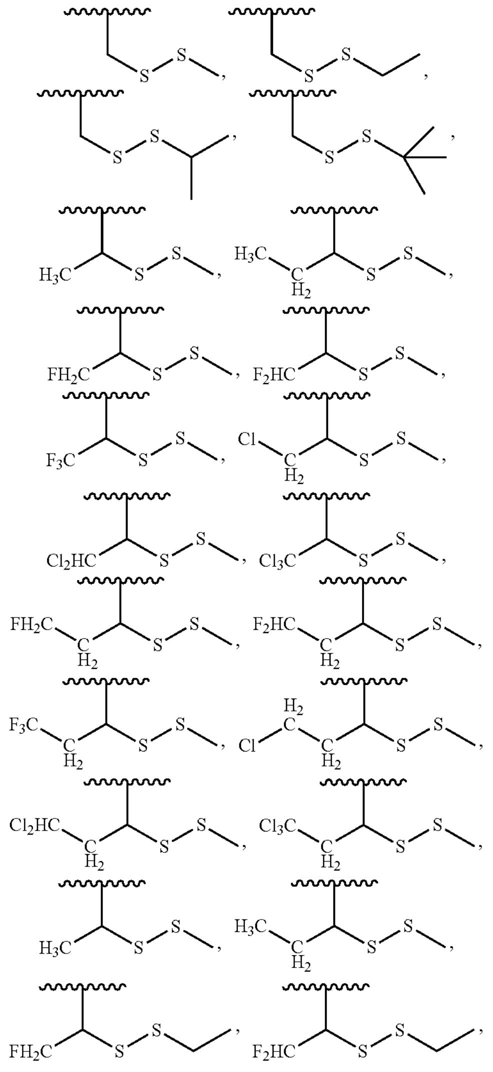

-continued

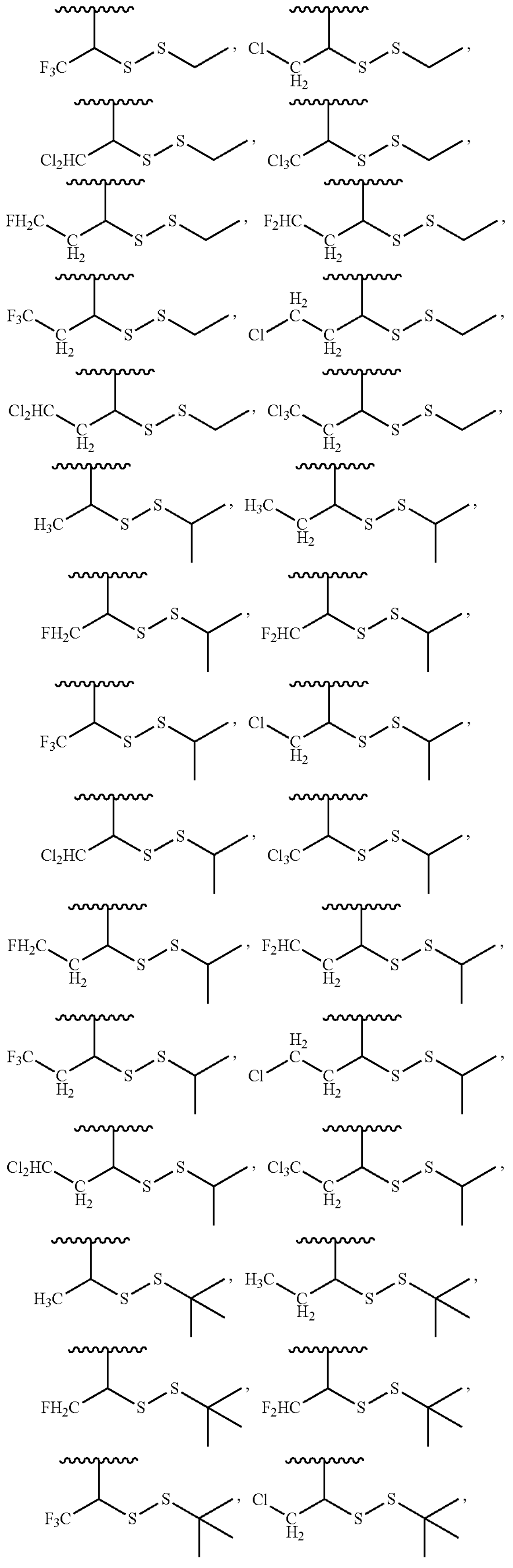

-continued

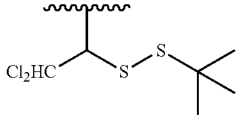
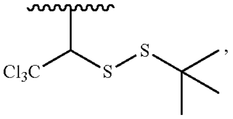
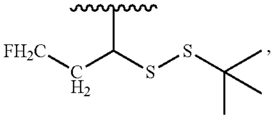
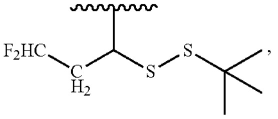
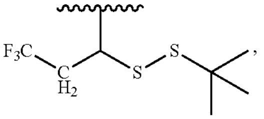
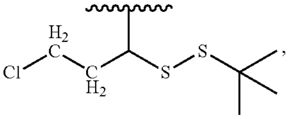
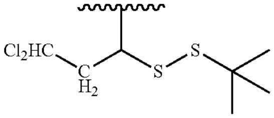
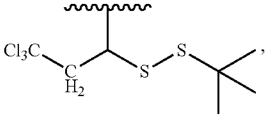
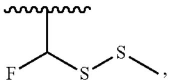
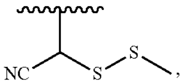
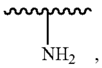
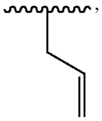
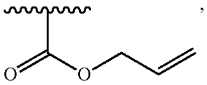
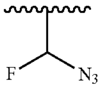
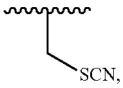
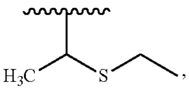
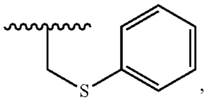
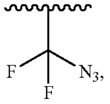
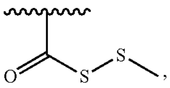
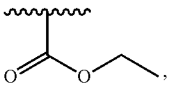
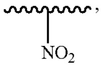
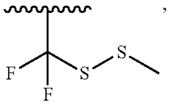
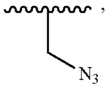
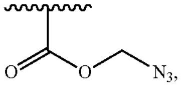
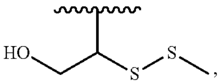
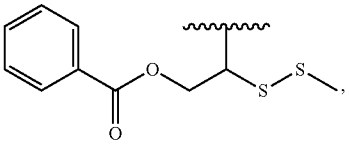
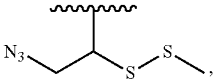
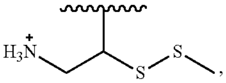
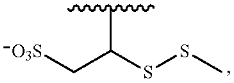
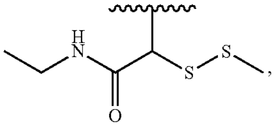
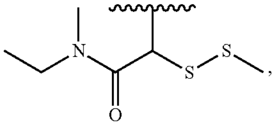
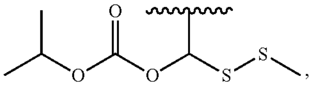

-continued

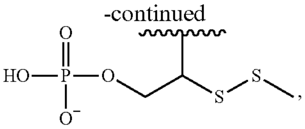
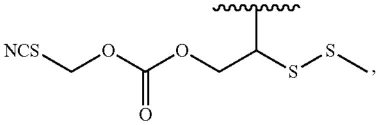
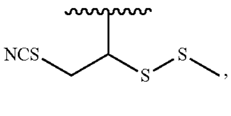
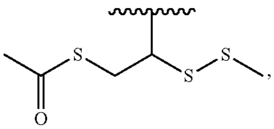
or
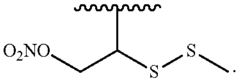

Embodiment P-30. A method for sequencing a nucleic acid, comprising: (i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label; (ii) detecting said unique detectable label of each incorporated compound, so as to thereby identify each incorporated compound in said extension strand, thereby sequencing the nucleic acid; wherein each of said four different compounds is independently a compound of one of embodiments P-1 to P-29.

Embodiment P-31. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of one of embodiments P-1 to P-29.

Embodiment P-32. A nucleic acid polymerase complex comprising a nucleic acid polymerase, wherein said nucleic acid polymerase is bound to a compound of one of embodiments P-1 to P-29.

Embodiment P-33. A method of preparing or synthesizing a compound of Formula (I)

(I)

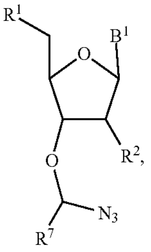

said method comprising mixing compound A1, compound B1, and an azidolating reagent together in a reaction vessel, wherein compound (A) has the formula:

(A)

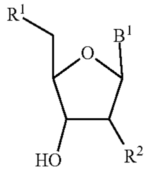

and compound (B) has the formula:

(B)

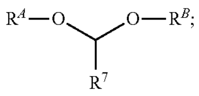

wherein $B^1$ is a nucleobase; $R^1$ is a polyphosphate moiety, 5'-O-nucleoside protecting group, monophosphate moiety, nucleic acid moiety, hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a polymerase-compatible cleavable moiety; $R^A$ and $R^B$ are independently hydrogen or substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^7$ is substituted or unsubstituted cycloalkyl, substituted or unsubstituted heterocycloalkyl, substituted or unsubstituted aryl, or substituted or unsubstituted heteroaryl.

Embodiment P-34. The compound of embodiment P-13, wherein $L^{101}$ is

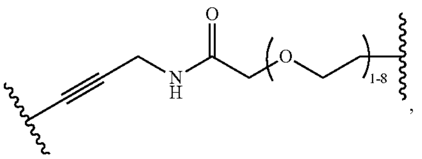

-continued

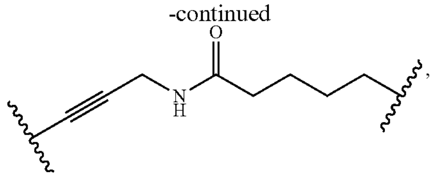

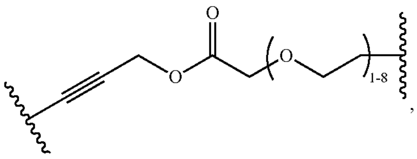

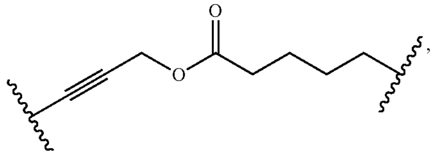

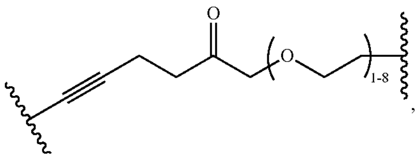

or

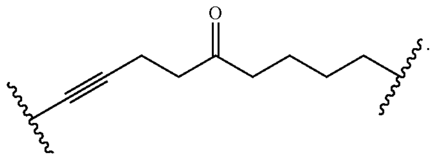

Embodiment P-35. The compound of embodiment P-13, wherein $L^{101}$ is

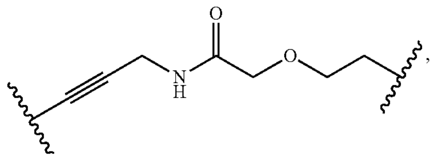

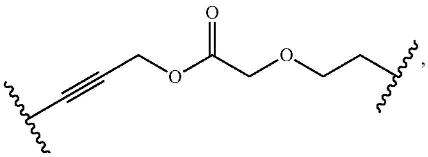

or

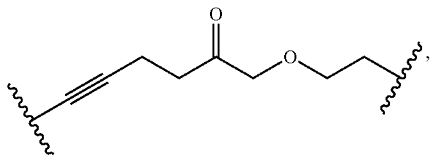

Embodiment P-36. The compound of embodiment P-24, wherein $L^{101}$ is

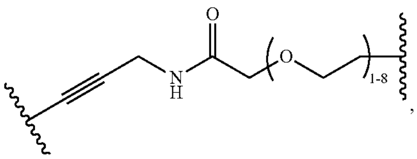

-continued

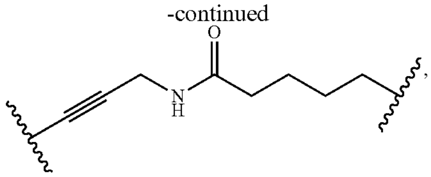

,

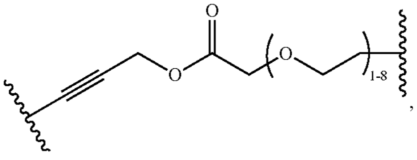

,

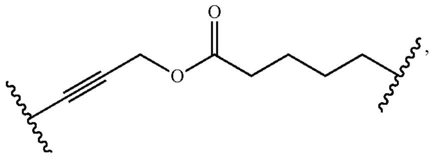

,

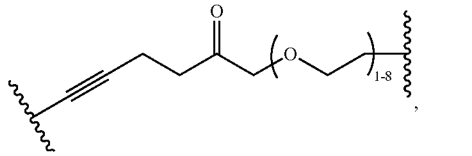

, or

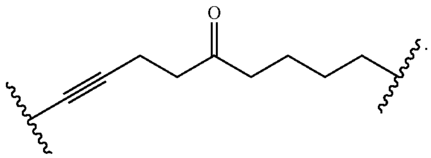

.

Embodiment P-37. The compound of embodiment P-24, wherein $L^{101}$ is

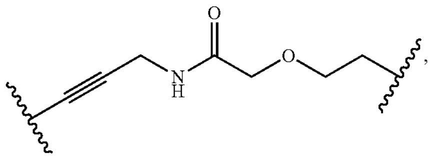

,

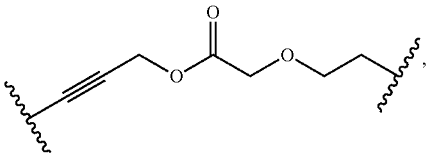

, or

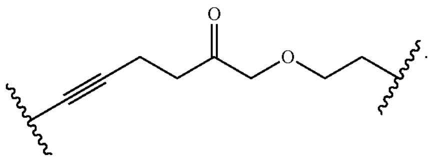

.

Additional Embodiments

Embodiment 1. A compound having the formula:

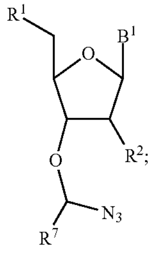

(I)

wherein $B^1$ is a nucleobase; $R^1$ is a polyphosphate moiety, 5'-O-nucleoside protecting group, monophosphate moiety, nucleic acid moiety, hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a polymerase-compatible cleavable moiety; and $R^7$ is substituted or unsubstituted cycloalkyl, substituted or unsubstituted heterocycloalkyl, substituted or unsubstituted aryl, or substituted or unsubstituted heteroaryl.

Embodiment 2. The compound of embodiment 1, wherein $R^2$ is hydrogen.

Embodiment 3. The compound of any one of embodiments 1 to 2, wherein $R^1$ is $-OH$, a 5'-O-nucleoside protecting group, monophosphate moiety, polyphosphate moiety, or nucleic acid moiety.

Embodiment 4. The compound of any one of embodiments 1 to 3, wherein $B^1$ is

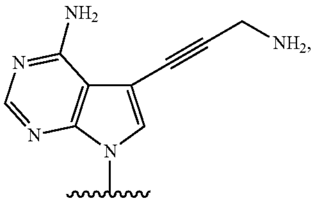

-continued

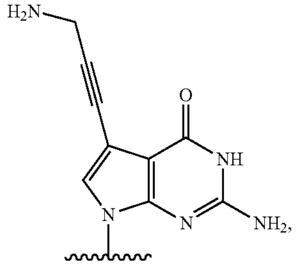

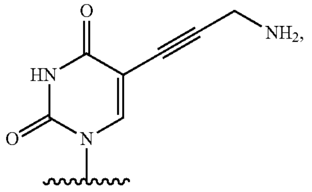

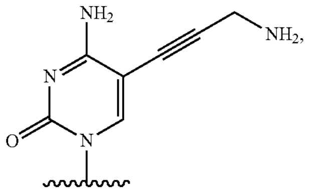

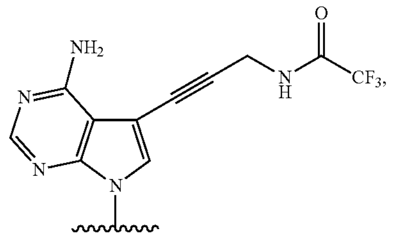

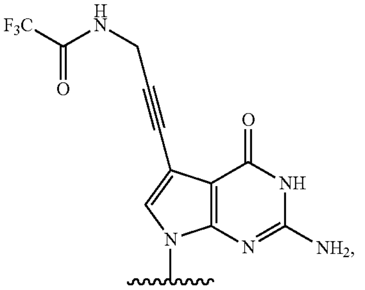

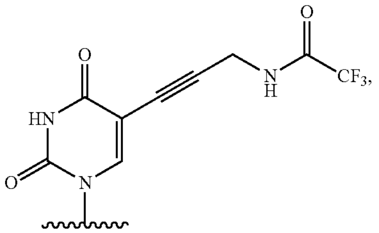

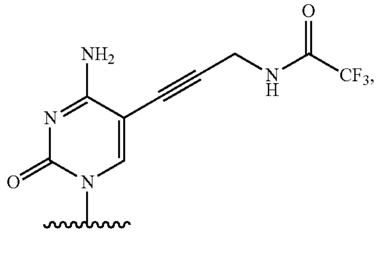

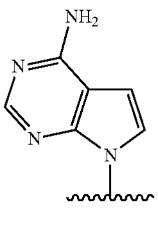
,

-continued

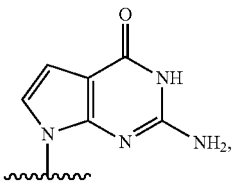

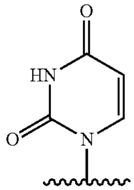
,

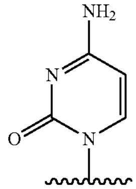
,

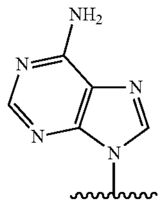
,

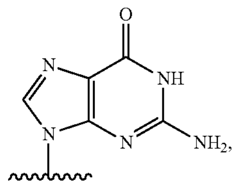
or

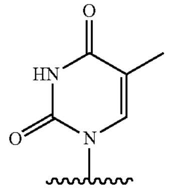
.

Embodiment 5. The compound of any one of embodiments 1 to 4, wherein $B^1$ is —B-$L^{100}$-$R^4$; B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof, $L^{100}$ is a divalent linker; and $R^4$ is a detectable moiety.

Embodiment 6. The compound of embodiment 5, wherein $L^{100}$ is a divalent linker comprising

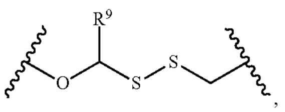
,

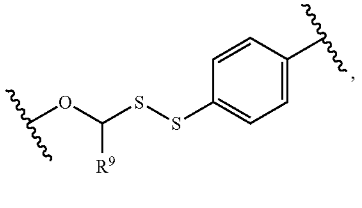
,

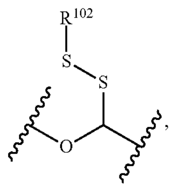
,

-continued

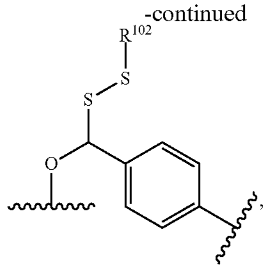

or

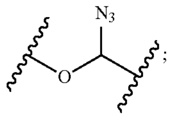

wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{102}$ is substituted or unsubstituted alkyl.

Embodiment 7. The compound of embodiment 5, wherein $L^{100}$ is $-L^{101}-L^{102}-L^{103}-L^{104}-L^{105}-$; and $L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 8. The compound of embodiment 5 or embodiment 7, wherein $L^{100}$ is

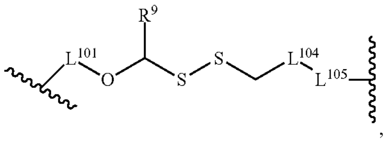

,

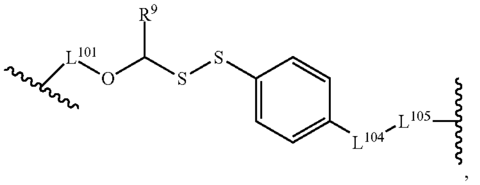

,

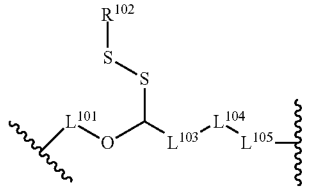

, or

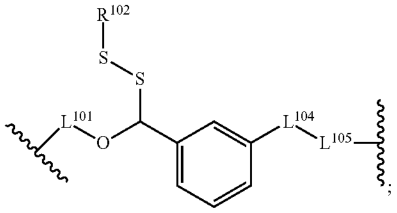

;

wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{102}$ is substituted or unsubstituted alkyl.

Embodiment 9. The compound of any one of embodiments 1 to 8, wherein $R^7$ is substituted or unsubstituted 5 to 6 membered heteroaryl.

Embodiment 10. The compound of any one of embodiments 1 to 8, wherein $R^7$ is

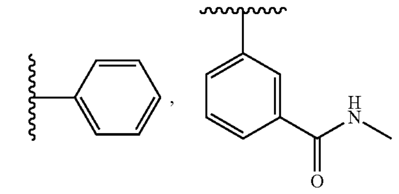

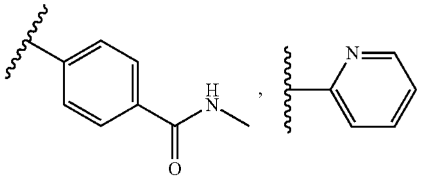

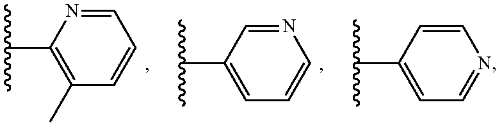

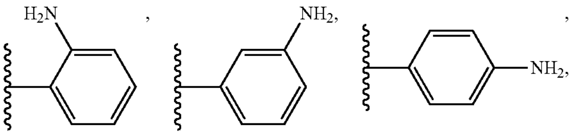

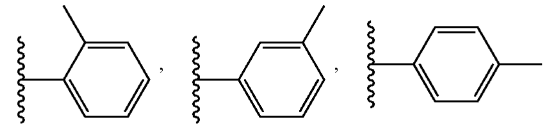

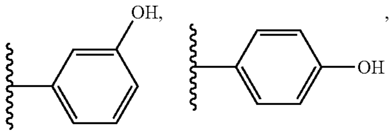

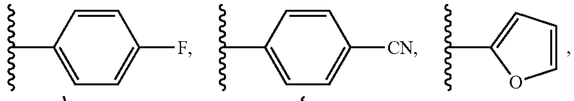

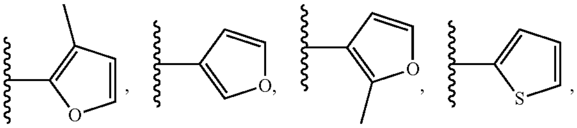

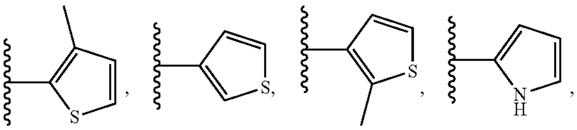

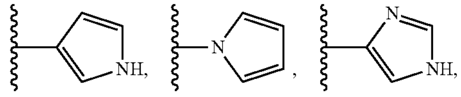

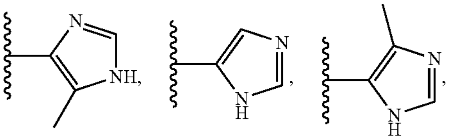

-continued
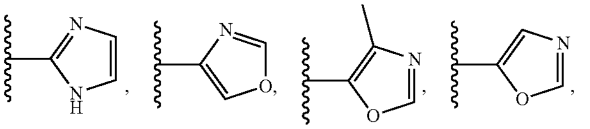
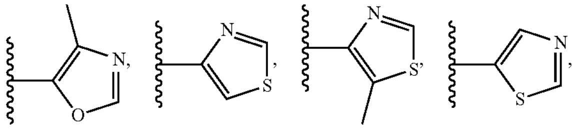
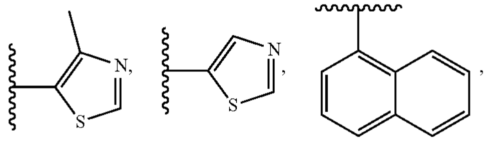
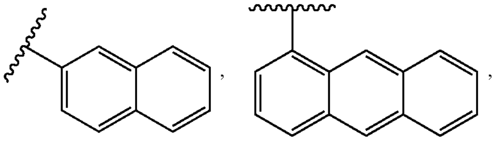
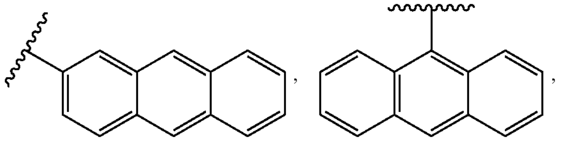
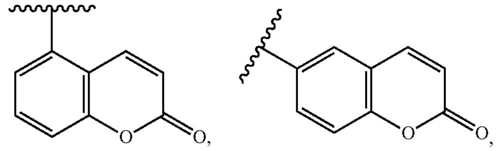
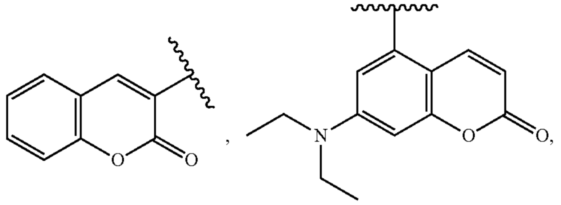
-continued
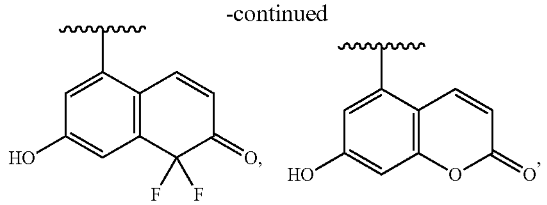
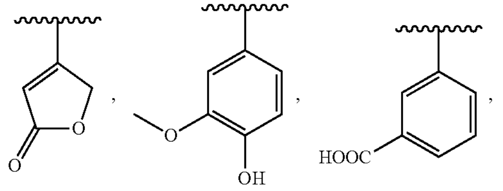
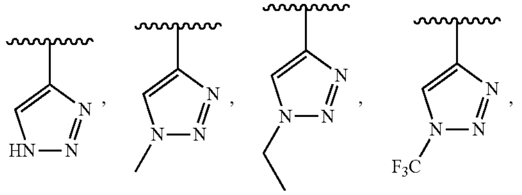
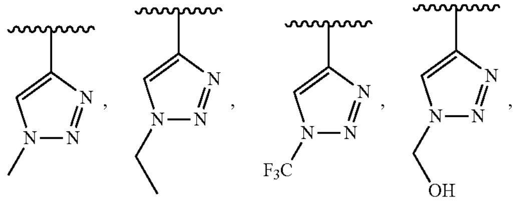
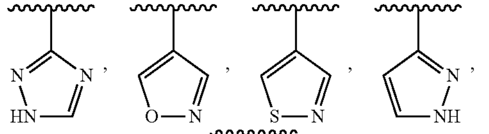
or
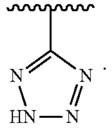
Embodiment 11. The compound of embodiment 1, having the formula:
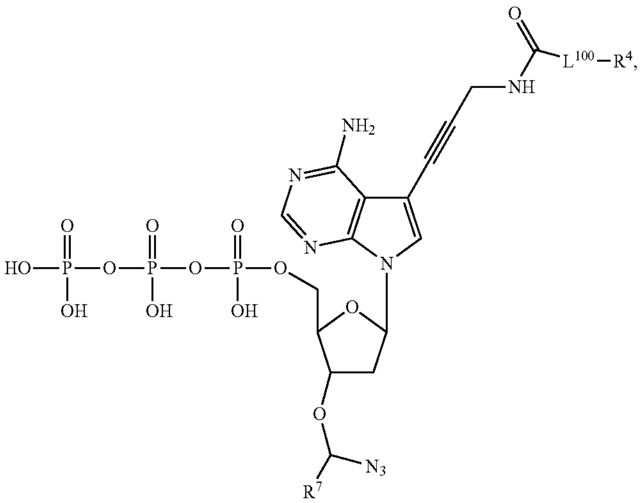

-continued
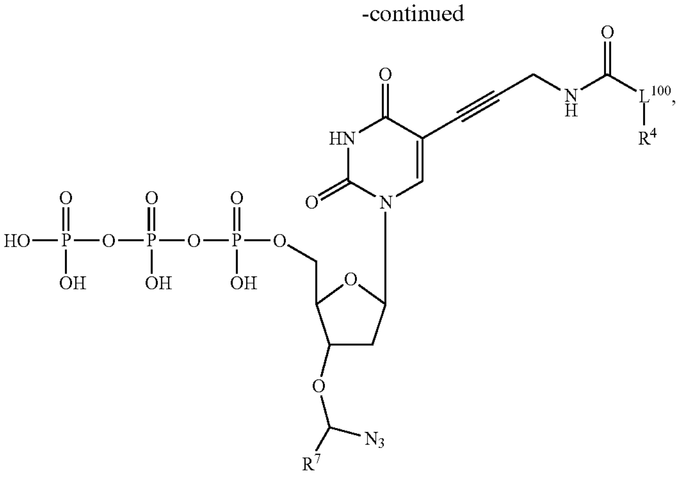
,
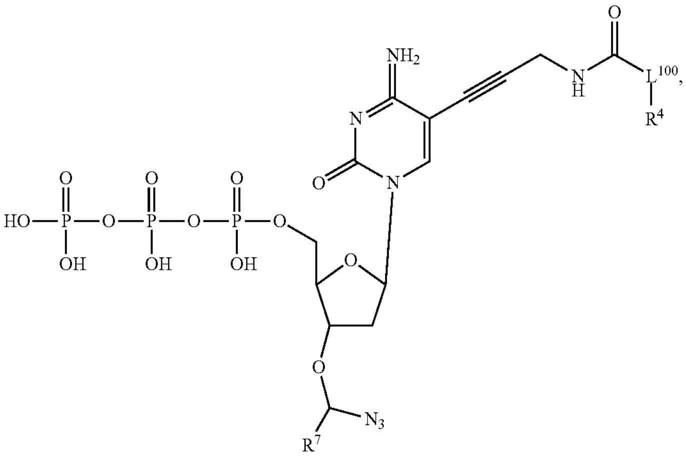
, or
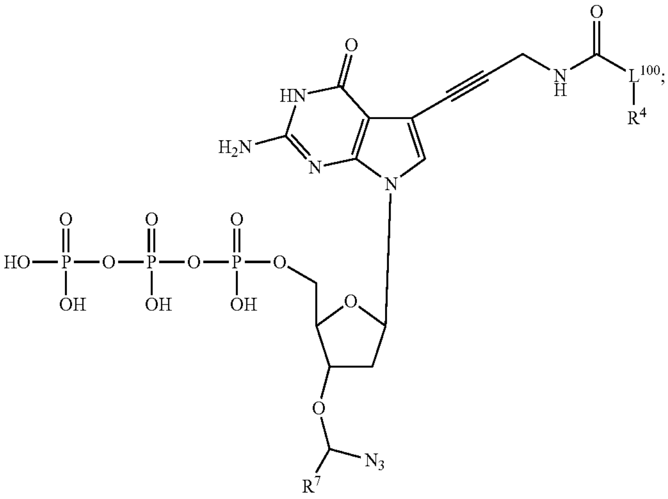
;
wherein $L^{100}$ is a cleavable linker; and $R^4$ is a detectable moiety.

Embodiment 12. A compound having the formula:

(II)

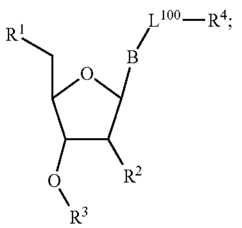

wherein B is a divalent nucleobase; $R^1$ is a polyphosphate moiety, 5'-O-nucleoside protecting group, monophosphate moiety, nucleic acid moiety, hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety; $R^3$ is a polymerase-compatible cleavable moiety; $R^4$ is a detectable moiety; $L^{100}$ is a divalent linker comprising

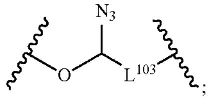

and $L^{103}$ is substituted or unsubstituted cycloalkylene, substituted or unsubstituted heterocycloalkylene, substituted or unsubstituted arylene, substituted or unsubstituted heteroarylene.

Embodiment 13. The compound of embodiment 12, having the formula:

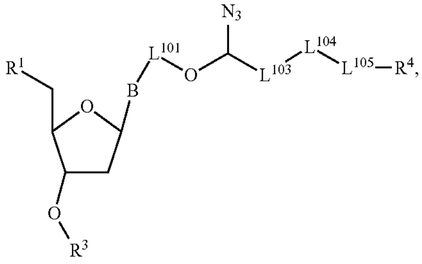

wherein $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 14. The compound of embodiment 12 or embodiment 13, wherein $R^1$ is —OH, a 5'-O-nucleoside protecting group, monophosphate moiety, polyphosphate moiety, or nucleic acid moiety.

Embodiment 15. The compound of any one of embodiments 12 to 14, wherein the polymerase-compatible cleavable moiety is independently:

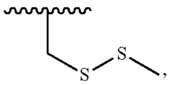 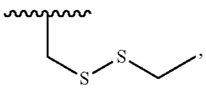

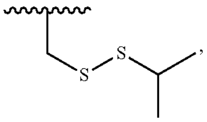 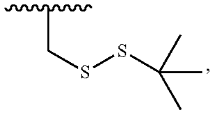

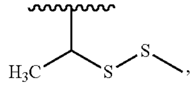 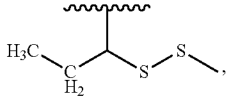

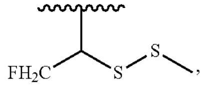 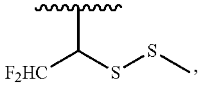

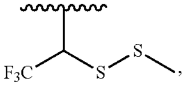 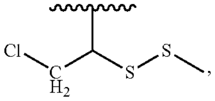

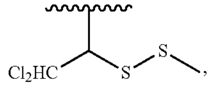 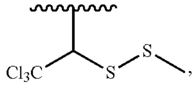

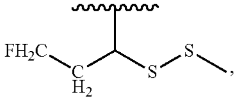 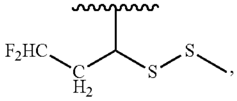

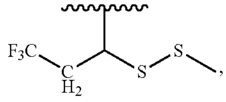 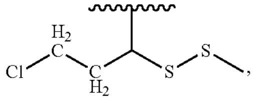

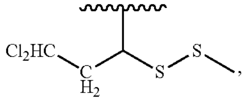 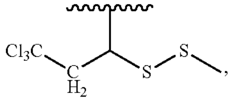

-continued
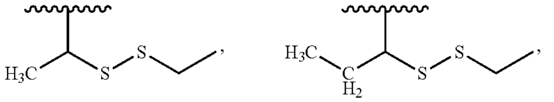
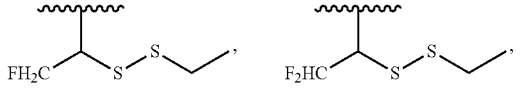
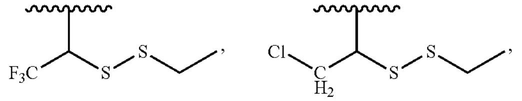
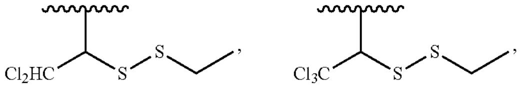
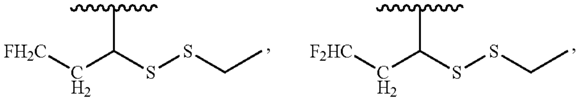
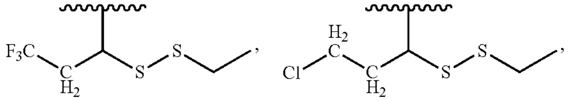
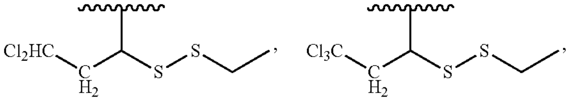
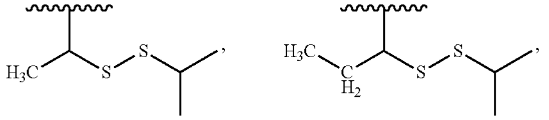
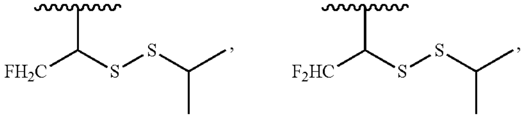
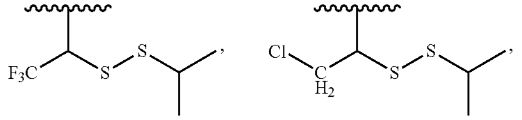
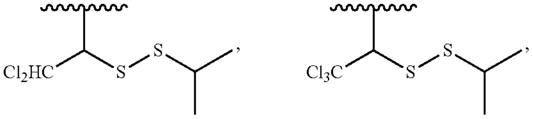
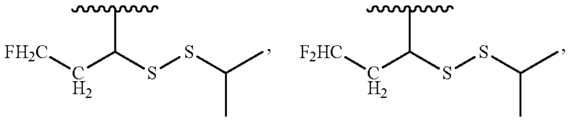
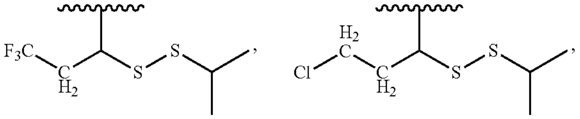
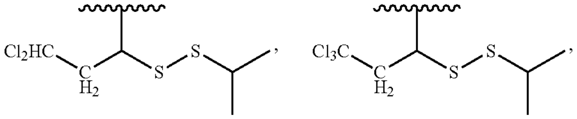
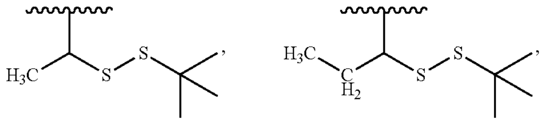
-continued
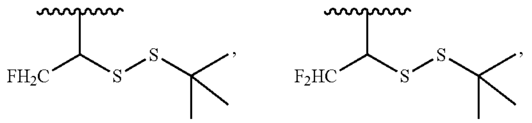
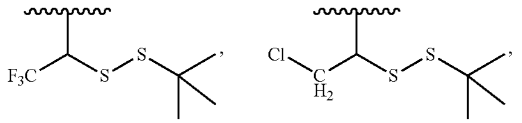
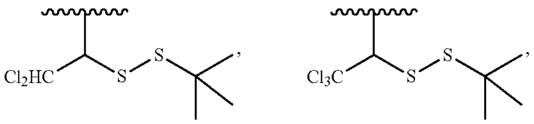
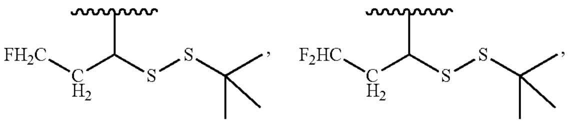
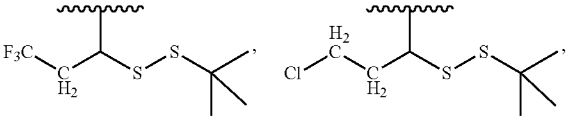
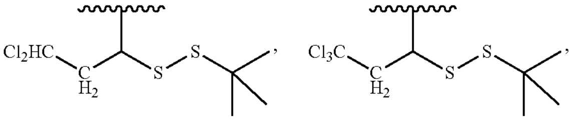
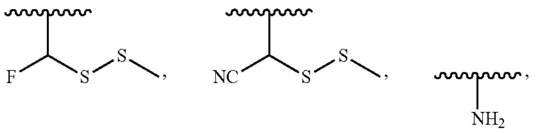
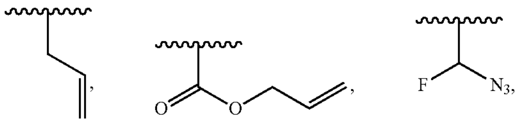
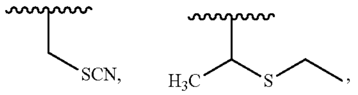
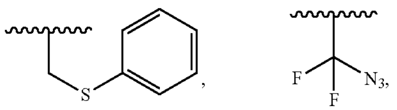
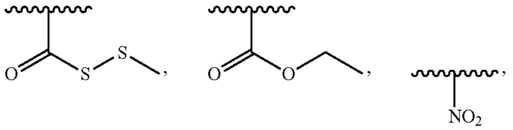
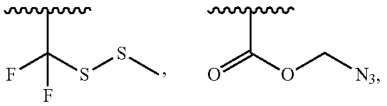
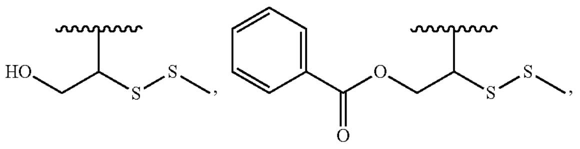
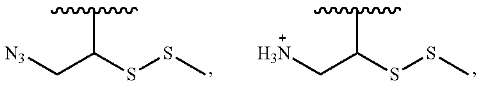

-continued

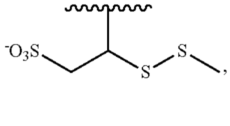
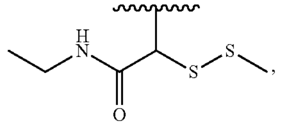
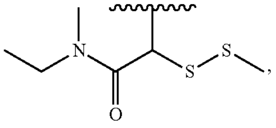
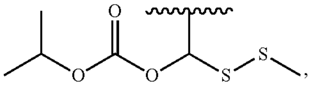
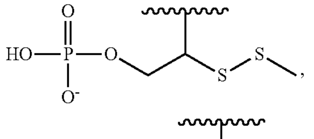
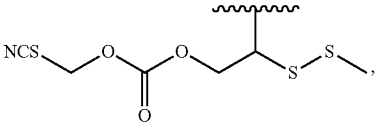
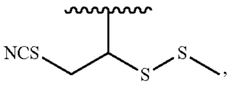
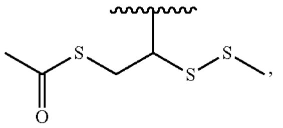
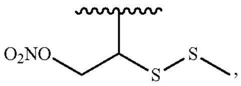
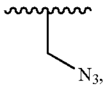

or

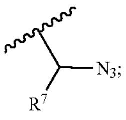

and $R^7$ is substituted or unsubstituted cycloalkyl, substituted or unsubstituted heterocycloalkyl, substituted or unsubstituted aryl, substituted or unsubstituted heteroaryl.

Embodiment 16. A method for sequencing a nucleic acid, comprising: (i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label; and (ii) detecting said unique detectable label of each incorporated compound, so as to thereby identify each incorporated compound in said extension strand, thereby sequencing the nucleic acid; wherein each of said four different compounds is independently a compound of any one of embodiments 1 to 15.

Embodiment 17. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of any one of embodiments 1 to 15.

Embodiment 18. A nucleic acid polymerase complex comprising a nucleic acid polymerase, wherein said nucleic acid polymerase is bound to any one of embodiments 1 to 15.

Embodiment 19. A method of preparing or synthesizing a compound of Formula (I)

(I)

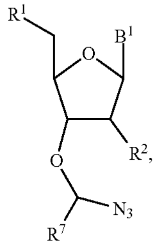

said method comprising mixing compound (A), compound (B), and an azidolating reagent together in a reaction vessel, wherein compound (A) has the formula:

(A)

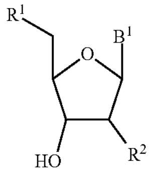

and compound (B) has the formula:

(B)

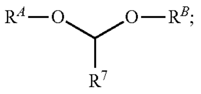

wherein $B^1$ is a nucleobase; $R^1$ is a polyphosphate moiety, 5'-O-nucleoside protecting group, monophosphate moiety, nucleic acid moiety, hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a polymerase-compatible cleavable moiety; $R^A$ and $R^B$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^7$ is substituted or unsubstituted cycloalkyl, substituted or unsubstituted heterocycloalkyl, substituted or unsubstituted aryl, or substituted or unsubstituted heteroaryl.

Embodiment 20. The compound of embodiment 8 or embodiment 13, wherein $L^{101}$ is

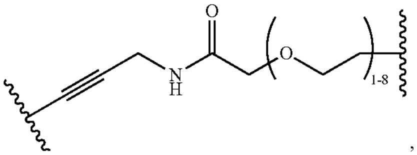

,

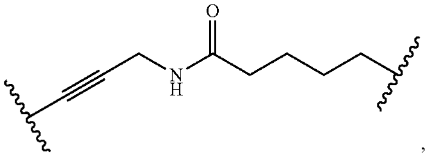

,

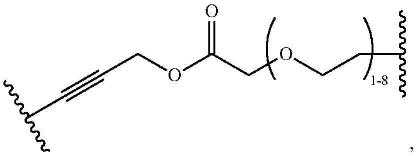

,

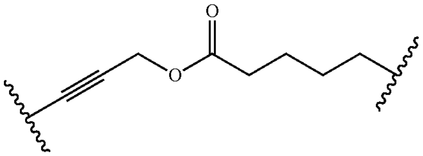

,

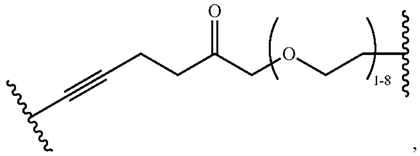

, or

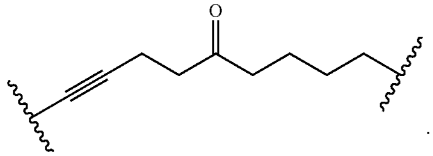

.

What is claimed is:

1. A compound having the formula:

(I)

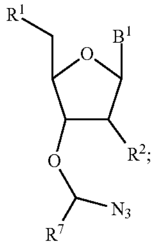

wherein $B^1$ is a nucleobase;

$R^1$ is a polyphosphate moiety, 5'-O-nucleoside protecting group, monophosphate moiety, nucleic acid moiety, hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a polymerase-compatible cleavable moiety; and $R^7$ is substituted or unsubstituted cycloalkyl, substituted or unsubstituted heterocycloalkyl, substituted or unsubstituted aryl, or substituted or unsubstituted heteroaryl.

2. The compound of claim 1, wherein $R^2$ is hydrogen.

3. The compound of claim 1, wherein $R^1$ is $-OH$, a 5'-O-nucleoside protecting group, monophosphate moiety, polyphosphate moiety, or nucleic acid moiety.

4. The compound of claim 1, wherein $B^1$ is

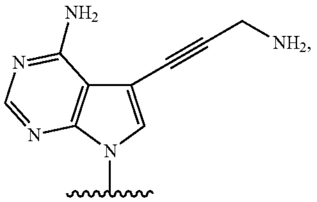

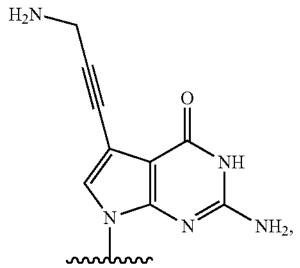

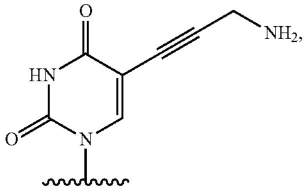

-continued

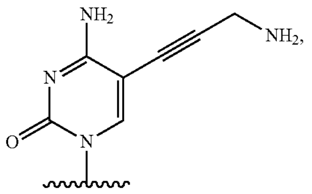

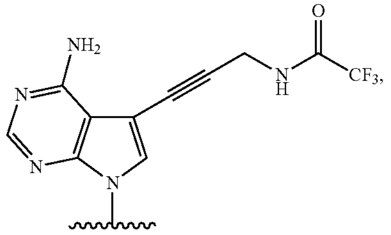

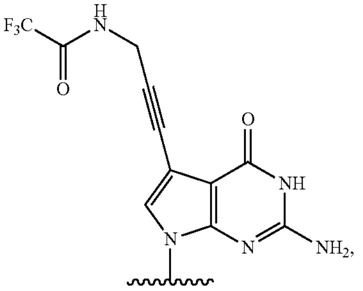

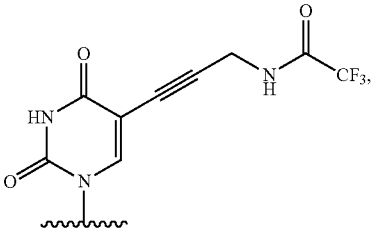

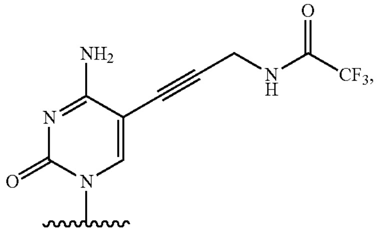

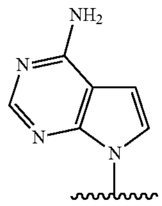
,

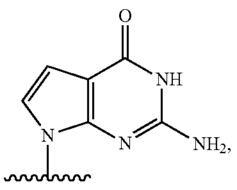

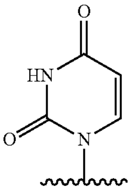
,

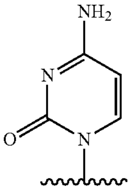
,

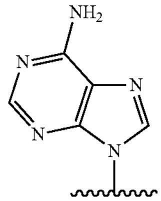
,

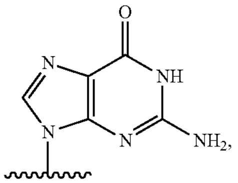
or

-continued

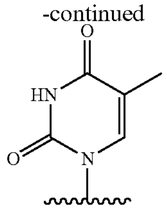
.

5. The compound of claim 1, wherein $B^1$ is —B-$L^{100}$-$R^4$;

B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof;

$L^{100}$ is a divalent linker; and $R^4$ is a detectable moiety.

6. The compound of claim 5, wherein L100 is a divalent linker comprising

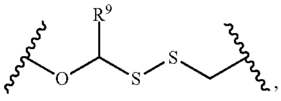

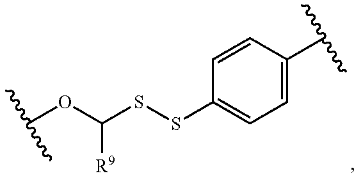
,

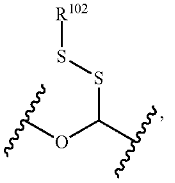

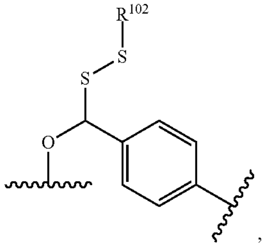
, or

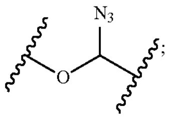

wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{102}$ is substituted or unsubstituted alkyl.

7. The compound of claim 5, wherein $L^{100}$ is $-L^{101}-L^{102}-L^{103}-L^{104}-L^{105}-$; and $L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

8. The compound of claim 7, wherein $L^{100}$ is

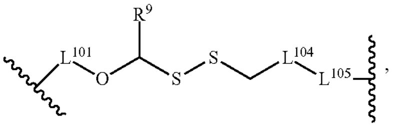

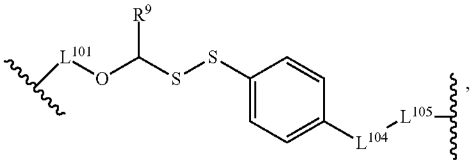

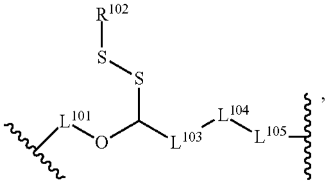

or

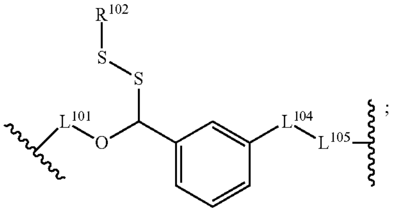

wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{102}$ is substituted or unsubstituted alkyl.

9. The compound of claim 1, wherein $R^7$ is substituted or unsubstituted 5 to 6 membered heteroaryl.

10. The compound of claim 1, wherein $R^7$ is

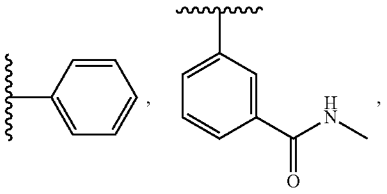

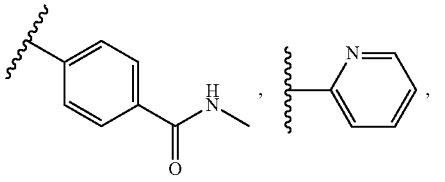

-continued

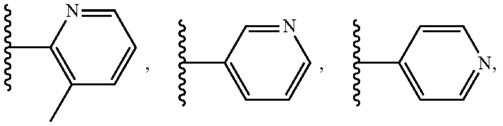

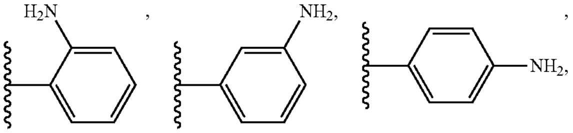

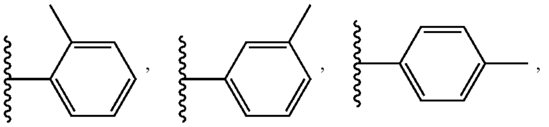

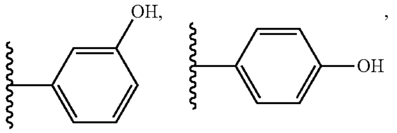

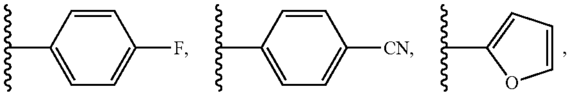

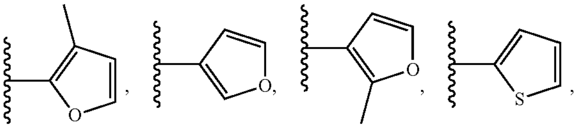

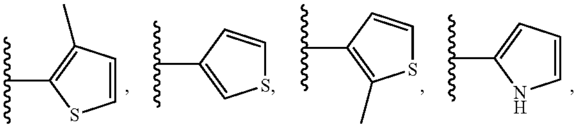

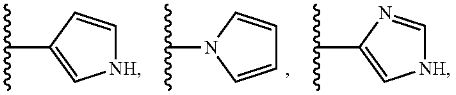

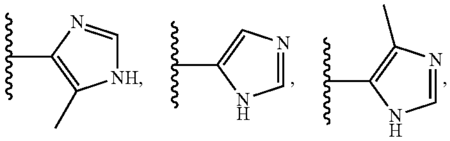

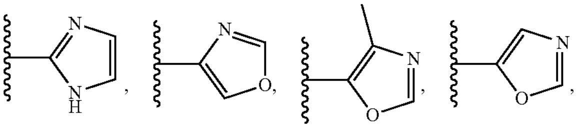

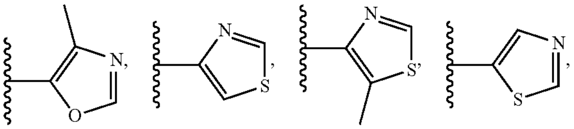

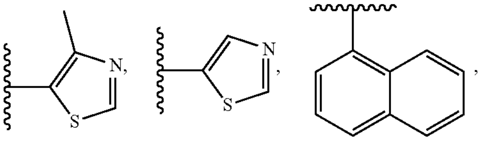

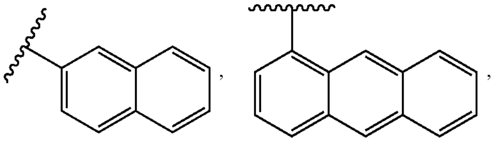

-continued
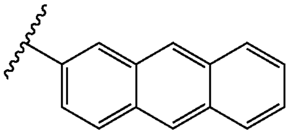, 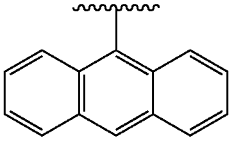,
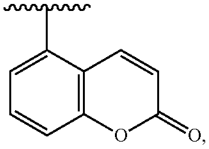 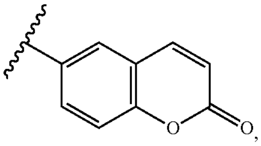
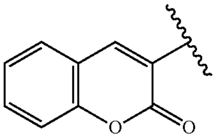, 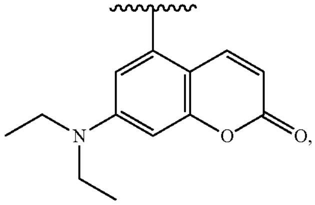
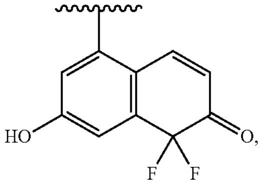 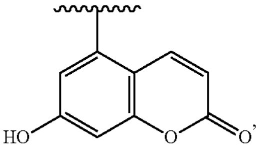
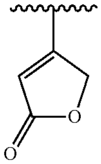, 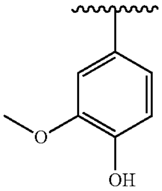, 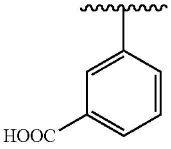,
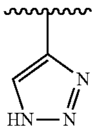, 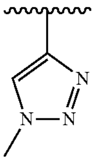, 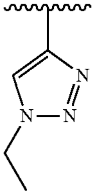, 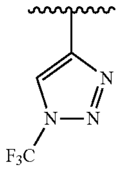,
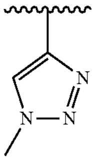, 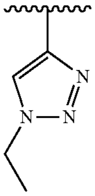, 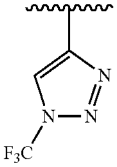, 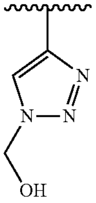,
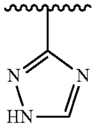, 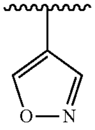, 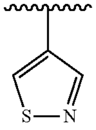, 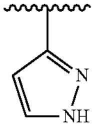, or
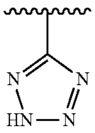.
11. The compound of claim 1, having the formula:
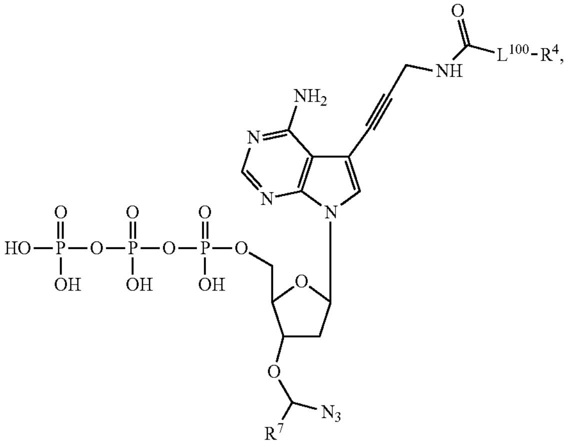
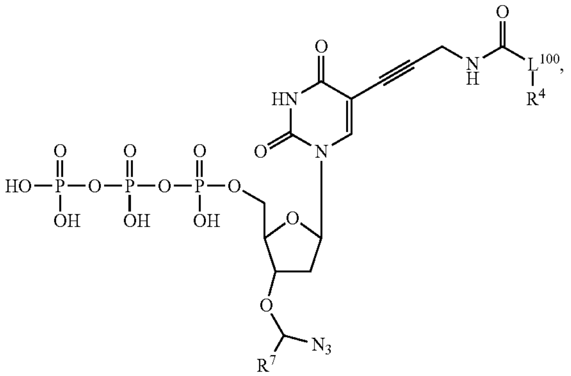
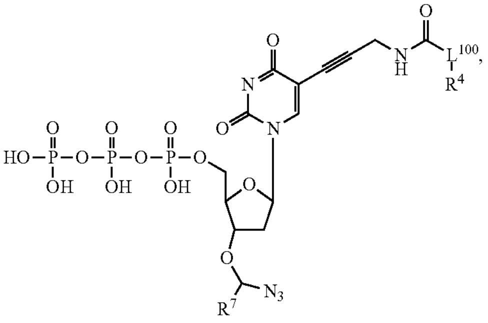 or
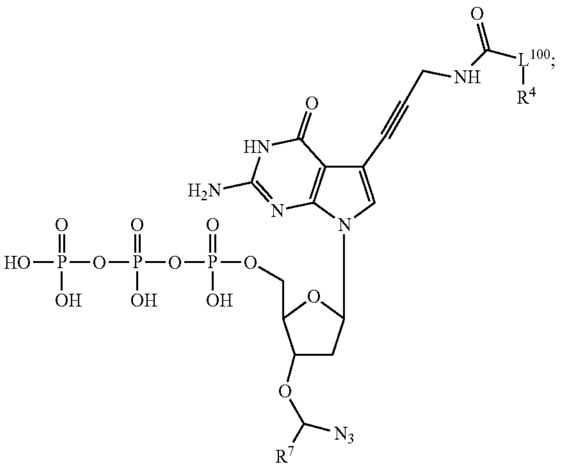

wherein $L^{100}$ is a cleavable linker; and $R^4$ is a detectable moiety.

12. A method for sequencing a nucleic acid, comprising:

(i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label; and (ii) detecting said unique detectable label of each incorporated compound, so as to thereby identify each incorporated compound in said extension strand, thereby sequencing the nucleic acid;

wherein each of said four different compounds is independently a compound of claim 1.

13. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of claim 1.

14. A nucleic acid polymerase complex comprising a nucleic acid polymerase, wherein said nucleic acid polymerase is bound to a compound of claim 1.

15. A method of preparing or synthesizing a compound of Formula (I)

(I)

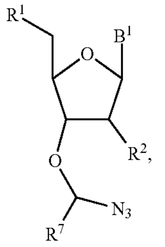

said method comprising mixing compound (A), compound (B), and an azidolating reagent together in a reaction vessel, wherein compound (A) has the formula:

(A)

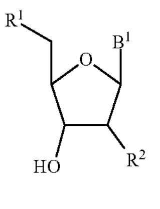

and compound (B) has the formula:

(B)

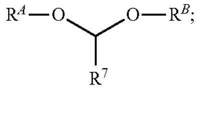

wherein $B^1$ is a nucleobase;

$R^1$ is a polyphosphate moiety, 5'-O-nucleoside protecting group, monophosphate moiety, nucleic acid moiety, hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a polymerase-compatible cleavable moiety;

$R^A$ and $R^B$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^7$ is substituted or unsubstituted cycloalkyl, substituted or unsubstituted heterocycloalkyl, substituted or unsubstituted aryl, or substituted or unsubstituted heteroaryl.

16. The compound of claim 8, wherein $L^{101}$ is

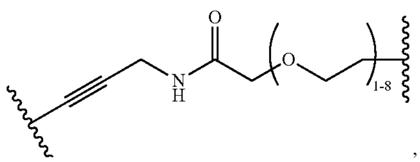

,

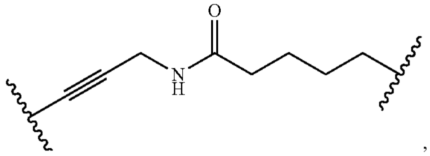

,

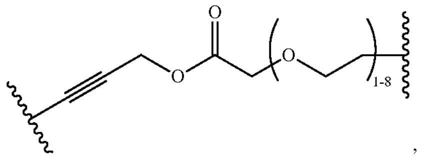

,

-continued
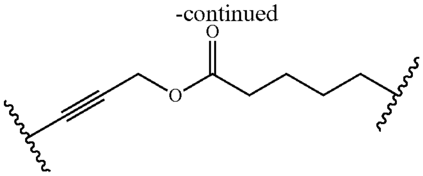
,
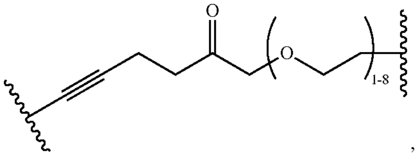
, or
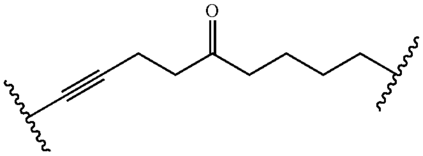
.
* * * * *